US010073348B2

(12) United States Patent
Nakagawa et al.

(10) Patent No.: US 10,073,348 B2
(45) Date of Patent: *Sep. 11, 2018

(54) RESIST-PATTERN-FORMING METHOD AND CHEMICALLY AMPLIFIED RESIST MATERIAL

(71) Applicants: OSAKA UNIVERSITY, Suita-shi (JP); TOKYO ELECTRON LIMITED, Tokyo (JP); JSR CORPORATION, Tokyo (JP)

(72) Inventors: Hisashi Nakagawa, Tokyo (JP); Takehiko Naruoka, Tokyo (JP); Tomoki Nagai, Tokyo (JP); Seiichi Tagawa, Suita (JP); Akihiro Oshima, Suita (JP); Seiji Nagahara, Tokyo (JP)

(73) Assignees: OSAKA UNIVERSITY, Suita-shi (JP); TOKYO ELECTRON LIMITED, Tokyo (JP); JSR CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/241,274

(22) Filed: Aug. 19, 2016

(65) Prior Publication Data

US 2017/0052448 A1    Feb. 23, 2017

(30) Foreign Application Priority Data

Aug. 20, 2015  (JP) .................................. 2015-163254

(51) Int. Cl.
*G03F 7/004*      (2006.01)
*G03F 7/20*       (2006.01)
(Continued)

(52) U.S. Cl.
CPC ............ *G03F 7/203* (2013.01); *C07C 303/32* (2013.01); *C07C 309/07* (2013.01);
(Continued)

(58) Field of Classification Search
CPC ...... G03F 7/004; G03F 7/2002; G03F 7/0397; G03F 7/32; G03F 7/38; H01L 21/0274;
(Continued)

(56) References Cited

U.S. PATENT DOCUMENTS 8,124,326 B2*   2/2012  Shirley ................. G03F 7/2022
                                                       430/322
8,900,791 B2*  12/2014  Tsuchimura .......... C07C 309/29
                                                     430/270.1
(Continued)

FOREIGN PATENT DOCUMENTS

EP    0 622 682 A1    11/1994
EP    2 960 926 A1    12/2015
(Continued)

OTHER PUBLICATIONS

S. Tagawa et al., "Super High Sensitivity Enhancement by Photo-Sensitized Chemically Amplified Resist (PS-CAR) Process", Journal of Photopolymer Science and Technology, vol. 26, No. 6 (2013), pp. 825-830.
(Continued)

*Primary Examiner* — Amanda C Walke
(74) *Attorney, Agent, or Firm* — Oblon, McClelland, Maier & Neustadt, L.L.P.

(57) ABSTRACT

A resist-pattern-forming method comprises: patternwise exposing a predetermined region of a resist material film to a first radioactive ray that is ionizing radiation or nonionizing radiation; floodwise exposing the resist material film to a second radioactive ray that is nonionizing radiation; baking the resist material film; and developing the resist material film to form a resist pattern. The resist material film is made from a photosensitive resin composition comprising a chemically amplified resist material. The chemically amplified resist material comprises a base component that is capable of being made soluble or insoluble in a developer
(Continued)

solution by an action of an acid and a generative component that is capable of generating a radiation-sensitive sensitizer and an acid upon an exposure. A van der Waals volume of the acid generated from the generative component is no less than $3.0 \times 10^{-28}$ m$^3$.

20 Claims, 9 Drawing Sheets

(51) Int. Cl.

| | |
|---|---|
| H01L 21/027 | (2006.01) |
| C07C 309/07 | (2006.01) |
| C07C 381/12 | (2006.01) |
| C08F 220/38 | (2006.01) |
| C07D 409/14 | (2006.01) |
| C07C 303/32 | (2006.01) |
| C08F 220/22 | (2006.01) |
| C08F 220/28 | (2006.01) |
| C08F 220/26 | (2006.01) |
| C08F 220/14 | (2006.01) |
| G03F 7/039 | (2006.01) |
| G03F 7/32 | (2006.01) |
| G03F 7/38 | (2006.01) |

(52) U.S. Cl.
CPC .......... *C07C 381/12* (2013.01); *C07D 409/14* (2013.01); *C08F 220/14* (2013.01); *C08F 220/22* (2013.01); *C08F 220/26* (2013.01); *C08F 220/28* (2013.01); *C08F 220/38* (2013.01); *G03F 7/0045* (2013.01); *G03F 7/0046* (2013.01); *G03F 7/0397* (2013.01); *G03F 7/2002* (2013.01); *G03F 7/2022* (2013.01); *G03F 7/322* (2013.01); *G03F 7/38* (2013.01); *H01L 21/0274* (2013.01)

(58) Field of Classification Search
CPC ... C07C 381/12; C07C 303/32; C07C 309/07; C08F 220/14; C08F 220/22; C08F 220/38; C08F 220/28; C08F 220/26; C07D 409/14
USPC .... 430/270.1, 322, 325, 329, 330, 331, 913; 560/1, 9, 103, 149, 83; 526/243, 281
See application file for complete search history.

(56) References Cited

U.S. PATENT DOCUMENTS

| | | | | |
|---|---|---|---|---|
| 9,045,398 | B2* | 6/2015 | Suzuki | C07C 309/06 |
| 9,156,785 | B2* | 10/2015 | Aqad | C07C 63/72 |
| 9,244,347 | B2* | 1/2016 | Komuro | C07C 381/12 |
| 9,593,060 | B2* | 3/2017 | Enomoto | C07D 317/22 |
| 9,720,323 | B2* | 8/2017 | Kotake | G03F 7/0392 |
| 2006/0269879 | A1* | 11/2006 | Elian | G03F 7/203 |
| | | | | 430/394 |
| 2011/0151540 | A1* | 6/2011 | Taran | C12N 9/16 |
| | | | | 435/197 |
| 2012/0315580 | A1* | 12/2012 | Masuyama | C07D 321/10 |
| | | | | 430/285.1 |
| 2013/0004740 | A1* | 1/2013 | Kataoka | G03F 7/0045 |
| | | | | 428/195.1 |
| 2013/0224659 | A1* | 8/2013 | Ohashi | C08F 220/18 |
| | | | | 430/285.1 |
| 2013/0344435 | A1* | 12/2013 | Utsumi | G03F 7/039 |
| | | | | 430/270.1 |
| 2014/0377706 | A1* | 12/2014 | Hatakeyama | G03F 7/32 |
| | | | | 430/296 |
| 2015/0086926 | A1* | 3/2015 | Ohashi | C07C 381/12 |
| | | | | 430/285.1 |
| 2015/0168829 | A1* | 6/2015 | Domon | G03F 7/322 |
| | | | | 430/285.1 |
| 2015/0241793 | A1 | 8/2015 | Carcasi et al. | |
| 2016/0004160 | A1* | 1/2016 | Tagawa | G03F 7/38 |
| | | | | 430/296 |
| 2016/0147144 | A1 | 5/2016 | Enomoto et al. | |
| 2016/0159953 | A1 | 6/2016 | Enomoto et al. | |
| 2016/0194300 | A1* | 7/2016 | Enomoto | H01L 21/0271 |
| | | | | 216/87 |
| 2016/0195809 | A1* | 7/2016 | Ochiai | G03F 7/038 |
| | | | | 430/270.1 |
| 2016/0357103 | A1 | 12/2016 | Nagahara et al. | |

FOREIGN PATENT DOCUMENTS

| | | |
|---|---|---|
| JP | H04-151156 A | 5/1992 |
| JP | H04-162040 A | 6/1992 |
| JP | H05-005995 A | 1/1993 |
| JP | H05-197148 A | 8/1993 |
| JP | H06-194834 A | 7/1994 |
| JP | H08-146608 A | 6/1996 |
| JP | H10-83079 A | 3/1998 |
| JP | 2002-174894 A | 6/2002 |
| JP | 2008-543033 A | 11/2008 |
| JP | 2014-224984 | 12/2014 |
| JP | 2015-061831 A | 4/2015 |
| JP | 2015-078366 A | 4/2015 |
| JP | 2015-098471 A | 5/2015 |
| JP | 2015-134904 A | 7/2015 |
| JP | 2015-187252 A | 10/2015 |
| WO | WO 2006/125509 A2 | 11/2006 |
| WO | WO 2011/086389 A1 | 7/2011 |
| WO | WO 2013/047528 A1 | 4/2013 |
| WO | WO 2014/129556 A1 | 8/2014 |
| WO | WO 2014/185065 A1 | 11/2014 |
| WO | WO 2014/208076 A1 | 12/2014 |
| WO | WO 2014/208102 A1 | 12/2014 |
| WO | WO 2014/208103 A1 | 12/2014 |
| WO | WO 2014/208104 A1 | 12/2014 |
| WO | WO 2015/019616 A1 | 2/2015 |
| WO | WO 2015/022779 A1 | 2/2015 |
| WO | WO 2015/049871 A1 | 4/2015 |
| WO | WO 2015/052914 A1 | 4/2015 |
| WO | WO 2015/125788 A1 | 8/2015 |
| WO | WO 2015/127353 A1 | 8/2015 |

OTHER PUBLICATIONS

Extended Search Report dated Jan. 20, 2017 in European Patent Application No. 16184899.9.
Seiichi Tagawa, et al., "Super High Sensitivity Enhancement by Photo-Sensitized Chemically Amplified Resist (PS-CAR) Process", Journal of Photopolymer Science and Technology, vol. 26, No. 6, 213, pp. 825-830.

* cited by examiner

BACKGROUND ART

US 10,073,348 B2

RESIST-PATTERN-FORMING METHOD AND CHEMICALLY AMPLIFIED RESIST MATERIAL

CROSS-REFERENCE TO RELATED APPLICATIONS

The present application claims priority to Japanese Patent Application No. 2015-163254, filed Aug. 20, 2015, the contents of which are incorporated herein by reference in their entirety.

BACKGROUND OF THE INVENTION

Field of the Invention

The present invention relates to a resist-pattern-forming method and a chemically amplified resist material.

Discussion of the Background

EUV (extreme-ultraviolet) lithography attracts attention as one of element technologies for manufacture of the next generation of semiconductor devices. The EUV lithography is a pattern formation technology in which EUV light having a wavelength of 13.5 nm is utilized as an exposure light. It is demonstrated that the EUV lithography enables an extremely fine pattern (no greater than 20 nm, for example) to be formed in an exposure step of a manufacture process of the semiconductor devices.

However, since hitherto-developed EUV light sources have low power, the exposure treatment requires a long time period, currently hindering practical application of the EUV lithography. In order to overcome the low power of the EUV light sources, increase of sensitivity of resist material (photosensitive resin) may be contemplated (see Japanese Unexamined Patent Application, Publication No. 2002-174894). Similar problems to those of EUV exist for power and sensitivity of lithography employing an electron beam, an ion beam and the like as a light source.

SUMMARY OF THE INVENTION

According to one aspect of the present invention, a resist-pattern-forming method comprises: patternwise exposing a predetermined region of a resist material film made from a photosensitive resin composition comprising a chemically amplified resist material to a first radioactive ray that is ionizing radiation or nonionizing radiation having a wavelength of no greater than 400 nm; floodwise exposing the resist material film patternwise exposed, to a second radioactive ray that is nonionizing radiation having a wavelength greater than the nonionizing radiation for the patternwise exposing and greater than 200 nm; baking the resist material film floodwise exposed; and developing the resist material film baked with a developer solution to form a resist pattern. The chemically amplified resist material comprises: a base component that is capable of being made soluble or insoluble in the developer solution by an action of an acid; and a generative component that is capable of generating a radiation-sensitive sensitizer and an acid upon an exposure. The generative component comprises: a radiation-sensitive acid-and-sensitizer generating agent; any two among the radiation-sensitive acid-and-sensitizer generating agent, a radiation-sensitive sensitizer generating agent, and a radiation-sensitive acid generating agent; or the radiation-sensitive acid-and-sensitizer generating agent, the radiation-sensitive sensitizer generating agent, and the radiation-sensitive acid generating agent. The radiation-sensitive acid-and-sensitizer generating agent generates, upon the exposure to the first radioactive ray, an acid, and a radiation-sensitive sensitizer absorbing the second radioactive ray, and substantially does not generate the acid and the radiation-sensitive sensitizer upon the exposure to the second radioactive ray, in light-unexposed regions that are not exposed to the first radioactive ray in the patternwise exposing. The radiation-sensitive sensitizer generating agent generates, upon the exposure to the first radioactive ray, a radiation-sensitive sensitizer absorbing the second radioactive ray, and substantially does not generate the radiation-sensitive sensitizer upon the exposure to the second radioactive ray, in light-unexposed regions that are not exposed to the first radioactive ray in the patternwise exposing. The radiation-sensitive acid generating agent generates an acid upon the exposure to the first radioactive ray, and substantially does not generate the acid upon the exposure to the second radioactive ray, in light-unexposed regions that are not exposed to the first radioactive ray in the patternwise exposing. A van der Waals volume of an acid generated from the generative component is no less than $3.0 \times 10^{-28}$ m$^3$.

According to another aspect of the present invention, a chemically amplified resist material comprises: a base component that is capable of being made soluble or insoluble in a developer solution by an action of an acid; and a generative component that is capable of generating a radiation-sensitive sensitizer and an acid upon an exposure. The generative component comprises: a radiation-sensitive acid-and-sensitizer generating agent; any two among the radiation-sensitive acid-and-sensitizer generating agent, a radiation-sensitive sensitizer generating agent, and a radiation-sensitive acid generating agent; or the radiation-sensitive acid-and-sensitizer generating agent, the radiation-sensitive sensitizer generating agent, and the radiation-sensitive acid generating agent. The radiation-sensitive acid-and-sensitizer generating agent is capable of generating, upon an exposure to a first radioactive ray that is ionizing radiation or nonionizing radiation having a wavelength of no greater than 400 nm, an acid, and a radiation-sensitive sensitizer absorbing a second radioactive ray that is nonionizing radiation having a wavelength greater than a wavelength of the first radioactive ray and greater than 200 nm, and substantially does not generate the acid and the radiation-sensitive sensitizer upon an exposure to the second radioactive ray without the exposure to the first radioactive ray. The radiation-sensitive sensitizer generating agent is capable of generating, upon the exposure to the first radioactive ray, a radiation-sensitive sensitizer absorbing the second radioactive ray, and substantially does not generate the radiation-sensitive sensitizer upon the exposure to the second radioactive ray without the exposure to the first radioactive ray. The radiation-sensitive acid generating agent is capable of generating an acid upon the exposure to the first radioactive ray, and substantially does not generate the acid upon the exposure to the second radioactive ray without the exposure to the first radioactive ray. A van der Waals volume of the acid generated from the generative component is no less than $3.0 \times 10^{-28}$ m$^3$.

BRIEF DESCRIPTION OF THE DRAWINGS

FIGS. 6A to 6C show cross-sectional views explaining an example of the manufacturing steps of the semiconductor device according to an embodiment of the present invention, in which FIG. 6A is a cross-sectional view illustrating the resist pattern forming step, FIG. 6B is a cross sectional view illustrating the etching step, and FIG. 6C is a cross sectional view illustrating the resist pattern removing step;

DESCRIPTION OF THE PREFERRED EMBODIMENTS

Figure 1:
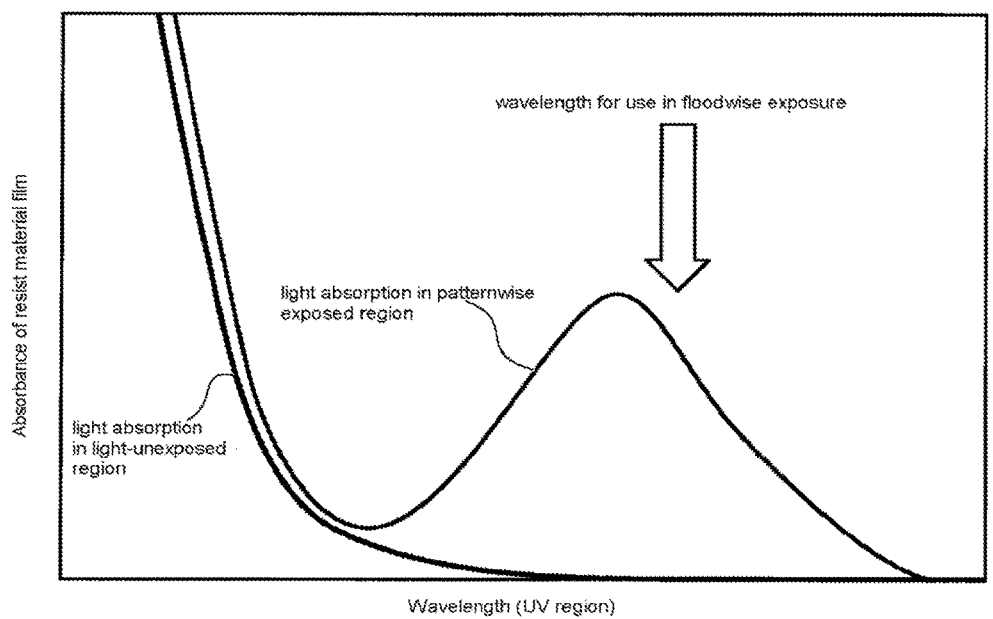
FIG. 1 shows a conceptual diagram showing the absorbance of the patternwise exposed regions and absorbance of the light-unexposed regions of the resist material film as a graph.

According to an embodiment of the invention, a chemically amplified resist material that is used as a photosensitive resin composition in a lithography process including: a patternwise exposure step of patternwise exposing a predetermined region of a resist material film formed by using a photosensitive resin composition to a first radioactive ray that is ionizing radiation or nonionizing radiation having a wavelength of no greater than 400 nm; a floodwise exposure step of floodwise exposing the resist material film obtained after patternwise exposure step, to a second radioactive ray that is nonionizing radiation having a wavelength greater than the nonionizing radiation for the patternwise exposure step and greater than 200 nm; a baking step of baking the resist material film obtained after the floodwise exposure step; and a development step of developing the resist material film obtained after the baking step with a developer solution to form a resist pattern, contains: (1) a base component that is capable of being made soluble or insoluble in the developer solution by an action of an acid, and (2) a component (may be also referred to as "generative component") that is capable of generating a radiation-sensitive sensitizer and an acid upon an exposure, wherein the component (2) contains the following component (a); any two among the following components (a) to (c); or all of the following components (a) to (c):

(a) a radiation-sensitive acid-and-sensitizer generating agent that is capable of generating, upon the exposure to the first radioactive ray, an acid, and a radiation-sensitive sensitizer absorbing the second radioactive ray, and substantially does not generate the acid and the radiation-sensitive sensitizer upon the exposure to the second radioactive ray, in light-unexposed regions that are not exposed to the first radioactive ray in the patternwise exposure step;

(b) a radiation-sensitive sensitizer generating agent that is capable of generating, upon the exposure to the first radioactive ray, a radiation-sensitive sensitizer absorbing the second radioactive ray, and substantially does not generate the radiation-sensitive sensitizer upon the exposure to the second radioactive ray, in light-unexposed regions that are not exposed to the first radioactive ray in the patternwise exposure step; and (c) a radiation-sensitive acid generating agent that is capable of generating an acid upon the exposure to the first radioactive ray, and substantially does not generate the acid upon the exposure to the second radioactive ray, in light-unexposed regions that are not exposed to the first radioactive ray in the patternwise exposure step, and wherein a van der Waals volume of an acid generated from the component (2) is no less than $3.0 \times 10^{-28}$ m$^3$.

According to another embodiment of the invention, a chemically amplified resist material contains (1) a base component that is capable of being made soluble or insoluble in the developer solution by an action of an acid, and (2) a component (may be also referred to as "generative component") that is capable of generating a radiation-sensitive sensitizer and an acid upon an exposure, wherein the component (2) contains: the following component (a); any two among the following components (a) to (c); or all of the following components (a) to (c):

(a) a radiation-sensitive acid-and-sensitizer generating agent that is capable of generating, upon an exposure to a first radioactive ray that is ionizing radiation or nonionizing radiation having a wavelength of no greater than 400 nm, an acid, and a radiation-sensitive sensitizer absorbing a second radioactive ray that is nonionizing radiation having a wavelength greater than a wavelength of the first radioactive ray and greater than 200 nm, and substantially does not generate the acid and the radiation-sensitive sensitizer upon an exposure to the second radioactive ray without the exposure to the first radioactive ray;

(b) a radiation-sensitive sensitizer generating agent that is capable of generating, upon the exposure to the first radioactive ray, a radiation-sensitive sensitizer absorbing the second radioactive ray, and substantially does not generate the radiation-sensitive sensitizer upon the exposure to the second radioactive ray without the exposure to the first radioactive ray;

(c) a radiation-sensitive acid generating agent that is capable of generating an acid upon the exposure to the first radioactive ray, and substantially does not generate the acid upon the exposure to the second radioactive ray without the exposure to the first radioactive ray, wherein a van der Waals volume of an acid generated from the component (2) is no less than $3.0 \times 10^{-28}$ m$^3$.

The term "substantially does not generate the acid and the radiation-sensitive sensitizer upon the exposure to (or, irradiation with) the second radioactive ray, in light-unexposed regions that are not exposed to (or, irradiated with) the first radioactive ray in the patternwise exposure step", "substantially does not generate the radiation-sensitive sensitizer upon the exposure to (or, irradiation with) the second radioactive ray, in light-unexposed regions that are not exposed to (or, irradiated with) the first radioactive ray in the patternwise exposure step", "substantially does not generate the acid upon the exposure to (or, irradiation with) the second radioactive ray, in light-unexposed regions that are not exposed to (or, irradiated with) the first radioactive ray in the patternwise exposure step", "substantially does not generate the acid and the radiation-sensitive sensitizer upon an exposure to (or, irradiation with) the second radioactive ray without the exposure to (or, irradiation with) the first radioactive ray", "substantially does not generate the radiation-sensitive sensitizer upon the exposure to (or, irradiation with) the second radioactive ray without the exposure to (or, irradiation with) the first radioactive ray", and "substantially does not generate the acid upon the exposure to (or, irradiation with) the second radioactive ray without the exposure to (or, irradiation with) the first radioactive ray" as referred to herein mean that the acid and/or the radiation-sensitive sensitizer is/are not generated through the exposure to (or, irradiation with) only the second radioactive ray, or that even in the case where the acid and/or the radiation-sensitive sensitizer is/are generated through the exposure to (or, irradiation with) only the second radioactive ray, the amount of the acid and/or the radiation-sensitive sensitizer generated in the regions unexposed to the patterning light through the exposure to (or, irradiation with) the second radioactive ray is so small that the difference in the concentration of the acid and/or the radiation-sensitive sensitizer between the light-exposed regions and the light-unexposed regions after the patternwise exposure can be maintained at a level to permit the pattern formation, and consequently the amount of the acid or radiation-sensitive sensitizer thus generated is so small that either the patternwise exposed regions or the patternwise unexposed regions alone can be dissolved in the developer solution in the development step.

The chemically amplified resist material of the embodiment of the present invention can achieve both high sensitivity and superior lithographic characteristics at a sufficiently high level. Formation of a fine pattern is thus possible even in the case of employing a low-power light source in the patternwise exposure step.

The embodiment of the present invention provides a chemically amplified resist material that can achieve both high sensitivity and superior lithographic characteristics in a pattern forming technique employing ionizing radiation such as EUV light, an electron beam and an ion beam, or nonionizing radiation having a wavelength no greater than 400 nm such as KrF excimer laser and ArF excimer laser.

Hereinafter, embodiments of the present invention will be described in detail. It is to be noted that the present invention is not limited to the following embodiments.

Chemically Amplified Resist Material

The chemically amplified resist material according to an embodiment of the present invention is used as a photosensitive resin composition in the two-step exposure lithography process. The two-step exposure lithography process comprises a patternwise exposure step, a floodwise exposure step, a baking step, and a development step. In the patternwise exposure step, a first radioactive ray, which is ionizing radiation or nonionizing radiation having a wavelength less than 400 nm, is emitted. And in the floodwise exposure step, a second radioactive ray, which is nonionizing radiation having wavelength greater than that of the nonionizing radiation in the patternwise exposure step and greater than 200 nm, is emitted.

The chemically amplified resist material according to the embodiment of the present invention may be any of a positive resist material and a negative resist material, and is appropriately selected by selecting a base component, a developer solution and the like described later. Here, a resist material that allows a patternwise exposed regions to be diffused in the development after the patternwise exposure, leaving a patternwise unexposed region (light shielding part) is referred to as a positive resist material, while a resist material that allows a light-unexposed regions to be diffused, leaving a light-exposed region (light shielding part) is referred to as a negative resist material.

The chemically amplified resist material according to the embodiment of the present invention (hereinafter may also be referred to merely as "resist material") contains a base component (1) that is capable of being made soluble or insoluble in the developer solution by an action of an acid, and a component (2) that is capable of generating a radiation-sensitive sensitizer and an acid upon an exposure.

(1) Base Component

In the embodiment of the present invention, the base component (1) may be either an organic compound or an inorganic compound. The organic compound may be either a polymer compound or a low molecular weight compound. In addition, the polymer compound may be a polymer whose solubility in a developer solution is altered by an action of an acid. Such a polymer is widely used as a base component for a resist material. Furthermore, the base component (1) is preferably a component that does not excessively absorb the first radioactive ray in the patternwise exposure and that can achieve formation of a resist pattern that has a shape with sufficiently high verticality. In addition, the base component (1) has preferably low absorption of the second radioactive ray in the floodwise exposure, and is preferably less likely to induce an unnecessary sensitization reaction in the light-unexposed regions upon the floodwise exposure. Alternatively, the base component (1) may be a base component (1') that has an acid-and-radiation-sensitive-sensitizer generating group (d), a radiation-sensitive sensitizer precursor group (e), and/or a radiation-sensitive acid generating group (f) described later.

The weight average molecular weight of the polymer compound is preferably no less than 1,000 and no greater than 200,000, more preferably no less than 2,000 and no greater than 50,000, and still more preferably no less than 2,000 and no greater than 20,000. In addition, in the polymer compound, a patternwise exposed region is made soluble or insoluble in a developer solution in the development step, through an acid-catalyzed reaction in the baking step (refer to FIG. 4) following the floodwise exposure.

Examples of the polymer compound include a polymer compound having a polar group (for example, an acidic functional group), a polymer compound having a polar group (for example, an acidic functional group) in which the polar group is protected by an acid-labile group. The polymer compound having a polar group is soluble in an alkaline developer solution, but is made insoluble in the alkaline developer solution through a reaction by an action of a crosslinking agent (described later) and an acid in the baking step. In this case, a resist material film in the patternwise unexposed regions is made removable by the alkaline developer solution in the development step. Therefore, in the case of developing a resist material film formed by using the polymer compound with the alkaline developer solution, the resist material functions as a negative resist material.

On the other hand, the polymer compound having a polar group in which the polar group is protected by an acid-labile group is soluble in an organic developer solution but insoluble or hardly soluble in an alkaline developer solution. The polymer compound having a polar group in which the polar group is protected by an acid-labile group, whose acid-labile group is dissociated (i.e., deprotection) by an action of an acid in the baking step, is polarized and made soluble in the alkaline developer solution and insoluble in the organic developer solution. In this case, the resist material film of the patternwise unexposed regions is made removable by the organic developer solution, while the patternwise exposed regions is made removable by the alkaline developer solution. Therefore, in the case of developing the resist material film formed by using the polymer compound having a protected polar group with the organic developer solution, the resist material functions as the negative resist material. On the other hand, in the case of developing the resist material film formed by using the polymer compound having a protected polar group with the alkaline developer solution, the resist material functions as the positive resist material.

Examples of the polymer compound include a phenol resin, a (meth)acrylic resin, a vinyl acetal resin, a urethane resin, an amide resin, an epoxy resin, a styrene resin, an ester resin. As the polymer compound, a phenol resin, a (meth)acrylic resin and a styrene based resin are preferred and a (meth)acrylic resin is more preferred.

The (meth)acrylic resin is preferably a polymer compound having at least one of structural units represented by the following formulae (VII) and (VIII).

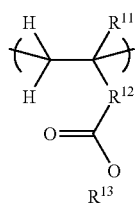
(VII)

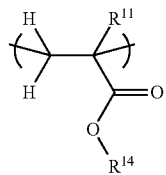
(VIII)

In the formulae (VII) and (VIII), $R^{11}$ represents a hydrogen atom; a fluorine atom; a methyl group; a trifluoromethyl group; a linear, branched, or cyclic alkylene group having 1 to 20 carbon atoms that may have a hydroxyl group, an ether bond, an ester bond or a lactone ring; a phenylene group; or a naphthylene group. $R^{12}$ represents a methylene group, a phenylene group, a naphthylene group, or a divalent group represented by C(=O)—O—$R^{12t}$—. $R^{12t}$ represents a linear, branched or cyclic alkylene group having 1 to 20 carbon atoms that may have any one of a hydroxyl group, an ether bond, an ester bond and a lactone ring; a phenylene group; or a naphthylene group. $R^{13}$ and $R^{14}$ each independently represent a hydrogen atom; a hydroxyl group; a cyano group; a carbonyl group; a carboxyl group; an alkyl group having 1 to 35 carbon atoms; and a protecting group (acid-labile group) having at least one type of structure selected from the group consisting of an ether bond, an ester bond, a sulfonic acid ester bond, a carbonate bond, a lactone ring, a sultone ring and dehydrated two carboxyl groups.

As the phenol resin, a polymer compound having a structural unit represented by the following formula (XXV) is preferred.

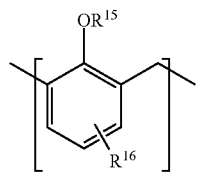
(XXV)

In the formula (XXV), $R^{15}$ represents a hydrogen atom; a hydroxyl group; a cyano group; a carbonyl group; a carboxyl group; an alkyl group having 1 to 35 carbon atoms; and a protecting group (acid-labile group) having at least one type of structure selected from the group consisting of an ether bond, an ester bond, a sulfonic acid ester bond, a carbonate bond, a lactone ring, a sultone ring and two dehydrated carboxyl group.

$R^{16}$ represents a hydrogen atom, an alkyl group having 1 to 35 carbon atoms, or the like. $R^{16}$ is preferably a methyl group, and more preferably bonded in a meta position.

The styrene resin is preferably a hydroxystyrene resin, and more preferably a polymer compound having a structural unit represented by the following formula (XXVI).

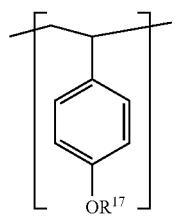
(XXVI)

In the formula (XXVI), $R^{17}$ represents a hydrogen atom; a hydroxyl group; a cyano group; a carbonyl group; a carboxyl group; an alkyl group having 1 to 35 carbon atoms; and a protecting group (acid-labile group) having at least one structure selected from the group consisting of an ether bond, an ester bond, a sulfonic acid ester bond, a carbonate bond, a lactone ring, a sultone ring and two dehydrated carboxyl groups.

Examples of the protecting group which may be contained in $R^{13}$, $R^{14}$, $R^{15}$, and $R^{17}$ include the groups shown below, but not limited thereto. In the following formulae, * denotes a site where $R^{13}$, $R^{14}$, $R^{15}$, and $R^{17}$ bond to oxygen.

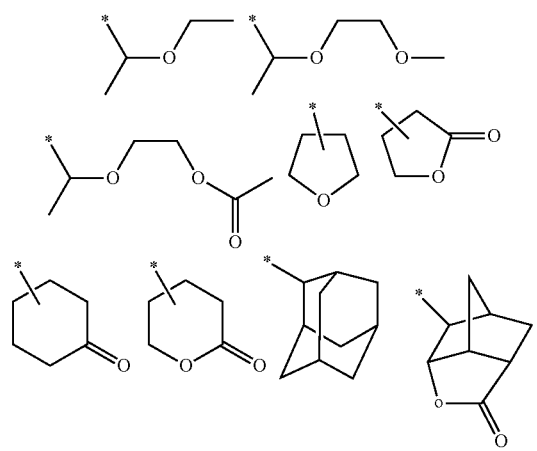

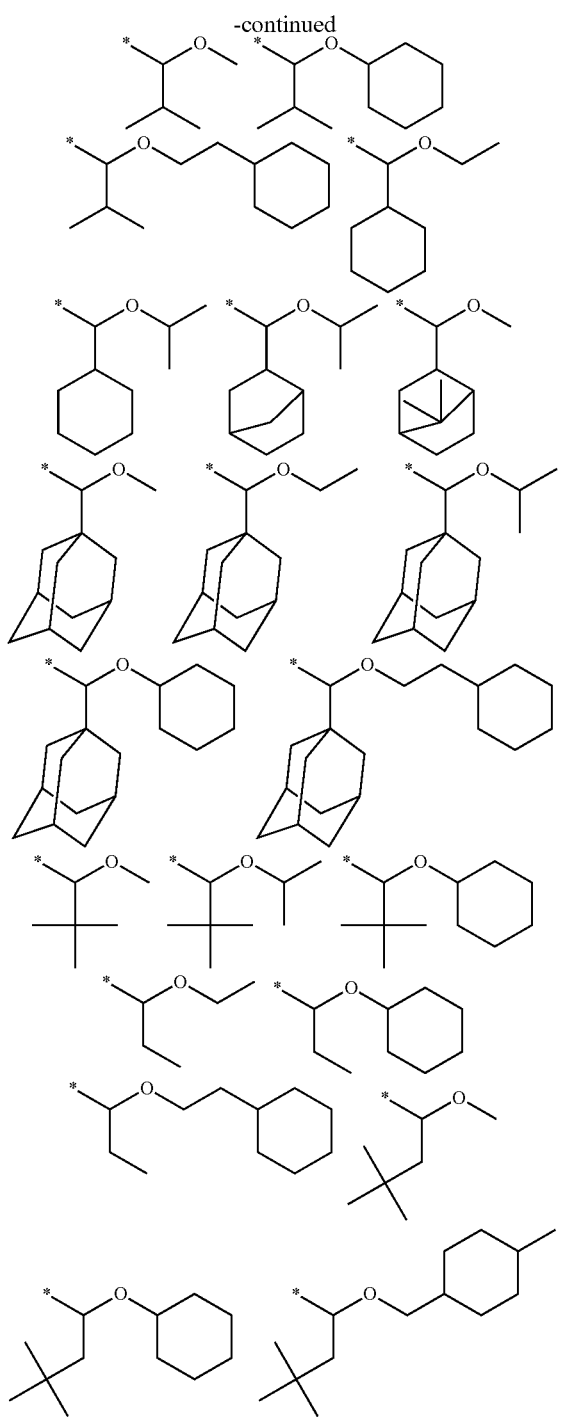

The structural unit may be included in a molecule alone or in combination of a plurality thereof.

The molecular weight of the low molecular weight compound is preferably no less than 300 and no greater than 3,000, more preferably no less than 500 and no greater than 2,000. In addition, the low molecular weight compound makes a patternwise exposed regions soluble or insoluble in a developer solution in the development step, by an acid-catalyzed reaction in the baking step (refer to FIG. 4) following the floodwise exposure.

Examples of the low molecular weight compound include: a star-shaped molecule such as a truxene derivative; a calixarene derivative; Noria; and a dendrimer.

Examples of the inorganic compound include: metal oxide such as cobalt oxide, hafnium oxide and zirconium oxide; and an organic metal compound such as a complex. The metal oxide may be either in a particulate form or a nanoparticle having a nanoorder particle diameter. In addition, the particle of the metal oxide may be coordinated with carboxylic acid and the like. An example of solubility change in the case of using an inorganic compound as the base component (1) is presented hereinafter. For example, in the case of using the nanoparticle of carboxylic acid-coordinated metal oxide as the base component (1), an anion of an acid generated upon the exposure coordinates to the metal oxide in place of the carboxylic acid anion. As a result, interaction between the metal oxide particles is increased and the base component (1) is thus gelated, thereby inhibiting dissolution of the light-exposed regions in the case of dissolution of the light-unexposed regions alone in the development step.

(2) Component Generating Radiation-Sensitive Sensitizer and Acid Upon Exposure

The component generates a radiation-sensitive sensitizer and an acid upon an exposure (radioactive ray irradiation). Among three components: a radiation-sensitive acid-and-sensitizer generating agent (a); a radiation-sensitive sensitizer generating agent (b); and a radiation-sensitive acid generating agent (c), the component contains component (a), any two among components (a) to (c), or all of components (a) to (c). In other words, in the resist material, the component (2) is blended with the base component (1).

The radiation-sensitive acid-and-sensitizer generating agent (a) and the radiation-sensitive acid generating agent (c) generate an acid by a first radioactive ray in the patternwise exposure step. Since the chemically amplified resist material according to the embodiment of the present invention contains at least one of the radiation-sensitive acid-and-sensitizer generating agent (a) and the radiation-sensitive acid generating agent (c), in the resist film formed by using the chemically amplified resist material according to the embodiment of the present invention, an acid is generated in the light-exposed regions in the patternwise exposure step.

The lower limit of the van der Waals volume of the acid is $3.0 \times 10^{-28}$ m$^3$, preferably $3.32 \times 10^{-28}$ m$^3$, and more preferably $3.5 \times 10^{-28}$ m$^3$. On the other hand, the upper limit of the van der Waals volume is preferably $1.0 \times 10^{-27}$ m$^3$ and more preferably $6.0 \times 10^{-28}$ m$^3$.

With the van der Waals volume of no less than the lower limit, the chemically amplified resist material of the embodiment of the present invention can achieve both of high sensitivity and superior lithography characteristics in a sufficiently high level and can particularly make a shape of a fine pattern favorable. Although the reason for the chemically amplified resist material of the embodiment of the present invention having the above described configuration to provide the above described effect has not been made clear, the following reason can be speculated: with the van der Waals volume of no less than the lower limit, the acid being generated does not move much within the resist material film. As a result, diffusion of the acid from the light-exposed regions to the light-unexposed regions can be appropriately inhibited, a contrast between the light-exposed regions and the light-unexposed regions can thus be secured even in a fine pattern, and superior lithography performance can be exerted.

Meanwhile, with the van der Waals volume of no greater than the upper limit, the acid being generated can be diffused more appropriately within the resist film, and a shape of the pattern to be formed can thus be made favorable in a case where both the patternwise exposure and the floodwise exposure are performed.

(a) Radiation-Sensitive Acid-and-Sensitizer Generating Agent

The radiation-sensitive acid-and-sensitizer generating agent (a) generates, through the irradiation with the first radioactive ray, an acid and a radiation-sensitive sensitizer that absorbs the second radioactive ray, while, in the light-unexposed regions not irradiated with the first radioactive ray in the patternwise exposure step, substantially does not generate the acid and the radiation-sensitive sensitizer through the irradiation with the second radioactive ray. The radiation-sensitive acid-and-sensitizer generating agent (a) having the above-described properties can therefore inhibit generation of the acid and the radiation-sensitive sensitizer caused through the irradiation with the second radioactive ray in the floodwise exposure step.

In addition, in a case where the acid and the radiation-sensitive sensitizer are generated by irradiating the radiation-sensitive acid-and-sensitizer generating agent (a) with the second radioactive ray, the lower limit of the wavelength of the second radioactive ray that can maintain the amount of the acid and the radiation-sensitive sensitizer generated through the irradiation with the second radioactive ray so small that that the difference in the concentration of the acid and the radiation-sensitive sensitizer between the light-exposed regions and the light-unexposed regions after the patternwise exposure can be maintained at a level to permit the pattern formation is preferably 300 nm, more preferably 320 nm, and still more preferably 350 nm. By making the wavelength of the second radioactive ray no less than the lower limit in a case where the radiation-sensitive acid-and-sensitizer generating agent (a) generates the acid and the radiation-sensitive sensitizer through the irradiation with the second radioactive ray, the acid is generated upon the irradiation with the second radioactive ray in the patternwise exposed regions irradiated with the first radioactive ray by sensitization action of the radiation-sensitive sensitizer being generated, while generation of the acid upon the irradiation with the second radioactive ray is inhibited in the patternwise unexposed regions not irradiated with the first radioactive ray. As a result, sensitivity and a contrast between the patternwise exposed regions and the patternwise unexposed regions can be improved.

Examples of the radiation-sensitive acid-and-sensitizer generating agent (a) includes: an onium salt compound, a diazomethane compound, and a sulfonimide compound. In addition, examples the onium salt compound include a sulfonium salt compound, a tetrahydrothiophenium salt compound, and an iodonium salt compound. In light of high reduction potential, the radiation-sensitive acid-and-sensitizer generating agent (a) is preferably a sulfonium salt compound or an iodonium salt compound, and more preferably an iodonium salt compound. The sulfonium salt compound is composed of a sulfonium cation and an anion of an acid; the iodonium salt compound is composed of an iodonium cation and an anion of an acid.

As the sulfonium salt compound, at least one compound selected from the group consisting of compounds represented by the following formulae (I) to (III) is preferred.

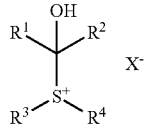
(I)

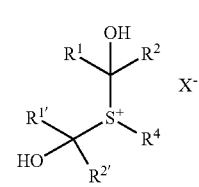
(II)

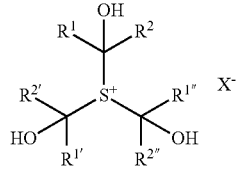
(III)

In the above formulae (I) to (III), $R^1$, $R^2$, $R^{1'}$, $R^{2'}$, $R^{1''}$, $R^{2''}$, $R^3$ and $R^4$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. In the above formulae (I) to (III), the hydrogen atom of the hydroxyl group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group. In a case where the hydrogen atom of the hydroxyl group is substituted, the sulfonium salt compound shall include a ketal compound group or an acetal compound group. In the formulae (I) to (III), any at least two of the groups represented by $R^1$, $R^2$, $R^{1'}$, $R^{2'}$, $R^{1''}$, $R^{2''}$, $R^3$, and $R^4$ may be taken together form a ring structure via a single bond or a double bond, or via a bond that includes —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. $R^e$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxyl group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group. $R^1$, $R^2$, $R^{1'}$, $R^{2'}$, $R^{1''}$, $R^{2''}$, $R^3$ and $R^4$ each independently represent preferably a phenyl group; a phenoxy group; a phenoxy group substituted with an alkyl group having 1 to 5 carbon atoms; or a phenyl group substituted with an alkoxy group having 1 to 5 carbon atoms or a hydroxyl group. In the formulae (I) to (III), $X^-$ represents an anion derived from an acid, preferably a strong acid, and more preferably a superacid.

In the above formulae (I) to (III), examples of the group represented by —C(—OH)$R^1R^2$, —C(—OH)$R^{1'}R^{2'}$, —C(—OH)$R^{1''}R^{2''}$ or the like include groups represented by the following formulae. It is to be noted that * in the formulae denotes a binding site to the sulfur ion in the above formulae (I) to (III). In the group represented by —C(—OH)$R^1R^2$, —C(—OH)$R^{1'}R^{2'}$, or —C(—OH)$R^{1''}R^{2''}$, the hydroxyl group and the carbon atom to which the hydroxyl group bonds are to give a carbonyl group upon the patternwise exposure. Thus, in the compounds represented by the above formulae (I) to (III), the group represented by —C(—OH)$R^1R^2$, —C(—OH)$R^{1'}R^{2'}$, or —C(—OH)$R^{1''}R^{2''}$ is dissociated after the patternwise exposure to generate the radiation-sensitive sensitizer.

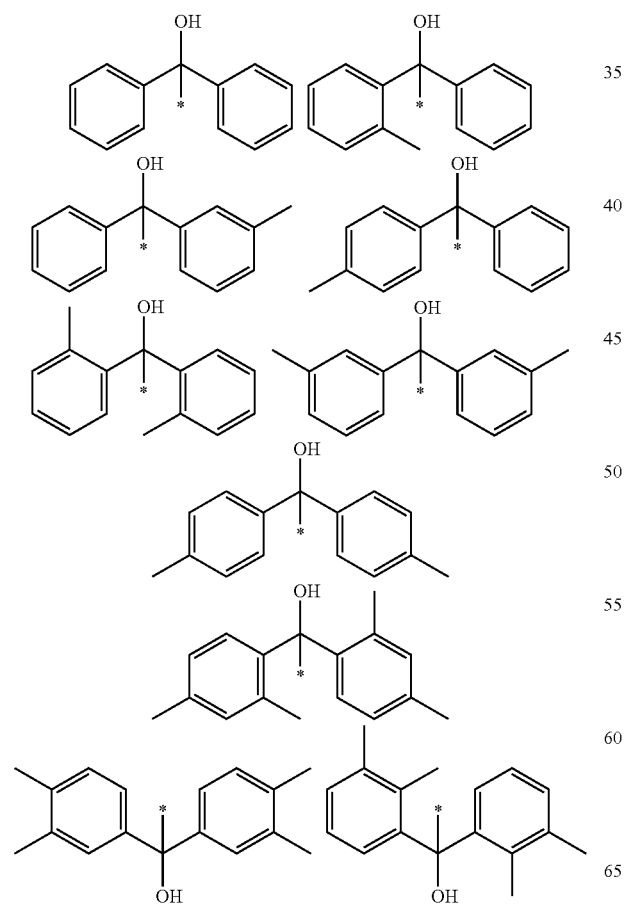

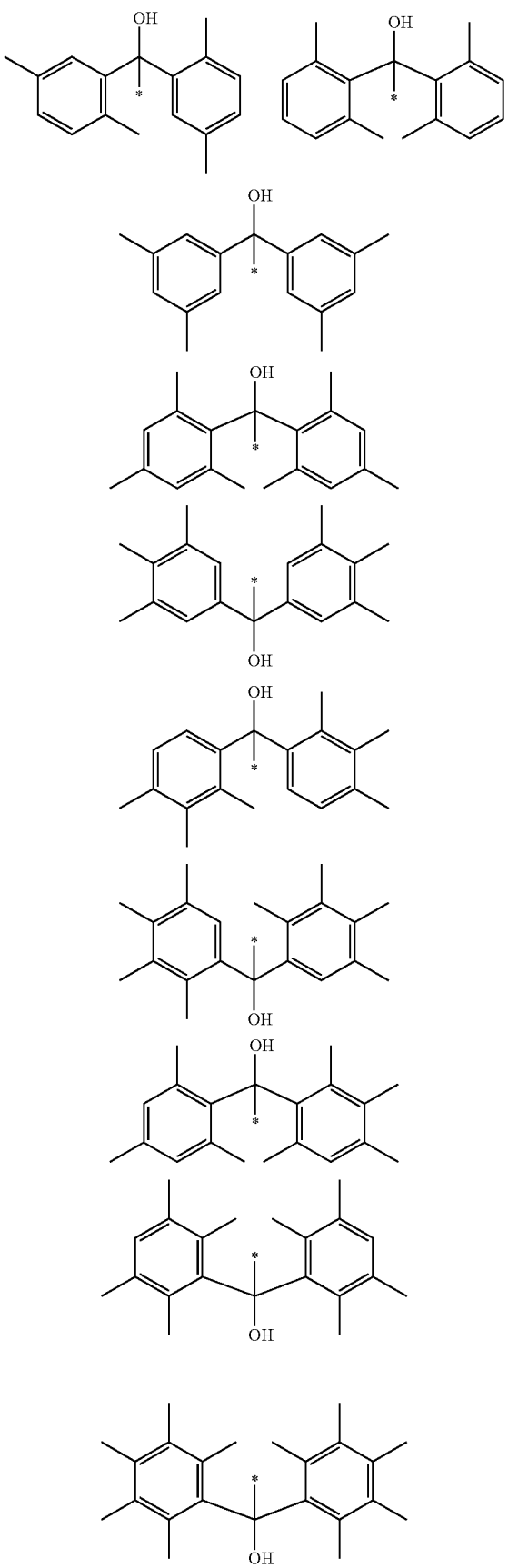

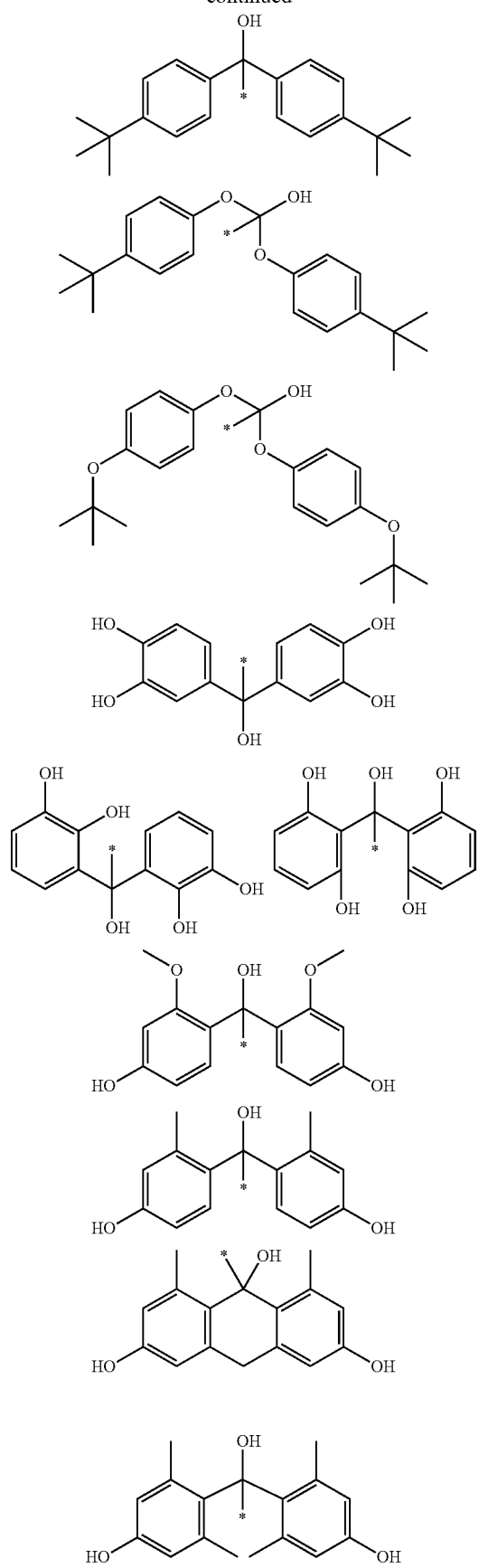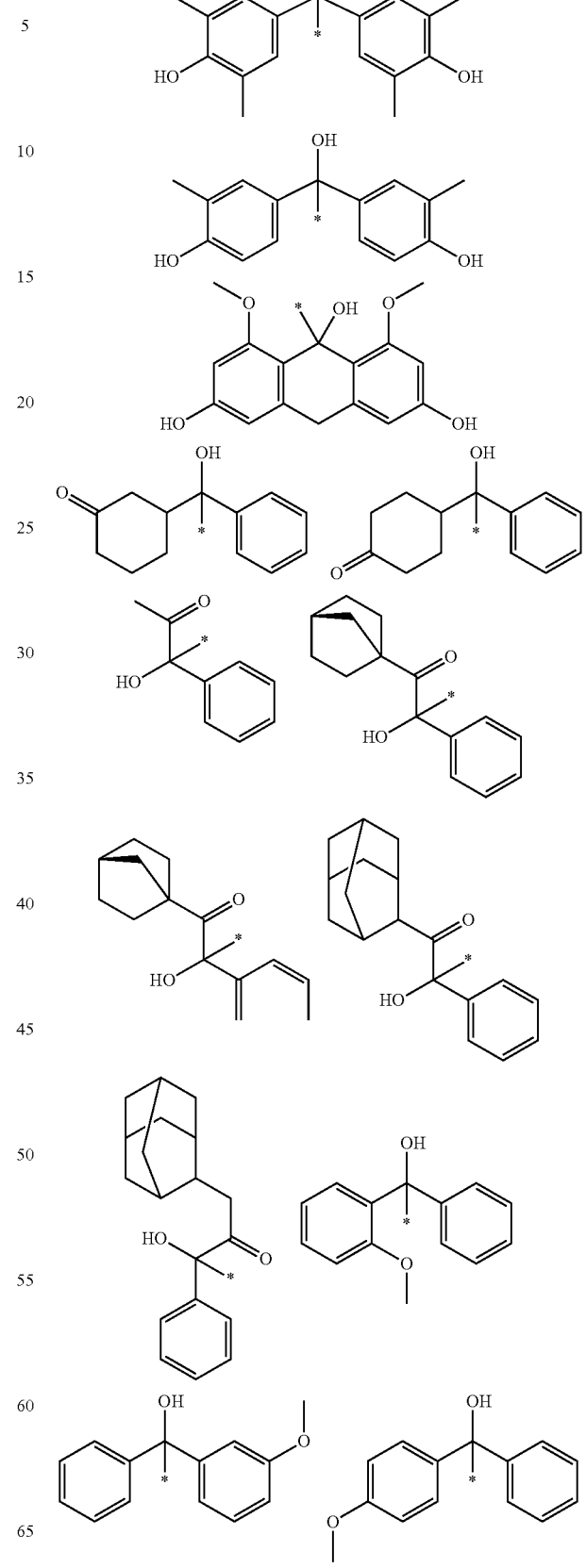

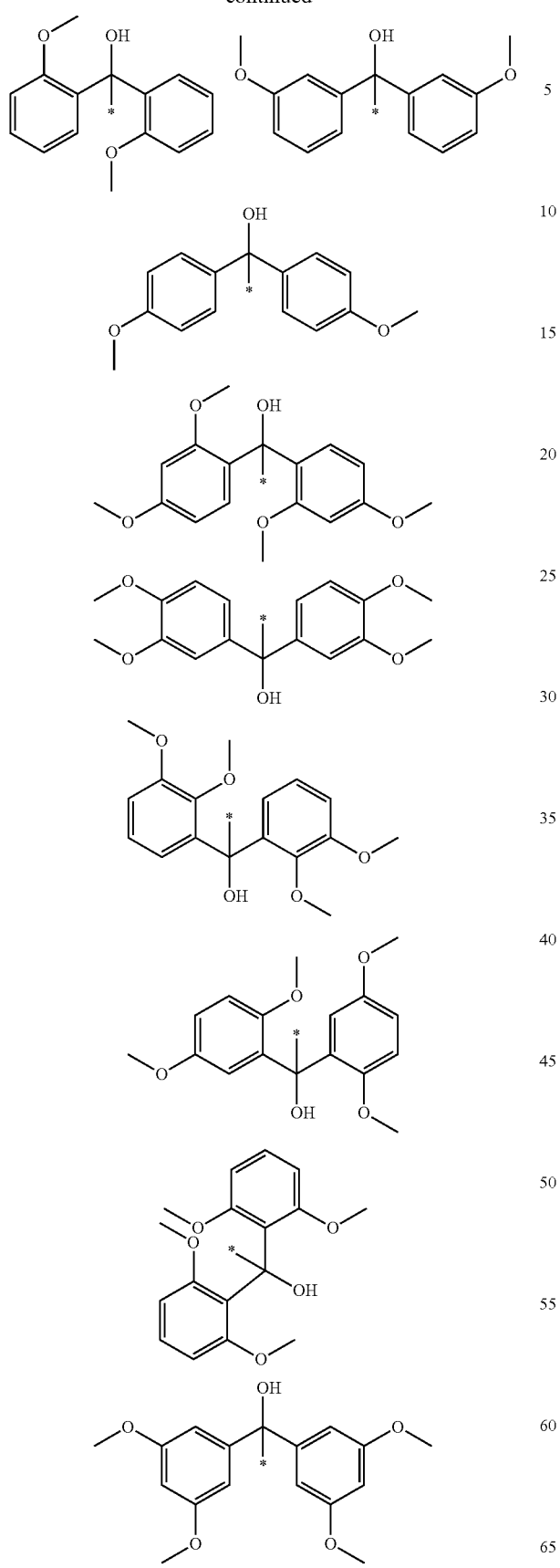
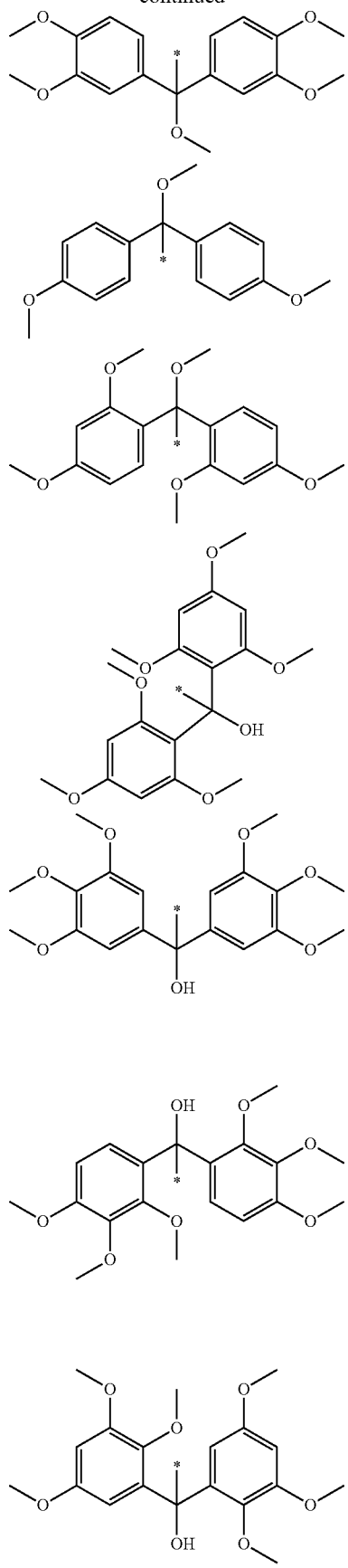

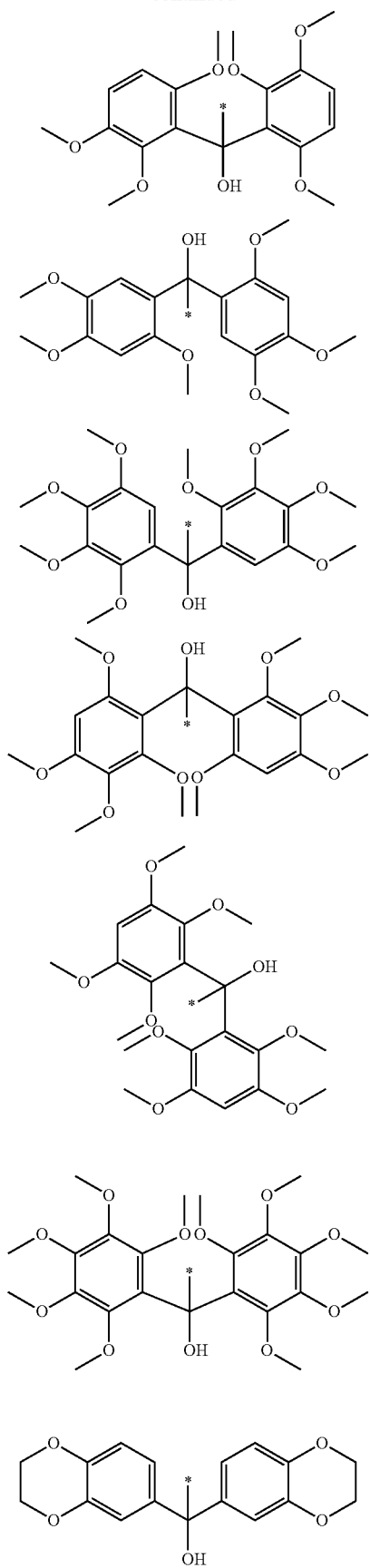

-continued
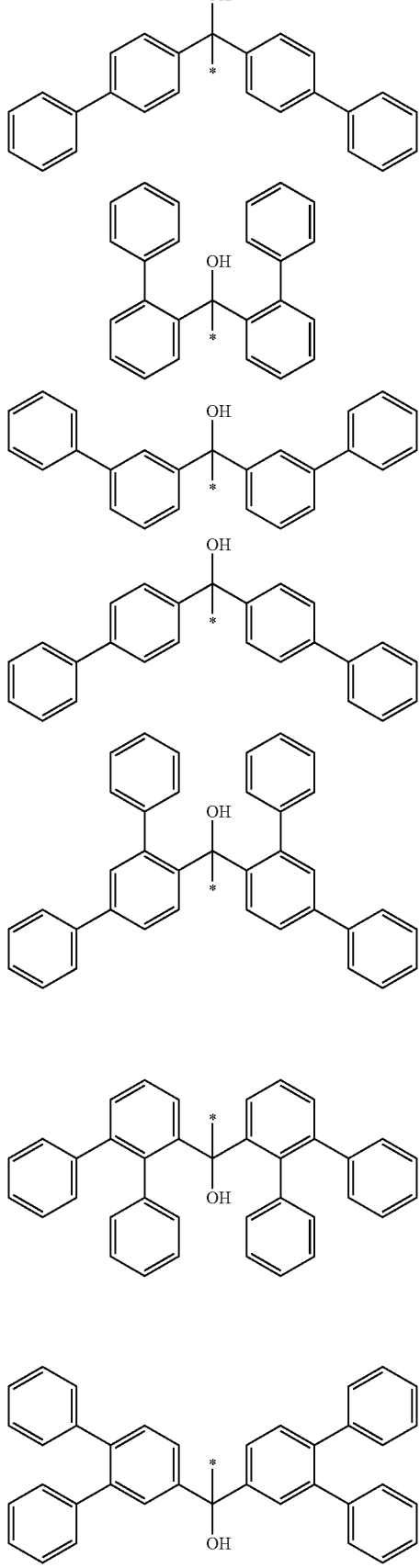
-continued
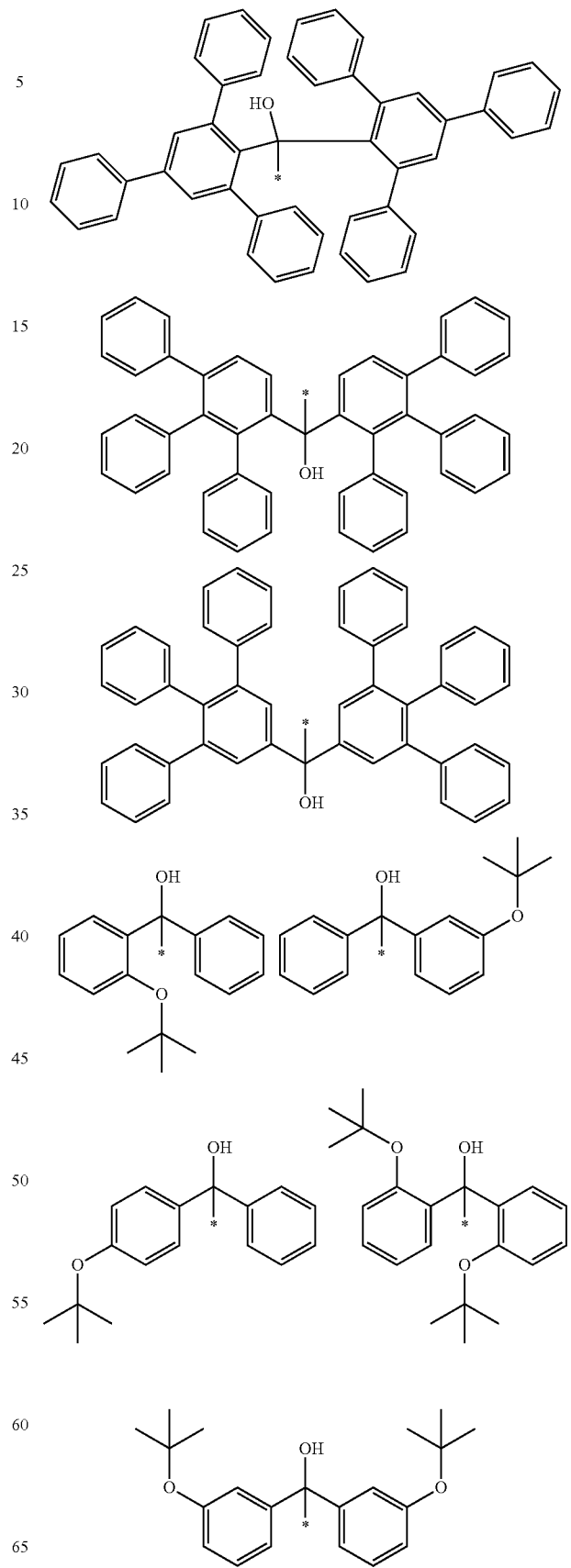

-continued
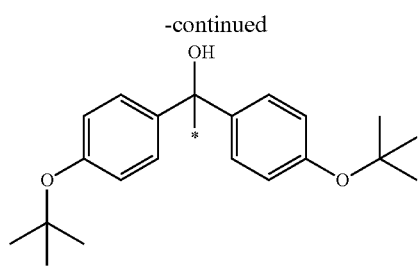
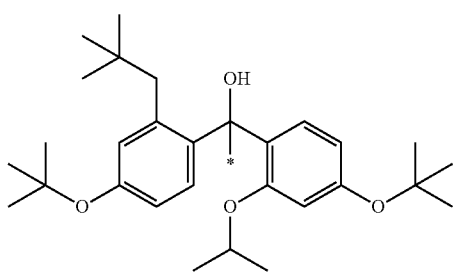
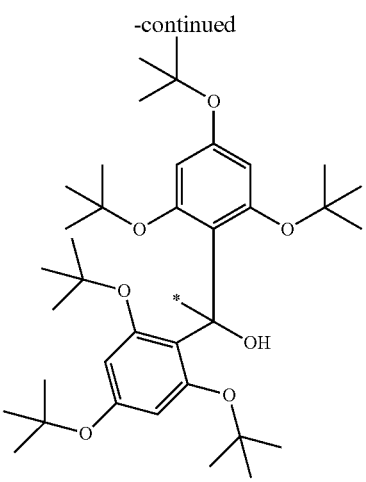
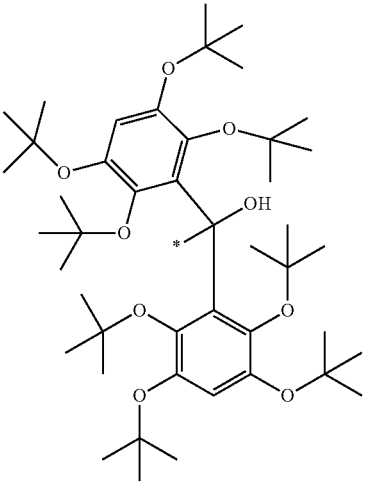
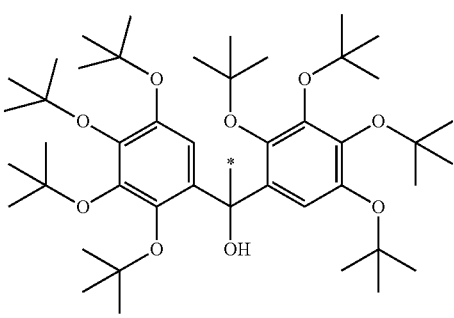
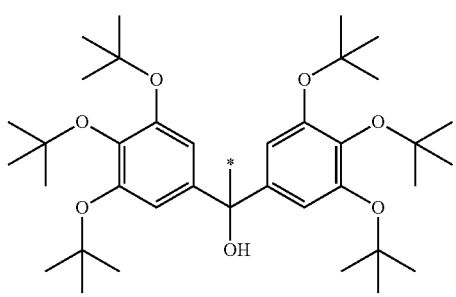
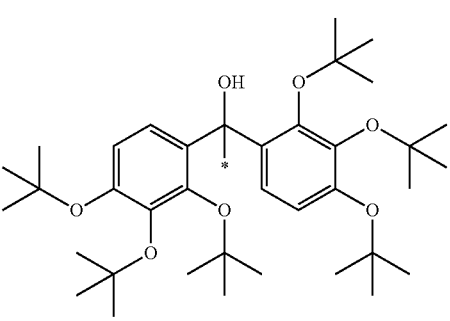

-continued

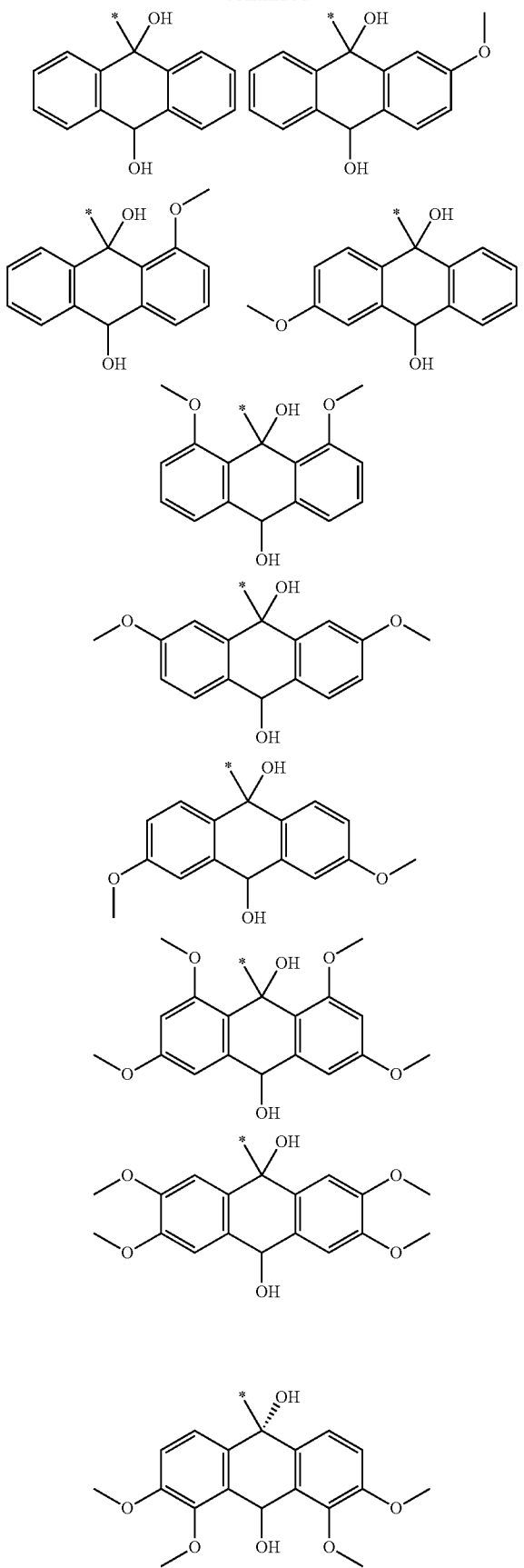

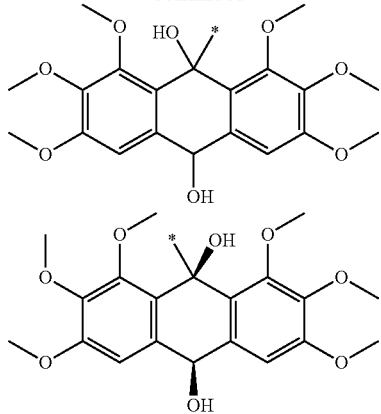

As the iodonium salt compound, at least one compound selected from the group consisting of compounds represented by the following formulae (IV) to (V) is preferred.

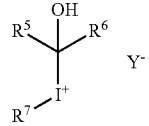

(IV)

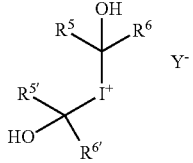

(V)

In the above formulae (IV) to (V), $R^5$, $R^6$, $R^{5'}$, $R^{6'}$, and $R^7$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group, preferably an alkyl group, having 1 to 30 carbon atoms, preferably 1 to 5 carbon atoms, substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. In the above formulae (IV) to (V), the hydrogen atom of the hydroxyl group may be substituted with: a phenyl group; a halogen atom; a saturated or unsaturated linear, branched or cyclic hydrocarbon group, preferably an alkyl group, having 1 to 30 carbon atoms, preferably 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group. In a case where the hydrogen atom of the hydroxyl group is substituted, the iodonium salt compound shall include a ketal compound group or an acetal compound group. In the formulae (IV) to (V), any at least two of the groups represented by $R^5$, $R^6$, $R^{5'}$, $R^{6'}$, and $R^7$ may be taken together form a ring structure via a single bond or a double bond, or via a bond that includes —$CH_2$—, —O—, —S—, —$SO_2NH$—, —C(=O)—, —C(=O)O—, —NHCO—, —NHC(=O)NH—, —$CHR^f$—, —$CR^f_2$—, —NH— or —$NR^f$—. $R^f$ represents: a phenyl group; a phenoxy group; a halogen atom; a saturated or unsaturated linear, branched or cyclic hydrocarbon group, preferably an alkyl group, having 1 to 30 carbon atoms, preferably 1 to 5 carbon atoms; a phenoxy group substituted with an alkoxy group having 1 to 5 carbon atoms, a hydroxyl group, or an alkyl group having 1 to 5 carbon atoms; or a phenyl group substituted with a saturated or unsaturated linear, branched or cyclic hydrocarbon group, preferably an alkyl group, having 1 to 30 carbon atoms, preferably 1 to 5 carbon atoms, an alkoxy group having 1 to 5 carbon atoms, or a hydroxyl group. $R^5$, $R^6$, $R^{5'}$, $R^{6'}$, and $R^7$ each independently represent preferably: a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group. In the formulae (IV) to (V), $Y^-$ represents an anion derived from an acid, preferably a strong acid, and more preferably a superacid.

In the above formulae (IV) to (V), examples of the group represented by —C(—OH)$R^5R^6$ or —C(—OH)$R^{5'}R^{6'}$ include groups similar to those exemplified as the group represented by —C(—OH)$R^1R^2$, —C(—OH)$R^{1'}R^{2'}$, —C(—OH)$R^{1''}R^{2''}$ or the like in connection with the above formulae (I) to (III).

The lower limit of the energy released from a radiation-sensitive onium cation included in the radiation-sensitive acid-and-sensitizer generating agent (a) upon reduction into radical is preferably 5.0 eV, more preferably 5.1 eV, and still more preferably 5.2 eV. The released energy less than the lower limit leads to an insufficient amount of the generated acid, and may make a shape of the pattern to be formed unfavorable.

The lower limit of the reduction potential of the radiation-sensitive onium cation included in the radiation-sensitive acid-and-sensitizer generating agent (a) is preferably −1.3 V, more preferably −1.0 V, and still more preferably −0.9 V. On the other hand, the upper limit of the reduction potential is preferably 0.0 V, and more preferably −0.2 V. The reduction potential less than the lower limit leads to insufficient strength of the generated acid, and may make a shape of the pattern to be formed unfavorable. To the contrary, the reduction potential exceeding the upper limit leads to excessive strength of the generated acid, and may risk facilitating diffusion of the acid into the patternwise unexposed regions.

As the anion represented by the above $Y^-$, for example, acid anions represented by the following general formulae (XX), (XXI) and (XXII) are preferred, and an acid anion represented by the following general formula (XX) is more preferred.

(XX)
(XXI)
(XXII)

In the above general formulae (XX), (XXI) and (XXII), $R^{18}$ to $R^{21}$ each independently represent an organic group. The organic group is exemplified by an alkyl group, an aryl group, a group obtained by linking a plurality of alkyl groups and/or aryl groups, and the like. The organic group is preferably an alkyl group substituted with a fluorine atom or a fluoroalkyl group in 1-position, or a phenyl group substituted with a fluorine atom or a fluoroalkyl group. When the organic group includes the fluorine atom or the fluoroalkyl group, the acidity of the acid generated upon the exposure tends to increase, leading to an improvement of the sensitivity. However, it is preferred that the organic group does not include the fluorine atom as the substituent at an end thereof.

The acid anion preferably includes at least one anion group selected from the group consisting of a sulfonic acid anion, a carboxylic acid anion, a sulfonylimide anion, a bis(alkylsulfonyl)imide anion, and a tris(alkylsulfonyl)methide anion. The acid anion is exemplified by an anion represented by the general formula "$R^{22}$—$SO_3^-$", wherein $R^{22}$ represents a linear, branched or cyclic alkyl group, a halogenated alkyl group, an aryl group, or an alkenyl group, wherein the linear, branched or cyclic alkyl group, the halogenated alkyl group, the aryl group and the alkenyl group may include a substituent. The number of carbon atoms of the linear or branched alkyl group which may be represented by $R^{22}$ is preferably no less than 1 and no greater than 10. In a case where $R^{22}$ represents the alkyl group, for example, the acid anion is exemplified by alkylsulfonates such as methanesulfonate, n-propanesulfonate, n-butanesulfonate, n-octanesulfonate, 1-adamantanesulfonate, 2-norbornanesulfonate and d-camphor-10-sulfonate. The halogenated alkyl group which may be represented by $R^{22}$ is a group obtained by substituting a part or all of hydrogen atoms of the alkyl group with a halogen atom, and the number of carbon atoms of the alkyl group is preferably no less than 1 and no greater than 10. Among the alkyl groups, linear or branched alkyl groups are more preferred, and a methyl group, an ethyl group, a propyl group, an isopropyl group, an n-butyl group, a tert-butyl group, a tert-pentyl group, and an isopentyl group are still more preferred. Moreover, examples of the halogen atom substituting the hydrogen atom include a fluorine atom, a chlorine atom, an iodine atom, a bromine atom, and the like. In regard to the halogenated alkyl group, it is preferred that no less than 50% and no greater than 100% of the total number of hydrogen atoms included in the alkyl group (alkyl group in its unhalogenated state) are substituted with the halogen atom, and it is more preferred that all hydrogen atoms are substituted with the halogen atom. In this regard, the halogenated alkyl group is preferably a fluorinated alkyl group. The number of carbon atoms of the fluorinated alkyl group is preferably no less than 1 and no greater than 10, more preferably no less than 1 and no greater than 8, and most preferably no less than 1 and no greater than 4. In addition, the degree of fluorination of the fluorinated alkyl group is preferably no less than 10% and no greater than 100%, and more preferably no less than 50% and no greater than 100%, and in particular, all of the hydrogen atoms are preferably substituted with the fluorine atom in light of an increase of the strength of the acid. Examples of the preferred fluorinated alkyl group include a trifluoromethyl group, a heptafluoro-n-propyl group, a nonafluoro-n-butyl group, and the like.

$R^{22}$ may also include a substituent. The substituent includes a divalent linking group containing an oxygen atom. Examples of the linking group include: non-hydrocarbon-based oxygen atom-containing linking groups such as an oxygen atom (ether bond: —O—), an ester bond (—C(=O)—O—), an amide bond (—C(=O)—NH—), a carbonyl group (—C(=O)—), a sulfonyl group (—SO$_2$—), and a carbonate bond (—O—C(=O)—O—).

In addition, the radiation-sensitive acid-and-sensitizer generating agent (a) is preferably the compound represented by the following formula (1). In other words, the anion of the acid represented by Y preferably has a structure shown in the following formula (1).

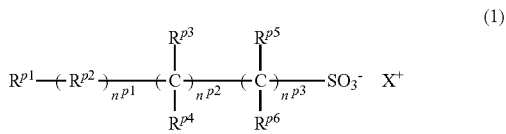

(1)

In the above formula (1), $R^{p1}$ represents a monovalent group that includes a ring structure having 6 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; $n^{p3}$ is an integer of 1 to 10, wherein in a case where $n^{p1}$ is no less than 2, a plurality of $R^{p2}$s may be identical or different, wherein in a case where $n^{p2}$ is no less than 2, a plurality of $R^{p3}$s may be identical or different, and a plurality of $R^{p4}$s may be identical or different, and wherein in a case where $n^{p3}$ is no less than 2, a plurality of $R^{p5}$s may be identical or different, and a plurality of $R^{p6}$s may be identical or different; and $X^+$ represents a monovalent radiation-sensitive onium cation.

Here, the number of "ring atoms" as referred to herein means the number of atoms constituting a ring included in the aromatic ring structure, the aromatic heterocyclic ring structure, the alicyclic structure, and the aliphatic heterocyclic ring structure, and in the case of polycyclic ring structures, the number of "ring atoms" means the number of atoms constituting the plurality of rings. The "hydrocarbon group" as referred to includes a chain hydrocarbon group, an alicyclic hydrocarbon group and an aromatic hydrocarbon group. The "hydrocarbon group" may be either a saturated hydrocarbon group or an unsaturated hydrocarbon group. The "chain hydrocarbon group" as referred to means a hydrocarbon group not containing a cyclic structure and constituted only of a chain structure, and includes both of a linear hydrocarbon group and a branched hydrocarbon group. The "alicyclic hydrocarbon group" as referred to means a hydrocarbon group containing only an alicyclic structure as the ring structure and not containing an aromatic ring structure, including both of a monocyclic alicyclic hydrocarbon group and a polycyclic alicyclic hydrocarbon group. However, the alicyclic hydrocarbon group is not required to be constituted only of an alicyclic structure, and may also contain a chain structure in a part thereof. The "aromatic hydrocarbon group" as referred to means a hydrocarbon group containing an aromatic ring structure as the ring structure. However, the aromatic hydrocarbon group is not required to be constituted only of an aromatic ring structure, and may also contain a chain structure and an alicyclic structure in a part thereof.

The monovalent group that includes ring structure having 6 or more ring atoms, which is represented by $R^{p1}$ is exemplified by a monovalent group that includes an alicyclic structure having 6 or more ring atoms, a monovalent group that includes an aliphatic heterocyclic structure having 6 or more ring atoms, a monovalent group that includes an aromatic ring structure having 6 or more ring atoms, a monovalent group that includes an aromatic heterocyclic structure having 6 or more ring atoms, and the like.

Examples of the alicyclic structure having 6 or more ring atoms include:

monocyclic cycloalkane structures such as a cyclohexane structure, a cycloheptane structure, a cyclooctane structure, a cyclononane structure, a cyclodecane structure and a cyclododecane structure;

monocyclic cycloalkene structures such as a cyclohexene structure, a cycloheptene structure, a cyclooctene structure and a cyclodecene structure; polycyclic cycloalkane structures such as a norbornane structure, an adamantane structure, a tricyclodecane structure and a tetracyclododecane structure;

polycyclic cycloalkene structures such as a norbornene structure and a tricyclodecene structure; and the like.

Examples of the aliphatic heterocyclic structure having 6 or more ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic ring structure having 6 or more ring atoms include: a benzene structure, a naphthalene structure, a phenanthrene structure, an anthracene structure and the like.

Examples of the aromatic heterocyclic structure having 6 or more ring atoms include: oxygen atom-containing heterocyclic structures such as a furan structure, a pyran structure and a benzopyran structure; nitrogen atom-containing heterocyclic structures such as a pyridine structure, a pyrimidine structure and an indole structure; and the like.

The lower limit of the number of ring atoms of the ring structure in $R^{p1}$ is preferably 7, more preferably 8, still more preferably 9, and particularly preferably 10. On the other hand, the upper limit of the number of ring atoms of the ring structure in $R^{p1}$ is preferably 15, more preferably 14, still more preferably 13, and particularly preferably 12. When the number of ring atoms falls within the above range, the abovementioned diffusion length of the acid can be decreased further moderately, and consequently LWR performance and the like of the resist material of the embodiment of the present invention can be more improved.

A part or all of hydrogen atoms included in the ring structure in $R^{p1}$ may be substituted with a substituent. Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like. Of these, a hydroxy group is preferred.

Of these, $R^{p1}$ represents preferably a monovalent group that includes an alicyclic structure having 6 or more ring atoms or a monovalent group that includes an aliphatic heterocyclic structure having 6 or more ring atoms, more preferably a monovalent group that includes an alicyclic structure having 9 or more ring atoms or a monovalent group that includes an aliphatic heterocyclic structure having 9 or more ring atoms, still more preferably an adamantyl group, a hydroxyadamantyl group, a norbornanelacton-yl group, a norbornanesultone-yl group or a 5-oxo-4-oxatricyclo[4.3.1.1$^{3,8}$]undecan-yl group, and particularly preferably an adamantyl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. The divalent linking group represented by $R^{p2}$ is preferably a carbonyloxy group, a sulfonyl group, an alkanediyl group or a cycloalkanediyl group, more preferably a carbonyloxy group or a cycloalkanediyl group, still more preferably a carbonyloxy group or a norbornanediyl group, and particularly preferably a carbonyloxy group.

The monovalent hydrocarbon group having 1 to 20 carbon atoms which may be represented by $R^{p3}$ or $R^{p4}$ is exemplified by an alkyl group having 1 to 20 carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each independently represent preferably a hydrogen atom, the fluorine atom or the fluorinated alkyl group, more preferably the fluorine atom or the perfluoroalkyl group, and still more preferably the fluorine atom or the trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

The lower limit of $n^{p1}$ is preferably 0. On the other hand, the upper limit of $n^{p1}$ is preferably 5, more preferably 3, still more preferably 2, and particularly preferably 1.

The lower limit of $n^{p2}$ is preferably 0. On the other hand, the upper limit of $n^{p2}$ is preferably 5, more preferably 2, and still more preferably 1.

The lower limit of $n^{p3}$ is preferably 1. On the other hand, the upper limit of $n^{p3}$ is preferably 5, more preferably 4, still more preferably 3, and particularly preferably 2.

The anion of the acid represented by $Y^-$ may be exemplified by, but not limited to, anions represented by the following formulae, for example.

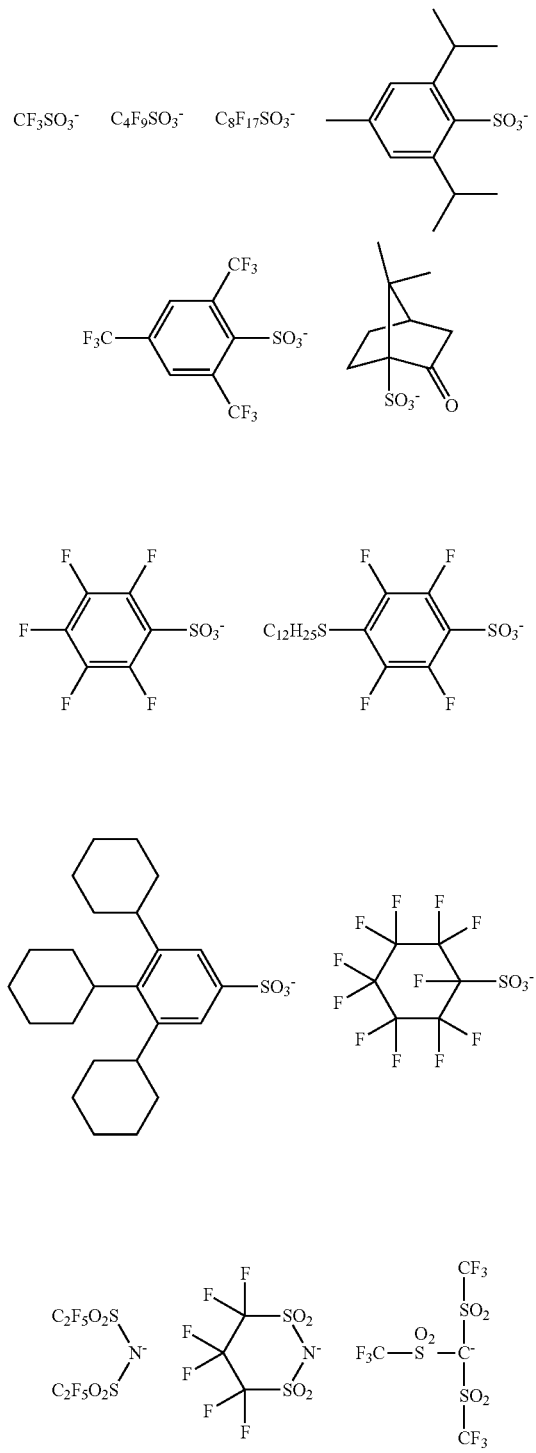

In addition, the anion shown in the above formula (1) may be exemplified by the following, for example.

33
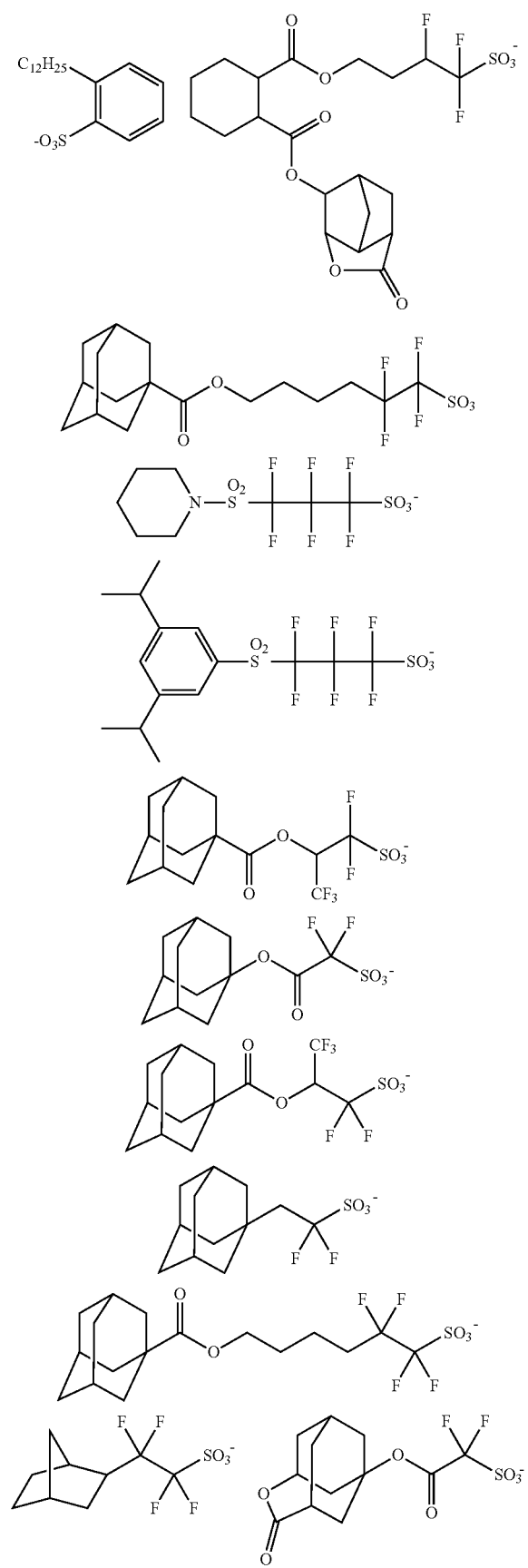
34
-continued
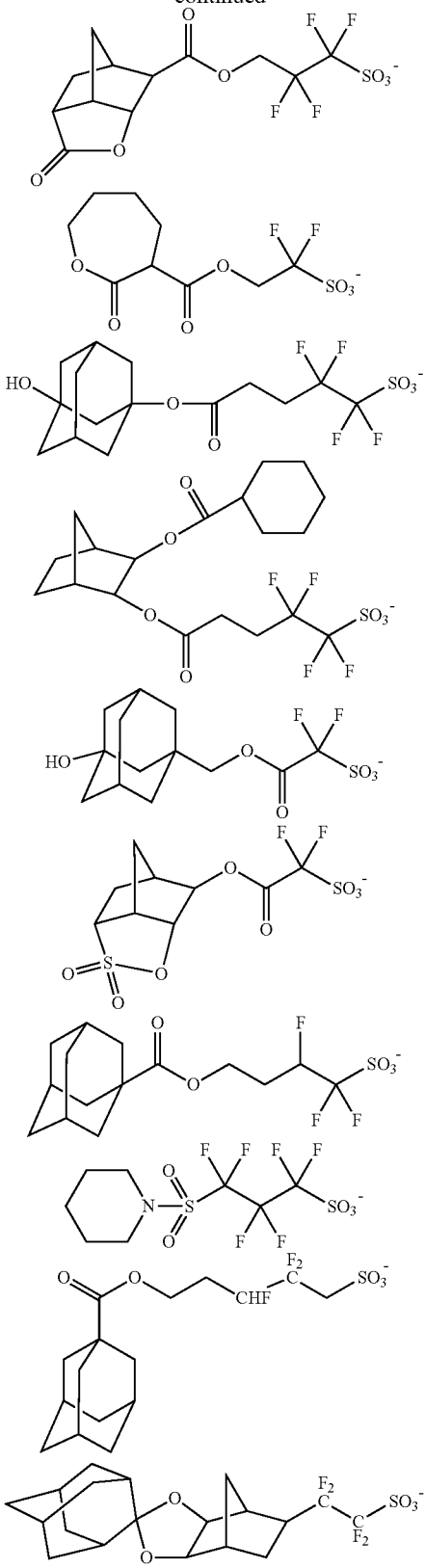
(b) Radiation-Sensitive Sensitizer Generating Agent
The radiation-sensitive sensitizer generating agent (b) generates, upon the irradiation with the first radioactive ray, a radiation-sensitive sensitizer that absorbs the second radioactive ray, and the radiation-sensitive sensitizer generating agent (b) substantially does not generate the radiation-sensitive sensitizer upon the irradiation with the second radioactive ray in light-unexposed regions which are not irradiated with the first radioactive ray in the patternwise exposure step; thus, the radiation-sensitive sensitizer generating agent (b) is different from the radiation-sensitive acid-and-sensitizer generating agent (a). According to the pattern-forming method of the embodiment of the present invention, in the patternwise exposure step, the chemical structure of the radiation-sensitive sensitizer generating agent (b) is altered through a direct or indirect reaction to generate a radiation-sensitive sensitizer that assists in the generation of the acid in the floodwise exposure step. Since the peak wavelength of the nonionizing radiation to be absorbed is shifted after the patternwise exposure step, a contrast of the absorption of the second radioactive ray in the floodwise exposure step can be attained more easily between the light-exposed regions where the radiation-sensitive sensitizer is generated and the light-unexposed regions. Furthermore, greater peak shift of the absorption wavelength provides a greater contrast of the absorption of the second radioactive ray in the floodwise exposure step.

In addition, in a case where the radiation-sensitive sensitizer is generated by irradiating the radiation-sensitive sensitizer generating agent (b) with the second radioactive ray, the lower limit of the wavelength of the second radioactive ray that can maintain the amount of the radiation-sensitive sensitizer generated through the irradiation with the second radioactive ray so small that that the difference in the concentration of the radiation-sensitive sensitizer between the light-exposed regions and the light-unexposed regions after the patternwise exposure can be maintained at a level to permit the pattern formation is preferably 300 nm, more preferably 320 nm, and still more preferably 350 nm. By making the wavelength of the second radioactive ray no less than the lower limit in a case where the radiation-sensitive sensitizer generating agent (b) generates the radiation-sensitive sensitizer through the irradiation with the second radioactive ray, the acid is generated upon the irradiation with the second radioactive ray in the patternwise exposed regions irradiated with the first radioactive ray by sensitization action of the radiation-sensitive sensitizer being generated, while generation of the acid upon the irradiation with the second radioactive ray is inhibited in the patternwise unexposed regions not irradiated with the first radioactive ray. As a result, sensitivity and a contrast between the patternwise exposed regions and the patternwise unexposed regions can be improved.

The radiation-sensitive sensitizer generating agent (b) is preferably a compound that, through the irradiation with the first radioactive ray in the patternwise exposure step, gives a compound (carbonyl compound) containing a carbonyl group that absorbs nonionizing radiation longer than the nonionizing radiation in the patternwise exposure step and longer than 200 nm, that is, the second radioactive ray in the floodwise exposure step. Examples of the carbonyl compound includes: aldehyde, ketone, carboxylic acid, and carboxylic acid ester. By the above described reaction, shift of the peak of absorption wavelength of the radioactive ray takes place only in the radiation-sensitive sensitizer generating agent (b) in the patternwise exposed regions. Therefore, following the patternwise exposure, by performing the floodwise exposure with the radioactive ray having a wavelength that can be absorbed only by the patternwise exposed regions, selective sensitization of the patternwise exposed regions alone is possible. The radiation-sensitive sensitizer generating agent (b) is preferably an alcohol compound represented by the following formula (VI), and may also be a secondary alcohol compound. It is to be noted that as referred to herein, the "alcohol compound" as referred to means not only a compound containing an alcoholic hydroxyl group, but may also be a ketal compound and an acetal compound as well as an ortho ester compound and the like, which are obtained by substitution of an hydrogen atom in the alcoholic hydroxyl group. In the case of the radiation-sensitive sensitizer generating agent (b) being a ketal compound or an acetal compound, heating may take place between the patternwise exposure and the floodwise exposure, in order to accelerate a hydrolysis reaction of a carbonyl compound by an acid catalyst generated upon the patternwise exposure.

(VI)

In the formula (VI), $R^8$, $R^9$ and $R^{10}$ each independently represent: a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); an alkoxy group having 1 to 5 carbon atoms substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; an alkylthio group having 1 to 5 carbon atoms substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a phenoxy group substituted with an alkoxy group having 1 to carbon atoms, a hydroxyl group, an amino group, an amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. The alcohol compound may also be a thiol compound, in which an alcoholic hydroxyl group (hydroxyl group) in the formula (VI) is a thiol group. In the above formula (VI), the hydrogen atom of the hydroxyl group or the thiol group may be substituted with: a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. In the formula, at least two arbitrary groups among $R^8$, $R^9$ and $R^{10}$ may form a ring structure via a single bond or a double bond, or via a bond including —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH— or —$NR^g$—. $R^g$ represents a phenyl group; a phenoxy group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. $R^8$, $R^9$ and $R^{10}$ each independently represent: preferably a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group.

It is to be noted that the ketal compound or the acetal compound, in which a hydrogen atom in the hydroxyl group in the formula (VI) is substituted, is preferably a compound represented by the following formula (XXXVI). In other words, the radiation-sensitive sensitizer generating agent (b) may also be a compound represented by the following formula (XXXVI). In the case of any one of $R^9$ and $R^{10}$ being a hydrogen atom, a compound represented by the following formula (XXXVI) can be considered to be an acetal compound.

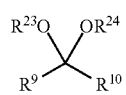

(XXXVI)

In the formula (XXXVI), $R^9$ and $R^{10}$ are respectively as defined in $R^9$ and $R^{10}$ in the above formula (VI). $R^9$ and $R^{10}$ may taken together represent a ring structure, similarly to $R^9$ and $R^{10}$ in the above formula (VI). In the formula (XXXVI), $R^{23}$ and $R^{24}$ each independently represent a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. $R^{23}$ and $R^{24}$ may also taken together represent a ring structure via a single bond, a double bond, or a bond including —$CH_2$—, —O—, —S—, —$SO_2$—, —$SO_2NH$—, —C(=O)—, —C(=O)O—, —NHCO—, NHC(=O)NH—, —$CHR^g$—, —$CR^g_2$—, —NH— or —$NR^g$—. $R^g$ is as defined in $R^g$ in the above formula (VI). The ketal compound or the acetal compound may also be a thioketal compound or a thioacetal compound, in which an oxygen atom bonding to $R^{23}$ and/or $R^{24}$ in the formula (XXXVI) is replaced with sulfur.

The ketal compound and the acetal compound can be obtained by reacting the carbonyl compound with alcohol. The reaction can be considered as a reaction of protecting a carbonyl group contributing to radioactive ray sensitization action, and $R^{23}$ and $R^{24}$ in the above formula (XXXVI) may be referred to as a protecting group for the carbonyl group. In this case, a reaction by which the radiation-sensitive sensitizer generating agent (b) gives the radiation-sensitive sensitizer by the radioactive ray and the like may be referred to as a deprotection reaction. An example of reactivity (likelihood of the deprotection reaction) of the protecting group is shown below. The reactivity of the protecting group increases from left to right. For example, in the case of a methoxy group being used as the protecting group of the carbonyl group, the reactivity toward the deprotection reaction is high and the deprotection reaction under an acid catalyst tends to proceed even at normal temperature. The deprotection reaction proceeding at normal temperature has an advantage that blurring of an image can be prevented. On the other hand, if the deprotection reaction takes place in the patternwise unexposed regions and the radiation-sensitive sensitizer is generated upon the patternwise exposure, contrast of the resist may be deteriorated. In order to prevent generation of the radiation-sensitive sensitizer in the patternwise unexposed regions, the protecting group may be selected such that activation energy of the deprotection reaction increases (such that reactivity of the protecting group decreases). In light of decreasing reactivity of the protecting group, a cyclic protecting group in which $R^{23}$ and $R^{24}$ in the formula (XXXVI) bind with each other to form a ring structure is more preferred. Examples of the ring structure include a 6-membered ring and a 5-membered ring, and the 5-membered ring is preferred. In the case of using the protecting group of low reactivity, the resist material preferably contain a first trapping agent as described later, and it is desirable to bake the resist material film between the patternwise exposure and the floodwise exposure. In the baking, an unnecessary acid in the patternwise unexposed regions is neutralized by the trapping agent and contrast of a latent image can be increased. In addition, the baking can compensate reduction in reactivity of the protecting group, and can diffuse a substance to reduce roughness of a latent image of an acid in the resist material film.

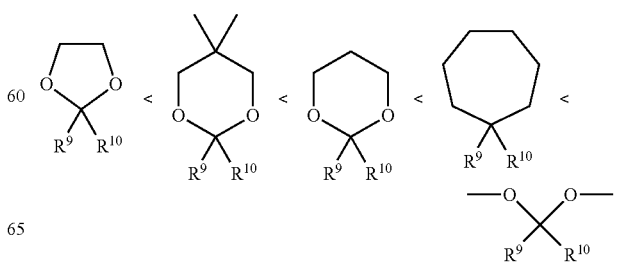

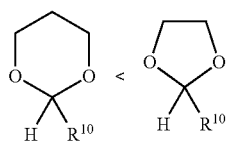

The ketal type radiation-sensitive sensitizer generating agent (b) may also be compounds represented by the following formulae (XXVII) to (XXX).

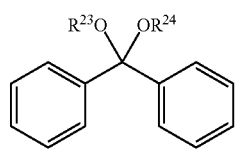

(XXVII)

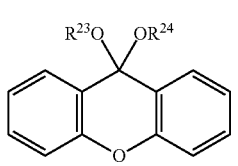

(XXVIII)

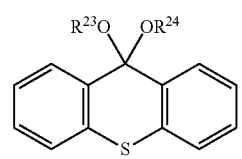

(XXIX)

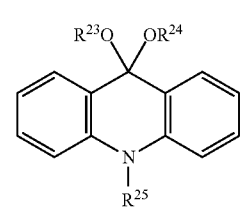

(XXX)

In the formulae (XXVII) to (XXX), $R^{23}$ and $R^{24}$ are respectively as defined in $R^{23}$ and $R^{24}$ in the formula (XXXVI). In the formulae (XXVII) to (XXX), a hydrogen atom in the aromatic ring may be substituted with an alkoxy group having 1 to 5 carbon atoms or an alkyl group having 1 to 5 carbon atoms, or the aromatic ring may be fused with another aromatic ring to form a naphthalene ring or an anthracene ring. $R^{25}$ represents an alkyl group having 1 to 5 carbon atoms. In the case of using a compound represented by the above formulae (XXVII) to (XXX) as the radiation-sensitive sensitizer generating agent (b), greater shift of radioactive ray absorption wavelength is realized upon transformation from the radiation-sensitive sensitizer generating agent (b) to the radiation-sensitive sensitizer, and more selective sensitization reaction may take place in the patternwise exposed regions.

It is to be noted that the ortho ester compound, in which a hydrogen atom in the hydroxyl group in the formula (VI) is substituted, is preferably a compound represented by the following formula (XLVI). In other words, the radiation-sensitive sensitizer generating agent (b) may also be a compound represented by the following formula (XLVI).

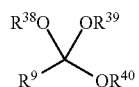

(XLVI)

In the formula (XLVI), $R^9$ is as defined in $R^9$ in the above formula (VI). In the formula (XLVI), $R^{38}$ to $R^{40}$ each independently represent: a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a linear, branched (chain) or cyclic saturated or unsaturated hydrocarbon group (preferably alkyl group) having 1 to 30 carbon atoms (preferably having 1 to 5 carbon atoms), an alkoxy group having 1 to 5 carbon atoms, or a hydroxyl group. $R^{38}$ to $R^{40}$ may form a ring structure via a single bond or a double bond, or via a bond including —$CH_2$—, —O—, —S—, —$SO_2$—, —$SO_2NH$—, —C(=O)—, —C(=O)O—, —NHCO—, —NHC(=O)NH—, —$CHR^g$—, —$CR^g_2$—, —NH— or —$NR^g$—. $R^g$ is as defined in $R^g$ in the above formula (VI).

The ortho ester compound degrades in the deprotection reaction upon the patternwise exposure, to transform into carboxylic acid ester or carboxylic acid containing for example a carbonyl group. The ortho ester compound is preferably an OBO ester compound represented by the following formula (XLVII) in which a carboxyl group moiety in the radiation-sensitive sensitizer containing a carboxyl group is substituted (protected) by OBO (e.g., 4-methyl-2,6,7-trioxabicyclo[2.2.2]octan-1-yl). The radiation-sensitive sensitizer generating agent (b) in which the carboxyl group is protected by OBO generates carboxylic acid by an acid catalyst generated upon the patternwise exposure, shifts the absorption wavelength of the radioactive ray, thereby functioning as the radiation-sensitive sensitizer upon the floodwise exposure. As carboxylic acid is generated from the radiation-sensitive sensitizer generating agent (b), in the patternwise exposed regions, the polarity of the resist is altered, for example from non-polar to polar. Given this, the ortho ester compound also functions as a dissolution accelerator in the development step, contributing to improvement of resist contrast. The radiation-sensitive sensitizer generating agent (b) containing the OBO ester compound can generate the radiation-sensitive sensitizer and cause a polarity changing reaction simultaneously.

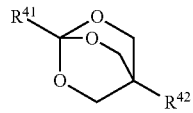

(XLVII)

In the formula (XLVII), $R^{41}$ and $R^{42}$ each independently represent a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. $R^{41}$ and $R^{42}$ each independently represent: preferably a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group.

Examples of the radiation-sensitive sensitizer generating agent (b) include the compounds represented by the following formulae. These compounds are alcohol compounds in which a hydrogen atom in an alcoholic hydroxyl group is not substituted, and transform into ketone compounds by a reaction upon the patternwise exposure.

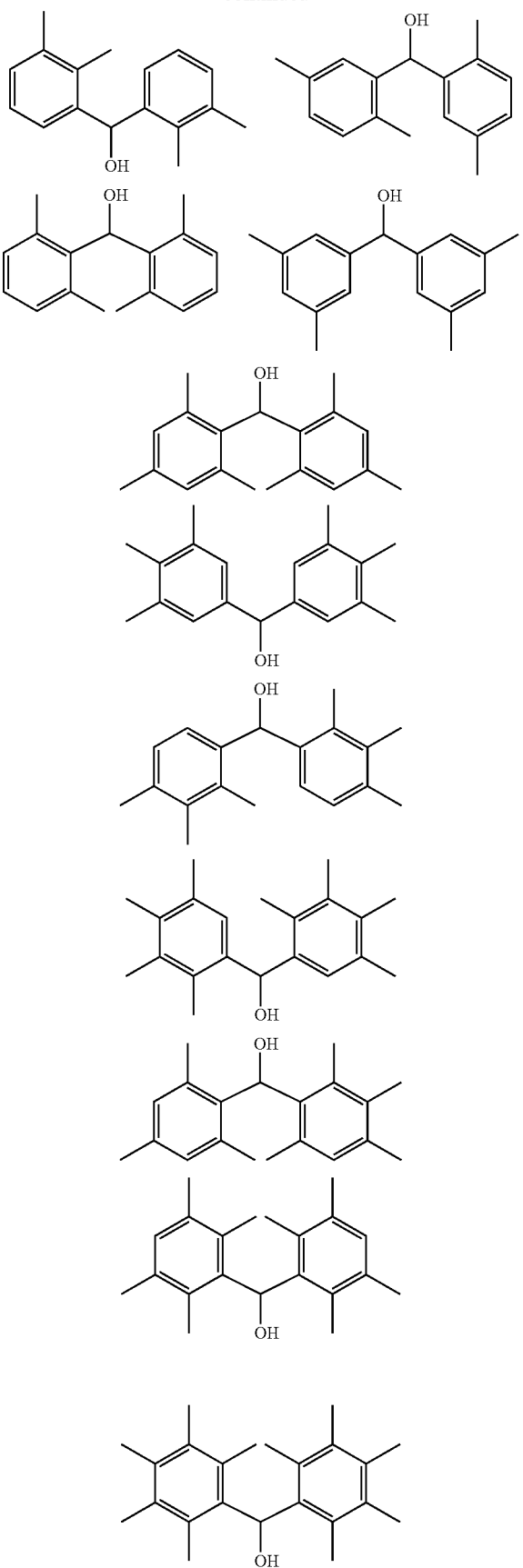

-continued
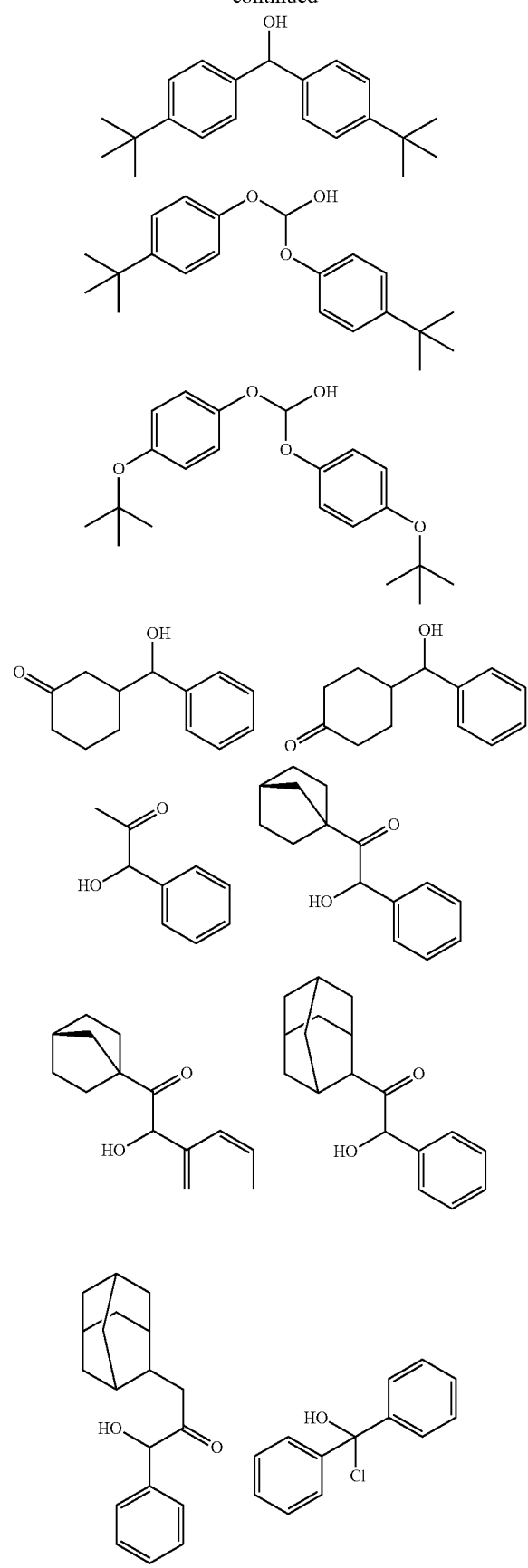
-continued
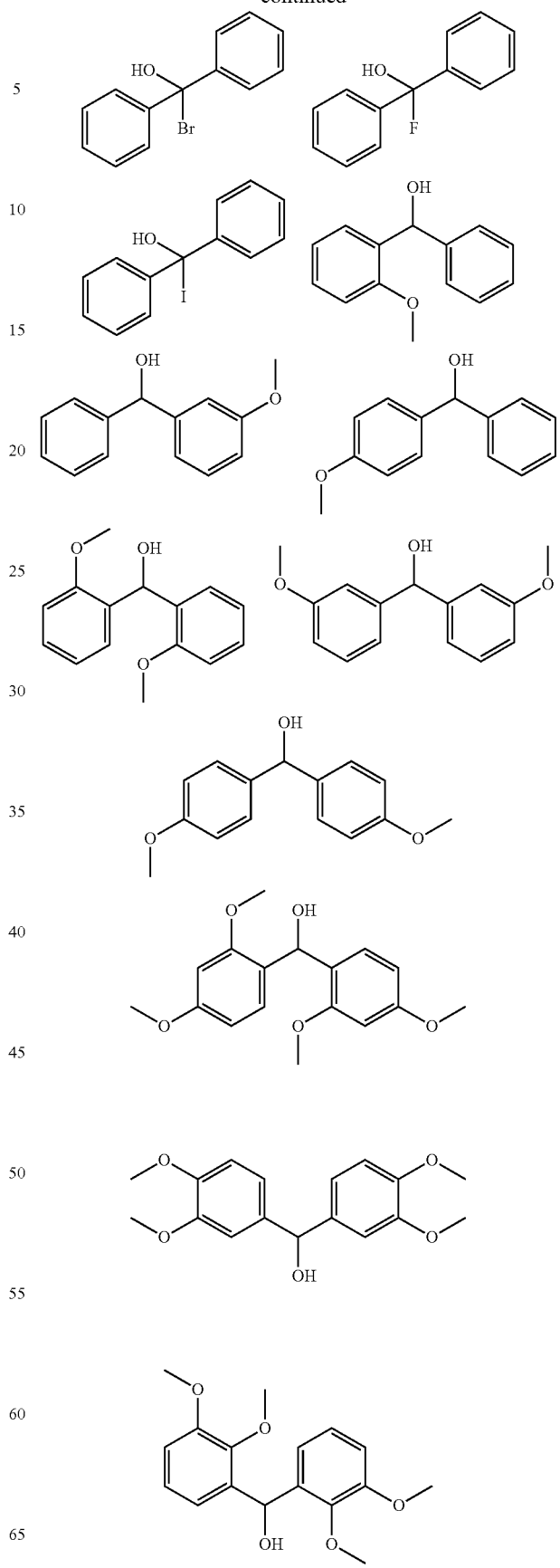

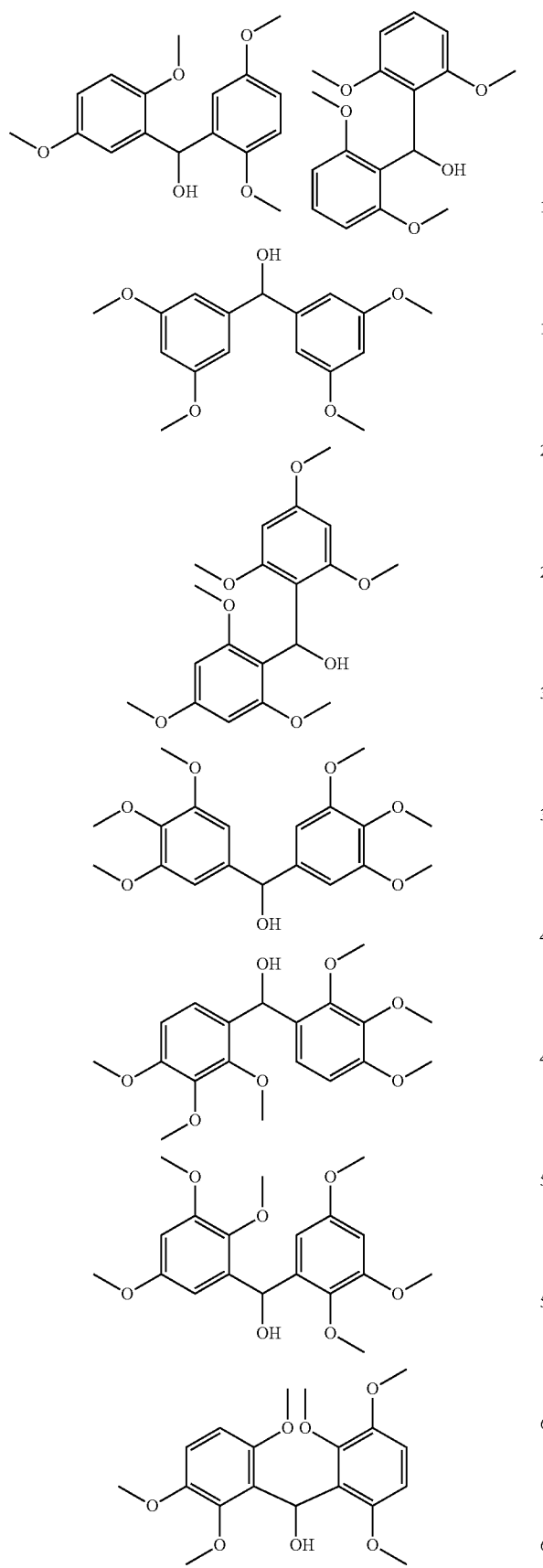
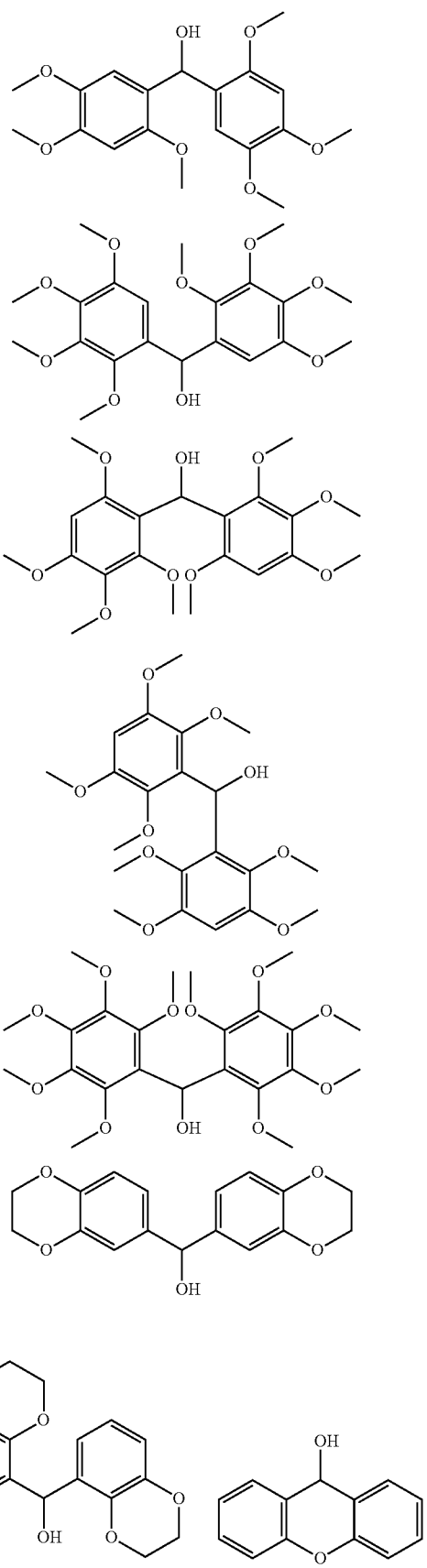

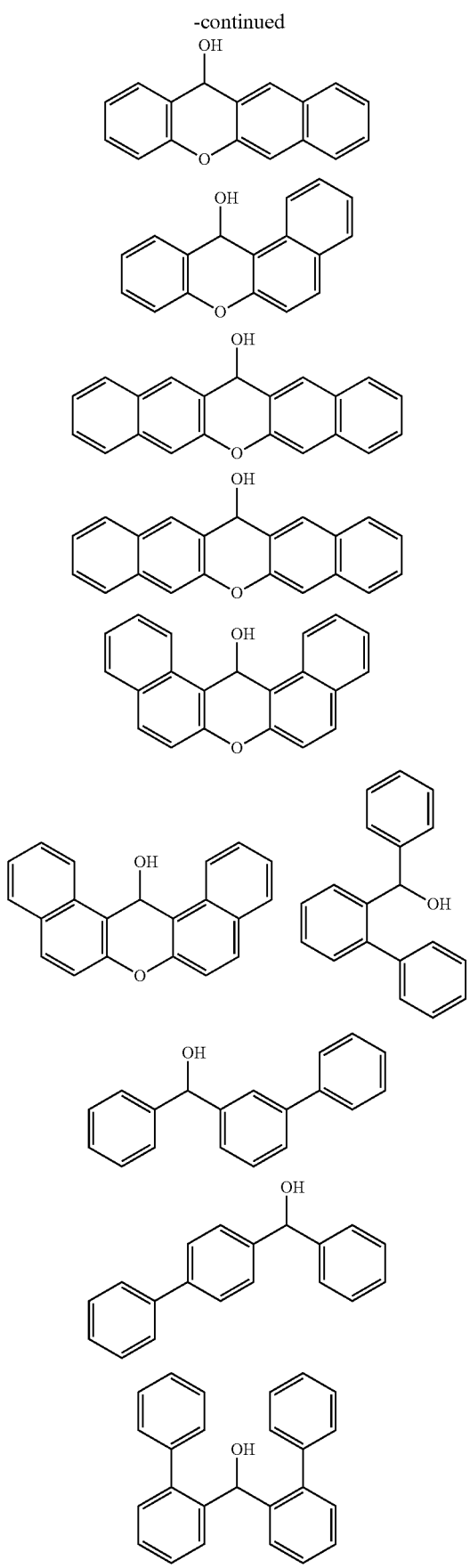

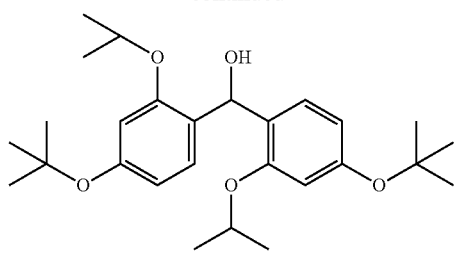
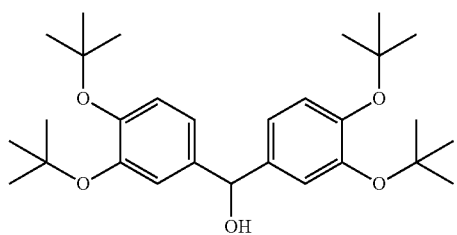
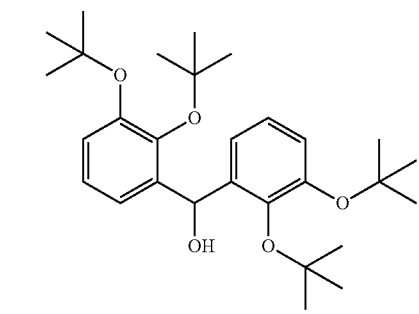
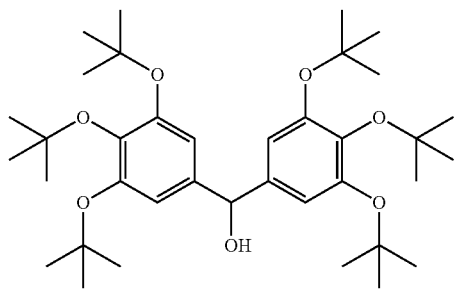
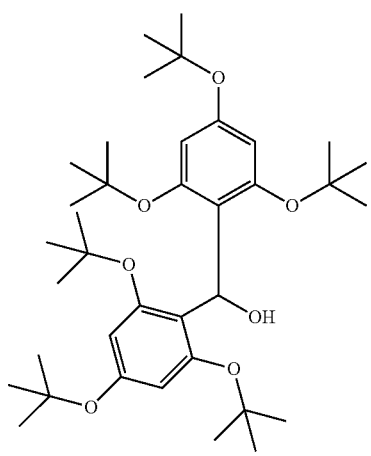
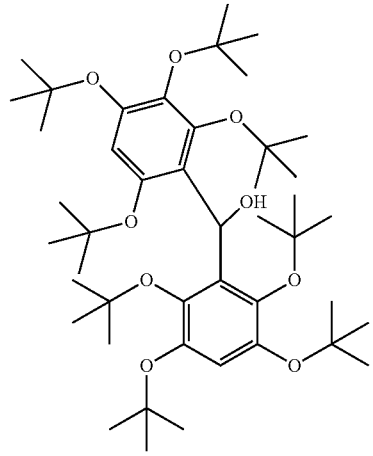
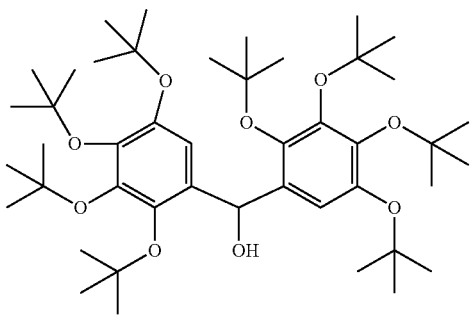
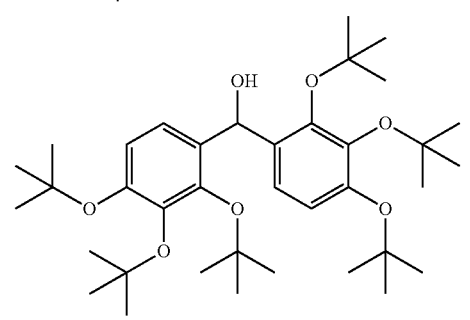
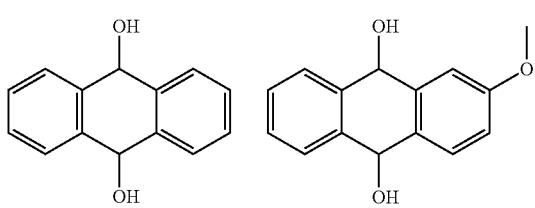
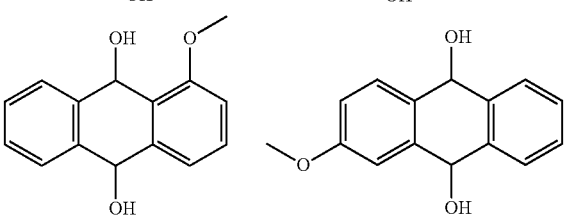
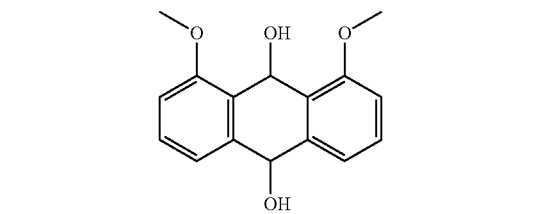

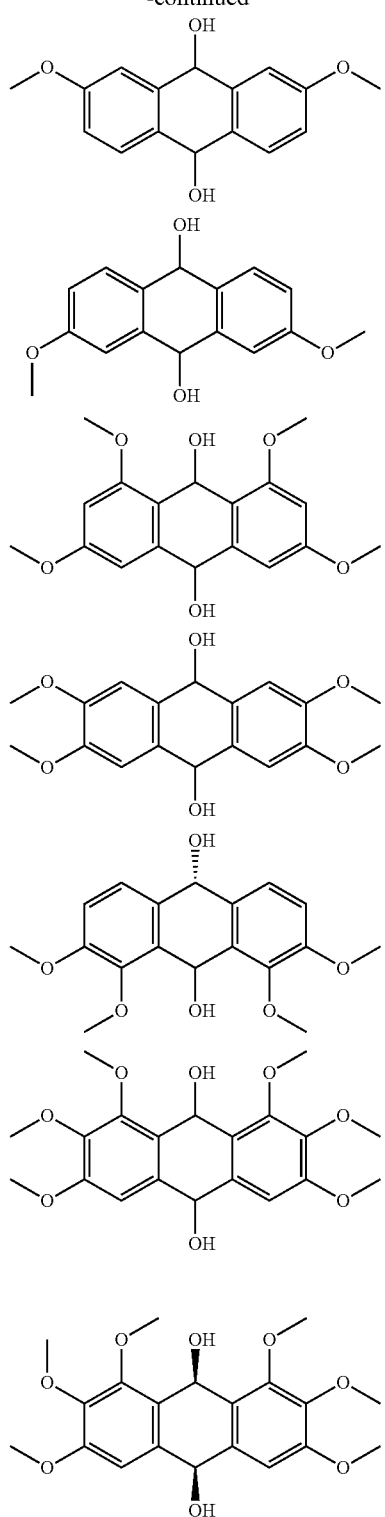
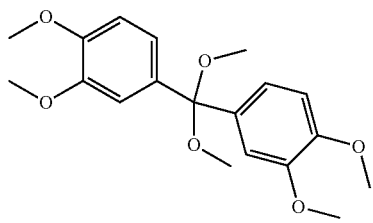
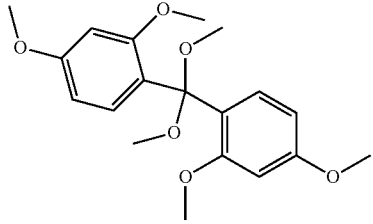
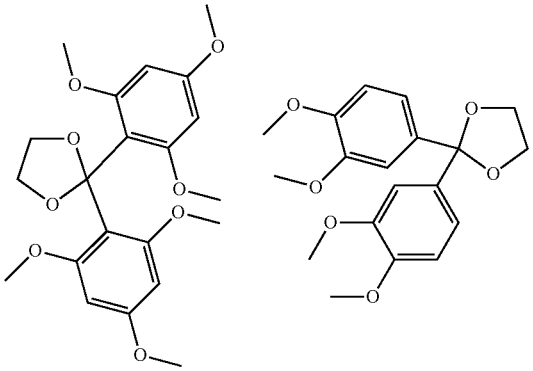
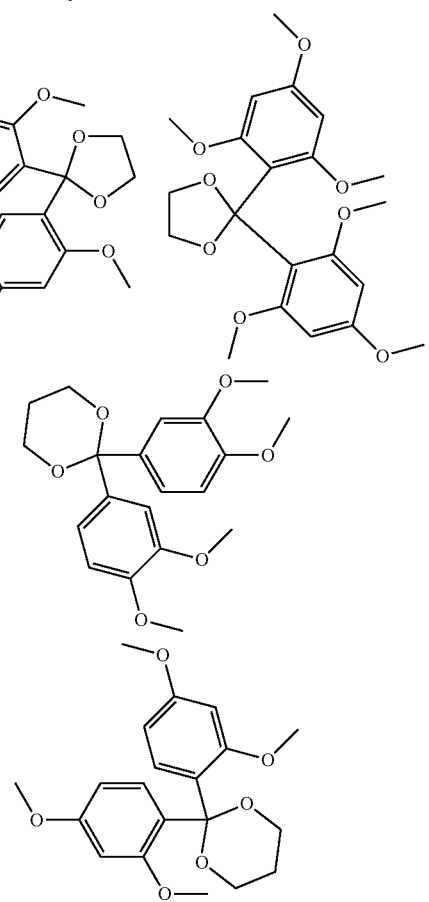
The following compounds are examples of the ketal compound or the acetal compound in which a carbonyl group in the radiation-sensitive sensitizer is protected. These compounds transform into radiation-sensitive sensitizer containing ketone in the patternwise exposed regions, under a catalytic action of an acid generated upon the patternwise exposure.

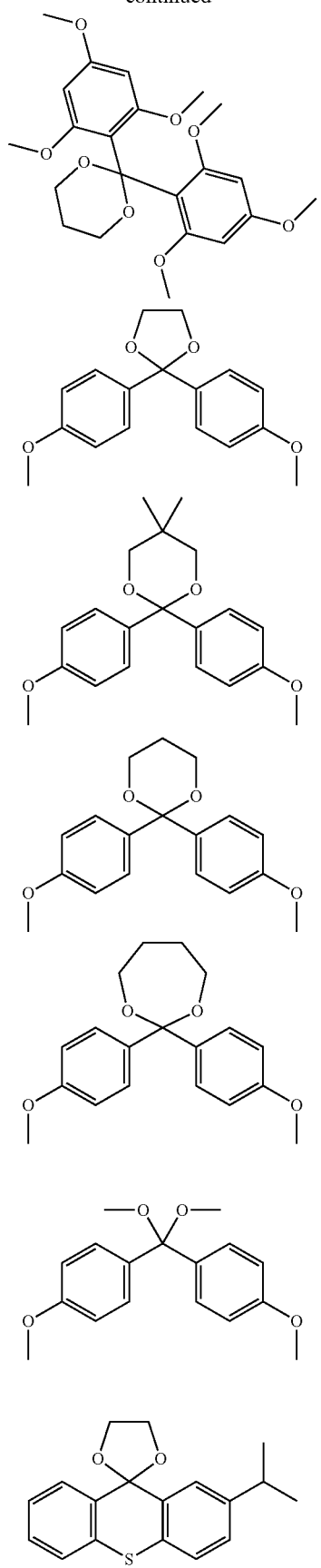
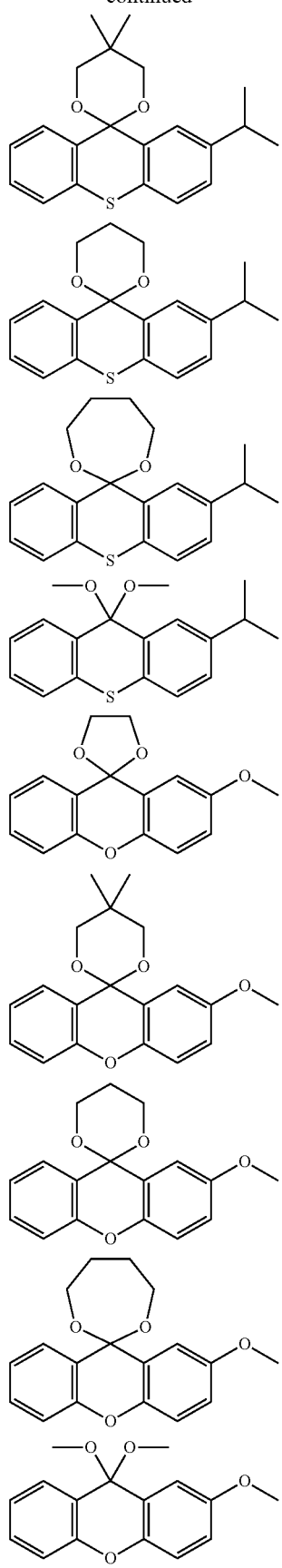

-continued
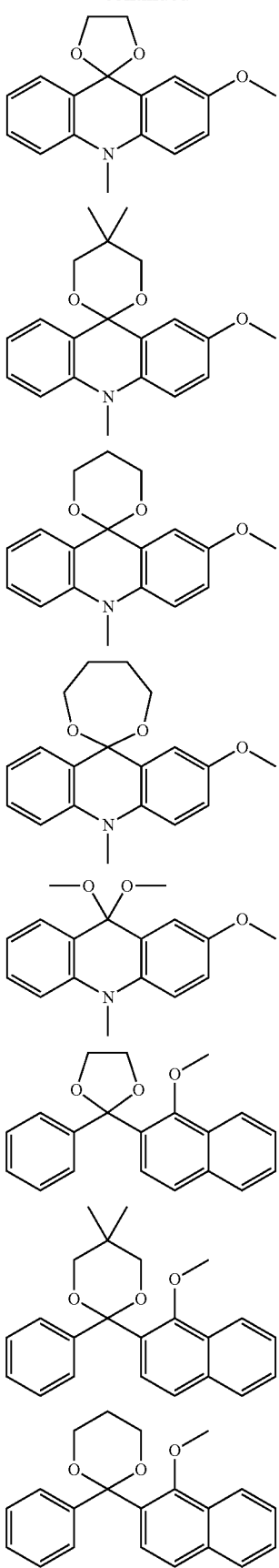
-continued
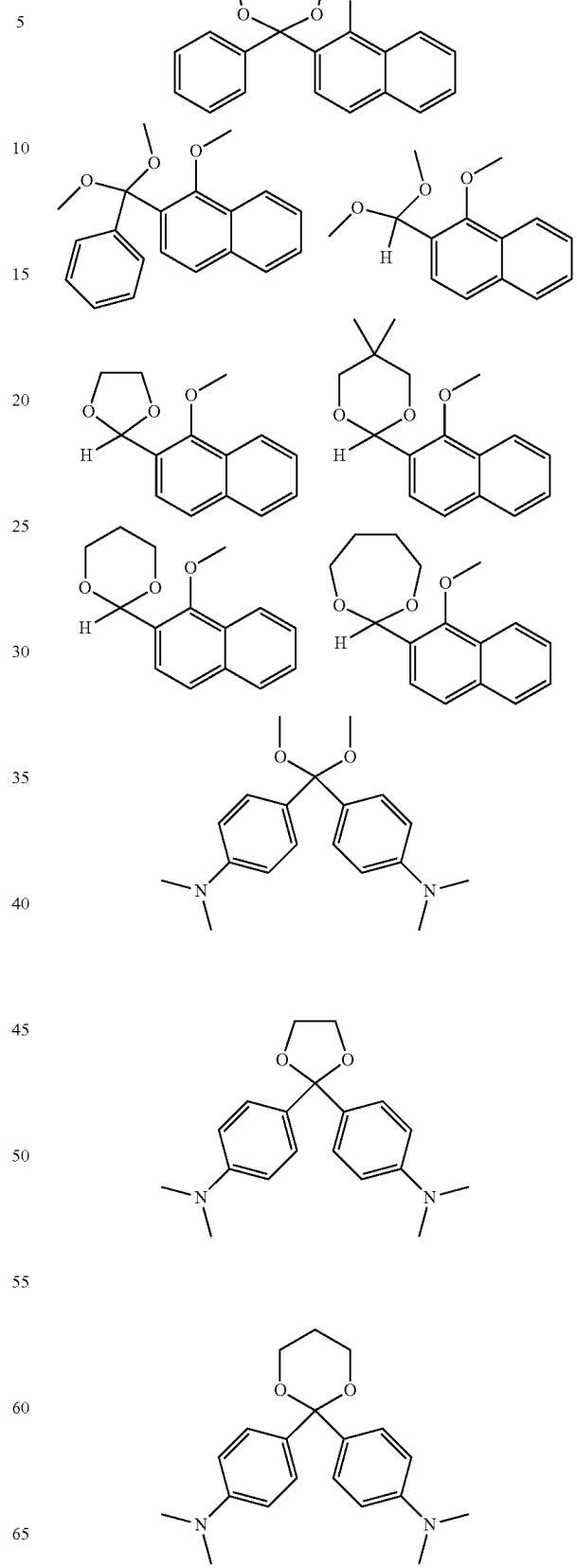

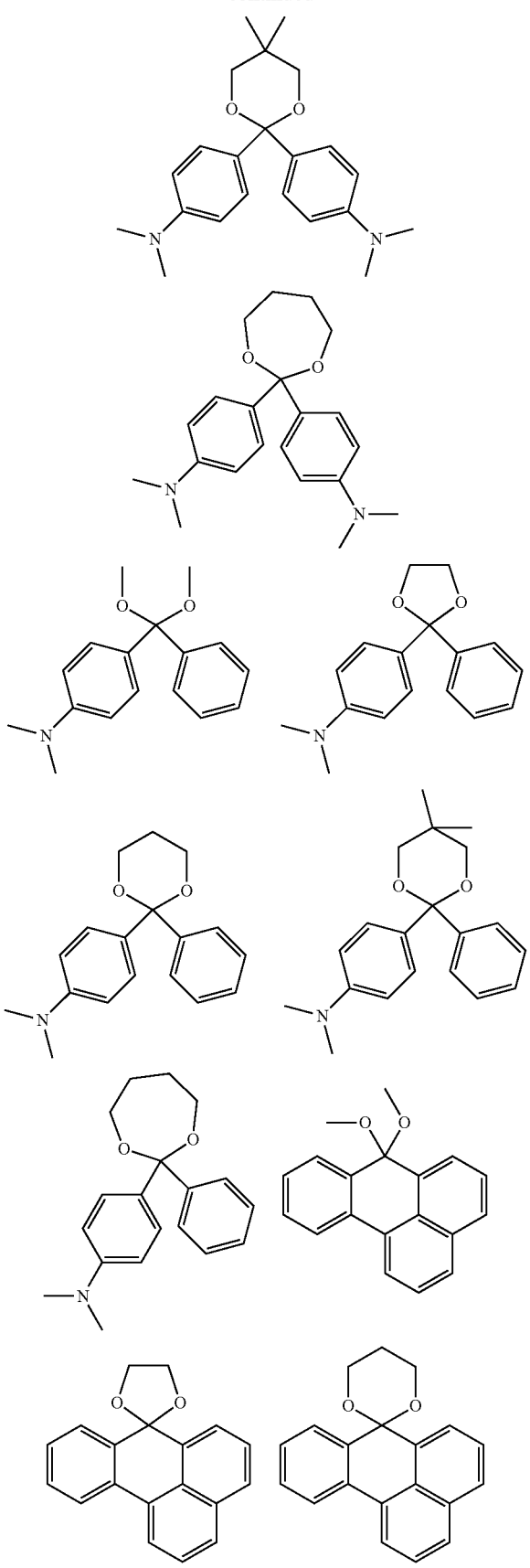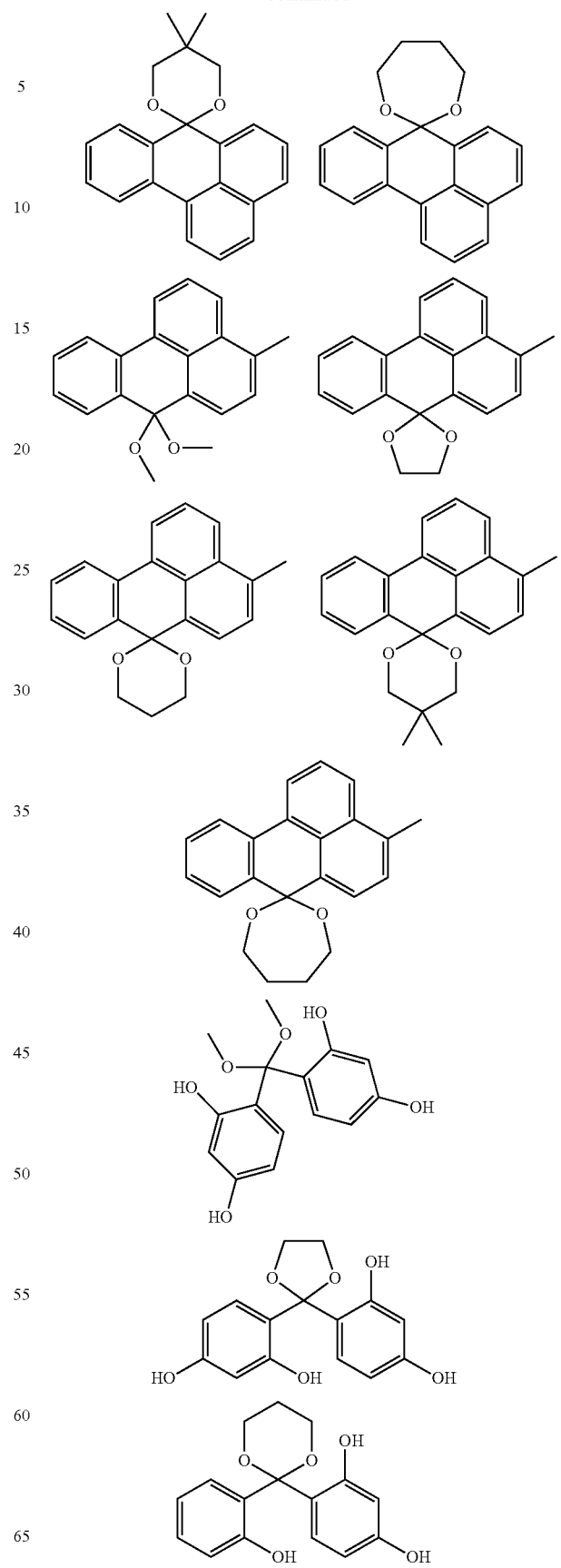

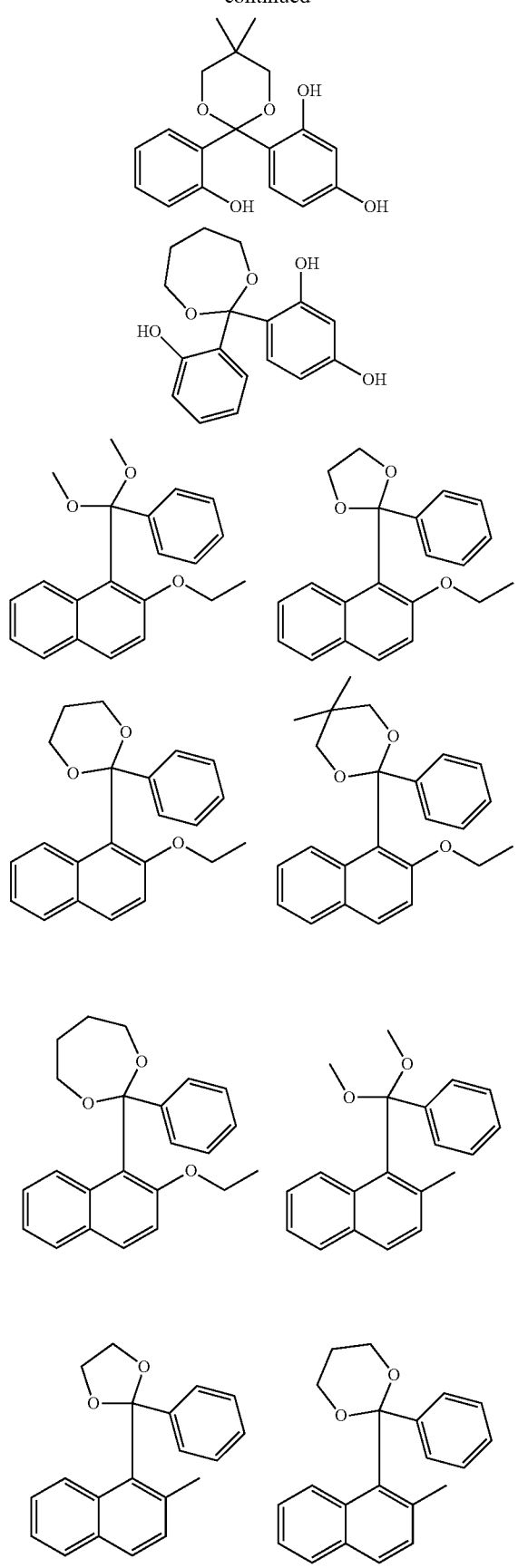
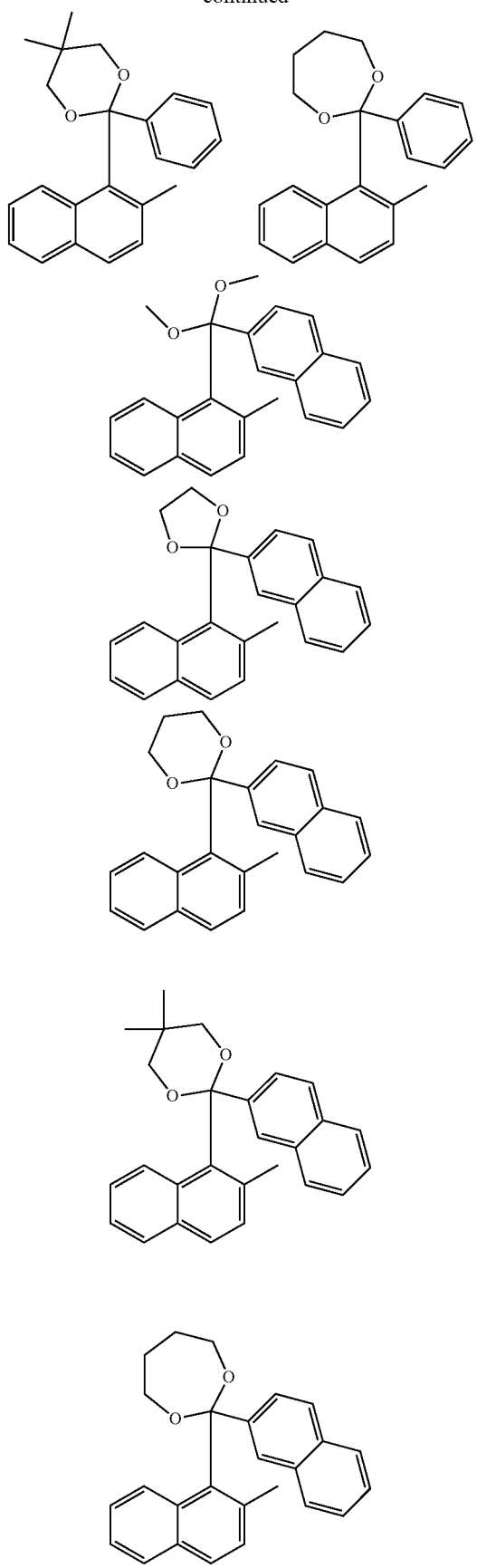

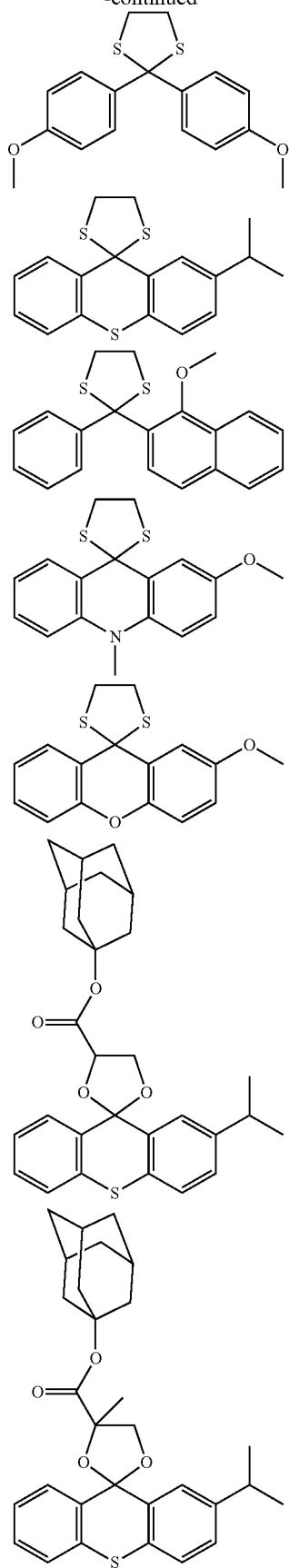
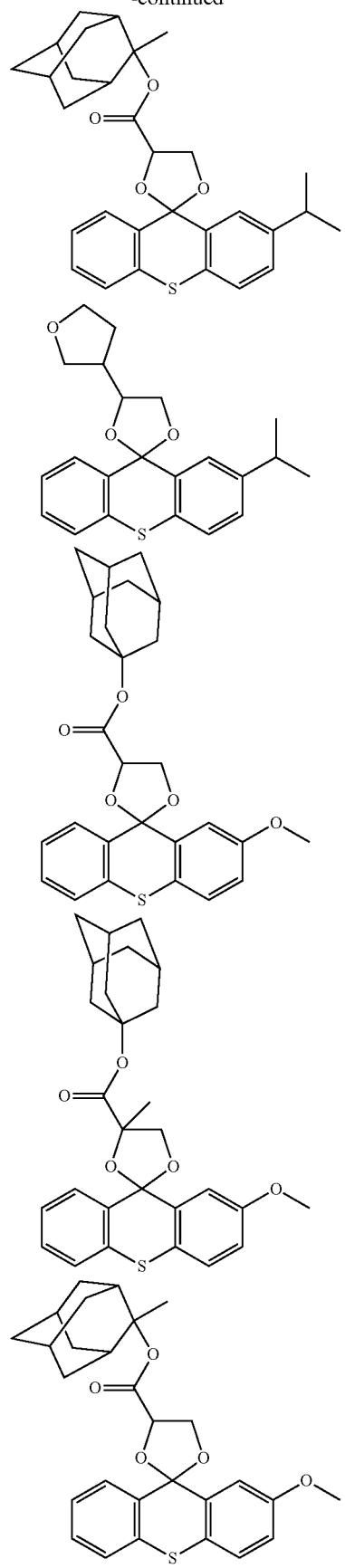

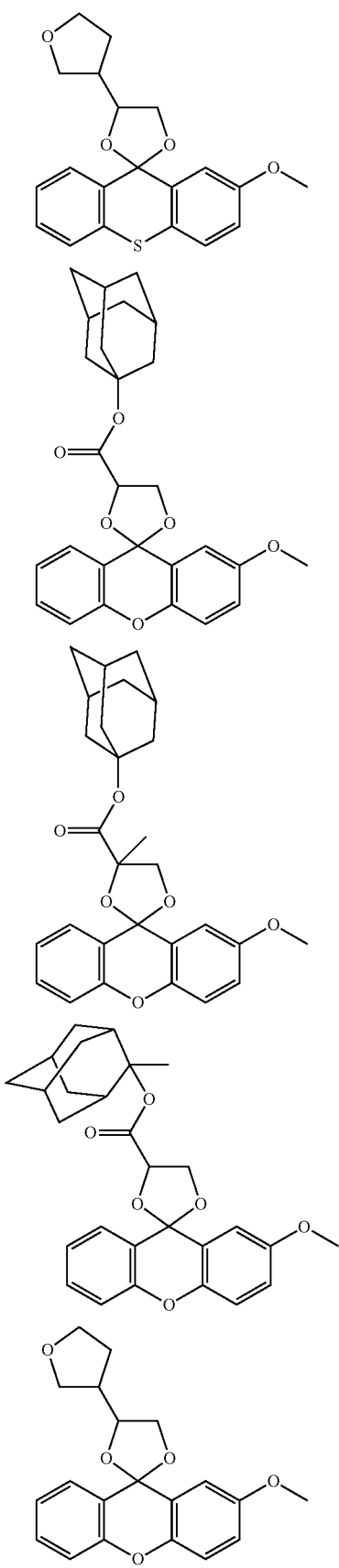
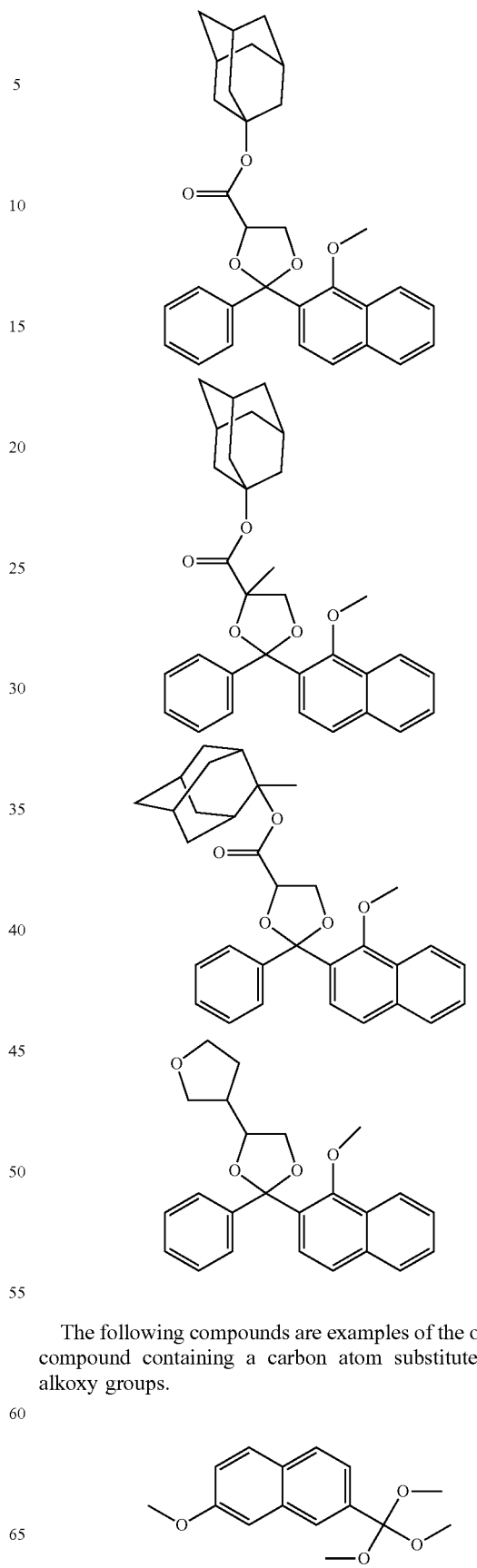
The following compounds are examples of the ortho ester compound containing a carbon atom substituted with 3 alkoxy groups.
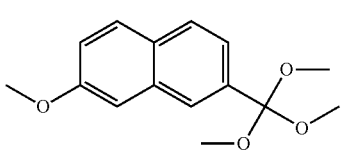

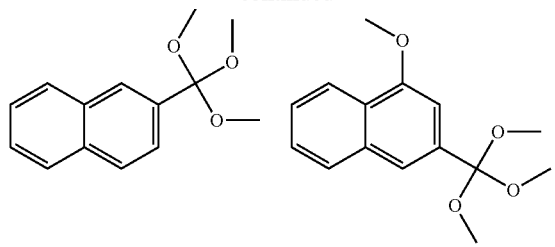
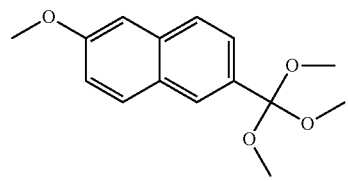
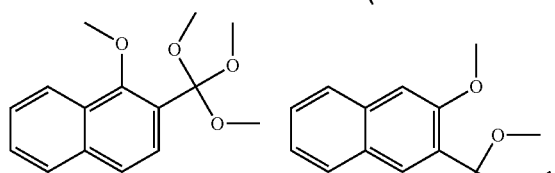
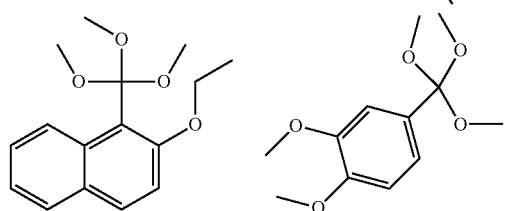
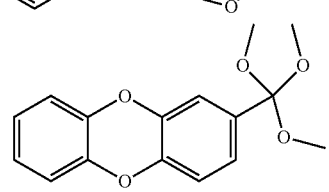
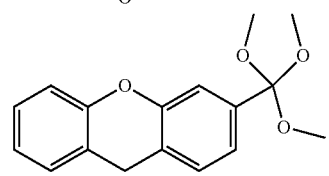
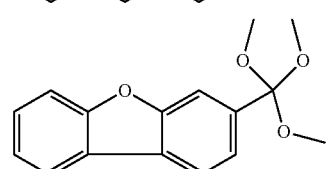
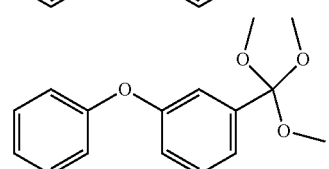
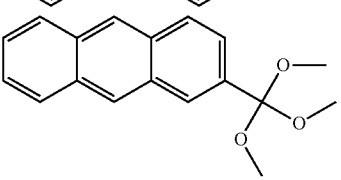
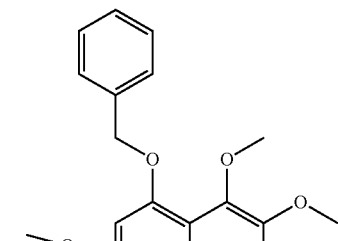
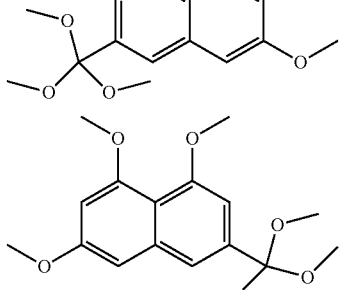
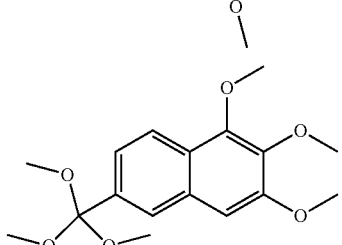
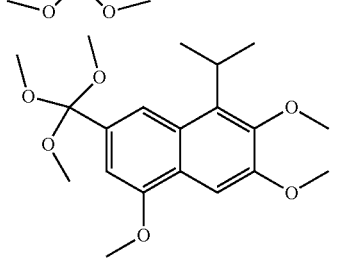
The ortho ester compound deprotects by the acid catalyst generated upon the patternwise exposure, to generate an ester containing a carbonyl group (in the following example, methyl carboxylate).
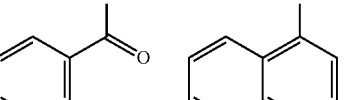
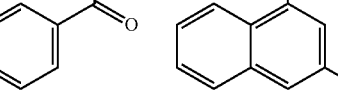
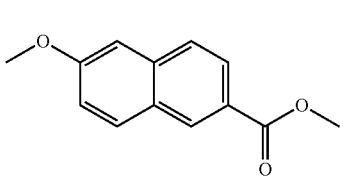

-continued
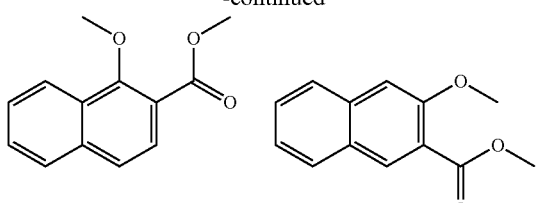
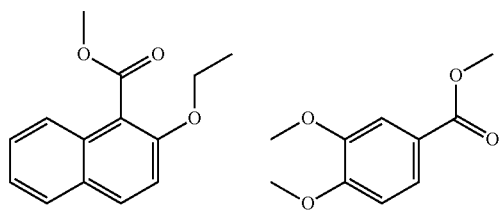
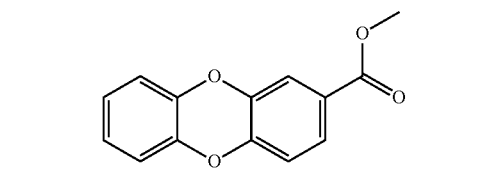
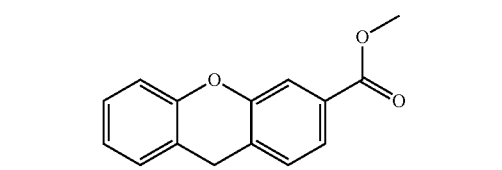
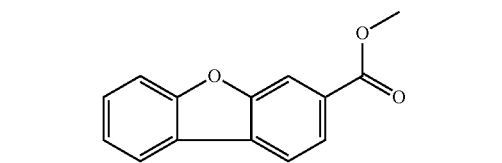
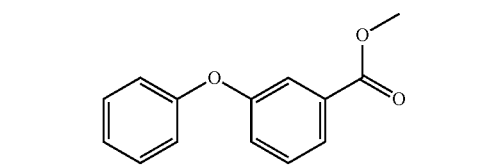
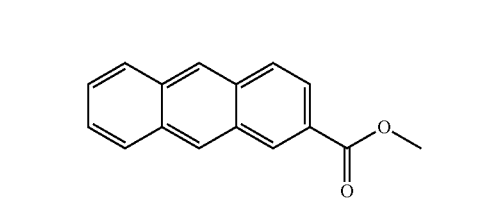
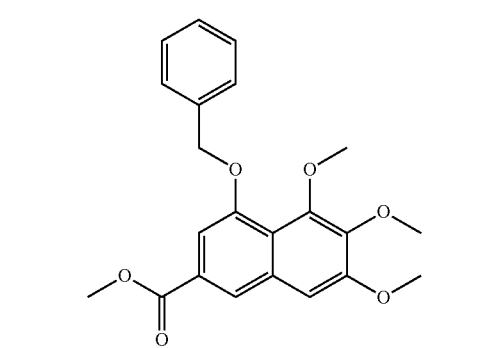
-continued
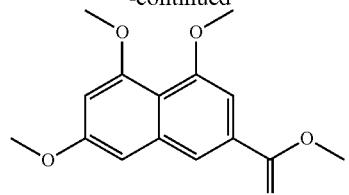
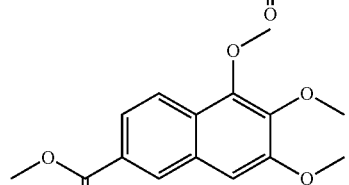
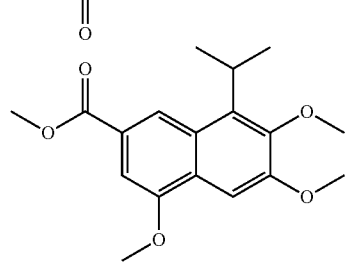
The following chemical formulae are examples of an OBO ester compound, which is a derivative in which a carboxyl group moiety of a carboxyl group-containing radiation-sensitive sensitizer is protected by OBO (e.g. 4-methyl-2,6,7-trioxabicyclo[2.2.2]octan-1-yl).
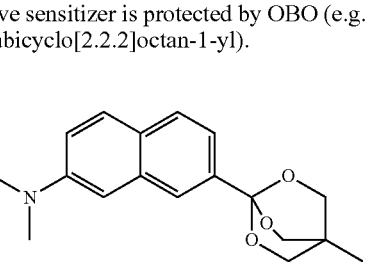
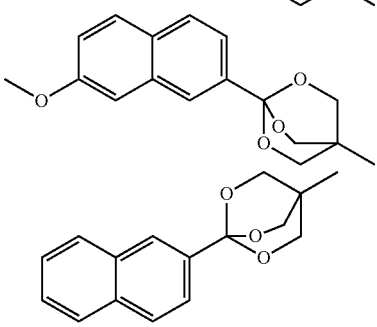
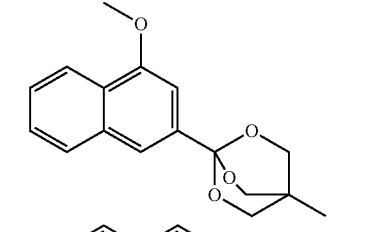
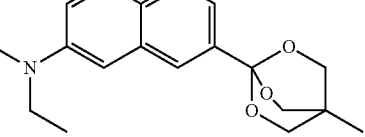

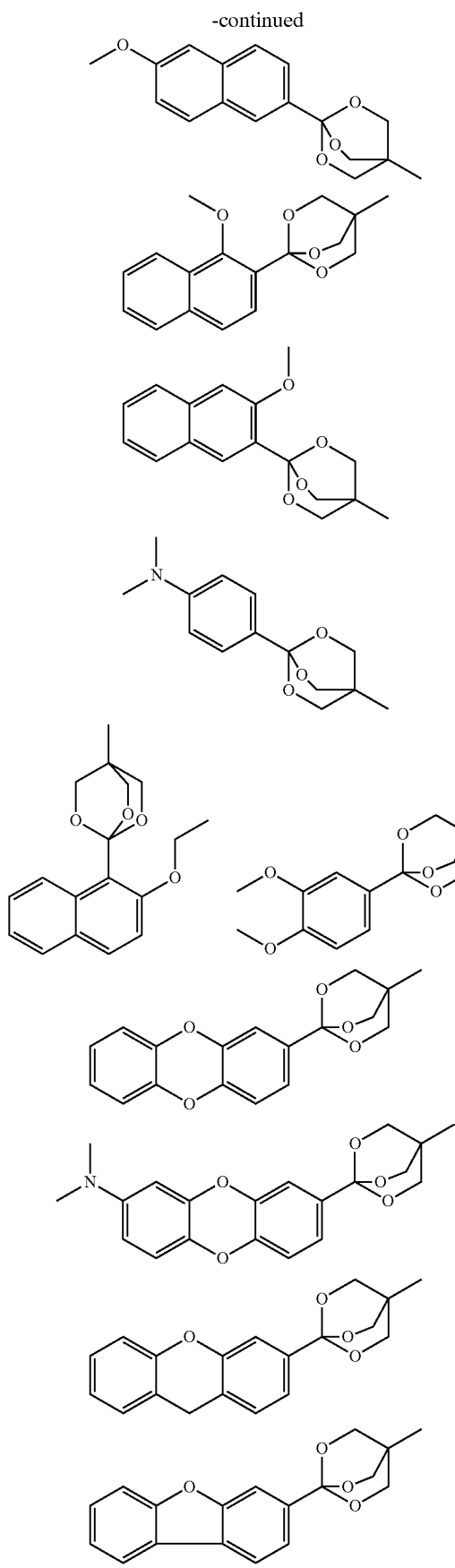
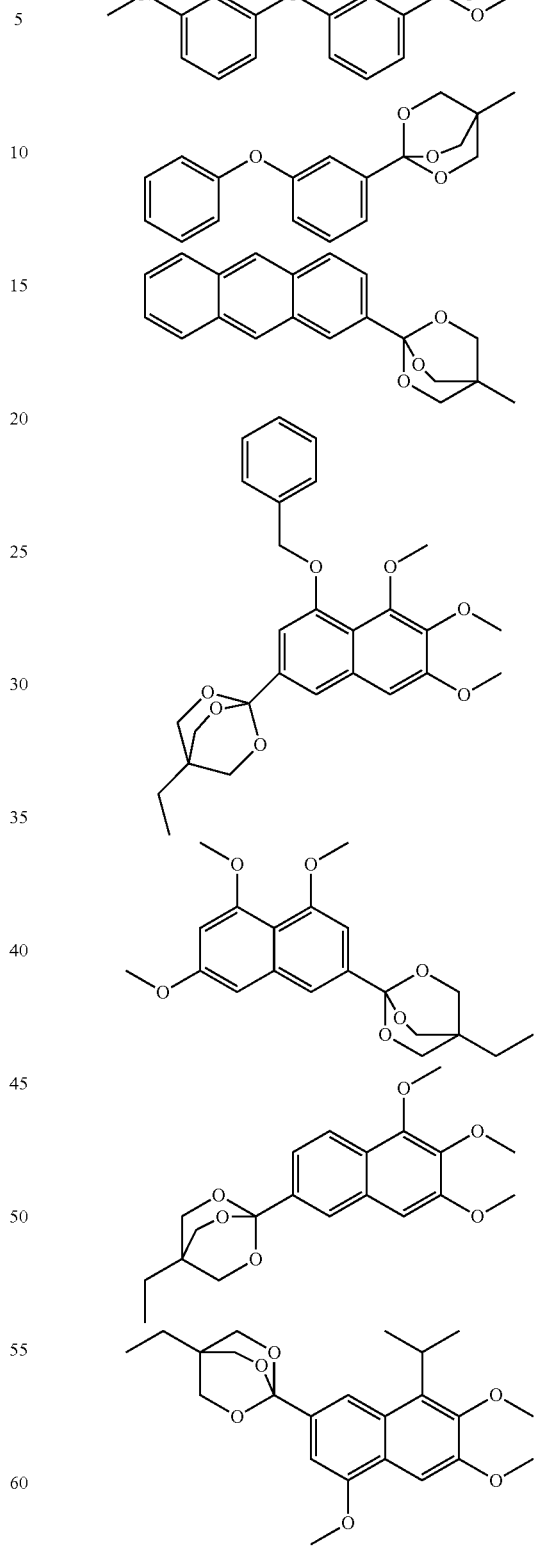
The OBO ester compound generates the following carboxylic acid by an acid catalyst generated upon the pattern-wise exposure.

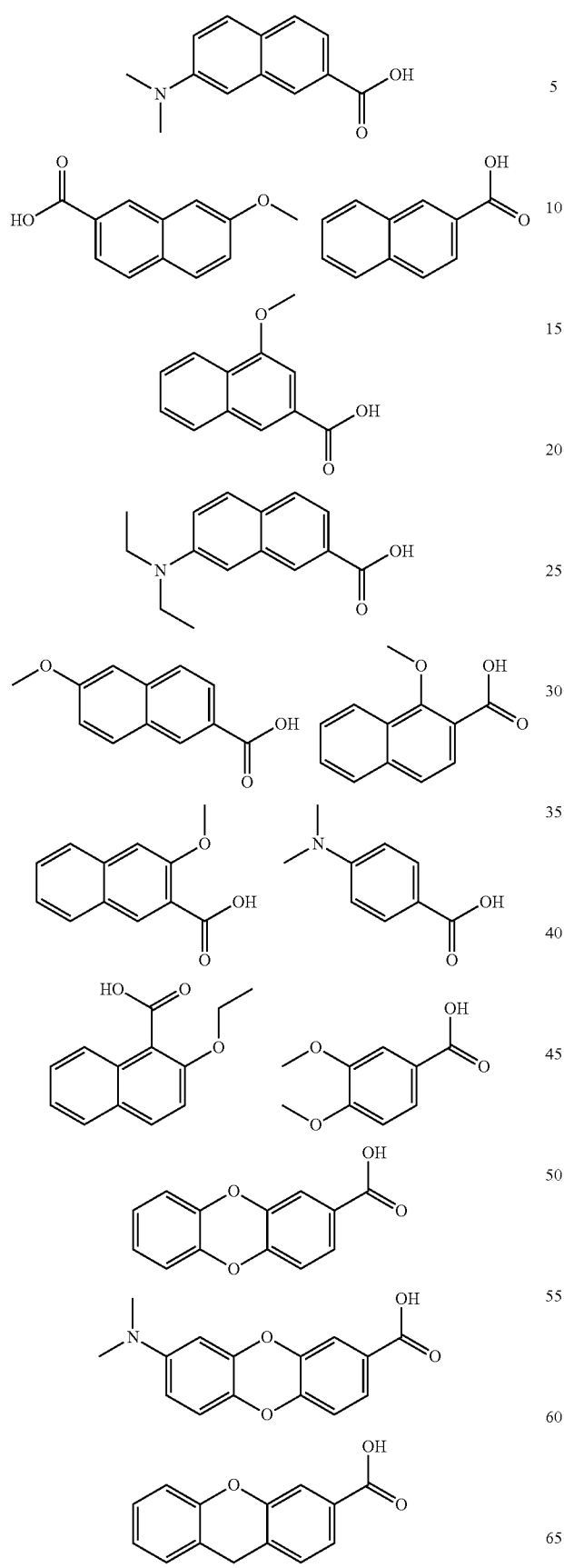
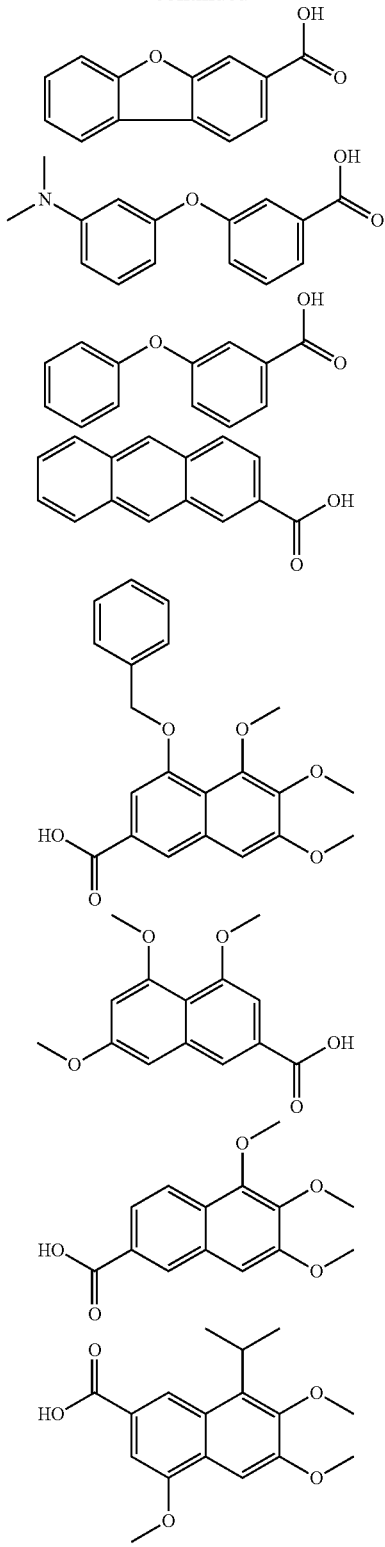
The radiation-sensitive sensitizer generated from the component (2) (that is, the radiation-sensitive acid-and-sensitizer generating agent (a) and the radiation-sensitive sensitizer generating agent (b)) upon the exposure must be capable of absorbing the second radioactive ray in the floodwise exposure step and degrading the radiation-sensitive acid generating agent (hereinafter may be also referred to "photosensitive acid generating agent" or "PAG"). For example, in the case of sensitization by generation of an acid from degradation of the PAG by electron transfer from the radiation-sensitive sensitizer to the PAG, it is preferable that the radiation-sensitive sensitizer satisfies the condition for causing the electron transfer. In other words, in order to cause the electron transfer with the wavelength of the radioactive ray for the floodwise exposure, it is preferable that oxidization potential of the radiation-sensitive sensitizer is sufficiently low, while the reduction potential of the PAG is sufficiently high. Free energy of the electron transfer reaction in the radioactive ray sensitization becomes negative, thereby facilitating the reaction. In the case of using an triplet sensitization reaction from the radiation-sensitive sensitizer to the PAG, it is preferable that the radiation-sensitive sensitizer is excitable to a singlet excited state by the wavelength of the second radioactive ray in the floodwise exposure step, and that an energy level of a triplet excited state of the radiation-sensitive sensitizer is higher than an energy level of a triplet excited state of the PAG. Examples of the radiation-sensitive sensitizer generated from the component (2) (that is, the radiation-sensitive acid-and-sensitizer generating agent (a) and the radiation-sensitive sensitizer generating agent (b)) upon the exposure include chalcone, 1,2-diketone, benzoin, benzophenone, fluorene, naphthoquinone, anthraquinone, xanthene, thioxanthene, xanthone, thioxanthone, cyanine, merocyanine, naphthalocyanine, subphthalocyanine, pyrylium, thiopyrylium, tetraphylline, annulene, spiropyran, spirooxazine, thiospiropyran, oxole, azine, thiazine, oxazine, indoline, azulene, azulenium, squarylium, porphyrin, porphyrazine, triarylmethane, phthalocyanine, acridone, coumarin, ketocoumarin, quinolinone, benzoxazole, acridine, thiazine, benzothiazole, phenothiazine, benzotriazole, perylene, naphthalene, anthracene, phenanthrene, pyrene, naphthacene, pentacene, coronene, and derivatives of these, and the like. In addition, the radiation-sensitive sensitizer generated from the component (2) upon the exposure preferably contains a carbonyl compound. The carbonyl compound preferably contains ketone, aldehyde, carboxylic acid, ester, amide, enone, carboxylic acid chloride, carboxylic anhydride, and the like as a carbonyl group. As the carbonyl compound, in light of separating the wavelength of the radioactive ray for the floodwise exposure sufficiently from the wavelength of the radioactive ray for the patternwise exposure to thereby improve resist contrast, a compound that absorbs the radioactive ray on the long-wavelength side of no less than 250 nm is preferred. Examples of the carbonyl compound include: a benzophenone derivative, a xanthone derivative, a thioxanthone derivative, a coumarin derivative, and an acridone derivative. In addition, the carbonyl compound may also be a naphthalene derivative or an anthracene derivative, and may also be an acridone derivative. In the radiation-sensitive sensitizer, hydrogen in the aromatic ring is preferably substituted with an electron-donating group. Substitution of hydrogen in the aromatic ring of the radiation-sensitive sensitizer by an electron-donating group tends to improve electron transfer efficiency by the sensitization reaction upon the floodwise exposure, and improve sensitivity of the resist. In addition, a difference between the radioactive ray absorption wavelength of the radiation-sensitive sensitizer (b) and the radioactive ray absorption wavelength of the radiation-sensitive sensitizer can be made greater and the radiation-sensitive sensitizer can be excited more selectively upon the floodwise exposure, and contrast of the latent image of the acid in the resist material thus tends to be improved. Examples of the electron-donating group include: a hydroxyl group, a methoxy group, an alkoxy group, an amino group, an alkylamino group, and an alkyl group.

Examples of benzophenone and its derivatives include the following compounds.

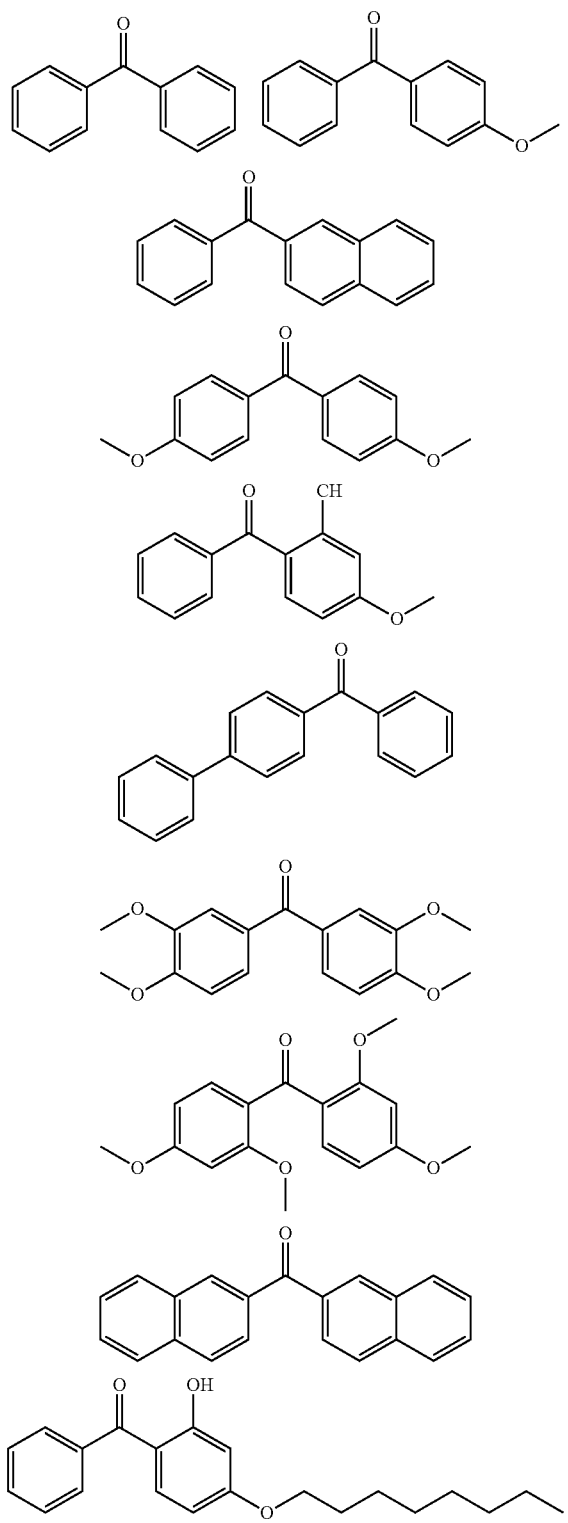

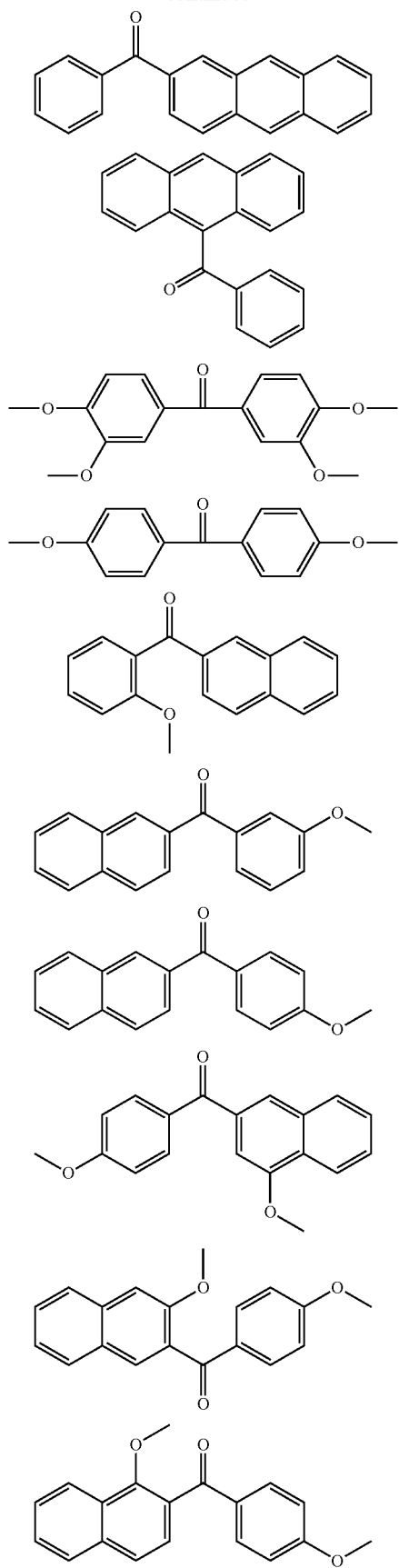
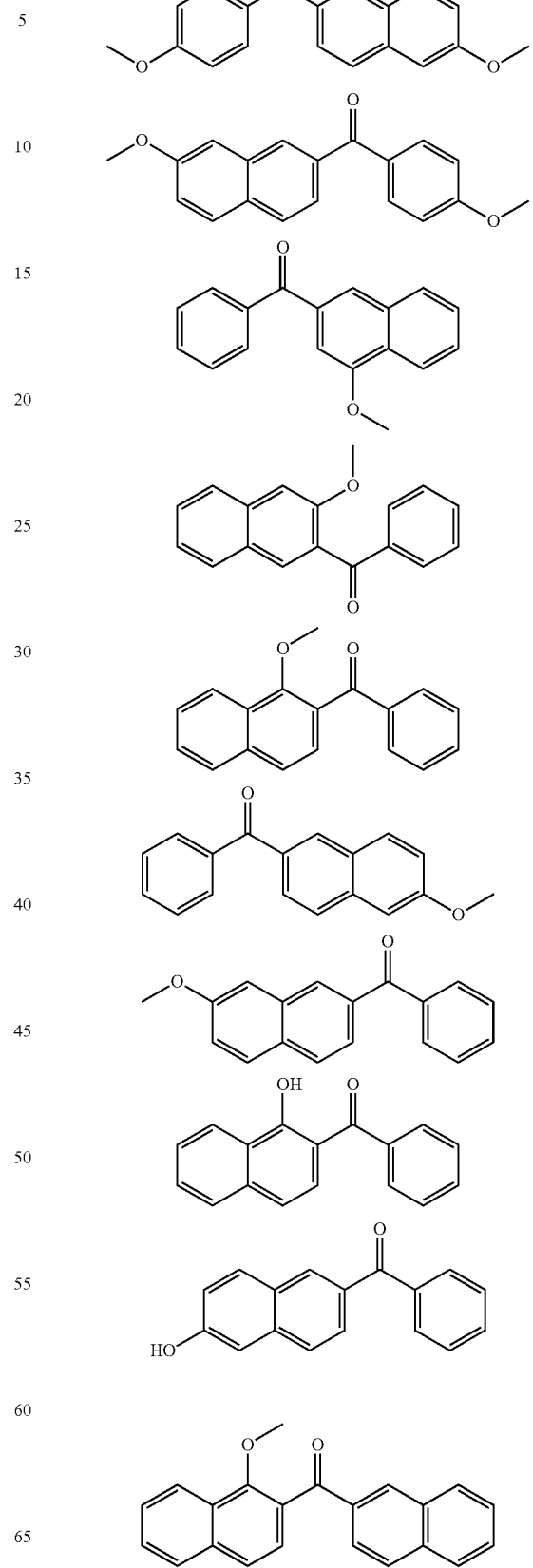

-continued
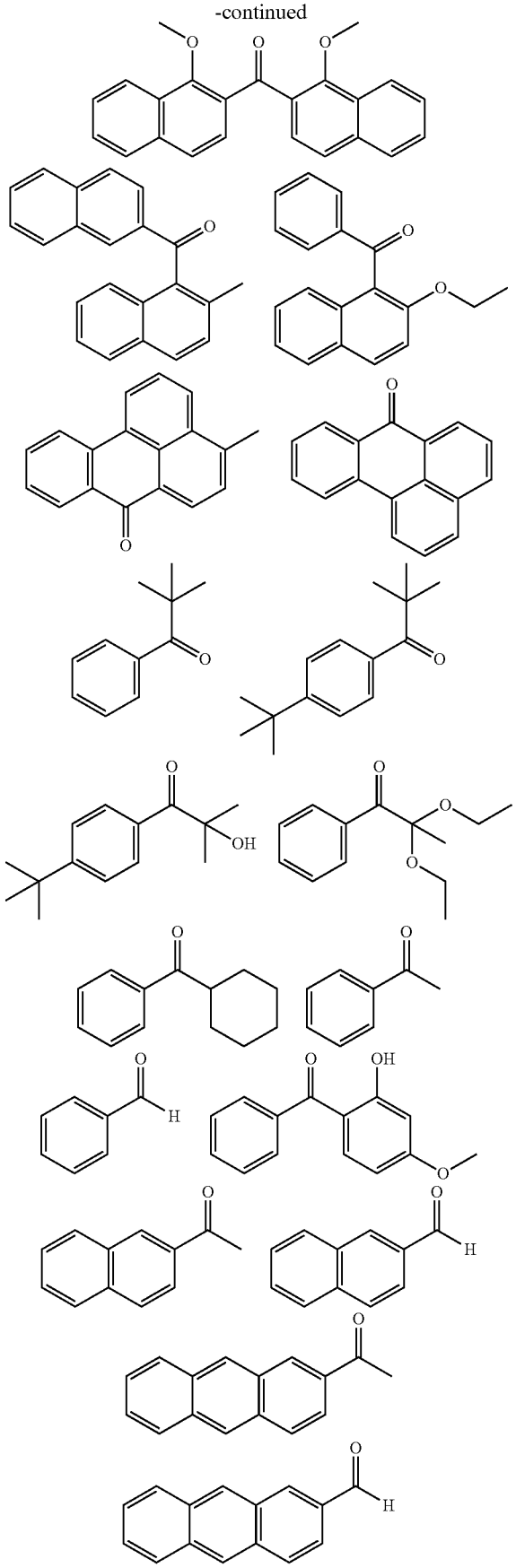
-continued
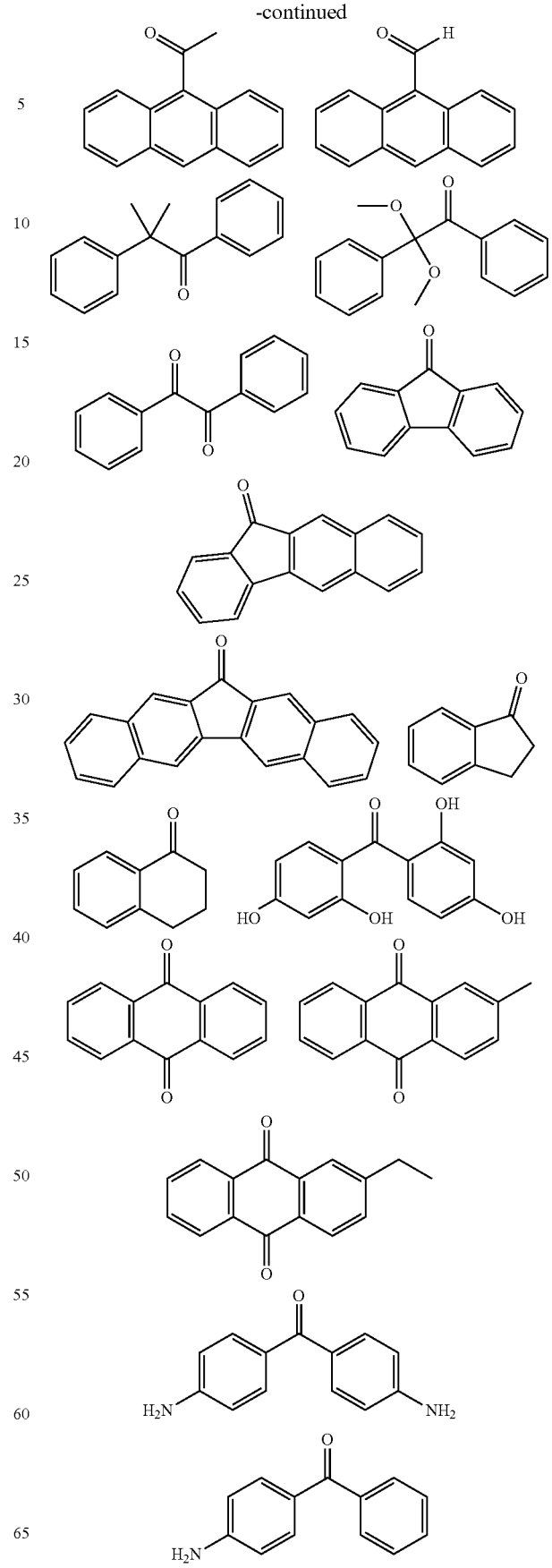

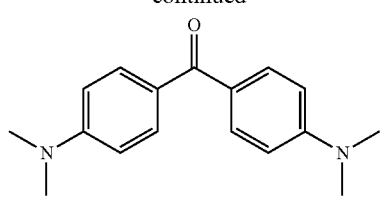
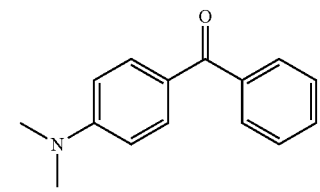
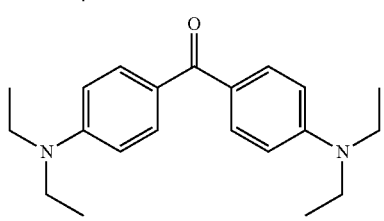
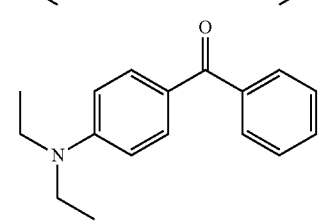
Examples of the thioxanthone and its derivatives include the following compounds.
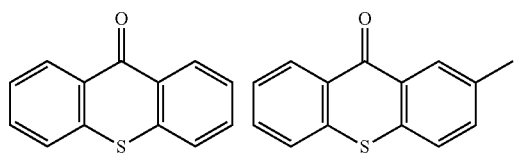
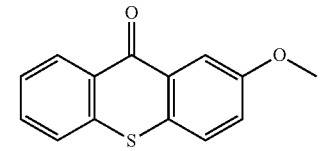
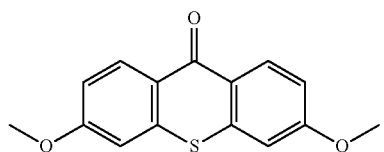
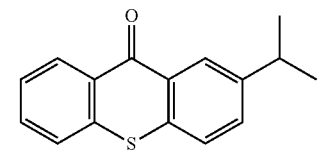
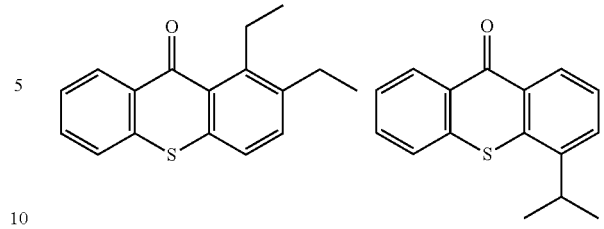
Examples of the xanthone and its derivatives include the following compounds.
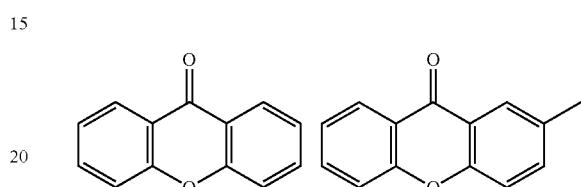
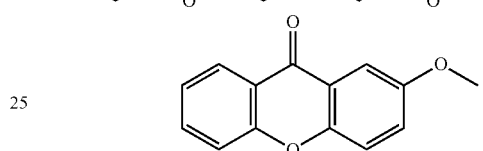
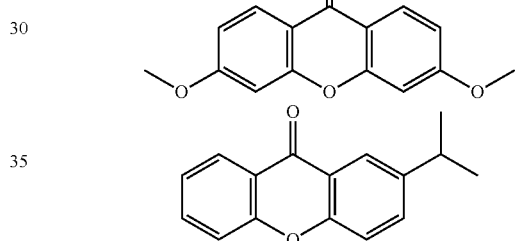
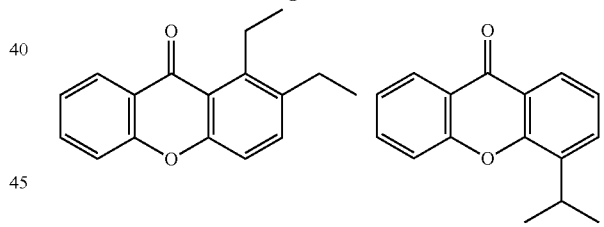
Examples of the acridone and its derivatives include the following compounds.
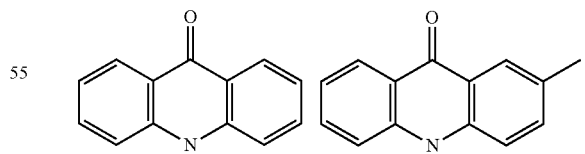
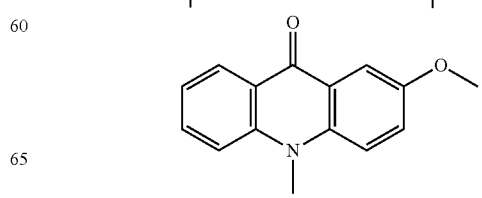

-continued

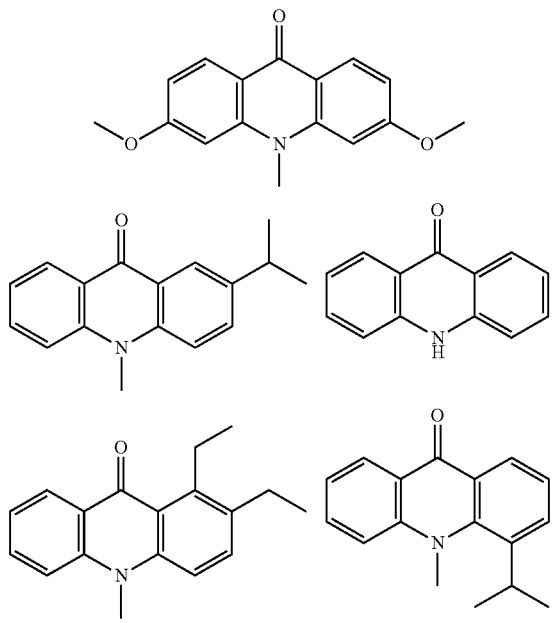

Examples of the coumarin and its derivatives include the following compounds.

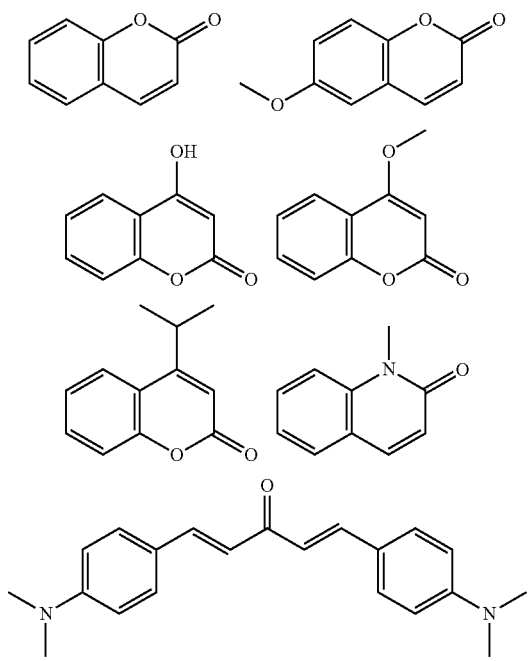

The radiation-sensitive sensitizer may also contain the following compounds.

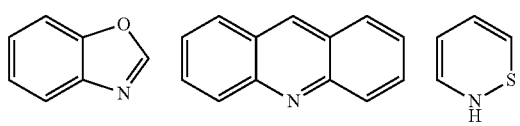

-continued

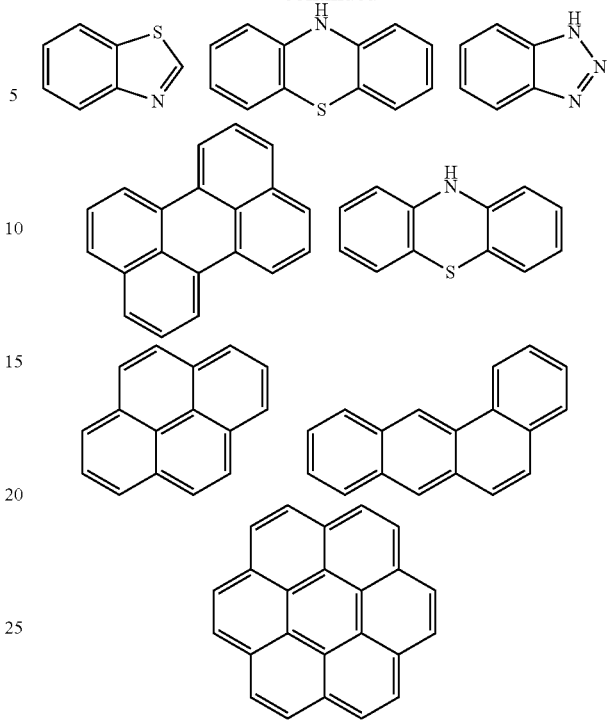

Examples of the radiation-sensitive sensitizer include acetophenone, 2,2-dimethoxy-2-phenylacetophenone, diethoxyacetophenone, 1-hydroxycyclohexyl phenyl ketone, 1,2-hydroxy-2-methyl-1-phenylpropan-1-one, α-hydroxycyclohexyl phenyl ketone, 2-hydroxy-2-methyl-1-phenylpropanone, 2-hydroxy-2-methyl-1-(4-isopropylphenyl)propanone, 2-hydroxy-2-methyl-1-(4-dodecylphenyl)propanone, 2-hydroxy-2-methyl-1-[(2-hydroxyethoxy)phenyl]propanone, benzophenone, 2-methylbenzophenone, 3-methylbenzophenone, 4-methylbenzophenone, 4-methoxybenzophenone, 2-chlorobenzophenone, 4-chlorobenzophenone, 4-bromobenzophenone, 2-carboxybenzophenone, 2-ethoxycarbonylbenzophenone, 4-benzoyl-4'-methyldiphenyl sulfide, benzophenonetetracarboxylic acid or the tetramethyl ester thereof, 4,4'-bis(dimethylamino)benzophenone, 4,4'-bis(dicyclohexylamino)benzophenone, 4,4'-bis(diethylamino)benzophenone, 4,4'-bis(dihydroxyethylamino)benzophenone, 4-methoxy-4'-dimethylaminobenzophenone, 4,4'-dimethoxybenzophenone, 4-dimethylaminobenzophenone, 4-dimethylaminoacetophenone, benzil, anthraquinone, 2-t-butylanthraquinone, 2-methylanthraquinone, phenanthraquinone, fluorenone, 2-benzyl-2-dimethylamino-1-(4-morpholinophenyl)-1-butanone, 2-(dimethylamino)-2-[(4-methylphenyl)methyl]-1-[4-(4-morpholinyl)phenyl]-1-butanone, 2-methyl-1-[4-(methylthio)phenyl]-2-morpholino-1-propanone, 2-hydroxy-2-methyl-[4-(1-methylvinyl)phenyl]propanol oligomer, benzoin, benzoin methyl ether, benzoin ethyl ether, benzoin propyl ether, benzoin isopropyl ether, benzoin isobutyl ether, benzoin phenyl ether, benzil dimethyl ketal, acridone, chloroacridone, N-methylacridone, N-butylacridone, N-butyl-chloroacridone, 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, 2-isopropylthioxanthone, 4-isopropylthioxanthone, 2,4-diethylthioxanthone, 2,4-dichlorothioxanthone, 1-chloro-4-propoxythioxanthone, benzoyl di-(2,6-dimethylphenyl)phosphonate, 1-[4-(phenylthio)phenyl]-1,2-octanedione-2-(O-benzoyloxime), 1-[9-ethyl-6-(2-methylbenzoyl)-9H-carbazol-3-yl]ethanone-1-(O-acetyloxime), 1-[9-ethyl-6-(2-methylbenzoyl)-9H-carbazol-3-yl]-3-cyclopentylpropanone-1-(O-acetyloxime), 1-[4-(phenylthio)phenyl]-3-cyclopentylpropane-1,2-dione-2-(O-benzoyloxime), 2,2-dimethoxy-1,2-diphenylethan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, phenyl-glyoxylic acid methyl ester, 2-methyl-1-(4-methylthiophenyl)-2-morpholinopropan-1-one, 2-benzyl-2-dimethylamino-1-(4-morpholinophenyl)-butanone-1, 1,2-octanedione, 1-[4-(phenylthio)-,2-(O-benzoyloxime)], ethanone, 1-[9-ethyl-6-(2-methylbenzoyl)-9H-carbazol-3-yl]-, 1-(O-acetyloxime), and the like.

Examples of the radiation-sensitive sensitizer and the radiation-sensitive sensitizer generating agent (b) that is capable of generating the radiation-sensitive sensitizer are provided hereinafter, respectively with an absorption ratio of the nonionizing radiation (wavelength: 365 nm) by the radiation-sensitive sensitizer with respect to the radiation-sensitive sensitizer generating agent (b). The absorption ratio is calculated with nonionizing radiation absorption capacity of the radiation-sensitive sensitizer generating agent (b) as a denominator and nonionizing radiation absorption capacity of the radiation-sensitive sensitizer as a numerator. Comparison of the nonionizing radiation absorption capacity between the radiation-sensitive sensitizer generating agent (b) and the radiation-sensitive sensitizer reveals that, through the structure alteration from the radiation-sensitive sensitizer generating agent (b) to the radiation-sensitive sensitizer, the nonionizing radiation absorption capacity increases more than 10-fold.

TABLE 1

| Radiation-sensitive sensitizer | Radiation-sensitive sensitizer generating agent (b) | Absorption ratio |
| --- | --- | --- |
| benzophenone derivative | ketal structure | >10-fold |
| naphthyl phenyl ketone derivative | ketal structure | >10-fold |
| thioxanthone derivative | ketal structure | >10-fold |
| acridone derivative | ketal structure | >10-fold |
| benzanthrone derivative | ketal structure | >10-fold |
| naphthoaldehyde derivative | acetal structure | >10-fold |
| naphthalenecarboxylic acid derivative | ortho ester structure | >10-fold |

(c) Radiation-Sensitive Acid Generating Agent

The radiation-sensitive acid generating agent (c) generates, upon the irradiation with the first radioactive ray, an acid, and the radiation-sensitive acid generating agent (c) substantially does not generate the acid upon the irradiation with the second radioactive ray in light-unexposed regions which are not irradiated with the first radioactive ray in the patternwise exposure step; thus, the radiation-sensitive acid generating agent (c) is different from the radiation-sensitive acid-and-sensitizer generating agent (a). The radiation-sensitive acid generating agent (c) having the above-described property can generate the acid only in the patternwise exposed regions of the resist material film through the radioactive ray sensitization reaction upon the floodwise exposure.

In addition, in a case where the acid is generated by irradiating the radiation-sensitive acid generating agent (c) with the second radioactive ray, the lower limit of the wavelength of the second radioactive ray that can maintain the amount of the acid generated through the irradiation with the second radioactive ray so small that that the difference in the concentration of the acid between the light-exposed regions and the light-unexposed regions after the patternwise exposure can be maintained at a level to permit the pattern formation is preferably 300 nm, more preferably 320 nm, and still more preferably 350 nm. By making the wavelength of the second radioactive ray no less than the lower limit in a case where the radiation-sensitive acid generating agent (c) generates the acid through the irradiation with the second radioactive ray, the acid is generated upon the irradiation with the second radioactive ray in the patternwise exposed regions irradiated with the first radioactive ray by sensitization action of the radiation-sensitive sensitizer being generated, while generation of the acid upon the irradiation with the second radioactive ray is inhibited in the patternwise unexposed regions not irradiated with the first radioactive ray. As a result, sensitivity and a contrast between the patternwise exposed regions and the patternwise unexposed regions can be improved.

The radiation-sensitive acid generating agent (c) is preferably a salt composed of a cation and an anion. Examples of the anion include: those exemplified as the anion of the acid in the description regarding the radiation-sensitive acid-and-sensitizer generating agent (a). In addition, the radiation-sensitive acid generating agent (c) is preferably the compound represented by the above formula (1), similarly to the radiation-sensitive acid-and-sensitizer generating agent (a). In other words, the anion in the radiation-sensitive acid generating agent (c) is preferably the anion shown in the above formula (1).

The cation in the radiation-sensitive acid generating agent (c) is a monovalent radiation-sensitive onium cation represented by $X^+$ and is degraded through the irradiation with the exposure light. In the light-exposed regions, sulfonic acid is generated from proton generated through degradation of the radiation-sensitive onium cation and a sulfonate anion. The cation does not generate the radiation-sensitive sensitizer.

Examples of the monovalent radiation-sensitive onium cation represented by $X^+$ include: a cation represented by the following formula (X-1) (hereinafter, may be also referred to as "cation (X-1)"), a cation represented by the following formula (X-2) (hereinafter, may be also referred to as "cation (X-2)"), and a cation represented by the following formula (X-3) (hereinafter, may be also referred to as "cation (X-3)").

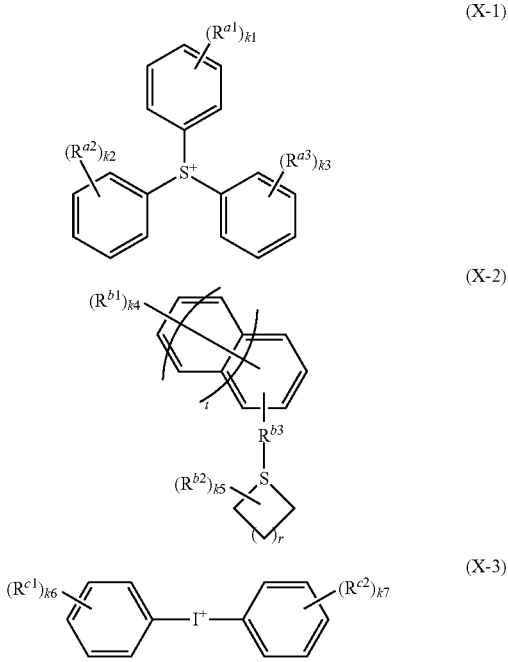

In the above formula (X-1), $R^{a1}$, $R^{a2}$ and $R^{a3}$ each independently represent: a substituted or unsubstituted linear or branched alkyl group having 1 to 12 carbon atoms; a substituted or unsubstituted aromatic hydrocarbon group having 6 to 12 carbon atoms; $-OSO_2-R^P$ or $-SO_2-R^Q$; or at least two of $R^{a1}$, $R^{a2}$ and $R^{a3}$ taken together represent a ring structure. $R^P$ and $R^Q$ each independently represents: a substituted or unsubstituted linear or branched alkyl group having 1 to 12 carbon atoms; a substituted or unsubstituted alicyclic hydrocarbon group having 5 to 25 carbon atoms; or a substituted or unsubstituted aromatic hydrocarbon group having 6 to 12 carbon atoms. k1, k2 and k3 are each independently an integer of 0 to 5. In a case in which $R^{a1}$ to $R^{a3}$ and $R^P$ and $R^Q$ are present in a plurality of number respectively, the plurality of $R^{a1}$s to $R^{a3}$s and $R^P$s and $R^Q$s may be either identical to or different from each other, respectively.

In the above formula (X-2), $R^{b1}$ represents a substituted or unsubstituted linear or branched alkyl group having 1 to 8 carbon atoms, or a substituted or unsubstituted aromatic hydrocarbon group having 6 to 8 carbon atoms. k4 is an integer of 0 to 7. In a case in which $R^{b1}$ is present in a plurality of number, the plurality of $R^{b1}$s may be either identical or different, and the plurality of $R^{b1}$s may taken together represent a ring structure. $R^{b2}$ represents a substituted or unsubstituted linear or branched alkyl group having 1 to 7 carbon atoms, or a substituted or unsubstituted aromatic hydrocarbon group having 6 or 7 carbon atoms. k5 is an integer of 0 to 6. In a case in which $R^{b2}$ is present in a plurality of number, the plurality of $R^{b2}$S may be either identical or different, and the plurality of $R^{b2}$s may taken together represent a ring structure. r is an integer of 0 to 3. $R^{b3}$ is a single bond or a divalent organic group having 1 to 20 carbon atoms. t is an integer of 0 to 2.

In the above formula (X-3), $R^{c1}$ and $R^{c2}$ each independently represent: a substituted or unsubstituted linear or branched alkyl group having 1 to 12 carbon atoms, a substituted or unsubstituted aromatic hydrocarbon group having 6 to 12 carbon atoms, $-OSO_2-R^R$ or $-SO_2-R^S$; or $R^{c1}$ and $R^{c2}$ taken together represent a ring structure. $R^R$ and $R^S$ each independently represent: a substituted or unsubstituted linear or branched alkyl group having 1 to 12 carbon atoms; a substituted or unsubstituted alicyclic hydrocarbon group having to 25 carbon atoms; or a substituted or unsubstituted aromatic hydrocarbon group having 6 to 12 carbon atoms. k6 and k7 are each independently an integer of 0 to 5. In a case in which $R^{c1}$, $R^{c2}$, $R^R$ and $R^S$ are present in a plurality of number respectively, the plurality of $R^{c1}$s, $R^{c2}$s, $R^R$s and $R^S$s may be either identical to or different from each other, respectively.

Examples of the unsubstituted linear alkyl group which may be represented by $R^{a1}$ to $R^{a3}$, $R^{b1}$, $R^{b2}$, $R^{c1}$ and $R^2$ include: a methyl group, an ethyl group, an n-propyl group, and an n-butyl group.

Examples of the unsubstituted branched alkyl group which may be represented by $R^{a1}$ to $R^{a3}$, $R^{b1}$, $R^{b2}$, $R^{c1}$ and $R^{c2}$ include: an i-propyl group, an i-butyl group, a sec-butyl group, and a t-butyl group.

Examples of the unsubstituted aromatic hydrocarbon group which may be represented by $R^{a1}$ to $R^{a3}$, $R^{c1}$ and $R^{c2}$ include: an aryl group such as a phenyl group, a tolyl group, a xylyl group, a mesityl group, and a naphthyl group; an aralkyl group such as a benzyl group, and a phenethyl group.

Examples of the unsubstituted aromatic hydrocarbon group which may be represented by $R^{b1}$ and $R^{b2}$ include: a phenyl group, a tolyl group, and a benzyl group.

Examples of the divalent organic group which may be represented by $R^{b3}$ include: a divalent chain hydrocarbon group, a divalent alicyclic hydrocarbon group, and a divalent aromatic hydrocarbon group.

Examples of the divalent chain hydrocarbon group include:

an alkanediyl group such as a methanediyl group, an ethanediyl group, a propanediyl group, and a butanediyl group;

an alkenediyl group such as an ethenediyl group, a propenediyl group, and a butenediyl group; and an alkynediyl group such as an ethynediyl group, a propynediyl group, and a butynediyl group.

Examples of the divalent alicyclic hydrocarbon group include:

a monocyclic cycloalkanediyl group such as a cyclopropanediyl group, a cyclobutanediyl group, a cyclopentanediyl group, and a cyclohexanediyl group;

a monocyclic cycloalkenediyl group such as a cyclopropenediyl group, a cyclobutenediyl group;

a polycyclic cycloalkanediyl group such as a norbornanediyl group, an adamantanediyl group, a tricyclodecanediyl group, and a tetracyclododecanediyl group; and a polycyclic cycloalkenediyl group such as a norbornenediyl group and a tricyclodecenediyl group.

Examples of the divalent aromatic hydrocarbon group include:

an arenediyl group such as a benzenediyl group, a toluenediyl group, a xylenediyl group, and a naphthalenediyl group; and an arenediyl(cyclo)alkanediyl group such as a benzenediylmethanediyl group and a naphthalenediylcyclohexancdiyl group.

The hetero atom-containing group as referred to means a group containing a divalent hetero atom having a valency of no less than 2 in its structure. The hetero atom-containing group may contain one or two or more hetero atoms.

The divalent hetero atom having a valency of no less than 2 contained in the hetero atom-containing group is not particularly limited as long as it is a hetero atom having a valency of no less than 2, and may be exemplified by, for example, an oxygen atom, a nitrogen atom, a sulfur atom, a silicon atom, a phosphorus atom, a boron atom and the like.

Examples of the hetero atom-containing group include:
a group constituted only of hetero atoms such as —SO—, —SO$_2$—, —SO$_2$O—, —SO$_3$—; and
a group of a combination of a carbon atom and hetero atoms such as —CO—, —COO—, —COS—, —CONH—, —OCOO—, —OCOS—, —OCONH—, —SCONH—, —SCSNH—, —SCSS—.

Examples of a substituent that may substitute for a hydrogen atom contained in the alkyl group and the aromatic hydrocarbon group, and of a substituent that may be contained in the organic group include: a halogen atom such as a fluorine atom, a chlorine atom, a bromine atom, and an iodine atom; a hydroxy group; a carboxy group; a cyano group; a nitro group; an alkoxy group; an alkoxycarbonyl group; an alkoxycarbonyloxy group; an acyl group; and an acyloxy group. Of these, a halogen atom is preferred and a fluorine atom is more preferred.

As $R^{a1}$ to $R^{a3}$, $R^{b1}$, $R^{b2}$, $R^{c1}$ and $R^{c2}$: an unsubstituted linear or branched alkyl group, a fluorinated alkyl group, an unsubstituted monovalent aromatic hydrocarbon group, —OSO$_2$—R" and —SO$_2$—R" are preferred; —SO$_2$—R", a fluorinated alkyl group, an unsubstituted linear or branched alkyl group, and unsubstituted monovalent aromatic hydrocarbon group are more preferred; —SO$_2$—R" and unsubstituted linear or branched alkyl group are still more preferred. R" represents an unsubstituted monovalent chain hydrocarbon group, an unsubstituted monovalent alicyclic hydrocarbon group, or an unsubstituted monovalent aromatic hydrocarbon group.

As k1, k2 and k3 in the formula (X-1), an integer of 0 to 2 is preferred, 0 and 1 are more preferred, and 0 is still more preferred. As k4 in the formula (X-2), an integer of 0 to 2 is preferred, 0 and 1 are more preferred, and 1 is still more preferred. As k5, an integer of 0 to 2 is preferred, 0 and 1 are more preferred, and 0 is still more preferred. As r, 2 and 3 is preferred, and 2 is more preferred. As t, 0 and 1 are preferred, and 0 is more preferred. As k6 and k7 in the formula (X-3), an integer of 0 to 2 is preferred, 0 and 1 are more preferred, and 0 is still more preferred.

Of these, the cation (X-1) and the cation (X-3) are preferred, and triphenylsulfonium cation, 4-methanesulfonylphenyldiphenylsulfonium cation, and bis(4-tert-butylphenyl)iodonium cation are more preferred as X$^+$.

Examples of the radiation-sensitive acid generating agent (c) include: an onium salt compound, a diazomethane compound, and a sulfonimide compound. In addition, examples of the onium salt compound include a sulfonium salt compound, a tetrahydrothiophenium salt compound, and an iodonium salt compound. The radiation-sensitive acid generating agent (c) has a sufficiently high reduction potential with respect to the electron transfer, and can generate an acid by degrading by accepting an electron from the radiation-sensitive sensitizer excited in the floodwise exposure. In addition, in a case in which an energy level of a triplet excited state of the radiation-sensitive sensitizer is higher than an energy level of a triplet excited state of the radiation-sensitive acid generating agent (c), a triplet sensitization reaction from the radiation-sensitive sensitizer to the radiation-sensitive acid generating agent (c) takes place more easily. As the radiation-sensitive acid generating agent (c), a sulfonium salt compound, an iodonium salt compound, sulfonyldiazomethane, N-sulfonyloxyimide, and an oxime-O-sulfonate radiation-sensitive acid generating agent are preferred, and a sulfonium salt compound and an iodonium salt compound are more preferred.

Examples of the sulfonium salt compound include: triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo [2.2.1]hept-2-yl-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-methanesulfonylphenyldiphenyl sulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, and 4-methanesulfonylphenyldiphenylsulfonium 2-bicyclo [2.2.1]hept-2-yl-1,1,2,2-tetrafluoroethanesulfonate.

Examples of the tetrahydrothiophenium salt compound include: 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(6-n-butoxynaphthalen-2-yl) tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl) tetrahydrothiophenium perfluoro-n-octanesulfonate, 1-(6-n-butoxynaphthalen-2-yl)tetrahydrothiophenium 2-bicyclo [2.2.1]hept-2-yl-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, and 1-(3,5-dimethyl-4-hydroxyphenyl)tetrahydrothiophenium 2-bicyclo[2.2.21]hept-2-yl-1,1,2,2-tetrafluoroethanesulfonate.

Examples of the iodonium salt compound include: diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, bis(4-t-butylphenyl) iodonium trifluoromethanesulfonate, bis(4-t-butylphenyl) iodonium nonafluoro-n-butanesulfonate, bis(4-t-butylphenyl)iodonium perfluoro-n-octanesulfonate, and bis (4-t-butylphenyl)iodonium 2-bicyclo[2.2.1]hept-2-yl-1,1,2, 2-tetrafluoroethanesulfonate.

Examples of the sulfonimide compound include: N-(trifluoromethanesulfonyloxy)bicyclo[2.2.1]hept-5-ene-2,3-dicarboxyimide, N-(nonafluoro-n-butanesulfonyloxy)bicyclo [2.2.1]hept-5-ene-2,3-dicarboxyimide, N-(perfluoro-n-octanesulfonyloxy)bicyclo[2.2.1]hept-5-ene-2,3-dicarboxyimide, and N-(2-bicyclo[2.2.1]hept-2-yl-1,1,2,2-tetrafluoroethanesulfonyloxy)bicyclo[2.2.1]hept-5-ene-2,3-dicarboxyimide.

Examples of the diazomethane compound includes: bis (n-propylsulfonyl)diazomethane, bis(isopropylsulfonyl)diazomethane, bis(n-butylsulfonyl)diazomethane, bis(tert-butylsulfonyl)diazomethane, bis(cyclopentylsulfonyl) diazomethane, bis(cyclohexylsulfonyl) diazomethane, bis (phenylsulfonyl)diazomethane, bis(4-chlorophenylsulfonyl) diazomethane, bis(p-tolylsulfonyl)diazomethane, bis(2,4-xylylsulfonyl)diazomethane, bis(4-isopropylphenylsulfonyl)diazomethane, bis(4-tertbutylphenylsulfonyl)diazomethane, bis(naphthylsulfonyl)diazomethane, and bis(anthracenylsulfonyl)diazomethane.

Suitable values of the energy released when a radiation-sensitive onium cation in the radiation-sensitive acid generating agent (c) is reduced into radical and the reduction potential of the radiation-sensitive onium cation are similar to those specified for the radiation-sensitive acid-sensitizer (a).

Base Component (1')

The base component (1') is a component that is capable of being made soluble or insoluble in a developer solution by an action of an acid. In other words, it is a component in which the patternwise exposed regions is made soluble or insoluble in the developer solution in the development step, by an acid-catalyzed reaction in the baking step (refer to FIG. 4) following the floodwise exposure step. The base component (1') may be either an organic compound or an inorganic compound. In addition, the organic compound may be either a polymer compound or a low molecular weight compound. Furthermore, the polymer compound may be a polymer. Examples of the organic compound and the inorganic compound in the base component (1') include compounds similar to those specified for the base component (1).

In addition, the base component (1') contains, among three groups: an acid-and-radiation-sensitive-sensitizer generating group (d); a radiation-sensitive sensitizer generating group (e); and a radiation-sensitive acid generating group (f), a group described in (d) below, any two groups from (d) to (f) below, or all of groups described in (d) to (f). In other words, the base component (1') is an organic compound or an inorganic compound containing a group described in (d) to (f) below. The base component (1') may contain a group described in (d) to (f) below in one molecule (or one particle) or in each of a plurality of molecules (or particles).

In other words, the base component (1') is a component that, similarly to the base component (1), is capable of being made soluble or insoluble in the developer solution by an action of an acid, and similarly to the component (2), that is capable of generating an acid and a radiation-sensitive sensitizer through the irradiation with the first radioactive ray in the patternwise exposure step.

The weight average molecular weight of the base component (1') being a polymer compound is preferably no less than 3,000 and no greater than 200,000, and more preferably no less than 5,000 and no greater than 30,000. Meanwhile, the molecular weight of the base component (1') being a low molecular weight compound is preferably no less than 500 and no greater than 3,000, and more preferably no less than 1,000 and no greater than 3,000. Hereinafter, the base component (1') will be described in detail, taking a polymer compound as an example.

Examples of the polymer compound in the base component (1') includes compounds that have groups represented by the (d) to (f) as, or as a part of, the groups (protecting groups) represented by $R^{11}$ to $R^{13}$ in the formula (VII), $R^{11}$ or $R^{14}$ in the formula (VIII), $R^{15}$ or $R^{16}$ in the formula (XXV), $R^{17}$ in the formula (XXVI) for the polymer compound in the base component (1).

(d) Acid-and-Radiation-Sensitive-Sensitizer Generating Group

An acid-and-radiation-sensitive-sensitizer generating group (d) is a group that is capable of generating an acid and a radiation-sensitive sensitizer, which absorbs the second radioactive ray, through the irradiation with the first radioactive ray, and that substantially does not generate the acid and the radiation-sensitive sensitizer in the light-unexposed regions that is not irradiated with the first radioactive ray in the patternwise exposure step. The acid-and-radiation-sensitive-sensitizer generating group (d) having the above described properties can inhibit generation of the acid and the radiation-sensitive sensitizer through the irradiation with the second radioactive ray in the floodwise exposure step.

In addition, in a case where the acid and the radiation-sensitive sensitizer are generated by irradiating the acid-and-radiation-sensitive-sensitizer generating group (d) with the second radioactive ray, the lower limit of the wavelength of the second radioactive ray that can maintain the amount of the acid and the radiation-sensitive sensitizer generated through the irradiation with the second radioactive ray so small that that the difference in the concentration of the acid and the radiation-sensitive sensitizer between the light-exposed regions and the light-unexposed regions after the patternwise exposure can be maintained at a level to permit the pattern formation is preferably 300 nm, more preferably 320 nm, and still more preferably 350 nm. By making the wavelength of the second radioactive ray no less than the lower limit in a case where the acid-and-radiation-sensitive-sensitizer generating group (d) generates the acid and the radiation-sensitive sensitizer through the irradiation with the second radioactive ray, the acid is generated upon the irradiation with the second radioactive ray in the patternwise exposed regions irradiated with the first radioactive ray by sensitization action of the radiation-sensitive sensitizer being generated, while generation of the acid upon the irradiation with the second radioactive ray is inhibited in the patternwise unexposed regions not irradiated with the first radioactive ray. As a result, sensitivity and a contrast between the patternwise exposed regions and the patternwise unexposed regions can be improved.

Examples of the acid-and-radiation-sensitive-sensitizer generating group (d) include: an onium salt compound group, a diazomethane compound group, and a sulfonimide compound group. Examples of the onium salt compound group include: a sulfonium salt compound group, an iodonium salt compound group, and a tetrahydrothiophenium salt compound. As the acid-and-radiation-sensitive-sensitizer generating group (d), in light of high reduction potential, a sulfonium salt compound group and an iodonium salt compound group are preferred and an iodonium salt compound group is more preferred. In addition, the acid-and-radiation-sensitive-sensitizer generating group (d) is preferably of an anion-bound type, in which an anion and the base component (1') are bound. The acid-radiation-sensitive sensitizer generating group being of the anion-bound type tends to be able to inhibit diffusion of the acid thus generated into the light-unexposed regions.

The sulfonium salt compound group is composed of a sulfonium cation and an anion of acid. The sulfonium salt compound group is preferably at least one type of group selected from the group consisting of groups represented by the following formulae (XIV) to (XVII). The groups represented by the following formulae (XIV) to (XVII) are of a cation-bound type in which a cation and the base component (1') are bound.

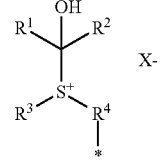

(XIV)

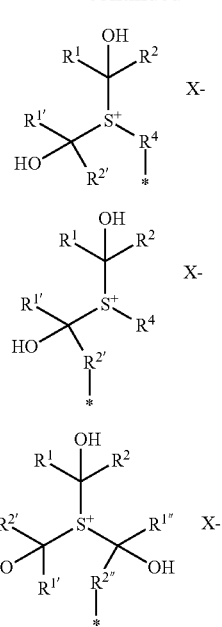

In the above formulae (XIV) to (XVII), $R^1$, $R^2$, $R^{1\prime}$, $R^{2\prime}$, $R^{1\prime\prime}$, $R^{2\prime\prime}$, $R^3$ and $R^4$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or, a carbonyl group to which an alkyl group having 1 to 12 carbon atoms is bound. In the above formulae (XIV) to (XVII), a hydrogen atom of the hydroxyl group may be substituted with a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or hydroxyl group. In the case of the hydrogen atom of the hydroxyl group being substituted, the sulfonium salt compound group contains a ketal compound group or an acetal compound group. In the formulae (XIV) to (XVII), at least two arbitrary groups among $R^1$, $R^2$, $R^{1\prime}$, $R^{2\prime}$, $R^{1\prime\prime}$, $R^{2\prime\prime}$, $R^3$, and $R^4$ may bind to each other to form a ring structure via a single bond, a double bond, or a bond including —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. $R^e$ represents a phenyl group; a phenoxy group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; or, a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. $R^1$, $R^2$, $R^{1\prime}$, $R^{2\prime}$, $R^{1\prime\prime}$, $R^{2\prime\prime}$, $R^3$ and $R^4$ each independently represent, preferably a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group. In the formulae (XIV) to (XVII), $X^-$ represents an anion of acid. The acid is preferably a strong acid, and more preferably a superacid. In the formulae (XIV) to (XVII), * denotes a binding site to the base component (1'). It is to be noted that in a case in which $R^{2\prime}$, $R^{2\prime\prime}$ and $R^4$ bind to the base component (1'), $R^{2\prime}$, $R^{2\prime\prime}$ and $R^4$ each independently represent a divalent group obtained by removing a hydrogen atom from: a phenyl group; a naphthyl group; an anthracenyl group; a phenoxy group; a naphthoxy group; an anthracenoxy group; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, or a hydroxyl group; or a carbonyl group to which an alkyl group having 1 to 12 carbon atoms bonds, preferably a divalent group obtained by removing a hydrogen atom from an alkoxy group having 1 to 5 carbon atoms, or a phenyl group substituted with an alkoxy group having 1 to 5 carbon atoms, an alkyl group having 1 to 5 carbon atoms, and a hydroxyl group.

As the sulfonium salt compound group, at least one type of group selected from the group consisting of groups represented by the following formulae (XXXI) to (XXXIII) is preferred. The groups represented by the following formulae (XXXI) to (XXXIII) are of an anion-bound type in which an anion and the base component (1') are bound. With an anion of acid being bound to the base component (1') even after the exposure, there is a tendency that diffusion of the acid after the exposure can be inhibited and blurring of an image can be reduced.

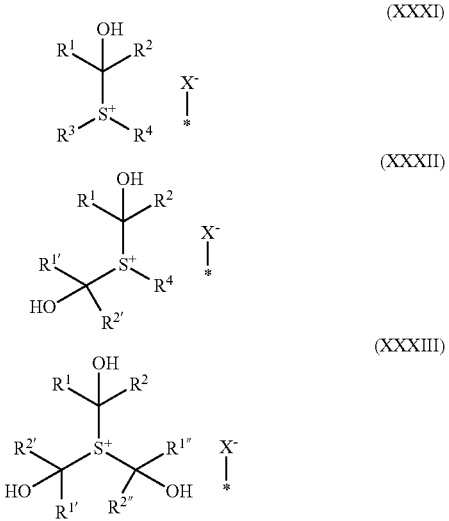

In the formulae (XXXI) to (XXXIII), $R^1$, $R^2$, $R^{1'}$, $R^{2'}$, $R^{1''}$, $R^{2''}$, $R^3$ and $R^4$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, an amino group, an amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or a carbonyl group to which an alkyl group having 1 to 12 carbon atoms bonds. In the formulae, an hydrogen atom in the hydroxyl group may be substituted with: a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. In the formulae (XXXI) to (XXXIII), at least two arbitrary groups among $R^1$, $R^2$, $R^{1'}$, $R^{2'}$, $R^{1''}$, $R^{2''}$, $R^3$, and $R^4$, may bind to each other to form a ring structure via a single bond, a double bond, or a bond including —$CH_2$—, —O—, —S—, —$SO_2$—, —$SO_2NH$—, —C(=O)—, —C(=O)O—, —NHCO—, —NHC(=O)NH—, —$CHR^e$—, —$CR^e_2$—, —NH— or —$NR^e$—. $R^e$ represents a phenyl group; a phenoxy group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or hydroxyl group. $R^1$, $R^2$, $R^{1'}$, $R^{2'}$, $R^{1''}$, $R^{2''}$, $R^3$ and $R^4$ each independently represent: preferably a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group. In the formulae (XXXI) to (XXXIII), $X^-$ represents an anion group of an acid. The acid is preferably a strong acid, and more preferably a superacid. In the formulae, * denotes a binding site to the base component (1').

Examples of groups represented by —C(—OH)$R^1R^2$, —C(—OH)$R^{1'}R^{2'}$, and —C(—OH)$R^{1''}R^{2''}$ in the above formulae (XIV) to (XVII) and formulae (XXXI) to (XXXIII) include groups similar to those exemplified for the above formulae (I) to (III).

The iodonium salt compound group is composed of an iodonium cation and an anion of acid. The iodonium salt compound group is preferably at least one type of group selected from the group consisting of groups represented by the following formulae (XVIII) to (XIX). The groups represented by the following formulae (XVIII) to (XIX) are of a cation-bound type in which a cation and the base component (1') are bound.

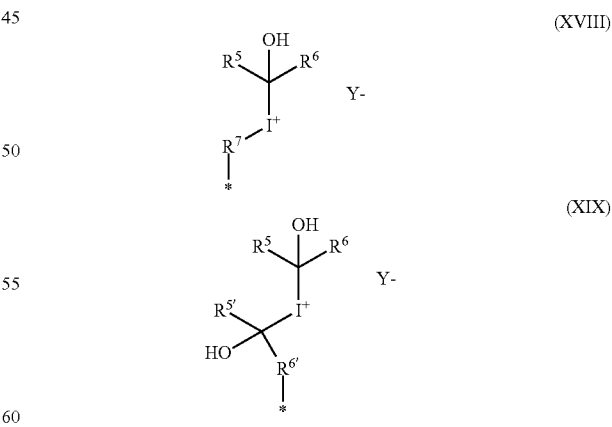

In the above formulae (XVIII) to (XIX), $R^5$, $R^6$ and $R^{5'}$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, amino group, amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, phenoxy group, naphthoxy group, an anthracenoxy group, an amino group, an amide group, or a hydroxyl group; or a carbonyl group to which an alkyl group having 1 to 12 carbon atoms bonds. In the above formulae (XVIII) to (XIX), a hydrogen atom of the hydroxyl group may be substituted with: a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. In a case in which a hydrogen atom of the hydroxyl group is substituted, the iodonium salt compound group contains a ketal compound group or an acetal compound group. In the formulae (XVIII) to (XIX), at least two arbitrary groups among $R^5$, $R^6$, $R^{5'}$, $R^{6'}$, and $R^7$ may form a ring structure via a single bond, a double bond, or a bond that includes —$CH_2$—, —O—, —S—, —$SO_2NH$—, —C(=O)—, —C(=O)O—, —NHCO—, —NHC(=O)NH—, —$CHR^f$—, —$CR^f{}_2$—, —NH— or —$NR^f$—. $R^f$ represents a phenyl group; a phenoxy group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; or, a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. $R^5$, $R^6$, and $R^{5'}$ each independently represent: preferably a phenyl group; a phenoxy group; a phenoxy group substituted with an alkoxy group having 1 to 5 carbon atoms, a hydroxyl group, or an alkyl group having 1 to 5 carbon atoms; or, a phenyl group substituted with an alkoxy group having 1 to 5 carbon atoms, or a hydroxyl group. In the formulae (XVIII) to (XIX), $Y^-$ represents an anion of an acid, preferably a strong acid, more preferably a superacid. In the formulae (XVIII) to (XIX), * denotes a binding site to the base component (1'). $R^{6'}$ and $R^7$ each independently represent a divalent group obtained by removing a hydrogen atom from: a phenyl group; a naphthyl group; an anthracenyl group; a phenoxy group; a naphthoxy group; an anthracenoxy group; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, an alkyl group having 1 to 5 carbon atoms, or hydroxyl group; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group; a naphthoxy group substituted with an alkoxy group having 1 to 5 carbon atoms, an alkyl group having 1 to 5 carbon atoms, or a hydroxyl group; an anthracenoxy group substituted with an alkoxy group having 1 to 5 carbon atoms, an alkyl group having 1 to 5 carbon atoms, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, or a hydroxyl group; or a carbonyl group to which an alkyl group having 1 to 12 carbon atoms bonds, preferably a divalent group obtained by removing a hydrogen from: an alkoxy group having 1 to 5 carbon atoms, or a phenyl group substituted with an alkoxy group having 1 to 5 carbon atoms, an alkyl group having 1 to 5 carbon atoms, and a hydroxyl group.

As the iodonium salt compound group, at least one type of group selected from the group consisting of groups represented by the following formulae (XXXIV) to (XXXV) is preferred. The groups represented by the following formulae (XXXIV) to (XXXV) are of an anion-bonded type in which an anion and the base component (1') are bound. With an anion of acid being bound to the base component (1') even after the exposure, there is a tendency that diffusion of the acid after the exposure can be inhibited and blurring of an image can be reduced.

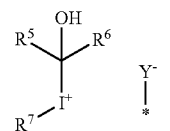

(XXXIV)

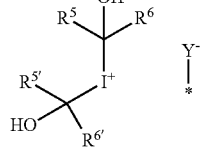

(XXXV)

In the formulae (XXXIV) to (XXXV), $R^5$, $R^6$, $R^{5'}$, $R^{6'}$, and $R^7$ each independently represent: a hydrogen atom; a phenyl group; a naphthyl group; an anthracenyl group; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, amino group, amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or, a carbonyl group to which an alkyl group having 1 to 12 carbon atoms bonds. In the formulae (XXXIV) to (XXXV), a hydrogen atom of the hydroxyl group may be substituted with a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. In a case in which a hydrogen atom of the hydroxyl group is substituted, the iodonium salt compound group contains a ketal compound group or an acetal compound group. In the formulae (XXXIV) to (XXXV), at least two arbitrary groups among $R^5$, $R^6$, $R^{5'}$, $R^{6'}$, and $R^7$ may form a ring structure via a single bond, a double bond, or a bond that includes —$CH_2$—, —O—, —S—, —$SO_2NH$—, —C(=O)—, —C(=O)O—, —NHCO—, —NHC(=O)NH—, —$CHR^f$—, —$CR^f_2$—, —NH— or —$NR^f$—. $R^f$ represents a phenyl group; a phenoxy group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; or, a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. $R^5$, $R^6$, $R^{5'}$, $R^{6'}$, and $R^7$ each independently represent: preferably a phenyl group; a phenoxy group; a phenoxy group substituted with an alkoxy group having 1 to 5 carbon atoms, a hydroxyl group, or an alkyl group having 1 to 5 carbon atoms; or, a phenyl group substituted with an alkoxy group having 1 to 5 carbon atoms, or a hydroxyl group. In the formulae (XXXIV) to (XXXV), $Y^-$ represents an anion group of an acid, preferably a strong acid, more preferably a superacid. In the formulae (XXXIV) to (XXXV), * denotes a binding site to the base component (1'). In the formulae, * denotes a binding site in the base component (1').

In the above formulae (XVIII) to (XIX) and formulae (XXXIV) to (XXXV), examples of the groups represented by —C(—OH)$R^5R^6$ and —C(—OH)$R^{5'}R^{6'}$ include groups similar to those represented by —C(—OH)$R^1R^2$, —C(—OH)$R^{1'}R^{2'}$, —C(—OH)$R^{1''}R^{2''}$, and the like exemplified in the above formulae (I) to (III).

Examples of the anion of a superacid in the sulfonium salt compound group and the iodonium salt compound group include anions exemplified in the sulfonium salt compound and the iodonium salt compound. The anion group in an acid of the sulfonium salt compound group and the iodonium salt compound group is a group that may function as an anion of acid. Examples of the anion group of an acid include: a sulfonic acid anion group, a carboxylic acid anion group, a bis(alkylsulfonyl)amide anion group, and a tris(alkylsulfonyl)methide anion group, and preferred is the anion group of an acid represented by the following general formulae (XXXVII), (XXXVIII) or (XXXIX), and more preferred is the anion group of an acid represented by the following general formula (XXXVII).

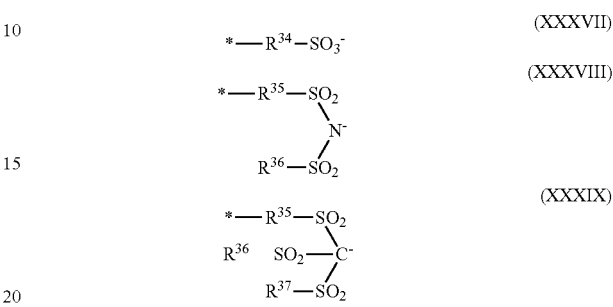

In the above general formulae (XXXVII), (XXXVIII), and (XXXIX), $R^{34}$ to $R^{35}$ each independently represent: a divalent organic group, and $R^{36}$ to $R^{37}$ represent a monovalent organic group. * denotes a binding site to the base component (1'). Examples of the divalent organic group include: an alkylene group, an arylene group, and a group in which a plurality of these groups are linked. Examples of the monovalent organic group include: an alkyl group, an aryl group, and a group in which a plurality of these groups are linked. As the monovalent organic group, an alkyl group in which a hydrogen atom in position 1 is substituted with a fluorine atom or a fluoroalkyl group, and a phenyl group substituted with a fluorine atom or a fluoroalkyl group is preferred. As the divalent organic group, an alkylene group in which a hydrogen atom in position 1 (on an anion side) is substituted with a fluorine atom or a fluoroalkyl group, and a phenylene group substituted with a fluorine atom or a fluoroalkyl group are preferred. With the organic group having a fluorine atom or a fluoroalkyl group, there is a tendency that acidity of the acid generated upon the exposure is increased, and sensitivity is improved. It is to be noted that the monovalent organic group preferably does not contain a fluorine atom as a substituent at a terminal. In addition, in the divalent organic group, an atom bonding to the base component (1') preferably does not bond to a fluorine atom.

An example of a chemical structure of the base component (1') (polymer compound) having the anion-bound type sulfonium salt compound group will be shown hereinafter. Through the irradiation with the first radioactive ray in the patternwise exposure step, the sulfonium salt compound group is degraded, the anion is bound to a polymer compound and remains, and the cation is degraded to generate an acid.

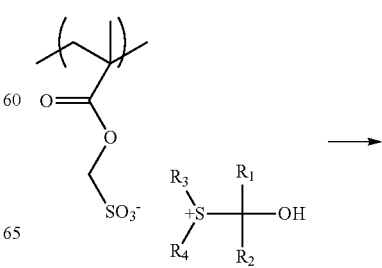

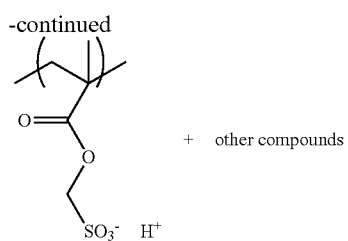 + other compounds

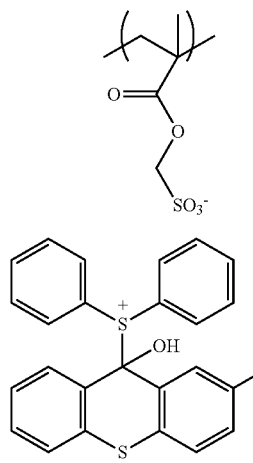

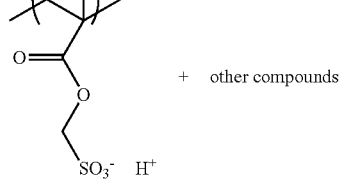 + other compounds (e) Radiation-Sensitive Sensitizer Precursor Group The radiation-sensitive sensitizer precursor group (e) is a group that is capable of generating, upon the irradiation with the first radioactive ray, a group having a function of radiation-sensitive sensitizer that absorbs a second radioactive ray, and that substantially does not generate the radiation-sensitive sensitizer in the light-unexposed regions that is not irradiated with the first radioactive ray in the patternwise exposure step. In addition, the radiation-sensitive sensitizer precursor group (e) is different from the group discussed in the (d). According to the pattern-forming method of the embodiment of the present invention, in the patternwise exposure step, the chemical structure of the radiation-sensitive sensitizer precursor group (e) is altered through a direct or indirect reaction to generate a group having a function of radiation-sensitive sensitizer that assists in the generation of the acid in the floodwise exposure step. Particularly in a case in which the radiation-sensitive sensitizer precursor group (e) is bound to a polymer compound, since the group having a function of radiation-sensitive sensitizer is fixed to the polymer compound, an effect of inhibiting diffusion from the patternwise exposed regions and of improving contrast of the latent image of acid between the patternwise exposed regions and the light-unexposed regions after the floodwise exposure can be obtained.

In addition, in a case where the group having a function of radiation-sensitive sensitizer is generated by irradiating the radiation-sensitive sensitizer precursor group (e) with the second radioactive ray, the lower limit of the wavelength of the second radioactive ray that can maintain the amount of the group having a function of radiation-sensitive sensitizer generated through the irradiation with the second radioactive ray so small that that the difference in the concentration of the radiation-sensitive sensitizer between the light-exposed regions and the light-unexposed regions after the patternwise exposure can be maintained at a level to permit the pattern formation is preferably 300 nm, more preferably 320 nm, and still more preferably 350 nm. By making the wavelength of the second radioactive ray no less than the lower limit in a case where the radiation-sensitive sensitizer precursor group (e) generates the group having a function of radiation-sensitive sensitizer through the irradiation with the second radioactive ray, the acid is generated upon the irradiation with the second radioactive ray in the patternwise exposed regions irradiated with the first radioactive ray by sensitization action of the group having a function of radiation-sensitive sensitizer being generated, while generation of the acid upon the irradiation with the second radioactive ray is inhibited in the patternwise unexposed regions not irradiated with the first radioactive ray. As a result, sensitivity and a contrast between the patternwise exposed regions and the patternwise unexposed regions can be improved.

The radiation-sensitive sensitizer precursor group (e) is preferably a group that, through the irradiation with the first radioactive ray in the patternwise exposure step, gives a carbonyl compound group (group obtained by removing a hydrogen atom from a carbonyl compound) containing a carbonyl group that absorbs nonionizing radiation longer than the nonionizing radiation in the patternwise exposure step and longer than 200 nm, that is, the second radioactive ray in the floodwise exposure step. In addition, the carbonyl compound group is preferably bound to the base component (1') even after the exposure. With the carbonyl compound group being bound to the base component (1') even after the exposure, there is a tendency that diffusion of the acid after the exposure can be inhibited and blurring of an image can be reduced. As the radiation-sensitive sensitizer precursor group (e), an alcohol compound group represented by the following formula (XXIV) and groups represented by the following formula (XXIII) are more preferred.

(XXIV)

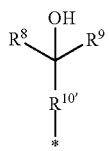

(XXIII)

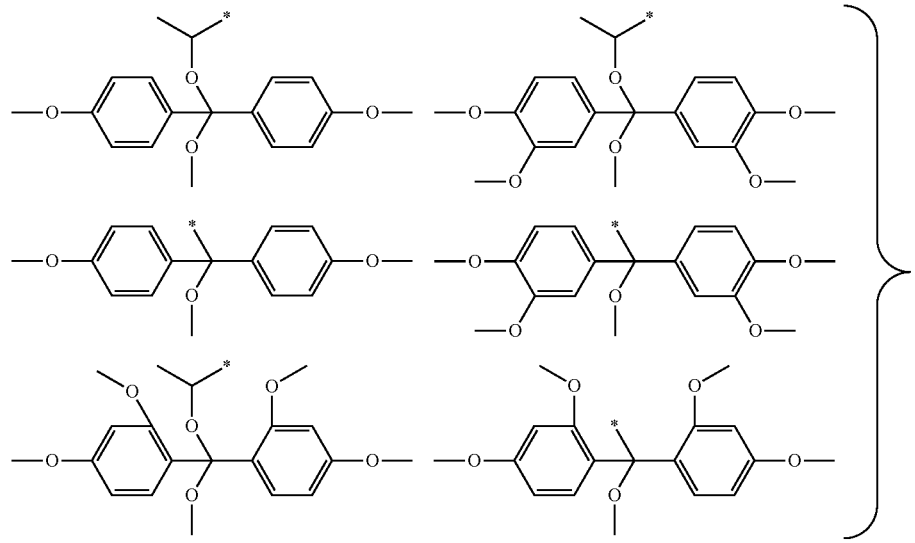

In the formula (XXIV), $R^8$ and $R^9$ each independently represent: a hydrogen atom; a phenyl group; a naphthyl group; an anthracenyl group; an alkoxy group having 1 to 5 carbon atoms; an alkylthio group having 1 to 5 carbon atoms; a phenoxy group; a naphthoxy group; an anthracenoxy group; an amino group; an amide group; a halogen atom; a saturated or unsaturated linear, branched or cyclic hydrocarbon group (preferably alkyl group) having 1 to 30 carbon atoms (preferably having 1 to 5 carbon atoms); an alkoxy group having 1 to 5 carbon atoms substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; an alkylthio group having 1 to 5 carbon atoms substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a phenoxy group substituted with an alkoxy group having 1 to carbon atoms, a hydroxyl group, an amino group, an amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, a phenoxy group, a naphthoxy group, an anthracenoxy group, an amino group, an amide group, or a hydroxyl group; or, a carbonyl group to which an alkyl group having 1 to 12 carbon atoms bonds. $R^{10\prime}$ represents a divalent group obtained by removing a hydrogen atom from: a phenyl group; a naphthyl group; an anthracenyl group; a phenoxy group; a naphthoxy group; an anthracenoxy group; an amino group; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, amino group, amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, an amino group, an amide group, or a hydroxyl group; a naphthoxy group substituted with an alkoxy group having 1 to 5 carbon atoms, an alkyl group having 1 to 5 carbon atoms, an amino group, an amide group, or a hydroxyl group; an anthracenoxy group substituted with an alkoxy group having 1 to 5 carbon atoms, an alkyl group having 1 to 5 carbon atoms, an amino group, an amide group, or a hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, phenoxy group, a naphthoxy group, an anthracenoxy group, an amino group, an amide group, or a hydroxyl group; or a carbonyl group to which an alkyl group having 1 to 12 carbon atoms bonds. The alcohol compound group may be a thiol compound group in which an alcoholic hydroxyl group (hydroxyl group) in the formula (XXIV) is a thiol group. In the above formula (XXIV), a hydrogen atom of the hydroxyl group or the thiol group may be substituted with: a phenyl group; a halogen atom; a saturated or unsaturated linear, branched or cyclic hydrocarbon group (preferably alkyl group) having 1 to 30 carbon atoms (preferably having 1 to 5 carbon atoms); a saturated or unsaturated linear, branched or cyclic hydrocarbon group (preferably alkyl group) having 1 to 30 carbon atoms (preferably having 1 to 5 carbon atoms); or a phenyl group substituted with an alkoxy group having 1 to 5 carbon atoms, or a hydroxyl group. In a case in which a hydrogen atom of the hydroxyl group is substituted, the alcohol compound group contains a ketal compound group or an acetal compound group; and in a case in which a hydrogen atom of the thiol group is substituted, the thiol compound group contains a thioketal compound group or a thioacetal compound group. In the formula, at least two arbitrary groups among $R^8$, $R^9$ and $R^{10'}$ may form a ring structure via a single bond, a double bond, or a bond including —$CH_2$—, —O—, —S—, —$SO_2NH$—, —C(=O)—, —C(=O)O—, —NHCO—, —NHC(=O)NH—, —$CHR^g$—, —$CR^g{}_2$—, —NH— or —$NR^g$—. $R^g$ represents a phenyl group; a phenoxy group; a halogen atom; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, or an alkyl group having 1 to 5 carbon atoms; a saturated or unsaturated linear, branched or cyclic hydrocarbon group (preferably alkyl group) having 1 to 30 carbon atoms (preferably having 1 to 5 carbon atoms); or a phenyl group substituted with an alkoxy group having 1 to 5 carbon atoms, or a hydroxyl group. $R^8$ and $R^9$ represent, preferably, each independently a hydrogen atom; a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group. In addition, $R^{10'}$ represents preferably a divalent group obtained by removing a hydrogen atom from: a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms, or a hydroxyl group. In the formula (XXIV), * denotes a binding site to the base component (1').

It is to be noted that the ketal compound group or the acetal compound group in which a hydrogen atom of the hydroxyl group in the formula (XXIV) is preferably a compound group represented by the following formula (XL). In other words, the radiation-sensitive sensitizer precursor group (e) may also be a compound group represented by the following formula (XL). In a case in which any one of $R^8$ and $R^9$ is a hydrogen atom, a compound represented by the following formula (XL) can be considered as an acetal compound group.

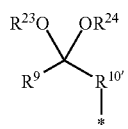

(XL)

In the formula (XL), $R^9$ and $R^{10'}$ are respectively as defined in $R^9$ and $R^{10'}$ in the above formula (XXIV). Similarly to the abovementioned ones, they may form a ring structure. In the formula (XL), $R^{23}$ and $R^{24}$ each independently represent: a phenyl group; a halogen atom; a saturated or unsaturated linear, branched or cyclic hydrocarbon group (preferably alkyl group) having 1 to 30 carbon atoms (preferably having 1 to 5 carbon atoms); or a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, or a hydroxyl group. $R^{23}$ and $R^{24}$ may taken together represent a ring structure via a single bond, a double bond, or a bond including —$CH_2$—, —O—, —S—, —$SO_2NH$—, —C(=O)—, —C(=O)O—, —NHCO—, —NHC(=O)NH—, —$CHR^g$—, —$CR^g{}_2$—, —NH— or —$NR^g$—. $R^g$ is as defined in $R^g$ in the above formula (XXIV). The ketal compound group or the acetal compound group may also be a thioketal compound group or a thioacetal compound group in which an oxygen atom bonding to $R^{23}$ and/or $R^{24}$ in the formula (XL) is replaced by sulfur.

The ketal compound group and the acetal compound group bonding to the base component (1') can be respectively obtained by reacting the carbonyl compound group bonding to the base component (1') with alcohol. The reaction can be considered as a reaction of protecting a carbonyl group contributing to radioactive ray sensitization action, and $R^{23}$ and $R^{24}$ in the above formula (XL) may be referred to as a protecting group for the carbonyl group. In this case, a reaction by which the radiation-sensitive sensitizer precursor group (e) gives the group having a function of radiation-sensitive sensitizer by the radioactive ray and the like may be referred to as a deprotection reaction. The reactivity of the protecting group is as discussed above for the radiation-sensitive sensitizer generating agent (b).

The radiation-sensitive sensitizer precursor group (e) may be compound groups represented by the following formulae (XLI) to (XLIV) or a derivative group thereof.

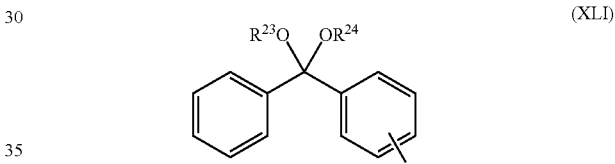

(XLI)

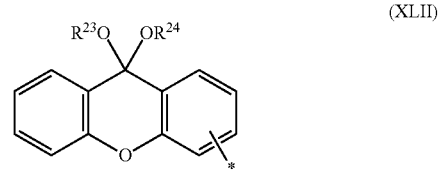

(XLII)

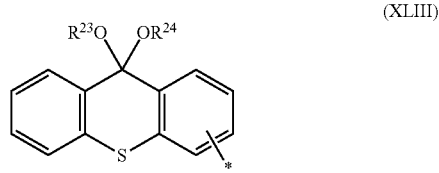

(XLIII)

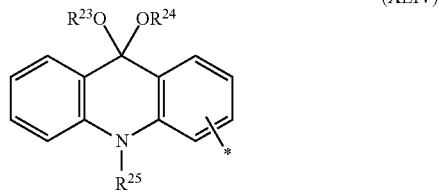

(XLIV)

In the formulae (XLI) to (XLIV), $R^{23}$ and $R^{24}$ are respectively as defined in $R^{23}$ and $R^{24}$ in the formula (XL). In the formulae (XLI) to (XLIV), a hydrogen atom in the aromatic ring may be substituted with an alkoxy group having 1 to 5 carbon atoms or an alkyl group having 1 to 5 carbon atoms, and the aromatic ring may fused with another aromatic ring to form a naphthalene ring or an anthracene ring. $R^{25}$ represents an alkyl group having 1 to 5 carbon atoms. In the formulae (XLI) to (XLIV), * denotes a binding site to the base component (1'). It is to be noted that in the formula (XLIV), $R^{25}$ may bond to the base component (1'). In the case of using the base component (1') to which a compound group represented by the formulae (XLI) to (XLIV) or a derivative group thereof bonds, greater shift of radioactive ray absorption wavelength is realized upon transformation from the radiation-sensitive sensitizer precursor group (e) to the group having a function of radiation-sensitive sensitizer, and more selective sensitization reaction can take place in the patternwise exposed regions.

The ortho ester compound group in which a hydrogen atom of the alcoholic hydroxyl group in the formula (XXIV) is substituted is preferably a compound group represented by the following formula (XLVIII). In other words, radiation-sensitive sensitizer precursor group (e) may be a compound group represented by the following formula (XLVIII).

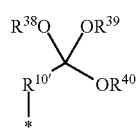

(XLVIII)

In the formula (XLVIII), $R^{38}$ to $R^{40}$ are, each independently, as defined in $R^{38}$ to $R^{40}$ the above formula (XLVI). In the formula (XLVIII), $R^{10'}$ is as defined in $R^{10'}$ in the formula (XXIV). At least two arbitrary groups among $R^{38}$ to $R^{40}$, may form a ring structure via a single bond, a double bond, or a bond including —$CH_2$—, —O—, —S—, —$SO_2NH$—, —C(=O)—, —C(=O)O—, —NHCO—, —NHC(=O)NH—, —$CHR^g$—, —$CR^g_2$—, —NH— or —$NR^g$—. $R^g$ is as defined in $R^g$ in the above formula (VI).

The ortho ester compound group degrades in the deprotection reaction upon the patternwise exposure, to transform into a carboxylic acid ester group or a carboxylic acid group containing for example a carbonyl group. The ortho ester compound group is preferably an OBO ester compound group represented by the following formula (XLIX). Examples of the OBO ester compound group include a group in which a carboxyl group moiety of the radiation-sensitive sensitizer containing a carboxyl group is substituted (protected) with OBO (for example, 4-methyl 2,6,7-trioxabicyclo[2.2.2]octan-1-yl). The radiation-sensitive sensitizer precursor group (e) in which a carboxyl group is protected by OBO generates a carboxylic acid group by an acid catalyst generated upon the patternwise exposure, and as the absorption wavelength of the radioactive ray shifts, functions as a group having a function of radiation-sensitive sensitizer upon the floodwise exposure. As carboxylic acid group is generated from the radiation-sensitive sensitizer precursor group (e), in the patternwise exposed regions, the polarity of the resist is altered, for example from non-polar to polar. Given this, the ortho ester compound group also functions as a dissolution accelerator in the development step, contributing to improvement of resist contrast. The radiation-sensitive sensitizer precursor group (e) containing the OBO ester compound group can generate the group having a function of radiation-sensitive sensitizer and cause a polarity changing reaction simultaneously.

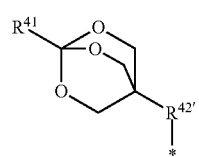

(XLIX)

In the formula (XLIX), $R^{41}$ is as defined in $R^{41}$ in the formula (XLVII). $R^{42'}$ represents a divalent group obtained by removing a hydrogen atom from: a phenyl group; a naphthyl group; an anthracenyl group; a phenoxy group; a naphthoxy group; an anthracenoxy group; an amino group; a saturated or unsaturated linear, branched or cyclic hydrocarbon group (preferably alkyl group) having 1 to 30 carbon atoms (preferably having 1 to 5 carbon atoms); a phenoxy group substituted with an alkoxy group having 1 to 5 carbon atoms, a hydroxyl group, amino group, amide group, or an alkyl group having 1 to 5 carbon atoms; a phenyl group substituted with a saturated or unsaturated linear, branched or cyclic hydrocarbon group (preferably alkyl group) having 1 to 30 carbon atoms (preferably having 1 to 5 carbon atoms), an alkoxy group having 1 to 5 carbon atoms, amino group, amide group, or hydroxyl group; a naphthoxy group substituted with an alkoxy group having 1 to 5 carbon atoms, an alkyl group having 1 to 5 carbon atoms, amino group, amide group, or hydroxyl group; an anthracenoxy group substituted with an alkoxy group having 1 to 5 carbon atoms, an alkyl group having 1 to 5 carbon atoms, amino group, amide group, or hydroxyl group; a saturated or unsaturated linear, branched or cyclic hydrocarbon group (preferably alkyl group) having 1 to 30 carbon atoms (preferably having 1 to 5 carbon atoms) substituted with an alkoxy group having 1 to 5 carbon atoms, phenoxy group, naphthoxy group, anthracenoxy group, amino group, amide group, or hydroxyl group; or a carbonyl group to which an alkyl group having 1 to 12 carbon atoms bonds. $R^{41}$ preferably represents a hydrogen atom; a phenyl group; a phenoxy group; a phenoxy group substituted with an alkoxy group having 1 to 5 carbon atoms, a hydroxyl group, or an alkyl group having 1 to 5 carbon atoms; or, a phenyl group substituted with an alkoxy group having 1 to 5 carbon atoms, or hydroxyl group. $R^{42'}$ preferably represents a divalent group obtained by removing a hydrogen atom from: a phenyl group; a phenoxy group; a phenoxy group substituted with an alkoxy group having 1 to 5 carbon atoms, a hydroxyl group, or an alkyl group having 1 to 5 carbon atoms; or a phenyl group substituted with an alkoxy group having 1 to 5 carbon atoms or a hydroxyl group.

Examples of the radiation-sensitive sensitizer precursor group (e) include a group obtained by removing a hydrogen atom from the compound exemplified as the radiation-sensitive sensitizer generating agent (b).

Examples of a chemical structure of the base component (1') (polymer compound) having the radiation-sensitive sensitizer precursor group (e) will be shown hereinafter. In the patternwise exposure step, the acid catalyst generated upon the patternwise exposure, a protecting group is removed from the radiation-sensitive sensitizer precursor group (e) and a carbonyl group is generated. In other words, the base component (1') to which the group having a function of radiation-sensitive sensitizer bonds is generated. With the group having a function of radiation-sensitive sensitizer bonding to the base component (1'), diffusion of the radiation-sensitive sensitizer upon the floodwise exposure step can be inhibited and the contrast of the latent image of acid in the resist material film can be improved.
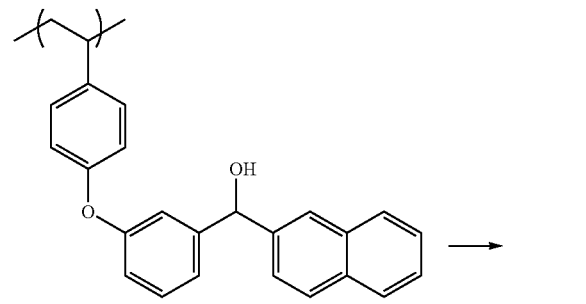
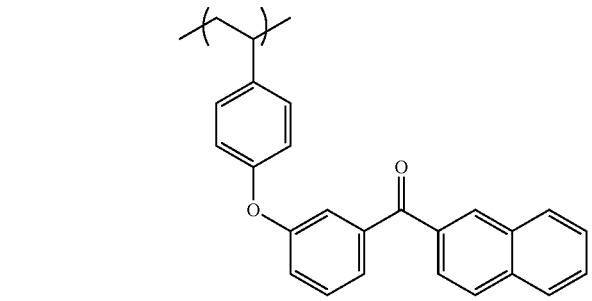
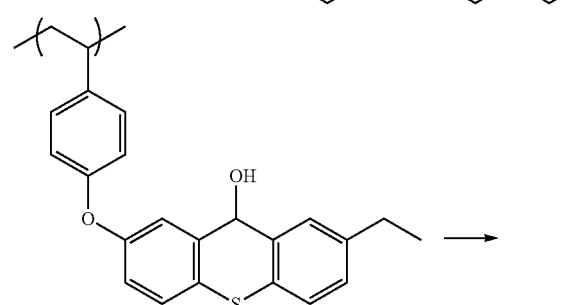
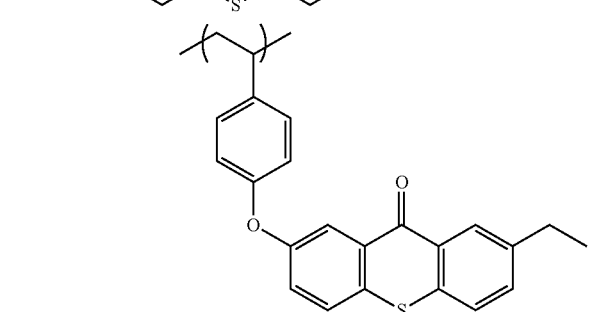
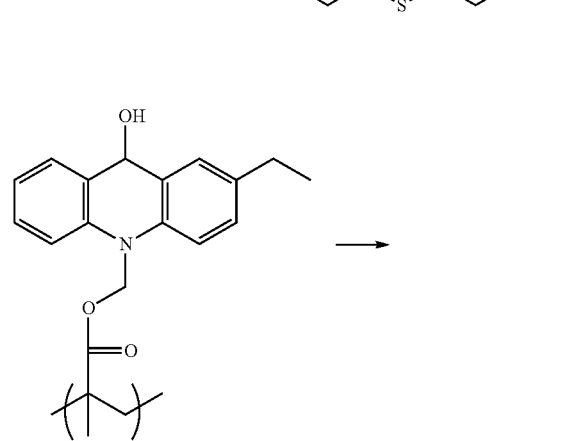
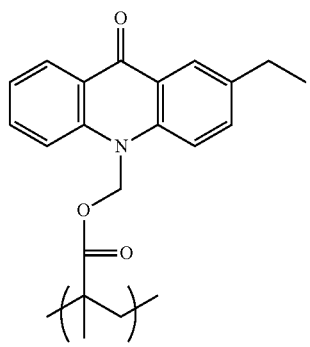
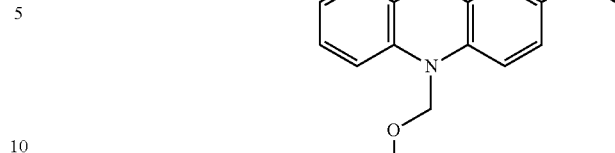
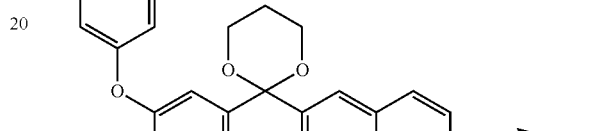
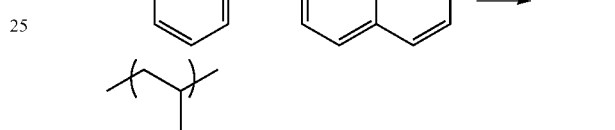
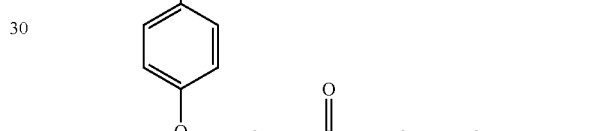
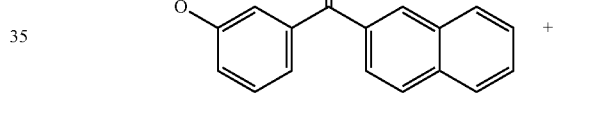
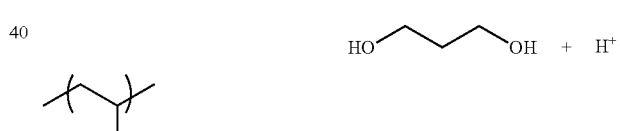
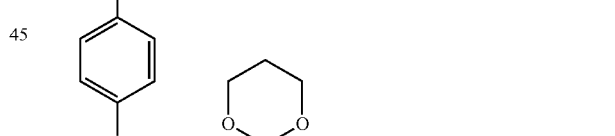
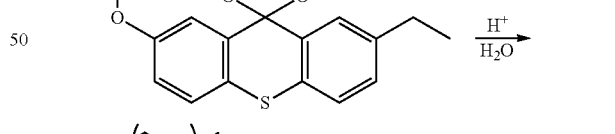
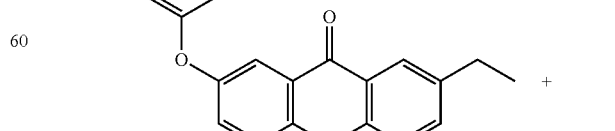
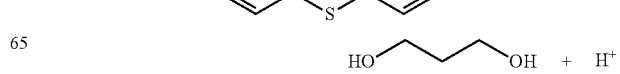

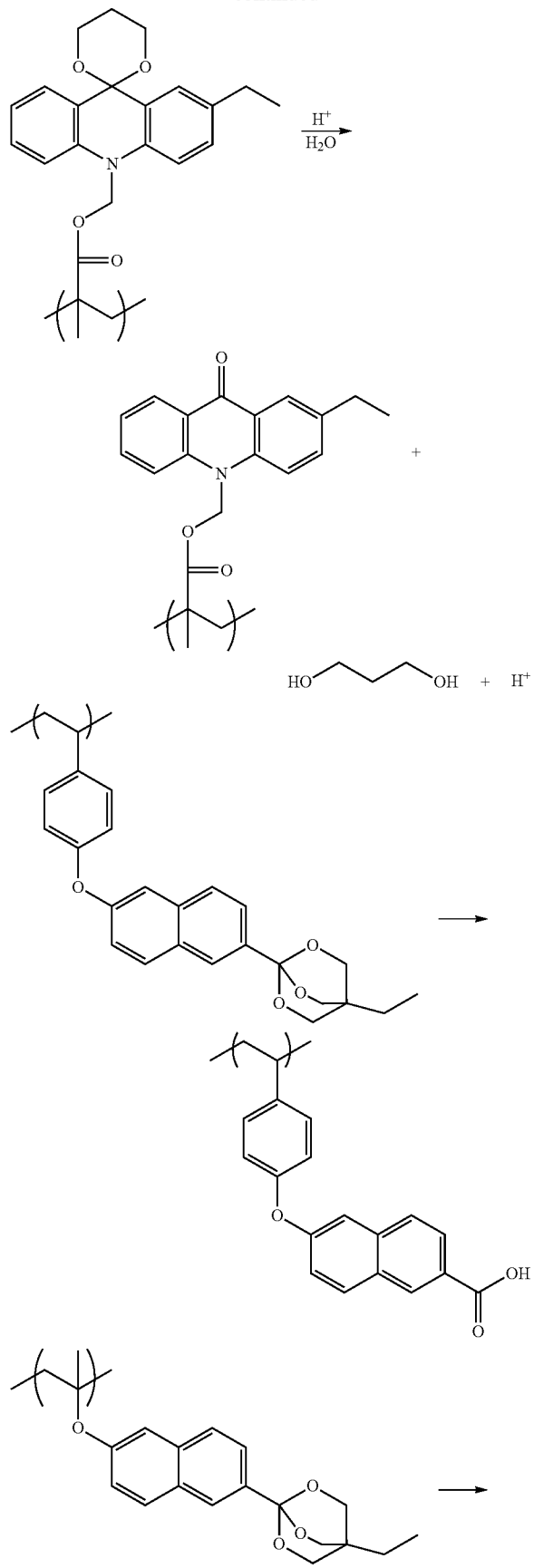
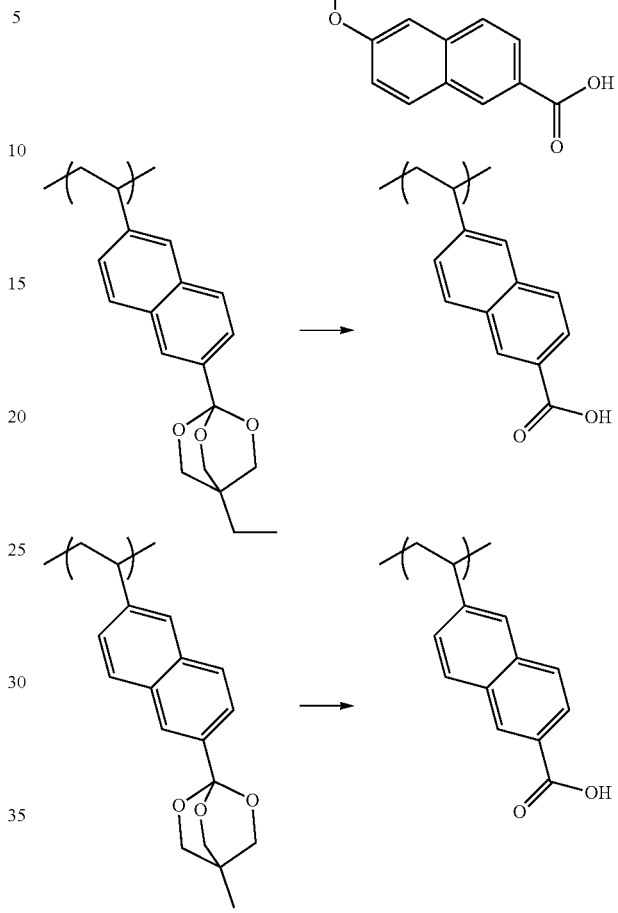

(f) Radiation-Sensitive Acid Generating Group

A radiation-sensitive acid generating group (f) is a group that is capable of generating an acid through the irradiation with the first radioactive ray, and that substantially does not generate the acid through the irradiation with the second radioactive ray in the light-unexposed regions that is not irradiated with the first radioactive ray in the patternwise exposure step, the group being different from the group described above in the (d).

In addition, in a case where the acid is generated by irradiating the radiation-sensitive acid generating group (f) with the second radioactive ray, the lower limit of the wavelength of the second radioactive ray that can maintain the amount of the acid generated through the irradiation with the second radioactive ray so small that that the difference in the concentration of the acid between the light-exposed regions and the light-unexposed regions after the patternwise exposure can be maintained at a level to permit the pattern formation is preferably 300 nm, more preferably 320 nm, and still more preferably 350 nm. By making the wavelength of the second radioactive ray no less than the lower limit in a case where the radiation-sensitive acid generating group (f) generates the acid through the irradiation with the second radioactive ray, the acid is generated upon the irradiation with the second radioactive ray in the patternwise exposed regions irradiated with the first radioactive ray by sensitization action of the radiation-sensitive sensitizer being generated, while generation of the acid upon the irradiation with the second radioactive ray is inhibited in the patternwise unexposed regions not irradiated with the first radioactive ray. As a result, sensitivity and a contrast between the patternwise exposed regions and the patternwise unexposed regions can be improved.

The radiation-sensitive acid generating group (f) preferably has a similar structure to the compound exemplified in the radiation-sensitive acid generating agent (c) (a salt constituted of a cation and an anion), and it is preferable that a part of the cation or the anion bonds to the base component (1'), and it is more preferable that a part of the anion bonds to the base component (1') (anion-bound type). In addition, in the radiation-sensitive acid generating group (f), it is more preferable that a part of the anion bonds to the base component (1') even after exposure. With the anion of acid being bound to the base component (1') even after the exposure, there is a tendency that diffusion of the acid after the exposure can be inhibited and blurring of an image can be reduced.

Examples of the radiation-sensitive acid generating group (f) include a group obtained by removing a hydrogen atom from the compound exemplified as the radiation-sensitive acid generating agent (c).

Examples of a chemical structure of the component (1') (polymer compound) having the radiation-sensitive acid generating group (f) will be shown hereinafter. In the following examples, the radiation-sensitive acid generating group (f) is degraded by patternwise exposure, and an anion group remains in the base part after the degradation.

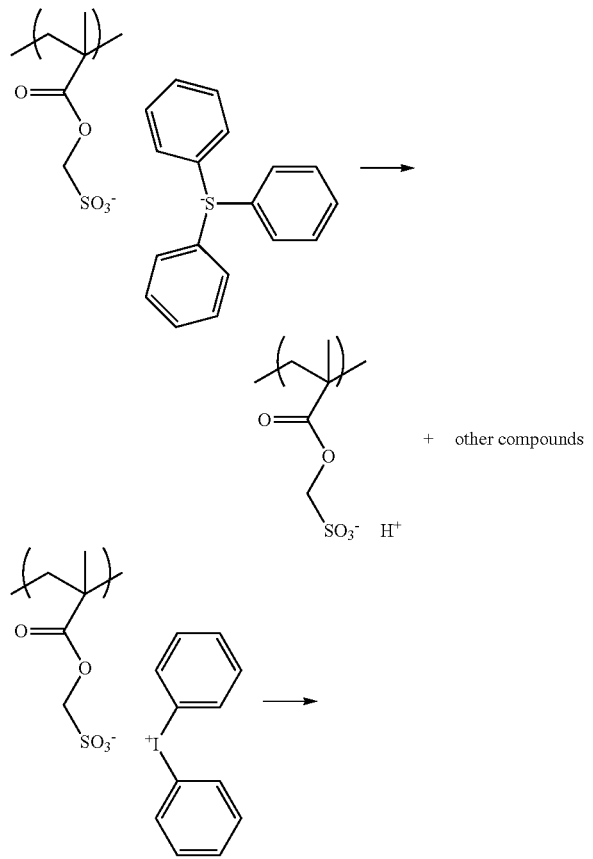

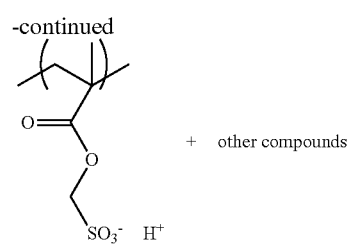

Suitable values of the energy released when a radiation-sensitive onium cation in the acid-and-radiation-sensitive-sensitizer generating group (d) or radiation-sensitive acid generating group (f) is reduced into radical and the reduction potential of the radiation-sensitive onium cation are similar to those specified for the radiation-sensitive acid-sensitizer (a).

A content of the groups shown in above (d) to (f) in the base component (1') is preferably no less than 0.1% by mass and no greater than 30% by mass, and more preferably no less than 0.2% by mass and no greater than 10% by mass with respect to the total mass of the base component (1').

In a case of the base component (1') being a polymer compound, the proportion of the group shown in the above (d) contained is preferably no less than 0.001 mol and no greater than 0.5 mol, more preferably no less than 0.002 mol and no greater than 0.3 mol, and still more preferably no less than 0.01 mol and no greater than 0.3 mol, with respect to 1 mol of the polymer compound. No greater than 0.5 mol of the group shown in the above (d) contained in the base component (1') facilitates obtaining a resist pattern having a superior shape, while no less than 0.001 mol of the group facilitates obtaining sufficient sensitivity.

In a case of the base component (1') being a polymer compound, the proportion of the group shown in the above (e) contained is preferably no less than 0.001 mol and no greater than 0.95 mol, more preferably no less than 0.002 mol and no greater than 0.3 mol, and still more preferably no less than 0.01 mol and no greater than 0.3 mol, with respect to 1 mol of the polymer compound. No greater than 0.5 mol of the group shown in the above (e) contained in the base component (1') facilitates obtaining a resist pattern having a superior shape, while no less than 0.001 mol of the group facilitates obtaining sufficient sensitivity.

In a case of the base component (1') being a polymer compound, the proportion of the group shown in the above (f) contained is preferably no less than 0.001 mol and no greater than 0.5 mol, more preferably no less than 0.002 mol and no greater than 0.3 mol, and still more preferably no less than 0.01 mol and no greater than 0.3 mol, with respect to 1 mol of the polymer compound. No greater than 0.5 mol of the group shown in the above (f) contained in the base component (1') facilitates obtaining a resist pattern having a superior shape, while no less than 0.001 mol of the group facilitates obtaining sufficient sensitivity.

In a case of the base component (1') being a low molecular weight compound, the proportion of the group shown in the above (d) contained is preferably no less than 0.001 mol and no greater than 0.5 mol, more preferably no less than 0.002 mol and no greater than 0.3 mol, and still more preferably no less than 0.01 mol and no greater than 0.3 mol, with respect to 1 mol of the low molecular weight compound. No greater than 0.5 mol of the group shown in the above (d) contained in the base component (1') facilitates obtaining a resist pattern having a superior shape, while no less than 0.001 mol of the group facilitates obtaining sufficient sensitivity.

In a case of the base component (1') being a low molecular weight compound, the proportion of the group shown in the above (e) contained is preferably no less than 0.001 mol and no greater than 0.5 mol, more preferably no less than 0.002 mol and no greater than 0.3 mol, and still more preferably no less than 0.01 mol and no greater than 0.3 mol, with respect to 1 mol of the low molecular weight compound. No greater than 0.5 mol of the group shown in the above (e) contained in the base component (1') facilitates obtaining a resist pattern having a superior shape, while no less than 0.001 mol of the group facilitates obtaining sufficient sensitivity.

In a case of the base component (1') being a low molecular weight compound, the proportion of the group shown in the above (f) contained is preferably no less than 0.001 mol and no greater than 0.5 mol, more preferably no less than 0.002 mol and no greater than 0.3 mol, and still more preferably no less than 0.01 mol and no greater than 0.3 mol, with respect to 1 mol of the low molecular weight compound. No greater than 0.5 mol of the group shown in the above (f) contained in the base component (1') facilitates obtaining a resist pattern having a superior shape, while no less than 0.001 mol of the group facilitates obtaining sufficient sensitivity.

It is to be noted that the amount of the group contained in the polymer compound or the low molecular weight compound is similar to the molar number of the monomer containing the groups shown in (d) to (f) with respect to 1 mol of the whole monomer used for synthesis.

In the case of the base component (1') being a polymer compound, examples of the method for synthesizing these polymer compound include a method of adding a polymerization initiator (for example, radical initiator) to a monomer having an unsaturated bond for obtaining a repeating unit in an organic solvent to cause thermal polymerization, which allows obtaining a polymer compound. Examples of the organic solvent used in the polymerization include: toluene, benzene, tetrahydrofuran, diethyl ether, and dioxane. Examples of the polymerization initiator include: 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The heating temperature in the polymerization is preferably no less than 50° C. and no greater than 80° C. The reaction time is preferably no less than 2 hrs and no greater than 100 hrs, more preferably no less than 5 hrs and no greater than 20 hrs. The groups shown in (d) to (f) which are introduced into a monomer may be used as is, or may form a bond by first eliminating an acid-labile group by an acid catalyst and then protecting or partially protecting.

In the case of the base component (1') being a low molecular weight compound, the groups shown in (d) to (f) may be used as is with respect to a reactive group of the low molecular weight compound, or may form a bond by first eliminating an acid-labile group by an acid catalyst and then protecting or partially protecting.

Other Components

The resist material of the embodiment of the present invention may also contain, in addition to the above described base component (1) and component (2), a first trapping agent (3), a second trapping agent (4), a crosslinking agent (5), an additive (6), a solvent (7) as appropriate.

(3) First Trapping Agent

The first trapping agent traps an acid and a cation, and functions as a quencher. As the resist material contains the first trapping agent, an acid generated in the resist material can be neutralized to improve a chemical contrast of a latent image of an acid between the patternwise exposed regions and the patternwise unexposed regions. In the case of the radiation-sensitive acid-and-sensitizer generating agent (a) containing a ketal compound group or an acetal compound group, or in a case of the radiation-sensitive sensitizer generating agent (b) containing a ketal compound or an acetal compound, a radiation-sensitive sensitizer is generated through an acid-catalyzed reaction at normal temperature. When the resist material contains the first trapping agent, the first trapping agent traps an acid that functions as a catalyst for the radiation-sensitive sensitizer generation reaction, and can improve a contrast of an amount of the radiation-sensitive sensitizer generated from the acetal compound and the like. In addition, in a case in which the radiation-sensitive sensitizer is generated through a reaction mechanism in which radioactive ray sensitization takes place via a cation intermediate generated upon the patternwise exposure step, the first trapping agent traps the cation intermediate, and an acid can be proliferated more selectively only in the patternwise exposed regions upon the floodwise exposure, and an effect of further ameliorating the chemical contrast of the latent image of the acid can thus be obtained. The first trapping agent can be classified into a radioactive ray-reactive trapping agent and a radioactive ray-unreactive trapping agent.

In the case of the first trapping agent being a radioactive ray-unreactive trapping agent, the first trapping agent is preferably a basic compound. Examples of the basic compound include: a hydroxide compound, a carboxylate compound, an amine compound, an imine compound, and an amide compound, and more specifically: primary to tertiary aliphatic amines, aromatic amine, heterocyclic amine, and a nitrogen-containing compound containing a carboxyl group; a nitrogen-containing compound containing a sulfonyl group; a nitrogen-containing compound containing a hydroxyl group; a nitrogen-containing compound containing a hydroxyphenyl group; an alcoholic nitrogen-containing compound; a nitrogen-containing compound containing a carbamate group; an amide compound; and an imide compound. As the basic compound, the nitrogen-containing compound containing a carbamate group is preferred. The basic compound may also be a Troger's base; a hindered amine such as diazabicycloundecene (DBU), diazabicyclononene (DBM) and the like; and an ionic quencher such as tetrabutylammonium hydroxide (TBAH), tetrabutylammonium lactate and the like.

Examples of the primary aliphatic amine include: ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of the secondary aliphatic amine include: dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyl tetraethylene pentamine. Examples of the tertiary aliphatic amine include: trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'- tetramethylmethylenediamine, N,N,N',N'-tetramethylethylenediamine, and N,N,N',N'-tetramethyltetraethylenepentamine.

Examples of the aromatic amine and the heterocyclic amine include: an aniline derivative such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine; diphenyl(p-tolyl)amine; methyldiphenylamine; triphenylamine; phenylenediamine; naphthylamine; diaminonaphthalene; a pyrrole derivative such as pyrrole, 2H-pyrrole, 1-methylpyrrole, 2,4-dimethylpyrrole, 2,5-dimethylpyrrole, N-methylpyrrole; an oxazole derivative such as oxazole and isoxazole; a thiazole derivative such as thiazole and isothiazole; an imidazole derivative such as imidazole, 4-methylimidazole, 4-methyl-2-phenylimidazole; pyrazole derivative; a furazane derivative; a pyrroline derivative such as pyrroline, 2-methyl-1-pyrroline; a pyrrolidine derivative such as pyrrolidine, N-methylpyrrolidine, pyrrolidinone, N-methylpyrrolidone; an imidazoline derivative; an imidazolidine derivative; a pyridine derivative such as pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, dimethylaminopyridine; a pyridazine derivative; a pyrimidine derivative; a pyrazine derivative; a pyrazoline derivative; a pyrazolidine derivative; a piperidine derivative; a piperazine derivative; a morpholine derivative; an indole derivative; an isoindole derivative; a 1H-indazole derivative; an indoline derivative; a quinolone derivative such as quinoline, 3-quinolinecarbonitrile; an isoquinoline derivative; a cinnoline derivative; a quinazoline derivative; a quinoxaline derivative; a phthalazine derivative; a purine derivative; a pteridine derivative; a carbazole derivative; a phenanthridine derivative; an acridine derivative; a phenazine derivative; a 1,10-phenanthroline derivative; an adenine derivative; an adenosine derivative; a guanine derivative; a guanosine derivative; an uracil derivative; and an uridine derivative.

Examples of the nitrogen-containing compound containing a carboxy group include: aminobenzoic acid; indolecarboxylic acid; an amino acid derivative such as nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine.

Examples of the nitrogen-containing compound containing a sulfonyl group include: 3-pyridinesulfonic acid, and pyridinium p-toluenesulfonate.

Examples of the nitrogen-containing compound containing a hydroxyl group, of the nitrogen-containing compound containing a hydroxyphenyl group, and of the alcoholic nitrogen-containing compound include: 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidineethanol, 1-aziridineethanol, N-(2-hydroxyethyl) phthalimide, and N-(2-hydroxyethyl)isonicotineamide.

Examples of the nitrogen-containing compound containing a carbamate group include: N-(tert-butoxycarbonyl)-L-alanine, N-(tert-butoxycarbonyl)-L-alanine methyl ester, (S)-(−)-2-(tert-butoxycarbonylamino)-3-cyclohexyl-1-propanol, (R)-(+)-2-(tert-butoxycarbonylamino)-3-methyl-1-butanol, (R)-(+)-2-(tert-butoxycarbonylamino)-3-phenylpropanol, (S)-(−)-2-(tert-butoxycarbonylamino)-3-phenylpropanol, (R)-(+)-2-(tert-butoxycarbonylamino)-3-phenyl-1-propanol, (S)-(−)-2-(tert-butoxycarbonylamino)-3-phenyl-1-propanol, (R)-(+)-2-(tert-butoxycarbonylamino)-1-propanol, (S)-(−)-2-(tert-butoxycarbonylamino)-1-propanol, N-(tert-butoxycarbonyl)-L-asparatic acid 4-benzyl ester, N-(tert-butoxycarbonyl)-O-benzyl-L-threonine, (R)-(+)-1-(tert-butoxycarbonyl)-2-tert-butyl-3-methyl-4-imidazolidinone, (S)-(−)-1-(tert-butoxycarbonyl)-2-tert-butyl-3-methyl-4-imidazolidinone, N-(tert-butoxycarbonyl)-3-cyclohexyl-L-alanine methyl ester, N-(tert-butoxycarbonyl)-L-cysteine methyl ester, N-(tert-butoxycarbonyl)ethanolamine, N-(tert-butoxycarbonyl)ethylenediamine, N-(tert-butoxycarbonyl)-D-glucoseamine, Nα-(tert-butoxycarbonyl)-L-glutamine, 1-(tert-butoxycarbonyl)imidazole, N-(tert-butoxycarbonyl)-L-isoleucine, N-(tert-butoxycarbonyl)-L-isoleucine methyl ester, N-(tert-butoxycarbonyl)-L-leucinol, Nα-(tert-butoxycarbonyl)-L-lysine, N-(tert-butoxycarbonyl)-L-methionine, N-(tert-butoxycarbonyl)-3-(2-naphthyl)-L-alanine, N-(tert-butoxycarbonyl)-L-phenylalanine, N-(tert-butoxycarbonyl)-L-phenylalanine methyl ester, N-(tert-butoxycarbonyl)-D-prolinal, N-(tert-butoxycarbonyl)-L-proline, N-(tert-butoxycarbonyl)-L-proline-N'-methoxy-N'-methylamide, N-(tert-butoxycarbonyl)-1H-pyrazole-1-carboxyamidine, (S)-(−)-1-(tert-butoxycarbonyl)-2-pyrrolidinemethanol, (R)-(+)-1-(tert-butoxycarbonyl)-2-pyrrolidinemethanol, 1-(tert-butoxycarbonyl)3-[4-(1-pyrrolyl)phenyl]-L-alanine, N-(tert-butoxycarbonyl)-L-serine, N-(tert-butoxycarbonyl)-L-serine methyl ester, N-(tert-butoxycarbonyl)-L-threonine, N-(tert-butoxycarbonyl)-p-toluenesulfonamide, N-(tert-butoxycarbonyl)-S-trityl-L-cysteine, N'-(tert-butoxycarbonyl)-L-tryptophan, N-(tert-butoxycarbonyl)-L-tyrosine, N-(tert-butoxycarbonyl)-L-tyrosine methyl ester, N-(tert-butoxycarbonyl)-L-valine, N-(tert-butoxycarbonyl)-L-valine methyl ester, N-(tert-butoxycarbonyl)-L-valinol, tert-butyl N-(3-hydroxypropyl)carbamate, tert-butyl N-(6-aminohexyl)carbamate, tert-butylcarbamate, tert-butyl carbazate, tert-butyl-N-(benzyloxy) carbamate, tert-butyl-4-benzyl-1-piperazinecarboxylate, tert-butyl (1S,4S)-(−)-2,5-diazabicyclo[2.2.1]heptane-2-carboxylate, tert-butyl-N-(2,3-dihydroxypropyl)carbamate, tert-butyl (S)-(−)-4-formyl-2,2-dimethyl-3-oxazolidinecarboxylate, tert-butyl[R—(R*,S*)]—N-[2-hydroxy-2-(3-hydroxyphenyl)-1-methylethyl] carbamate, tert-butyl-4-oxo-1-piperidinecarboxylate, tert-butyl 1-pyrrolecarboxylate, tert-butyl 1-pyrrolidinecarboxylate, and tert-butyl (tetrahydro-2-oxo-3-furanyl)carbamate.

Examples of the amide compound include: formamide, N-methylformamide, N,N-dimethylformamide, acetamide, N-methylacetamide, N,N-dimethylacetamide, propionamide, benzamide, and 1-cyclohexylpyrrolidone.

Examples of the imide compound include: phthalimide, succinimide, and maleimide.

The radioactive ray-reactive trapping agent may be the one that loses the function as a trapping agent by degrading by a radioactive ray reaction (radioactive ray-degradable trapping agent), or the one that acquires the function as a trapping agent, being generated through a radioactive ray reaction (radioactive ray-generable trapping agent), but the radioactive ray-degradable trapping agent is preferred.

In the case of the resist material containing the first trapping agent that loses the function as a trapping agent by degrading by the radioactive ray reaction, the first trapping agent degrades in the patternwise exposed regions following the patternwise exposure step, and does not degrade in the patternwise unexposed regions. Therefore, in the patternwise exposed regions, an action of trapping the acid and the cation is reduced, and action of trapping the acid and the cation is maintained in the patternwise unexposed regions. As a result, in the patternwise exposed regions, in a case in which the radiation-sensitive sensitizer is generated from the component (b) via a cation as an intermediate, and in a case in which the radiation-sensitive sensitizer is generated by an acid catalyst, the acid being generated is less likely to be trapped by the first trapping agent. As a result, the acid being generated is more likely to be used for degradation of the PAG and generation of the radiation-sensitive sensitizer, thereby improving the sensitization effect. On the other hand, upon the floodwise exposure, the first trapping agent traps unnecessary acid in the light-unexposed regions, thereby improving nanoedge roughness. As discussed above, as the first trapping agent loses the function as a trapping agent by the radioactive ray reaction, the chemical contrast of the latent image of acid can be improved. In the case of the first trapping agent being the one that loses the function as a trapping agent by degrading through the radioactive ray reaction, the first trapping agent is preferably a sulfonic acid salt and a carboxylic acid salt containing a radioactive ray-degradable cation. As the sulfonic acid in the sulfonic acid salt, a weaker acid is preferred, and a sulfonic acid that includes a hydrocarbon group having 1 to 20 carbon atoms, and not having a fluorine atom is more preferred. Examples of the sulfonic acid include sulfonic acids such as alkylsulfonic acids, benzenesulfonic acid and 10-camphorsulfonic acid. As the carboxylic acid in the carboxylic acid salt, a weaker acid is preferred, and a carboxylic acid having 1 to 20 carbon atoms is more preferred. Examples of the carboxylic acid include carboxylic acids such as formic acid, acetic acid, propionic acid, tartaric acid, succinic acid, cyclohexylcarboxylic acid, benzoic acid and salicylic acid. The radioactive ray-degradable cation in the carboxylic acid salt containing the radioactive ray-degradable cation is preferably an onium cation, and examples of the onium cation include iodonium cations, sulfonium cations, and the like.

In the case of the resist material containing the first trapping agent that is generated through the radioactive ray reaction and acquires the function as a trapping agent, the first trapping agent acquires the function as a trapping agent upon the patternwise exposure step in the patternwise exposed regions, and not in the patternwise unexposed regions. Therefore, an action of trapping the acid and the cation is exerted in the patternwise exposed regions, and the action of trapping the acid and the cation is not exerted in the patternwise unexposed regions. Alternatively, the radioactive ray-generable trapping agent may be the one that acquires the function of trapping agent upon the floodwise exposure. In this case, an exposure dose of the floodwise exposure is greater than an exposure dose of the patternwise exposure, and an amount of the trapping agent generated is comparatively greater in the floodwise exposure. As a result, in a case in which the radiation-sensitive sensitizer is generated from the radiation-sensitive sensitizer generating agent (b) via a cation as the intermediate, and in a case in which the radiation-sensitive sensitizer is generated by the acid catalyst, a function of the cation and the acid as trapping agent can be minimized prior to the floodwise exposure, and the radiation-sensitive sensitizer can be efficiency generated. On the other hand, if a most part of the first trapping agent degrades upon the floodwise exposure, the first trapping agent thus degraded traps unnecessary acid in the light-unexposed regions upon subsequent PEB, inhibiting diffusion of the acid, thereby improving the chemical contrast of the latent image of acid in the resist.

In the case of the first trapping agent being the one that is generated and acquires the function of trapping agent by the radioactive ray reaction, the carboxylic acid salt of the radioactive ray-degradable cation is preferably a compound that is capable of generating a base upon the floodwise exposure (radiation-sensitive base generating agent), and more preferably a nitrogen-containing organic compound that is capable of generating an amino group. In addition, the carboxylic acid salt is preferably a carboxylic acid ester. In comparison with a usual resist, in the chemically amplified resist, it is desirable that the content of the first trapping agent with respect to PAG is small upon the patternwise exposure, in order to leave place for the generation of acid by the radioactive ray sensitization upon the floodwise exposure. In other words, it is difficult to make the resist material contain the first trapping agent at a high concentration. On the other hand, a large amount of the first trapping agent is desirable for inhibiting the polarity changing reaction or diffusion of acid in the patternwise unexposed regions. The radioactive ray-generable trapping agent that is capable of generating a base upon the floodwise exposure is expected to satisfy both of these demands. Generation of a base upon the floodwise exposure may be caused by directly absorbing radioactive ray of the floodwise exposure, or by the radioactive ray sensitization. When the radioactive ray sensitization causes the generation, the first trapping agent functions also as a trapping agent of the acid or the cation in the radioactive ray sensitization in the floodwise exposure reaction, and can inhibit the radioactive ray sensitization reaction in regions where patternwise exposure is low, thereby further improving the contrast of the latent image of acid in the resist.

Examples of the compound that is capable of generating a base upon the floodwise exposure (radiation-sensitive base generating agent) include compounds disclosed in Japanese Unexamined Patent Application, Publication Nos. H4-151156, H4-162040, H5-197148, H5-5995, H6-194834, H8-146608 and H10-83079, and European patent No. 622682. The radiation-sensitive base generating agent is exemplified by a compound that includes a carbamate group (urethane bond), a compound that includes an acyloxyimino group, an ionic compound (anion-cation complex), a compound that includes a carbamoyloxyimino group, and the like, and a compound that includes a carbamate group (urethane bond), a compound that includes an acyloxyimino group, and an ionic compound (anion-cation complex) are preferred. In addition, as the radiation-sensitive base generating agent, a compound having a ring structure within a molecule is preferred. Examples of the ring structure include: benzene, naphthalene, anthracene, xanthone, thioxanthone, anthraquinone, and fluorene.

As the radiation-sensitive base generating agent, in light of radioactive ray degradation properties, a compound represented by the following general formula (XLV) is more preferred. When the compound is exposed, at least a bond between a nitrogen atom and a carbon atom in the carbonyl group adjacent thereto in the formula (XLV) is disconnected, and an amine or ammonia, as well as carbon dioxide are generated. Following the degradation, it is preferable that the boiling point of the product including —N($R^{26}$)($R^{27}$) is high. In addition, it is preferable that the product including —N($R^{26}$)($R^{27}$) has a high molecular weight, or has a bulky skeleton, from the viewpoint of diffusion control upon PEB.

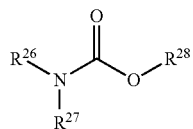

(XLV)

In the formula, $R^{26}$ and $R^{27}$ each independently represent a monovalent hydrocarbon group that may contain a hydrogen atom or a hetero atom, and $R^{26}$ and $R^{27}$ may taken together represent a ring structure together with the nitrogen atom to which $R^{26}$ and $R^{27}$ bond. $R^{28}$ is a monovalent radiation-sensitive functional group.

Examples of the radiation-sensitive base generating agent include: 2-nitrobenzylcarbamate, 2,5-dinitrobenzyl cyclohexylcarbamate, N-cyclohexyl-4-methylphenylsulfonamide, and 1,1-dimethyl-2-phenylethyl-N-isopropylcarbamate.

The first trapping agent may also be the one that is generated and acquires the function of trapping agent by a thermal reaction (thermally generable trapping agent). In the case of the resist material containing the thermally generable trapping agent, it is preferable that baking during which the trapping agent is generated follows the floodwise exposure. Therefore, a temperature of the baking following the floodwise exposure is preferably higher than the heating temperature after application of the resist material prior to the patternwise exposure, and then the baking temperature after the patternwise exposure prior to the floodwise exposure. In a case in which the resist material contains the first trapping agent that is generated and acquires the function of trapping agent by the thermal reaction, or the radioactive ray reaction at a wavelength of the floodwise exposure, acid trapping power of the first trapping agent in the patternwise unexposed regions is increased and the chemical contrast of the latent image of acid can be improved.

(4) Second Trapping Agent

The second trapping agent traps a free radical, and functions as a free radical trapping agent. As the resist material contains the second trapping agent, an effect of further inhibiting generation of the radiation-sensitive sensitizer via a reaction by a radical in the resist material in regions where the patternwise exposure is low, and further improving the contrast of the latent image of the radiation-sensitive sensitizer can be obtained. As a result, an effect of further increasing the contrast of the latent image of acid between the patternwise exposed regions and the light-unexposed regions after the floodwise exposure is exerted.

Examples of the second trapping agent include: a phenol compound, a quinone compound, an amine compound and the like may be exemplified, and 2,6-di-t-butyl-p-cresol, 2,2-methylene-bis(4-methyl-6-t-butylphenol), 1,1,3-tris(2-methyl-4-hydroxy-5-t-butylphenyl)butane, 1,3,5-trimethyl-2,4,6-tris(3,5-di-t-butyl-4-hydroxybenzyl)benzene, such as 1,3,5-tris(3',5'-di-t-butyl-4-hydroxybenzyl)-S-triazine-2,4,6-(1H,3H,5H)trione, 2,2,6,6-tetramethyl-1-piperidinyloxy (TEMPO), 2-tert-butyl-4-hydroxyanisole, 3-tert-butyl-4-hydroxyanisole, 3,4,5-trihydroxybenzoic acid propyl ester, 2-(1,1-dimethylethyl)-1,4-benzenediol, diphenyl picrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis (methylene(3,5-di-tert-butyl)-4-hydroxy-hydrocinnamate) methane, phenothiazine, alkylamidoisourea, thiodiethylenebis(3,5-di-tert-butyl-4-hydroxy-hydrocinnamate, 1,2-bis(3,5-di-tert-butyl-4-hydroxyhydrocinnamoyl) hydrazine, tris(2-methyl-4-hydroxy-5-tert-butylphenyl)butane, cyclic neopentane tetraylbis(octadecyl phosphite), 4,4'-thiobis(6-tert-butyl-m-cresol), 2,2'-methylenebis(6-tert-butyl-p-cresol), oxalyl bis(benzylidenehydrazide)methyl 5-doxyl stearate, hydroquinone, 2-t-butylhydroquinone, hydroquinone monomethyl ether, metaquinone, benzoquinone, bis(2,2,6,6-tetramethyl-4-piperidyl)-sebacate, phenothiazine, a naturally-derived antioxidant such as untreated seed oil, wheat germ oil, tocophenol, and rubber.

(5) Crosslinking Agent

The crosslinking agent is designed to trigger a crosslinking reaction between base component molecules in the baking step following the floodwise exposure through the acid-catalyzed reaction, to thereby increase molecular weight of the base component and make them insoluble to the developer solution, being different from the base component (1). As the resist material contains the crosslinking agent, a polar site is unpolarized simultaneously with crosslinking and the resist material is made insoluble to the developer solution, thereby providing a negative resist material.

The crosslinking agent is a compound having at least two functional groups. The functional group is preferably at least one selected from the group consisting of a (meth)acryloyl group, a hydroxymethyl group, an alkoxymethyl group, an epoxy group and a vinyl ether group.

Examples of the compound having at least two (meth) acryloyl groups include: trimethylolpropane tri(meth)acrylate, ditrimethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, glycerin tri(meth)acrylate, tris(2-hydroxyethyl)isocyanurate tri(meth)acrylate, ethylene glycol di(meth)acrylate, 1,3-butanediol di(meth)acrylate, 1,4-butanediol di(meth)acrylate, 1,6-hexanediol di(meth)acrylate, neopentyl glycol di(meth)acrylate, diethylene glycol di(meth)acrylate, triethylene glycol di(meth)acrylate, dipropylene glycol di(meth)acrylate, and bis(2-hydroxyethyl)isocyanurate di(meth)acrylate.

Examples of the compound having at least two alkoxymethyl groups or hydroxymethyl groups include: a hydroxymethyl group-containing phenol compound, an alkoxymethyl group-containing phenol compound, alkoxymethylated melamine, and an alkoxymethylated urea compound. The carbon number of the alkoxy group is preferably 1 to 5 for all. As the compound having at least two alkoxymethyl groups or hydroxymethyl groups, a methoxymethyl group-containing phenol compound, an ethoxymethyl group-containing phenol compound, methoxymethylated melamine and a methoxymethylated urea compound are preferred, and methoxymethylated melamine and methoxymethylated urea compound are more preferred. Examples of the methoxymethylated melamine include compounds represented by the following formulae (IX) to (X).

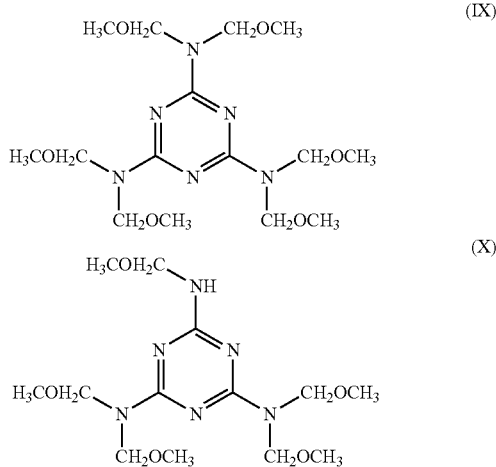

Examples of the methylated urea resin include compounds represented by the following formulae (XI) to (XIII).

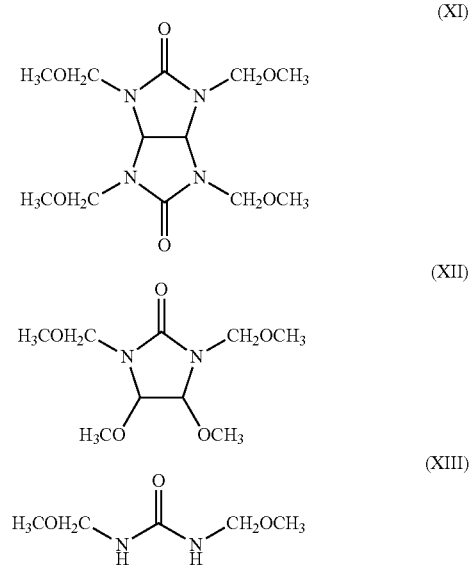

Examples of the compound having at least two epoxy groups include: a novolak-type epoxy resin, a bisphenol-type epoxy resin, an alicyclic epoxy resin, and an aliphatic epoxy resin.

Examples of the compound having at least two vinyl ether groups include: bis(4-(vinyloxymethyl)cyclohexylmethyl) glutarate, tri(ethylene glycol) divinyl ether, adipic acid divinyl ester, diethylene glycol divinyl ether, 1,2,4-tris(4-vinyloxybutyl)trimellitate, 1,3,5-tris(4-vinyloxybutyl)trimellitate, bis(4-(vinyloxy)butyl)terephthalate, bis(4-(vinyloxy)butyl)isophthalate, ethylene glycol divinyl ether, 1,4-butanediol divinyl ether, tetramethylene glycol divinyl ether, tetraethylene glycol divinyl ether, neopentyl glycol divinyl ether, trimethylolpropane trivinyl ether, trimethylolethane trivinyl ether, hexanediol divinyl ether, 1,4-cyclohexanediol divinyl ether, tetraethylene glycol divinyl ether, pentaerythritol divinyl ether, pentaerythritol trivinyl ether, and cyclohexanedimethanol divinyl ether.

(6) Additive

Examples of the additive include: a surfactant, an antioxidant, a dissolution inhibitor, a plasticizer, a stabilizer, a colorant, a halation inhibitor, and a dye. Well-known materials may be selected as the surfactant, the antioxidant, the dissolution inhibitor, the plasticizer, the stabilizer, the colorant, the halation inhibitor and the dye. As the surfactant, for example, an ionic and nonionic fluorochemical surfactant, a silicone surfactant, and the like may be used. Examples of the antioxidant include: a phenol antioxidant, an antioxidant composed of an organic acid derivative, a sulfur-containing antioxidant, a phosphorus antioxidant, an amine antioxidant, an antioxidant composed of amine-aldehyde condensate, and an antioxidant composed of amine-ketone condensate.

(7) Solvent

The solvent is designed to dissolve a composition of the resist material to facilitate formation of a resist material film by a coater by a method such as spin coating. It is to be noted that the compounds contained in the radiation-sensitive sensitizer generating agent (b) and the like are excluded from the solvent. Examples of the solvent include: ketones such as cyclohexanone and methyl 2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol monomethyl ether acetate, and propylene glycol mono-tert-butyl ether acetate.

Blend Ratio

The resist material is a radiation-sensitive resin composition containing the above described component. Upon preparation of the resist material, a blend ratio of each component may be appropriately selected according to an intended use, use conditions, and the like of the resist material.

The amount of the radiation-sensitive acid-and-sensitizer generating agent (a) blended with respect to 100 parts by mass of component (1) is preferably no less than 0.005 parts by mass and no greater than 50 parts by mass, and more preferably no less than 0.1 parts by mass and no greater than 30 parts by mass. The amount no less than 0.005 parts by mass facilitates obtaining sufficient sensitivity, while the amount no greater than 50 parts by mass improves compatibility with the resist and facilitates formation of the resist material film. The amount of the radiation-sensitive acid generating group (b) blended with respect to 100 parts by mass of component (1) is preferably no less than 0.005 parts by mass and no greater than 50 parts by mass, and more preferably no less than 0.1 parts by mass and no greater than 30 parts by mass. The amount no less than 0.005 parts by mass facilitates obtaining sufficient sensitivity, while the amount no greater than 50 parts by mass facilitates obtaining a rectangular resist pattern. The amount of the radiation-sensitive sensitizer (c) blended with respect to 100 parts by mass of component (1) is preferably no less than 0.01 parts by mass and no greater than 50 parts by mass, and more preferably no less than 0.1 parts by mass and no greater than 30 parts by mass. The amount no less than 0.01 parts by mass facilitates obtaining sufficient sensitivity, while the amount no greater than 50 parts by mass facilitates obtaining a rectangular resist pattern.

The amount of the first trapping agent (3) blended with respect to 100 parts by mass of component (1) is preferably no less than 0.001 parts by mass and no greater than 20 parts by mass, and more preferably no less than 0.01 parts by mass and no greater than 10 parts by mass. The amount no greater than parts by mass is more likely to inhibit excessive reduction of sensitivity. The amount no less than 0.001 parts by mass is more likely to provide the above described effect from blending the first trapping agent. The usage ratio of the whole radiation-sensitive acid generating agent (total of the radiation-sensitive acid-and-sensitizer generating agent (a) and the radiation-sensitive acid generating agent (c)) to the first trapping agent in the resist material is preferably as follows: whole radiation-sensitive acid generating agent/first trapping agent (molar ratio)=no less than 1.5 and no greater than 300. In other words, in light of sensitivity and resolution, the molar ratio is preferably no less than 1.5, while in light of inhibition of resist pattern dimension change over time between the exposure and the heat treatment, the molar ratio is preferably no greater than 300. Whole radiation-sensitive acid generating agent/first trapping agent (molar ratio) is more preferably no less than 5.0 and no greater than 200.

The amount of the second trapping agent (4) blended with respect to 100 parts by mass of component (1) is preferably no greater than 10 parts by mass, and more preferably no less than 0.0005 parts by mass and no greater than 5 parts by mass. The amount no greater than 10 parts by mass is less likely to inhibit generation of the radiation-sensitive sensitizer, and likely to increase sensitivity by the radiation-sensitive sensitizer upon the floodwise exposure. The amount no less than 0.0005 parts by mass is more likely to provide the above described effect from blending the second trapping agent.

The amount of the crosslinking agent (5) blended with respect to 100 parts by mass of component (1) is preferably no greater than 40 parts by mass, and more preferably no less than 0.1 parts by mass and no greater than 25 parts by mass. The amount no greater than 40 parts by mass increases solubility of the resist material and is more likely to inhibit decrease in contrast of image. The amount no less than 0.1 parts by mass is more likely to provide the above described effect from blending the crosslinking agent.

The amount of the additive (6) blended with respect to 100 parts by mass of component (1) is preferably no greater than 30 parts by mass, and more preferably no less than 0.1 parts by mass and no greater than 10 parts by mass. The amount no greater than 30 parts by mass is less likely to deteriorate characteristics of the resist material. The amount no less than 0.1 parts by mass is more likely to provide a superior process window of the resist material.

The amount of the solvent (7) blended with respect to 100 parts by mass of component (1) is preferably no less than 200 parts by mass and no greater than 10,000 parts by mass, and more preferably no less than 300 parts by mass and no greater than 5,000 parts by mass. The amount no greater than 10,000 parts by mass is less likely to deteriorate characteristics of the resist material. The amount no less than 200 parts by mass facilitates formation of the resist material film.

The resist material of the embodiment of the present invention can be manufactured by mixing the components (1) to (7) by a well-known method.

Pattern-Forming Method

The resist material is suitably used in the two-step exposure lithography process. In other words, the lithography process (pattern-forming method) according to the embodiment of the present invention comprises: a film-forming step of forming a resist material film on a substrate using the resist material; a patternwise exposure step of patternwise exposing the resist material film to a first radioactive ray through a mask; a floodwise exposure step of floodwise exposing the resist material film obtained after the patternwise exposure step to a second radioactive ray; a baking step of baking the resist material film obtained after the floodwise exposure step; and a development step of developing the resist material film obtained after the baking step with a developer solution.

Figure 4:
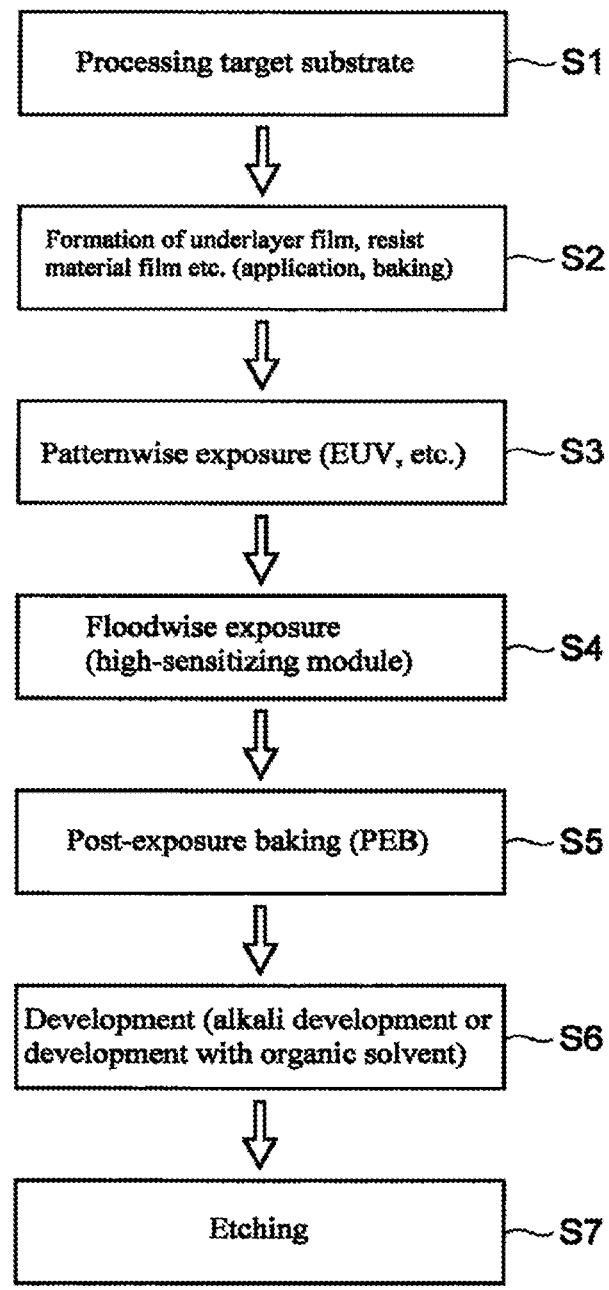
FIG. 4 shows a flow chart showing an embodiment of the pattern-forming method employing the chemically amplified resist material according to the present invention.
Figure 7:
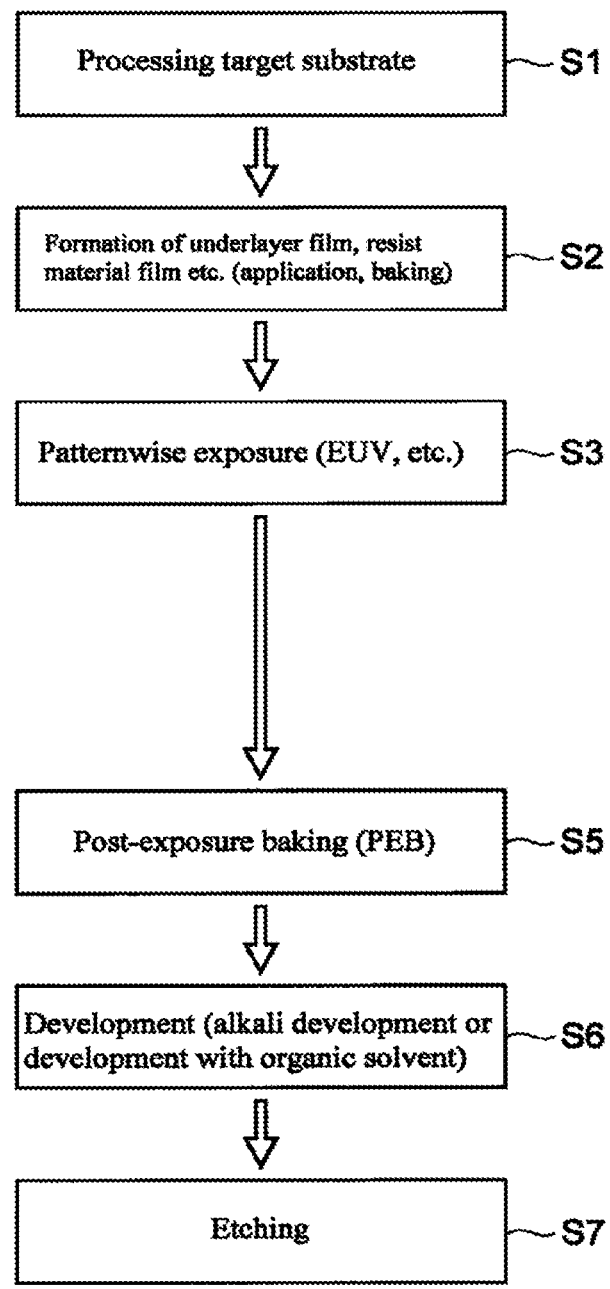
FIG. 7 shows a flow chart showing an example of the pattern-forming method employing the conventional chemically amplified resist material.

FIG. 4 is a flow chart showing a lithographic process according to the embodiment of the present invention. As shown in FIG. 4, the process comprises the following steps. FIG. 7 is a flow chart showing an example of the pattern-forming method using the conventional chemically amplified resist material.

Step S1: a step of preparing a substrate subjected to the process

Step S2: a step of forming an underlayer film and a resist material film (film-forming step)

Step S3: a step of generating an acid in light-exposed regions by patternwise exposure (patternwise exposure step)

Step S4: a step of proliferating the acid only in the patternwise exposed regions by the floodwise exposure (floodwise exposure step)

Step S5: a step of causing a polarity change reaction in the patternwise exposed regions by post-exposure baking (baking step)

Step S6: a step of forming a resist pattern by a developing treatment (development step)

Step S7: a step of transferring the pattern by etching

Step S1

A substrate subjected to the process in the following steps (processing target substrate) may be constituted of a semiconductor wafer such as a silicon substrate, a silicon dioxide substrate, a glass substrate, and an ITO substrate, or can be the semiconductor wafer with an insulating film layer being formed thereon.

Step S2: Film-Forming Step

The resist material film is formed by using the resist material of the embodiment of the present invention. Examples of the forming method of the resist material film include: a method of applying a liquid resist material by spin coating and the like, and a method of attaching a film-like (solid) resist material. In the case of applying the liquid resist material, heating (prebaking) may take place following the application to volatilize the solvent in the resist material. Formation conditions of the resist material film are appropriately selected according to properties of the resist material, thickness of the resist material film to be obtained, and the like. An average thickness of the resist material film is preferably no less than 1 nm and no greater than 5,000 nm, more preferably no less than 10 nm and no greater than 1,000 nm, and still more preferably no less than 30 nm and no greater than 200 nm.

Prior to forming the resist material film on the substrate, an underlayer film (antireflective film, film for ameliorating resist adhesiveness, film for ameliorating resist shape etc.) may be formed on the substrate. By forming the antireflective film, generation of standing wave due to reflection of the radioactive ray from the substrate and the like in the patternwise exposure step can be inhibited. By forming a film for ameliorating resist adhesiveness, adhesiveness between the substrate and the resist material film can be improved. By forming the film for ameliorating resist shape, a post-development resist shape can be further improved. In other words, trailing or constriction of the resist can be reduced.

On the other hand, in order to prevent deterioration of the resist shape due to generation of the standing wave of the radioactive ray of the floodwise exposure, it is preferable that the thickness of the underlayer film is designed to inhibit reflection of the radioactive ray of the floodwise exposure. It is desirable that the underlayer film does not absorb the radioactive ray of the floodwise exposure. If the underlayer film absorbs the radioactive ray of the floodwise exposure, a radioactive ray sensitization reaction would be caused in the resist material film due to energy transfer or electron transfer from the underlayer film, and an acid may thus be generated in the patternwise unexposed regions. Given this, a buffer layer that does not propagate the radioactive ray sensitization reaction may be provided between the resist material film and the underlayer film, to thereby prevent sensitization from the underlayer film having absorbed the radioactive ray.

A protective film may further be formed on the resist material film. By forming the protective film, deactivation of the radiation-sensitive sensitizer, the acid, and a reaction intermediate thereof generated in the patternwise exposure step S3 can be inhibited and process stability can be improved. The protective film may be an absorption film that absorbs at least a part of the wavelength of nonionizing radiation that is directly absorbed by the component (a) or (c) (radiation-sensitive acid generating agent), or a group shown in (d) or (f) (radiation-sensitive acid generating group), in order to prevent an acid generating reaction in the light-unexposed regions in the floodwise exposure step. By using the absorption film, out-of-band light (OOB light), which is a radioactive ray of an ultraviolet ray region generated upon EUV exposure, is prevented from entering into the resist material film, and degradation of the radiation-sensitive acid generating agent or the radiation-sensitive acid generating group in the patternwise unexposed regions can also be prevented. In addition, in the case of the absorption film being formed directly on the resist material film, in order to inhibit generation of an acid in the resist material film by the radioactive ray sensitization reaction in the patternwise unexposed regions, it is preferable that the radioactive ray sensitization reaction from the protective film is not triggered by the wavelength of the second radioactive ray in the floodwise exposure step. In addition, a buffer layer may be provided between the resist material film and the protective film to prevent sensitization from the absorption film having absorbed the radioactive ray, such that the radiation-sensitive sensitizer in the resist material film is not sensitized by energy transfer or electron transfer and the like from the protective film. By forming the absorption film on the resist material film following the patternwise exposure step S3 and prior to the floodwise exposure step S4, generation of an acid directly from the radiation-sensitive acid generating agent or the radiation-sensitive acid generating group remaining on the resist material film obtained after the patternwise exposure step S3 through the irradiation with the second radioactive ray in the floodwise exposure step S4 can further be inhibited.

Step S3: Patternwise Exposure Step

The patternwise exposure step S3 disposes a light shielding mask having a predetermined pattern on the resist material film formed in the film-forming step S2. Thereafter, the resist material film is irradiated with the first radioactive ray from an exposure system (radioactive ray irradiating module) including a projection lens, an electronic optics mirror, or a reflection mirror, through the mask (patternwise exposure).

The first radioactive ray used for the patternwise exposure is ionizing radiation or nonionizing radiation having wavelength no greater than 400 nm. The upper limit of the wavelength of the nonionizing radiation is preferably 250 nm, and more preferably 200 nm. On the other hand, the lower limit of the wavelength of the nonionizing radiation is preferably 150 nm, and more preferably 190 nm.

The ionizing radiation is a radioactive ray having sufficient energy for ionizing an atom or a molecule. Meanwhile, the nonionizing radiation is a radioactive ray not having sufficient energy for ionizing an atom or a molecule. Examples of the ionizing radiation include: gamma ray, X-ray, alpha ray, heavy particle ray, proton beam, beta ray, ion beam, electron beam, and extreme-ultraviolet ray. As the ionizing radiation used for the patternwise exposure, electron beam, extreme-ultraviolet ray and ion beam are preferred, and electron beam and extreme-ultraviolet ray are more preferred. Examples of the nonionizing radiation include: far-ultraviolet ray, near-ultraviolet ray, visible light ray, infrared ray, microwave, and low-frequency wave. As the nonionizing radiation used for the patternwise exposure, far ultraviolet ray (wavelength: 190 to 300 nm) is preferred.

As a light source for the patternwise exposure, for example, electron beam of 1 keV to 200 keV, extreme-ultraviolet ray (EUV) having a wavelength of 13.5 nm, excimer laser beam (ArF excimer laser beam) of 193 nm, and excimer laser beam (KrF excimer laser beam) of 248 nm are frequently used. Exposure dose in the patternwise exposure may be smaller than in the case of floodwise exposure using the chemically amplified resist of the embodiment of the present invention. By the patternwise exposure, the components (a) to (c) or groups shown in (d) to (f) in the resist material film degrade and generate an acid and the radiation-sensitive sensitizer that absorbs the second radioactive ray.

A step-and-scan exposure system called "scanner" is widely used for exposure. In the present method, by performing scanning exposure while synchronizing the mask with the substrate, a pattern is formed for every one shot. This exposure triggers a selective reaction in exposed sites in the resist.

In addition, prior to performing the floodwise exposure step S4, an absorption film that absorbs at least a part of the wavelength of nonionizing radiation that is directly absorbed by the radiation-sensitive acid generating agent in the component (a) or (c), or the radiation-sensitive acid generating group, which is a group shown in (d) or (f), may be formed on the resist material film after the patternwise exposure step S3. By forming the absorption film, generation of acid directly from the radiation-sensitive acid generating agent or the radiation-sensitive acid generating group remaining on the resist material film after the patternwise exposure step S3 through the irradiation with the second radioactive ray in the floodwise exposure step S4 described later can be further inhibited.

In the case of using the radiation-sensitive sensitizer generating agent (b) (or radiation-sensitive sensitizer precursor group (e)) having an alcoholic hydroxyl group in which a hydrogen atom is not substituted, it is preferable that the resist material film is placed under a vacuum atmosphere or an inert atmosphere containing nitrogen or argon, following the patternwise exposure step S3 and prior to performing the floodwise exposure step S4 described later. By placing the resist material film under the above described atmosphere, exposure of the resist material film to oxygen upon an exposure and stopping of the radical reaction by this oxygen can be inhibited, and quenching of the acid by a slight amount of a basic compound can be inhibited, leading to a tendency that the process is further stabilized. The upper limit of the time period from the completion of the patternwise exposure step S3 until performing the floodwise exposure step S4 (keeping time) is preferably 30 min and more preferably 10 min. The keeping time no greater than 30 min tends to inhibit decreases in sensitivity. On the other hand, in the case of using the radiation-sensitive sensitizer generating agent (b) (in other words, a ketal compound, an acetal compound, or an ortho ester compound, and the like) having an alcoholic hydroxyl group in which a hydrogen atom is substituted, after the patternwise exposure step S3 and prior to performing the floodwise exposure step S4 described later, an atmosphere in which the resist material film is present is preferably ambient air cleaned by an amine eliminating filter. In the case of using the radiation-sensitive sensitizer generating agent (b), the above described influence of oxygen is less likely, and treatment in the ambient air cleaned by the amine eliminating filter is therefore possible. By placing the resist material film in the above described atmosphere, quenching of the acid by a slight amount of a basic compound can be inhibited, leading to a tendency that the process is further stabilized. The upper limit of the time period from the completion of the patternwise exposure step S3 until performing the floodwise exposure step S4 (keeping time) is preferably 30 min and more preferably 10 min. The keeping time no greater than 30 min tends to inhibit decreases in sensitivity.

Figure 5:
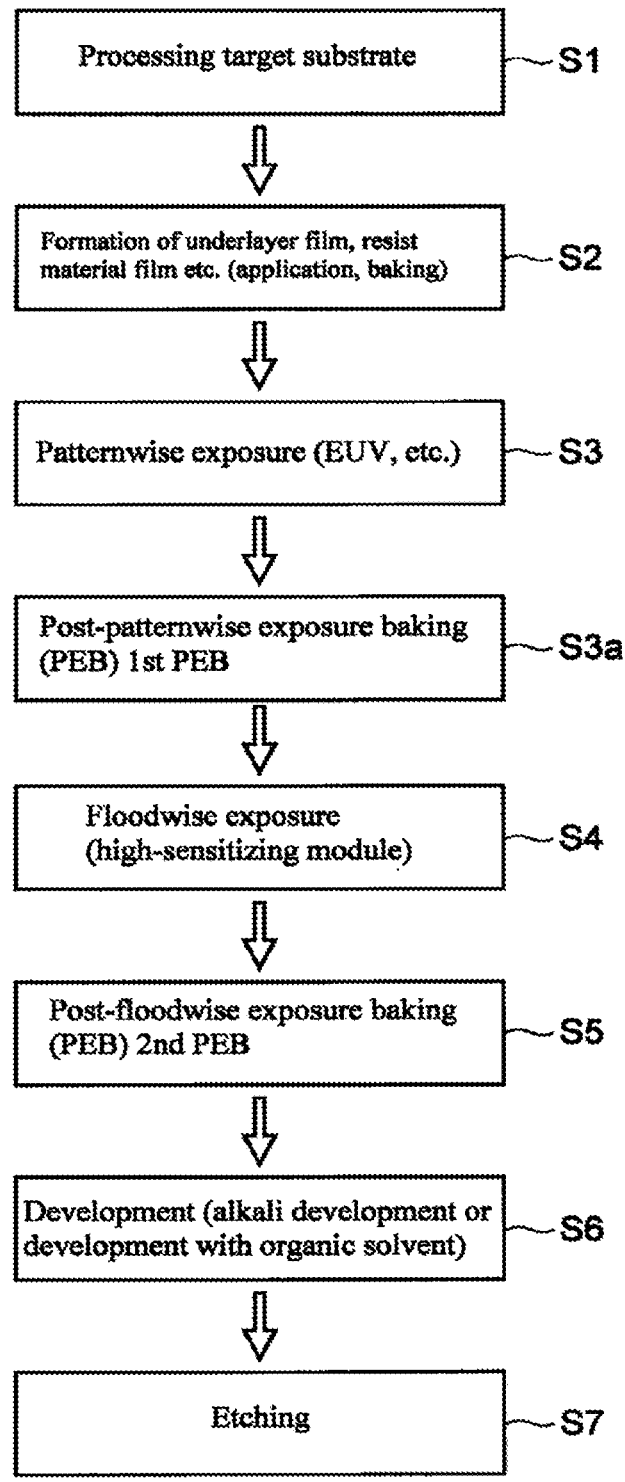
FIG. 5 shows a flow chart showing another embodiment of the pattern-forming method employing the chemically amplified resist material according to the present invention.

The pattern-forming method of the embodiment of the present invention may further comprise, following the patternwise exposure step S3 and prior to the floodwise exposure step S4 described later, a step of conveying the substrate from the exposure system in which the patternwise exposure step S3 takes place to the exposure system in which the floodwise exposure step S4 takes place. In addition, the floodwise exposure may take place in an in-line connected application developing apparatus, or in a module corresponding to an interface with an exposure device. It is to be noted that, in a case in which the component (2) contains a ketal compound, an acetal compound or an ortho ester compound, and in a case in which the base component (1') contains a ketal compound group, an acetal compound group or an ortho ester compound group, the pattern-forming method of the embodiment of the present invention may comprise a baking step S3a (may also be referred to as post-patterning exposure baking (PPEB or PEB)) following the patternwise exposure step S3 and prior to the floodwise exposure step S4 described later (refer to FIG. 5). The heating temperature in the baking step is preferably no less than 30° C. and no greater than 150° C., more preferably no less than 50° C. and no greater than 120° C., and still more preferably no less than 60° C. and no greater than 100° C. The heating time is preferably no less than 5 sec and no greater than 3 min, and more preferably no less than 10 sec and no greater than 60 sec. Furthermore, the baking preferably takes place in a humidity-controlled environment, since, in the case of using a hydrolysis reaction as the deprotection reaction for generating the radiation-sensitive sensitizer, humidity influences the reaction speed. The pattern-forming method comprising the baking step S3a can accelerate generation of the radiation-sensitive sensitizer by a hydrolysis reaction from an acetal compound, an ortho ester compound, or a ketal compound and the like to a carbonyl compound.

Step S4: Floodwise Exposure Step

In the floodwise exposure step S4, an entire surface (entire surface with both the patternwise exposed regions and the patternwise unexposed regions) of the resist material film after the patternwise exposure step S3 is irradiated with the second radioactive ray from a high-sensitizing module (may also be referred to as an exposure system or a radioactive ray irradiating module) having a projection lens (or a light source) (floodwise exposure). The floodwise exposure may be either an exposure of the entire face of the wafer, a combination of local exposures, or overlapping exposures. As a light source for the floodwise exposure, a general light source may be employed: in addition to an ultraviolet ray from a mercury lamp, a xenon lamp, and the like controlled to have a desired wavelength by a band-pass filter and a cut-off filter, a narrow-bandwidth ultraviolet ray from an LED light source, a laser diode, a laser light source and the like may also be used. In the floodwise exposure, only the radiation-sensitive sensitizer generated in the patternwise exposed regions in the resist material film absorbs the radioactive ray. As a result, in the floodwise exposure, absorption of radioactive ray takes place selectively in the patternwise exposed regions. This allows continuous generation of an acid only in the patternwise exposed regions upon the floodwise exposure, and significant improvement of sensitivity. On the other hand, since no acid is generated in the patternwise unexposed regions, improvement of sensitivity is possible while maintaining the chemical contrast in the resist material film.

In the case of the first radioactive ray being a nonionizing radiation, the second radioactive ray used for the floodwise exposure has a wavelength greater than the wavelength of the nonionizing radiation in the first radioactive ray. Furthermore, the second radioactive ray is a nonionizing radiation having a wavelength greater than 200 nm, is preferably a nonionizing radiation having a wavelength greater than 250 nm, and is more preferably a near ultraviolet ray (wavelength 200 to 450 nm).

In the floodwise exposure step S4, in order to inhibit the acid generating reaction in the patternwise unexposed regions, exposure with a radioactive ray having a wavelength greater than the wavelength of the radioactive ray that can be absorbed by the base component (1), the radiation-sensitive acid generating agent, and the radiation-sensitive sensitizer generating agent is necessary. In consideration of these, the lower limit of a wavelength of the nonionizing radiation for the floodwise exposure lower limit is more preferably 280 nm and still more preferably 320 nm. In the case of generating the radiation-sensitive sensitizer that can absorb the radioactive ray having a greater wavelength, the wavelength of the nonionizing radiation may be no less than 350 nm. However, if the wavelength of the nonionizing radiation is too long, efficiency of the radioactive ray sensitization reaction would be deteriorated; and therefore it is desirable to use a nonionizing radiation having a wavelength as short as possible that can be absorbed by the radiation-sensitive sensitizer, while avoiding a wavelength of the radioactive ray that can be absorbed by the base component, the radiation-sensitive acid generating agent, and the radiation-sensitive sensitizer generating agent. From such a viewpoint, the lower limit of the wavelength of the nonionizing radiation is preferably 450 nm and more preferably 400 nm.

The patternwise exposure step S3 and/or the floodwise exposure step S4 may be performed either by liquid immersion lithography (liquid immersion exposure) or by dry lithography (dry exposure). The "liquid immersion lithography" as referred to means an exposure performed in a state in which a liquid is interposed between the resist material film and a projection lens. On the other hand, the "dry lithography" as referred to means an exposure performed: in a state in which a gas is interposed between the resist material film and the projection lens; under a reduced pressure; or under vacuum.

In addition, the liquid immersion lithography in the patternwise exposure step S3 and/or the floodwise exposure step S4 may also be performed in a state in which a liquid whose refractive index is no less than 1.0 is interposed between the resist material film or the protective film formed in the film-forming step S2 and the projection lens. The protective film is preferably a film designated for reflection prevention or reaction stability improvement. In addition, the protective film is preferably a film capable of liquid penetration prevention, water repellency improvement on the film surface, and prevention of defect caused by the liquid in the liquid immersion lithography.

In the liquid immersion lithography in the floodwise exposure step S4, the liquid may also be a liquid that absorbs at least a part of the wavelength of the second radioactive ray directly absorbed by the component (a) or (c) (radiation-sensitive acid generating agent), or a group shown in (d) or (f) (radiation-sensitive acid generating group). By using the liquid in the liquid immersion lithography, generation of acid directly from the radiation-sensitive acid generating agent or the radiation-sensitive acid generating group remaining in the resist material film through the irradiation with the second radioactive ray in the floodwise exposure step S4 can further be inhibited.

In the case of performing the patternwise exposure step S3 and/or the floodwise exposure step S4 by dry lithography, these steps may be performed in any of: ambient air, under a vacuum atmosphere, and under an inert atmosphere, and preferably performed under a vacuum atmosphere or under an inert atmosphere containing nitrogen or argon, and the upper limit of the basic compound concentration in the atmosphere upon performing is preferably 20 ppb, more preferably 5 ppb, and still more preferably 1 ppb.

Step S5: Baking Step

In the baking step S5, the resist material film obtained after the floodwise exposure step S4 is heated (hereinafter may be also referred to as "post-flood exposure baking (PFEB)" or "post-exposure baking (PEB)"). It is to be noted that, if the pattern-forming method of the embodiment of the present invention includes the baking step S3a following the patternwise exposure step S3 and prior to the floodwise exposure step S4, hereinafter, the baking step S3a may be also referred to as "1st PEB step" and the baking step S5 may be also referred to as "2nd PEB step" (refer to FIG. 5). Baking conditions may be as follows, for example: in the ambient air, under an inert gas atmosphere of nitrogen, argon and the like, no lower than 50° C. and no higher than 200° C., no less than 10 sec and no more than 300 sec. The baking conditions within the above specified range are likely to be able to control diffusion of acid and to secure processing speed of the semiconductor wafer. In the baking step S5, a polarity change reaction such as a deprotection reaction of the base component (1) and the base component (1'), a crosslinking reaction, and the like are triggered by an acid generated in the patternwise exposure step S3 and the floodwise exposure step S4. In addition, although a resist side wall may be waved under influence of the standing wave of the radioactive ray in the resist material film, the baking step S5 can inhibit the waving through diffusion of the reactant.

Step S6: Development Step

In the development step S6, the resist material film obtained after the baking step S5 is brought into contact with the developer solution. Development takes place through a selective change in solubility to a developer solution in the patternwise exposed regions by a reaction within the resist material film in the baking step S5, to thereby form a resist pattern. The developer solution can be classified into a positive developer solution and a negative developer solution.

As the positive developer solution, an alkaline developer solution is preferred. The alkaline developer solution selectively dissolves high-polarity sites of the post-exposure resist material film. Examples of the alkaline developer solution include: potassium hydroxide, sodium hydroxide, sodium carbonate, potassium carbonate, sodium phosphate, sodium silicate, ammonia, amines (such as ethanolamine), and tetraalkylammonium hydroxide (TAAH). As the alkaline developer solution, TAAH is preferred. Examples of the TAAH include: tetramethylammonium hydroxide (TMAH), tetraethylammonium hydroxide, tetrapropylammonium hydroxide, tetrabutylammonium hydroxide, methyltriethylammonium hydroxide, trimethylethylammonium hydroxide, dimethyldiethylammonium hydroxide, trimethyl(2-hydroxyethyl)ammonium hydroxide (i.e. choline), triethyl(2-hydroxyethyl)ammonium hydroxide, dimethyldi(2-hydroxyethyl)ammonium hydroxide, diethyldi(2-hydroxyethyl)ammonium hydroxide, methyltri(2-hydroxyethyl)ammonium hydroxide, ethyltri(2-hydroxyethyl)ammonium hydroxide, and tetra(2-hydroxyethyl)ammonium hydroxide.

As the positive developer solution, a 2.38% by mass aqueous solution of tetramethylammonium hydroxide (TMAH) is widely used.

In alkaline development, a pattern is formed through a phenomenon in which carboxylic acid and the hydroxyl group generated in the resist material film following the exposure are ionized and eluted in the alkaline developer solution. Following the development, a water washing treatment called rinsing takes place in order to remove the developer solution remaining on the substrate.

As the negative developer solution, an organic developer solution is preferred. The organic developer solution selectively dissolves low-polarity sites of the post-exposure resist material film. The organic developer solution is used for improving resolving performance and a process window by a punching pattern such as hole and trench (groove). In this case, a dissolve contrast between the patternwise exposed regions and the patternwise unexposed regions is obtained through a difference in affinity between the solvent and the organic developer solution in the resist material film. A high-polarity site has low solubility to the organic developer solution and remains as a resist pattern. Examples of the organic developer solution include: 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

The resist pattern obtained after the development step S6 (including the rinsing treatment) may be heated (may also be referred to as "post-baking"). The post-baking can vaporize and remove a rinse agent remaining from the rinse treatment and can harden the resist pattern.

Step S7

In step S7, a pattern is formed by etching or ion implanting a substrate as a base, with the resist pattern obtained after the development step S6 as a mask. The etching may be either dry etching under atmosphere such as plasma excitement, or wet etching involving immersion into a chemical. Following formation of the pattern on the substrate by the etching, the resist pattern is removed.

Reaction Mechanism

A mechanism of reactions taking place in the lithography process according to the embodiment of the present invention will be explained hereinafter.

First, a typical lithography process of a conventional chemically amplified resist is as follows. The radiation-sensitive acid generating agent (may be also referred to "photosensitive acid generating agent" or "PAG") in the resist material film degrades and generates an acid following the patternwise exposure. Thereafter, an acid-catalyzed reaction resulting from heating alters the dissolution characteristic of the base component. As a result, the solubility of the resist material film in a developer solution is changed and enables development.

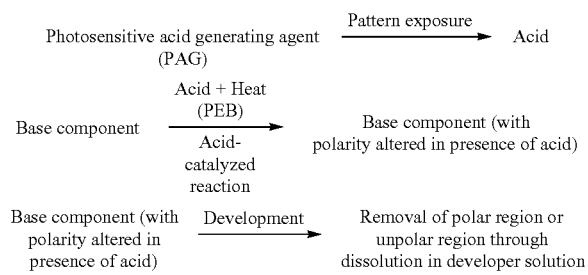

On the other hand, since the lithography process according to the embodiment of the present invention employs the radioactive ray sensitization to generate an acid, an amount of the acid generated can be increased, and sensitivity can be greatly amplified relative to the conventional process.

The reaction system in the lithography process according to the embodiment of the present invention can be classified into three as follows. For further improvement of characteristic, these systems may be combined with each other.

A first reaction system in the lithography process according to the embodiment of the present invention is a system in which the resist material contains the radiation-sensitive acid-and-sensitizer generating agent (a) as the component (2), or the resist material contains the base component (1') having the acid-and-radiation-sensitive-sensitizer generating group (d). In this system, both the acid and the radiation-sensitive sensitizer generate from the radiation-sensitive acid-and-sensitizer generating agent (a) upon an exposure. Since the radiation-sensitive sensitizer thus generated contains a carbonyl group and the like, the absorption wavelength of the radioactive ray shifts to a wavelength longer than the absorption wavelength of the radiation-sensitive acid-and-sensitizer generating agent (a). By performing the floodwise exposure with the nonionizing radiation having a wavelength that can be absorbed only by the generated radiation-sensitive sensitizer, and that can degrade the radiation-sensitive acid-and-sensitizer generating agent (a) by radioactive ray sensitization, an amount of the acid generated can be selectively amplified in the patternwise exposed regions. The acid-catalyzed reaction in the base component following the acid generation is similar to the reaction in the conventional lithography process.

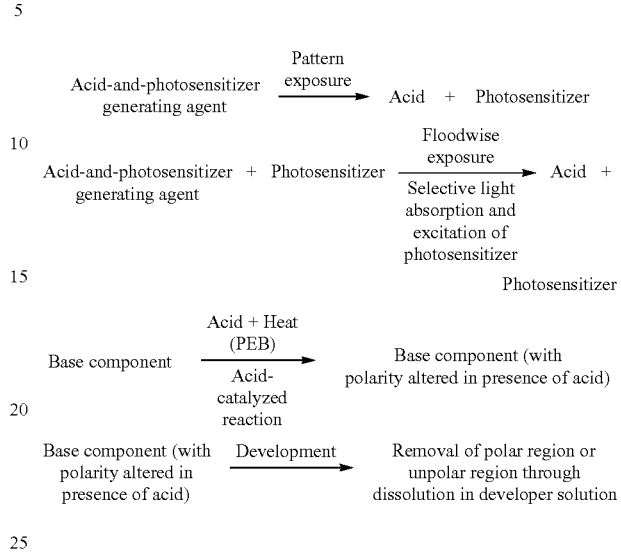

A second reaction system in the lithography process according to the embodiment of the present invention is a system in which the resist material contains the radiation-sensitive sensitizer generating agent (b) and the radiation-sensitive acid generating agent (c) as the component (2), or the resist material contains the base component (1') having the radiation-sensitive sensitizer precursor group (e) and radiation-sensitive acid generating group (f), and the component (b) or the group shown in (e) has an alcoholic hydroxyl group in which a hydrogen atom is not substituted. In this system, first, the acid is generated from the component (c) or the group shown in (f) upon the patternwise exposure, and the radiation-sensitive sensitizer is generated simultaneously from the component (b) or the group shown in (e). In a case in which the component (b) or the group shown in (e) has the alcoholic hydroxyl group in which a hydrogen atom is not substituted, the alcoholic hydroxyl group and the carbon atom, to which the alcoholic hydroxyl group bonds, form a carbonyl group contributing to the radioactive ray sensitization action. In this reaction, the radiation-sensitive sensitizer is generated via a short lifetime intermediate such as radical or cation, and the reaction may take place in a sufficiently shorter period of time within several seconds at a normal temperature. Since the radiation-sensitive sensitizer being generated contains a carbonyl group and the like, the absorption wavelength of the radioactive ray shifts toward a longer wavelength than the components (b) and (c) and the groups shown in (e) and (f). By performing the floodwise exposure with the nonionizing radiation having a wavelength that can be absorbed only by the generated radiation-sensitive sensitizer, and that can degrade the component (c) or the group shown in (f) by radioactive ray sensitization, an amount of the acid generated can be selectively amplified in the patternwise exposed regions. The acid-catalyzed reaction in the base component following the acid generation is similar to the reaction in the conventional lithography process.

-continued

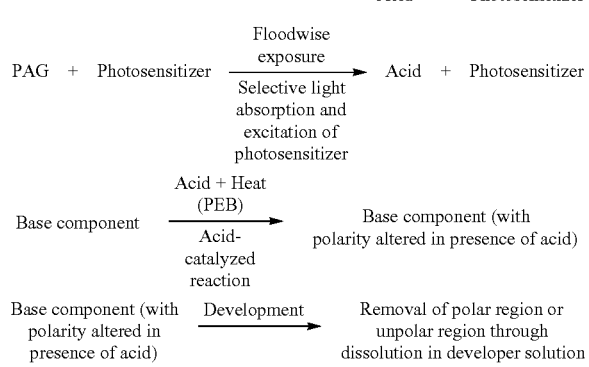

A third reaction system in the lithography process according to the embodiment of the present invention is a system in which the resist material contains the radiation-sensitive sensitizer generating agent (b) and radiation-sensitive acid generating agent (c) as the component (2), or the resist material contains the base component (1') having the radiation-sensitive sensitizer precursor group (e) and the radiation-sensitive acid generating group (f), and the component (b) or the group shown in (e) has an alcoholic hydroxyl group in which a hydrogen atom is substituted. In this system, first an acid is generated from the component (c) or the group shown in (f) upon the patternwise exposure, and the generated acid functions as a catalyst to generate radiation-sensitive sensitizer from the component (b) or the group shown in (e). Examples of the component (b) having the alcoholic hydroxyl group in which a hydrogen atom is substituted include: an acetal compound, a ketal compound and an ortho ester compound. The acetal compound and the ketal compound respectively generate aldehyde and ketone, which are radiation-sensitive sensitizers, by the acid-catalyzed reaction. In addition, the ortho ester compound generates a carboxylic acid ester, which is a radiation-sensitive sensitizer, by the acid-catalyzed reaction. In addition, the component (b) may generate carboxylic acid, which is a radiation-sensitive sensitizer, by a deprotection reaction of the OBO-protected carboxylic acid. In this reaction system, an acid generated in the patternwise exposure functions as a catalyst to generate the radiation-sensitive sensitizer, deactivation of the acid as a catalyst can therefore be inhibited, and the radiation-sensitive sensitizer generating reaction can thus be controlled. Since the radiation-sensitive sensitizer thus generated is a compound having a carbonyl group such as aldehyde, ketone, carboxylic acid ester, carboxylic acid and the like, the absorption wavelength of the radioactive ray shifts toward a longer wavelength than the components (b) and (c) and the groups shown in (e) and (f). By performing the floodwise exposure with the nonionizing radiation having a wavelength that can be absorbed only by the generated radiation-sensitive sensitizer, and that can degrade the component (c) or the group shown in (f) by radioactive ray sensitization, an amount of the acid generated can be selectively amplified in the patternwise exposed regions. The acid-catalyzed reaction in the base component following the acid generation is similar to the reaction in the conventional lithography process.

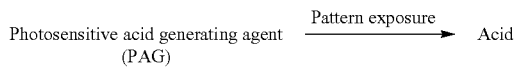

-continued

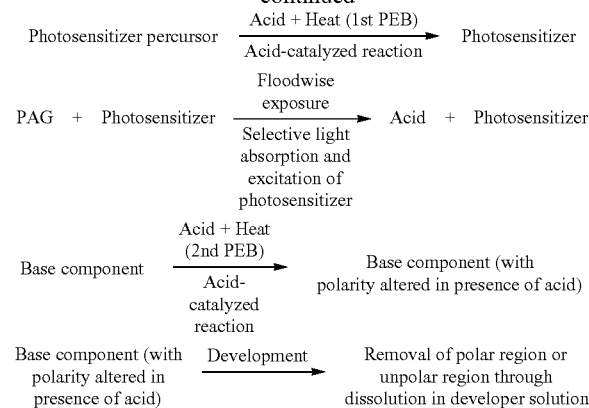

Next, reactions in lithography process according to the embodiment of the present invention will be explained for each step. The reaction is explained with reference mainly to the second reaction system, and reactions in the third and first reaction systems will be added as needed.

Reaction in Patternwise Exposure Step S3

In the patternwise exposure step S3, the resist material film is irradiated with the first radioactive ray (patternwise exposure). An example of a reaction expected in the case of the first radioactive ray being ionizing radiation will be shown below, mainly in the second reaction system. It should however be noted that the expected reaction is not limited to the reaction described below.

In the patternwise exposure step S3, the following reaction (first acid generating mechanism) takes place relating to the component (c) or the groups shown in (f). The component (c) is explained hereinafter as an example; however, the first acid generating mechanism likewise takes place in the group shown in (f).

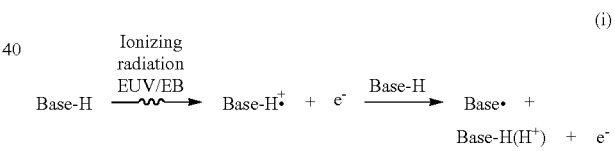

(i)

In the above formula (i), • denotes a free radical. In the above mentioned reaction, the base component (Base) is irradiated with the ionizing radiation (Ionizing radiation) such as extreme-ultraviolet rays (EUV)/electron beam (EB) and the like, to thereby ionize the base component and generate an electron.

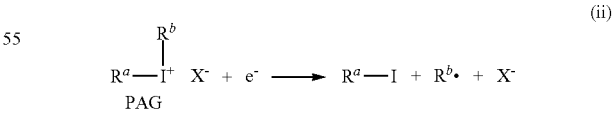

(ii)

$R^a R^b I^+ X^-$ in the above formula (ii) is an iodonium salt compound as an example of the component (c) (PAG). $X^-$ is an anion of acid, and $R^a$ and $R^b$ are as defined in $R^3$, $R^4$ and the like the above formula (1). In the above reaction, an electron generated from the above formula (i) is trapped by the component (c) or the group shown in (f), resulting in degradation as in the above formula. An anion of acid $X^-$ is thus generated.

(iii)

In the above reaction, a proton-added product of the base component generated in the above formula (i) reacts with the anion of acid X⁻ generated in the above formula (ii) and the like, to generate an acid. This is the first acid generating mechanism in the patternwise exposure step S3.

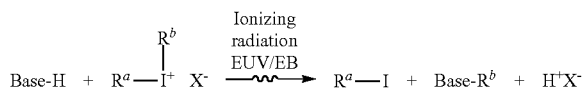
(iv)

The acid generating mechanism in the patternwise exposure step S3 can be assembled into the above formula (iv).

On the other hand, in the patternwise exposure step S3, for example, the following reaction (first radiation-sensitive sensitizer generating mechanism) takes place relating to the component (b) or the group shown in (e). It should however be noted that the reaction described herein is only a part and does not encompass all reaction mechanisms. The component (b) is explained hereinafter as an example; however, the first radiation-sensitive sensitizer generating mechanism likewise takes place in the group shown in (e). Hereinafter, a reaction example of the component (b) in the second reaction system, in other words the component (b) in a case in which the component (b) is an alcohol compound and a hydrogen atom in the hydroxyl group is not substituted, is explained.

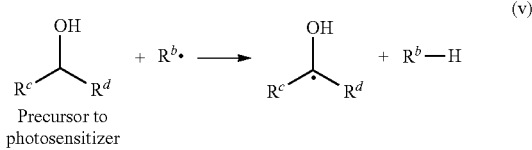
(v)

In the above formula (v), $R^cR^dCH(OH)$ is a secondary alcohol compound as an example of the component (b) (Precursor to photosensitizer). $R^c$ and $R^d$ are as defined in $R^8$ to $R^{10}$ and the like in the above formula (VI). In the above reaction, $R^b$. having a free radical generated in the above formula (ii) and the like reacts with the secondary alcohol compound to abstract hydrogen from the secondary alcohol compound and generate a secondary alcohol compound having a carbon radical on the carbon atom directly attached to the hydroxyl group.

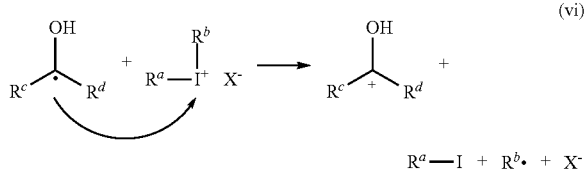
(vi)

In the above reaction, the carbon radical in the secondary alcohol compound passes an electron to the base component to which the component (c) or the group shown in (f) bonds, to degrade these. $R^b$ having a free radical generated through the degradation is further provided to a reaction of the above formula (v), and reactions of the above formulae (v) and (vi) thus proceed in a chain reaction. The chain reaction mechanism of the above formulae (v) and (vi) may be also referred to as a radical chain acid generating mechanism.

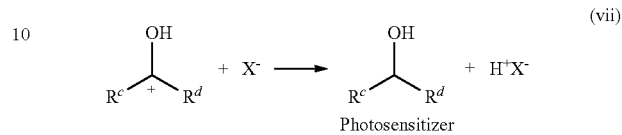
(vii)

A cation of the secondary alcohol compound generated in the above formula (vi) reacts with the anion of acid X⁻ generated in the above formula (vi) to generate a ketone compound, which is a radiation-sensitive sensitizer (Photosensitizer), and an acid. The ketone compound thus generated functions as the radiation-sensitive sensitizer in the floodwise exposure step S4. This is the first radiation-sensitive sensitizer generating mechanism in the patternwise exposure step S3.

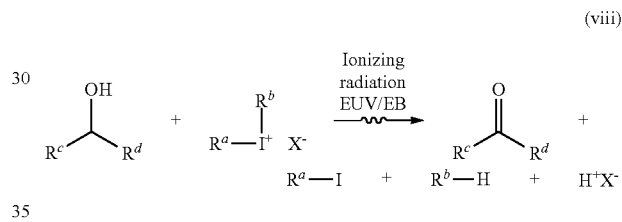
(viii)

The radiation-sensitive sensitizer generating mechanism of the alcohol compound in the patternwise exposure step S3 can be assembled into the above formula (viii).

Next, a reaction example of the case of the first radioactive ray being nonionizing radiation having a wavelength of no greater than 400 nm, preferably no greater than 250 nm, and more preferably no greater than 200 nm will be shown hereinafter.

In the patterning light exposing step S3, the following reaction (second acid generating mechanism) further takes place relating to the component (c) or the group shown in (f). The component (c) is explained hereinafter as an example; however, the second acid generating mechanism likewise takes place in the group shown in (f).

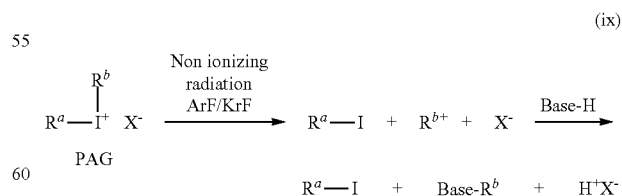
(ix)

In the above mentioned reaction, by irradiating an iodonium salt compound as an example of the component (c) (PAG) with an ionizing radiation such as ArF/KrF (Nonionizing radiation), the radiation-sensitive acid generating agent is directly excited and degrades to generate an acid. This is the second acid generating mechanism in the patternwise exposure step S3.

On the other hand, in the patternwise exposure step S3, the following reaction (radiation-sensitive sensitizer generating mechanism) takes place relating to the component (b) or the group shown in (e). The component (b) is explained hereinafter as an example; however, the second acid generating mechanism likewise takes place in the group shown in (e).

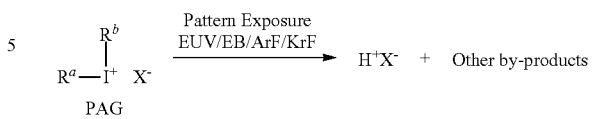

(xxvii)

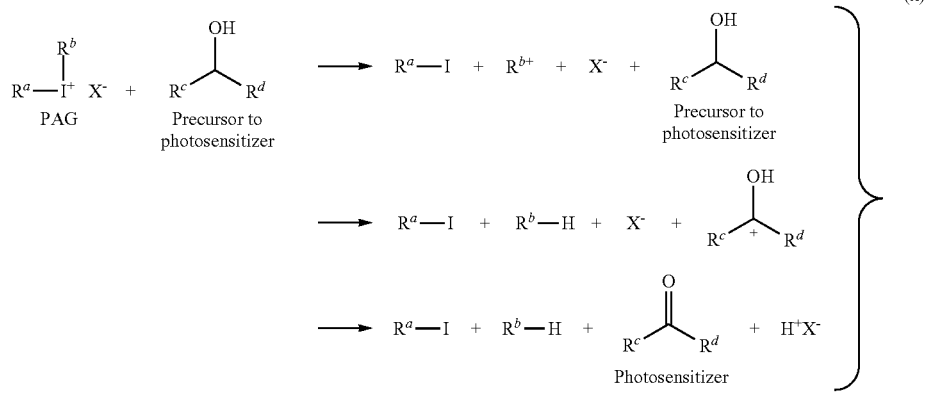

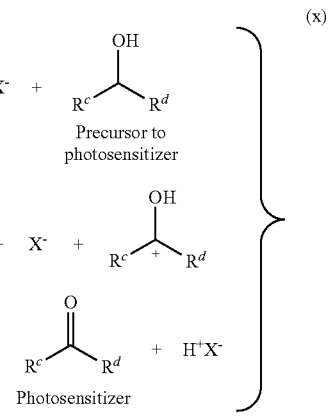

(x)

In the above described reaction, $R^{b+}$ cation generated from the iodonium salt compound abstracts hydrogen from a carbon atom directly attached to the hydroxyl group of the secondary alcohol compound, which is the component (b), thereby generating a carbocation of the secondary alcohol compound. As an anion $X^-$ of acid is paired with hydrogen ion of from the carbocation, an acid is generated and a ketone compound, which is a radiation-sensitive sensitizer, is simultaneously generated. This is an example of the second radiation-sensitive sensitizer generating mechanism in the patternwise exposure step S3. A ketone compound (carbonyl compound) that functions as a radiation-sensitive sensitizer can likewise be generated from an alcohol compound having an acetal compound group or a ketal compound group, through a hydrolysis deprotection reaction by a radioactive ray generating acid catalyst and the like.

In addition, in the case of the component (b) in the third reaction system, that is the component (b) being an acetal compound or a ketal compound, the radiation-sensitive sensitizer generating mechanism is partially different from the first radiation-sensitive sensitizer generating mechanism. First, the first and second radioactive ray acid generating mechanism generates an acid. The acid thus generated acts on the acetal compound or the ketal compound to generate a ketone compound, which is a radiation-sensitive sensitizer. In other words, the acid generated from the first and second radioactive ray acid generating mechanism functions as a catalyst for a reaction generating a ketone compound from the acetal compound or the ketal compound. The ketone compound thus generated acts as a radiation-sensitive sensitizer in the floodwise exposure step S4. This is the third radiation-sensitive sensitizer generating mechanism in the patternwise exposure step S3.

The third radiation-sensitive sensitizer generating mechanism in the patterning light exposing step S3 of the third reaction system will be described more specifically. First, as in the second system, an acid is generated as shown in the following formula (xxvii).

An acid generated upon the patternwise exposure acts as a catalyst to alter the structure of the component (b) or the group shown in (e), and a radiation-sensitive sensitizer is generated as described below. The reaction of changing the structure (deprotection reaction) can be accelerated by performing baking following the patternwise exposure, prior to the floodwise exposure. In addition, by performing the baking after reducing the reaction speed of the deprotection reaction by increasing activation energy of the structure alteration reaction, and trapping (neutralizing) an acid in the patternwise unexposed regions, contrast of the latent image of acid in the resist material film can be further improved. Furthermore, by increasing the activation energy of the deprotection reaction (bonding a protecting group hardly dissociated), storage stability of the chemically amplified resist material at normal temperature can be improved.

In the third reaction system, for example, the one with a carbonyl group substituted (protected) by a protecting group is considered as the component (b) or the group shown in (e). An acid generated upon the patternwise exposure acts as a catalyst to trigger a deprotection reaction of the component (b) or the group shown in (e), to generate a carbonyl compound as a radiation-sensitive sensitizer. In the radiation-sensitive sensitizer generated through this reaction, the absorption wavelength of the radioactive ray shifts toward a longer wavelength than the components (b) and (c) and the groups shown in (e) and (f). By performing the floodwise exposure with the nonionizing radiation having a wavelength that can be absorbed only by the generated radiation-sensitive sensitizer, the radiation-sensitive sensitizer can be selectively excited in the patternwise exposed regions.

Examples of the radiation-sensitive sensitizer generating agent that can be formed through protection of the carbonyl compound include: an acetal compound, a ketal compound, and an ortho ester compound.

In the case of using a ketal compound as the radiation-sensitive sensitizer generating agent, generation of the radiation-sensitive sensitizer through a deprotection reaction (acid-catalyzed hydrolysis reaction) takes place as in the following formula (xviii).

(xviii)

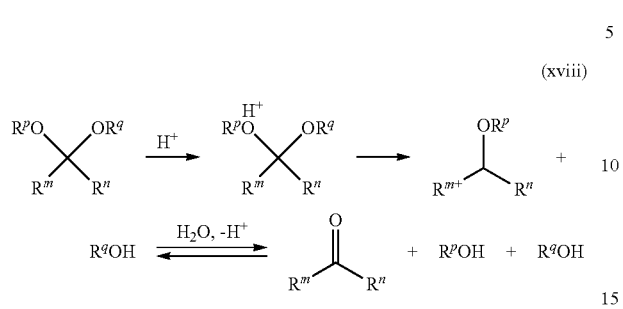

More specifically, the following acid-catalyzed hydrolysis reaction causes structure alteration from the ketal compound to the ketone compound.

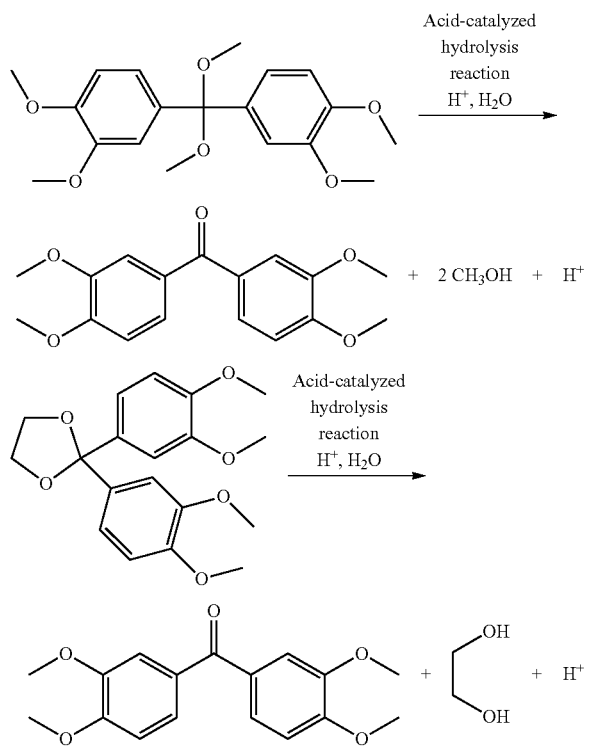

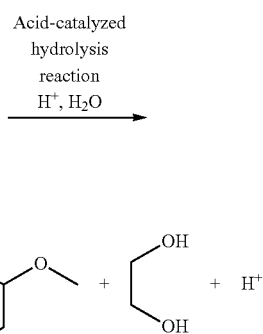

In the case of using an acetal compound as the radiation-sensitive sensitizer generating agent, generation of the radiation-sensitive sensitizer through a deprotection reaction (acid-catalyzed hydrolysis reaction) takes place as in the following formula (xix).

(xix)

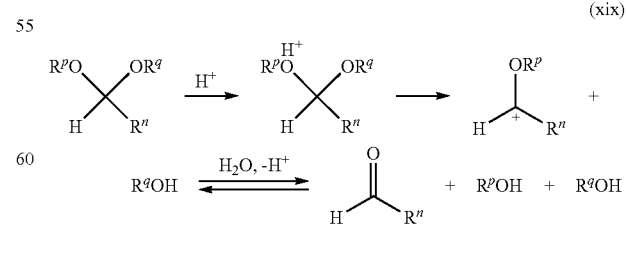

More specifically, the following acid-catalyzed hydrolysis reaction causes structure alteration from the acetal compound to the aldehyde compound.

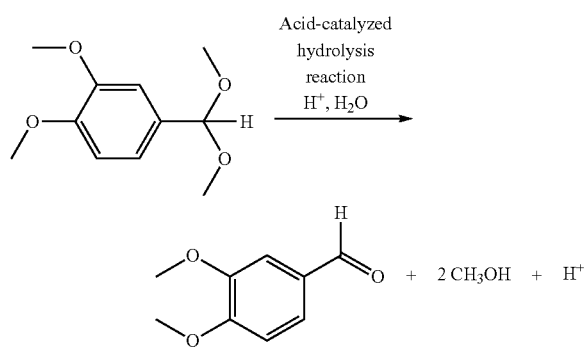

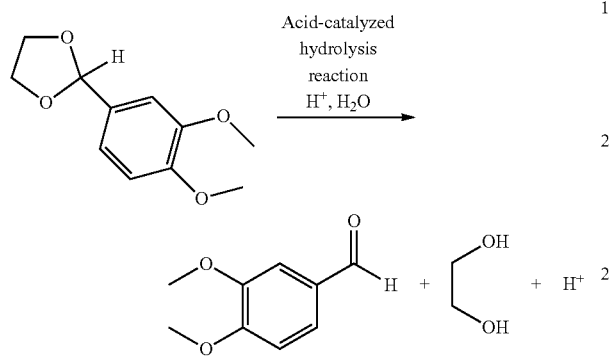

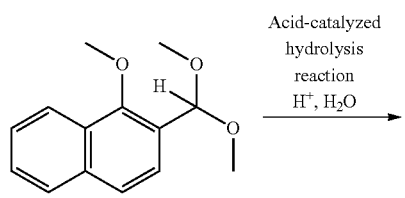

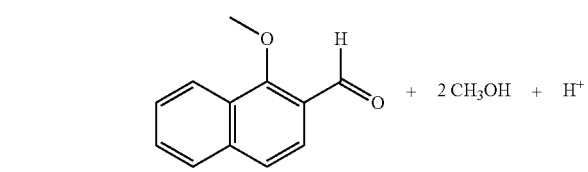

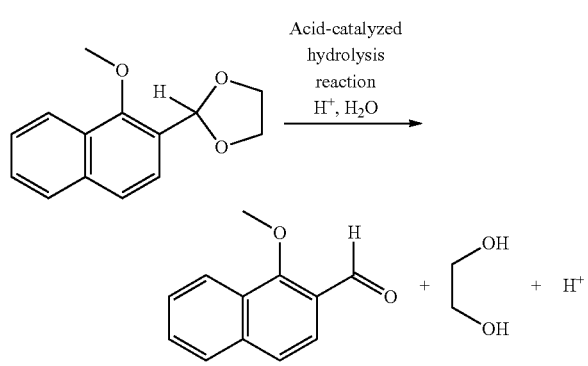

In the case of using an ortho ester compound as the radiation-sensitive sensitizer generating agent, generation of the radiation-sensitive sensitizer through a deprotection reaction (acid-catalyzed hydrolysis reaction) takes place as in the following formula (xx). The ortho ester compound is degraded to a carboxylic acid ester compound by the deprotection reaction.

(xx)

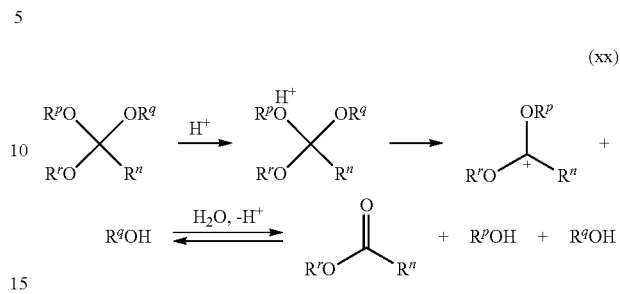

More specifically, the following acid-catalyzed hydrolysis reaction causes structure alteration from the ortho ester compound to the carboxylic acid ester compound.

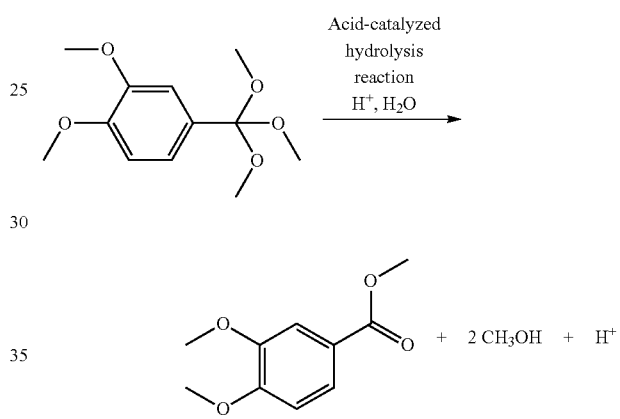

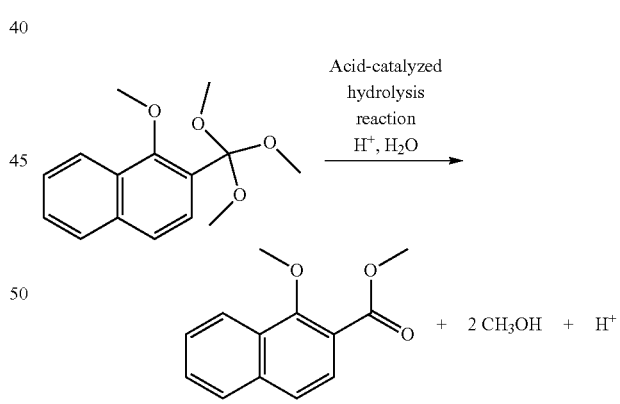

Among ortho ester compounds, an OBO ester compound in which carboxylic acid is protected by OBO (4-methyl-2,6,7-trioxabicyclo[2.2.2.2]octan-1-yl) generates carboxylic acid through a deprotection reaction as in the following formula (xxi). As a result, the radiation-sensitive sensitizer generating agent obtained by protecting by OBO can generate the radiation-sensitive sensitizer having a carboxyl group. By using this radiation-sensitive sensitizer, the radiation-sensitive sensitizer can be generated while increasing polarity of the resist material film, thereby improve dissolution contrast of the resist material film.

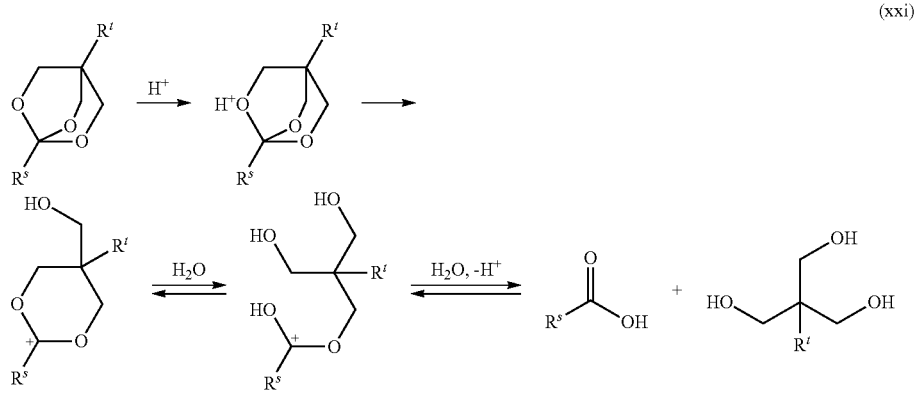

(xxi)

More specifically, the following acid-catalyzed hydrolysis reaction causes structure alteration from the OBO ester compound to the carboxylic acid.

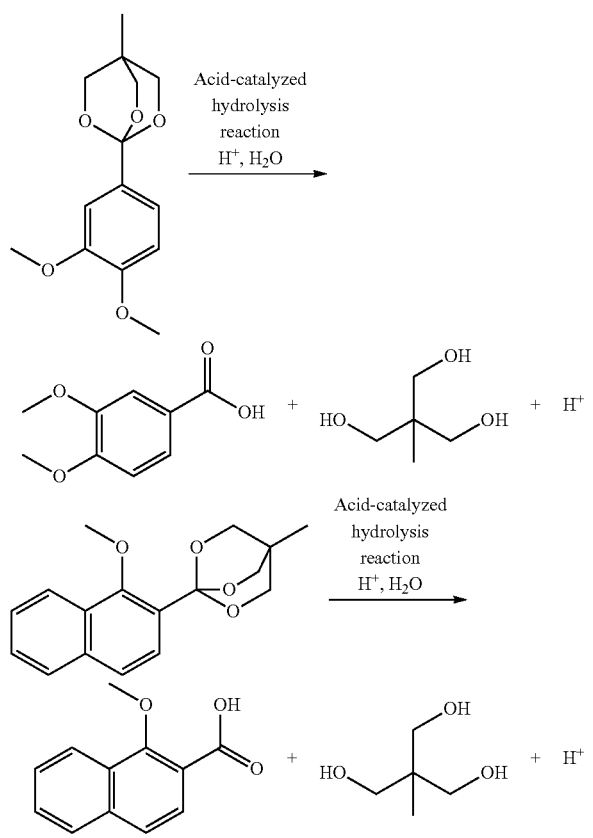

A reaction of generating the radiation-sensitive sensitizer in the first reaction system is as follows. In the first reaction system, the component (a), which generates an acid and a radiation-sensitive sensitizer by the patternwise exposure, generates the acid and the radiation-sensitive sensitizer simultaneously upon the patternwise exposure. An example will be shown below (sixth acid generating mechanism).

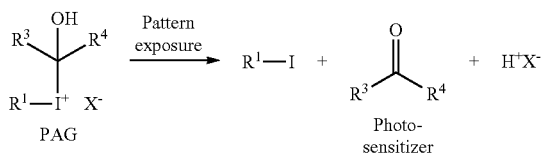

In the patternwise exposure step S3, both the acid generating mechanism and the radiation-sensitive sensitizer generating mechanism take place relating to the base component to which the component (a) or the group shown in (d) bonds.

In the embodiment of the present invention, the component (2) contains the component (a), any two among the components (a) to (c), or all of the components (a) to (c). Therefore, in the patternwise exposure step S3 in the embodiment of the present invention, both the acid generating mechanism and the radiation-sensitive sensitizer generating mechanism take place.

Reaction in Floodwise Exposure Step S4

In the floodwise exposure step S4, the resist material film is irradiated with the second radioactive ray (floodwise exposure). The radiation-sensitive sensitizer generating agent must have sufficiently small energy absorption of the patternwise exposure upon the patternwise exposure; however, energy of the patternwise exposure causes chemical structure alteration and generates the radiation-sensitive sensitizer. The chemical structure alteration shifts the light absorption spectrum in an ultraviolet ray region, and the radiation-sensitive sensitizer absorbs light on a longer-wavelength side than the radiation-sensitive sensitizer generating agent. It is desirable to select a material of the radiation-sensitive sensitizer generating agent so as to increase the light absorption shift through the chemical structure alteration. Examples of the chemical structure alteration include a chemical change from an alcohol compound or a ketal compound to a ketone compound. A reaction in the floodwise exposure step S4 will be shown below. The components (b) and (c) are explained hereinafter as examples; however, the same reaction takes place in the component (a), and the group shown in (d) to (f). With regard to amplification of the amount of the acid generated through the radioactive ray sensitization that takes place commonly in the first to third reaction systems, firstly examples in the second and third reaction systems will be mainly explained. These reactions involve excitation of the radiation-sensitive sensitizer by the floodwise exposure and acid generation through degradation of the radiation-sensitive acid generating agent caused by the excited radiation-sensitive sensitizer. Reaction mechanisms by which the excited radiation-sensitive sensitizer degrades the radiation-sensitive acid generating agent can be classified roughly into mechanisms that involve electron transfer and mechanisms that involve excitation transfer. Since these sensitization reactions take place as a chain reaction, an amount of acid generated upon the floodwise exposure can be greatly amplified and sensitivity of the resist is greatly improved.

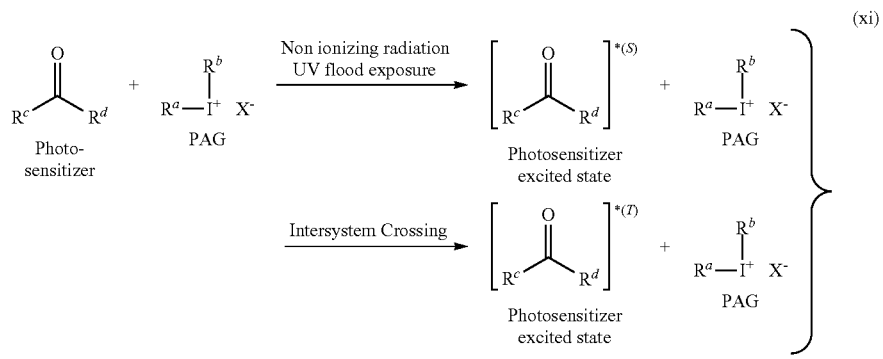

(xi)

S: Excitation to Singlet State, T: Excitation to Triplet State

In the formula (xi), $R^cR^dC=O$ is a ketone compound generated in the patternwise exposure step S3, and $R^aR^bI^+ X^-$ is an iodonium salt compound as an example of the component (c) (PAG) partially remaining after the patternwise exposure step S3. In addition, in the formula (xi), * denotes an excited state, *(S) denotes a singlet excited state and *(T) denotes a triplet excited state. In the above reaction, the ketone compound, which is a radiation-sensitive sensitizer generated in the patternwise exposure step S3, is excited through the irradiation with the nonionizing radiation. The excited ketone compound is firstly excited into a singlet excited state and then partially into a triplet excited state through intersystem crossing.

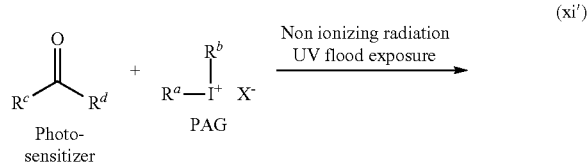

(xi')

The reaction of the above formula (xi) may also be expressed as the formula (xi') without specifying the singlet excited state and the triplet excited state.

In the floodwise exposure step S4, the radiation-sensitive sensitizer in the excited state indirectly degrades the component (c) (PAG) to generate an acid. As an acid generating mechanism in the floodwise exposure step S4, a third acid generating mechanism (electron transfer sensitizing type acid generating mechanism), a fourth acid generating mechanism (energy transfer sensitizing type acid generating mechanism), and a fifth acid generating mechanism (hydrogen abstracting type acid generating mechanism) may be mainly exemplified.

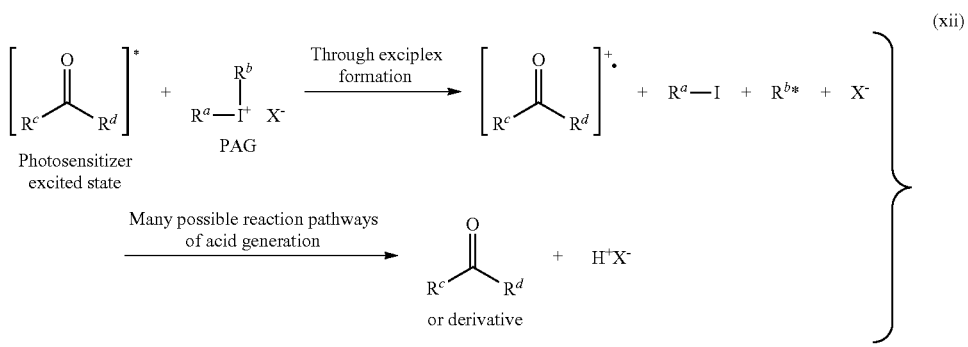

(xii)

The formula (xii) is a reaction formula representing the third acid generating mechanism (electron transfer sensitizing type acid generating mechanism). In the above reaction, an electron transfers from the excited ketone compound to the iodonium salt compound (PAG) remaining after the patternwise exposure step S3, and the iodonium salt compound degrades to generate a radiation-sensitive sensitizer and an acid. In order that the third acid generating mechanism may be realized through the electron transfer, it is necessary that oxidization potential of the radiation-sensitive sensitizer is sufficiently low, reduction potential of the PAG is sufficient high, energy of the floodwise exposure is high enough to permit the electron transfer, and free energy of the electron transfer reaction of the radioactive ray sensitization is negative and the reaction autonomously proceeds. In order to lower the oxidization potential of the radiation-sensitive sensitizer, use of a ketone compound in which conjugation extends to a ketone moiety and introduction of a highly electron-donating group are considered to be desirable.

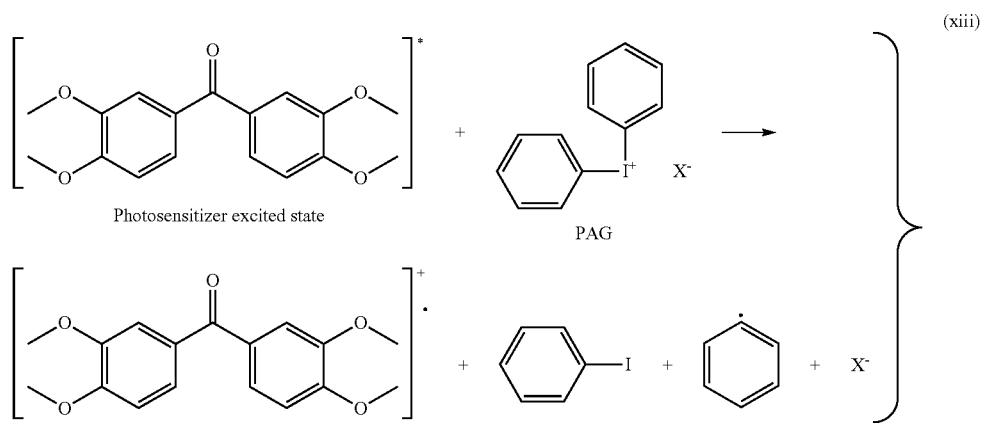

(xiii)

The above formula (xiii) is a specific example of the electron transfer that takes place in the third acid generating mechanism.

A cation radical of the radiation-sensitive sensitizer is generated through the electron transfer. A product of the formula (xiii) reacts as follows and generates an acid. The third acid generating mechanism (electron transfer sensitizing type acid generating mechanism) in a case in which a cation radical of the radiation-sensitive sensitizer has reacted with a phenyl radical is as follows.

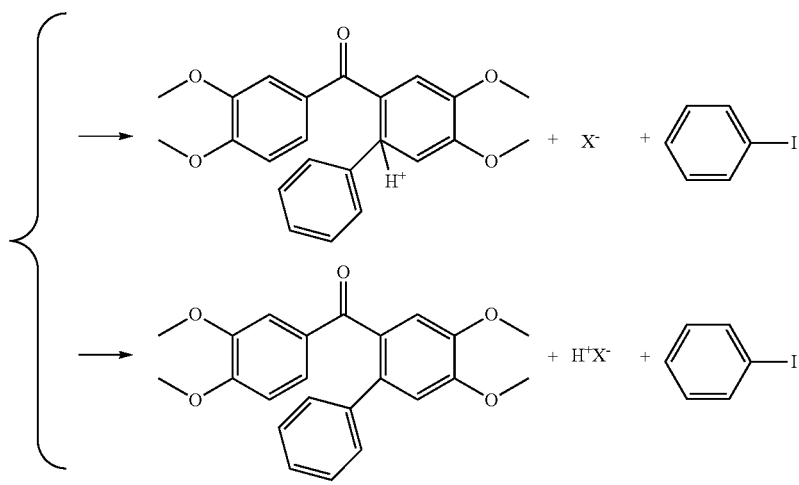

The third acid generating mechanism (electron transfer sensitizing type acid generating mechanism) in a case in which a cation radical of the radiation-sensitive sensitizer has reacted with a polymer (POLY-H) is as follows.

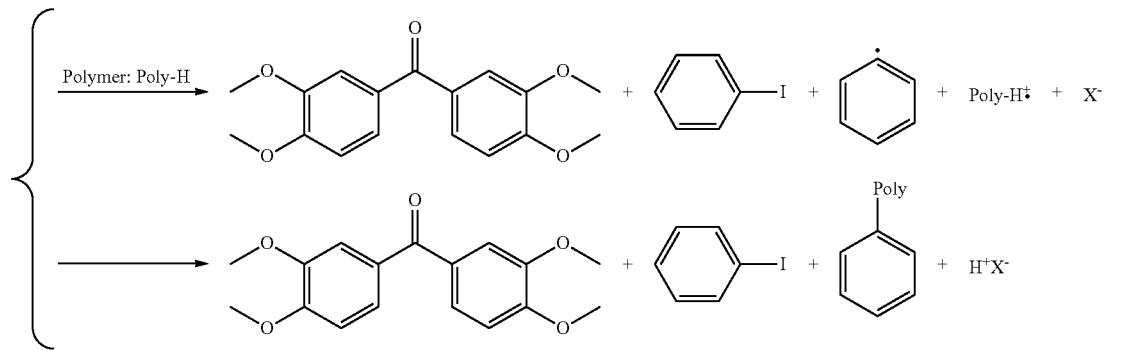

(xiv)

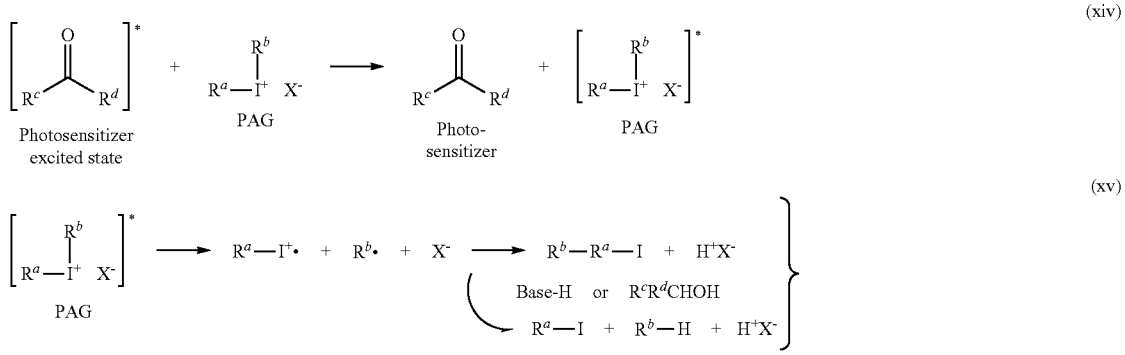

(xv)

The formula (xiv) and formula (xv) are reaction formulae representing the fourth acid generating mechanism (energy transfer sensitizing type acid generating mechanism). In the formula (xiv), an excited state is transferred from a ketone compound to an iodonium salt compound (triplet excitation transfer) and the radiation-sensitive sensitizer is generated, while in the formula (xv), an excited iodonium salt compound degrades to generate an acid. In the case of using the triplet sensitization reaction from the radiation-sensitive sensitizer to the PAG, it is necessary that the wavelength of the floodwise exposure is able to excite the radiation-sensitive sensitizer into a singlet excited state, and that an energy level of the triplet excited state of the radiation-sensitive sensitizer is higher than an energy level of the triplet excited state of the PAG.

(xvi)

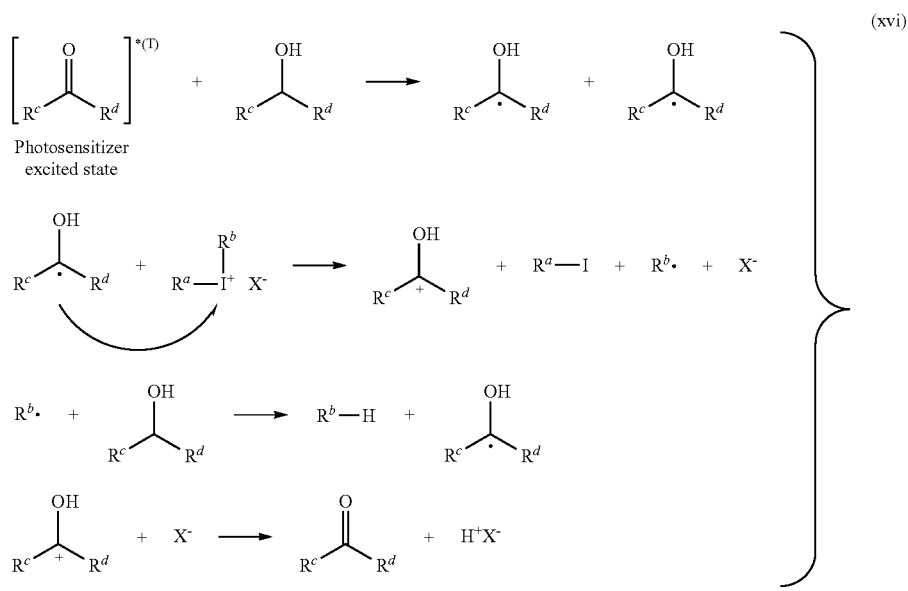

The formula (xvi) is a reaction formula representing a fifth acid generating mechanism (hydrogen abstracting type acid generating mechanism) in the case of the component (b) being a radiation-sensitive sensitizer generating agent having a hydroxyl group. In the above reaction, the excited ketone compound abstracts hydrogen from the secondary alcohol compound remaining after the patternwise exposure step S3 to generate a free radical, and an electron transfers from the generated radical to an iodonium salt compound to generate a radiation-sensitive sensitizer and an acid.

Also in the first reaction system, in the floodwise exposure, exposure is performed not with a radioactive ray having a wavelength mainly absorbed by the radiation-sensitive acid generating agent (PAG), which is the component (c), but with a radioactive ray having a wavelength mainly absorbed by the radiation-sensitive sensitizer. As a result, only in sites where the radiation-sensitive sensitizer is generated, an acid and a radiation-sensitive sensitizer (may be also referred to as "photosensitizer") are additionally generated (seventh acid generating mechanism). In the following formula, an iodonium salt is used as the radiation-sensitive acid generating agent (PAG); however, the acid is likewise generated even in the case of other radiation-sensitive acid generating agents such as sulfonium salt.

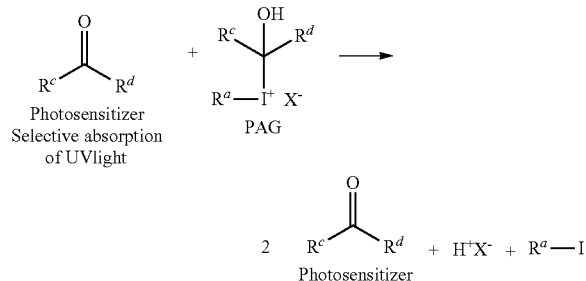

The pattern-forming method of the embodiment of the present invention including the patternwise exposure step S3 and the floodwise exposure step S4 can greatly increase the acid generated after exposure only in regions having been subjected to the patternwise exposure.

FIG. 1 is a graph showing absorbance of the patternwise exposed regions and the light-unexposed regions of the resist material film upon the floodwise exposure. A site not subjected to the patternwise exposure (patternwise unexposed region) of the resist material film exhibits absorbance of an ultraviolet ray having a comparatively short wavelength, while not exhibiting absorbance of an ultraviolet ray having a long wavelength. On the other hand, in a site subjected to the patternwise exposure (patternwise exposed regions) of the resist material film, the acid and the radiation-sensitive sensitizer are generated as described above. The radiation-sensitive sensitizer thus generated absorbs nonionizing radiation having a wavelength exceeding 200 nm, and exhibits absorbance of an ultraviolet ray having a comparatively long wavelength. In the floodwise exposure, unlike in the patternwise exposure, an entire surface of the resist material film is irradiated with a radioactive ray without using a mask; however, in the patternwise unexposed regions, absorbance of the second radioactive ray in the floodwise exposure step S4 is low. Therefore, in the floodwise exposure step S4, the above described third to fifth and seventh acid generating mechanisms take place in the patternwise exposed regions. As a result, upon the floodwise exposure, an acid can be continuously generated only in the patternwise exposed regions, and sensitivity can thus be improved while maintaining lithography characteristics.

Figure 2A:
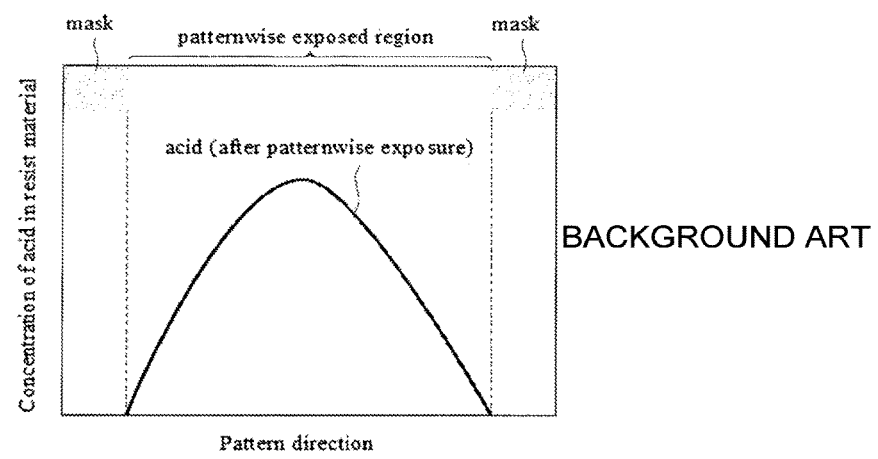
FIG. 2A shows a conceptual diagram showing the acid concentration distribution in the conventional chemically amplified resist material as a graph.
Figure 2B:
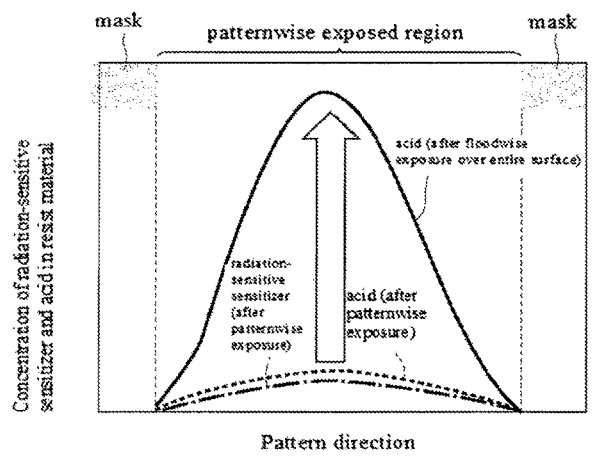
FIG. 2B is a conceptual diagram showing the radiation-sensitive sensitizer concentration distribution and the acid concentration distribution in the chemically amplified resist material according to an embodiment of the present invention as a graph.

FIG. 2A is a graph showing an acid concentration distribution in the conventional chemically amplified resist material. In the case of performing only the patternwise exposure with extreme-ultraviolet rays (EUV) and the like as in FIG. 7, a sufficient acid cannot be generated and sensitivity is lowered. Increasing the exposure dose for improving sensitivity deteriorates a latent image of the resist pattern (reduces lithography characteristics), thereby making it difficult to provide sensitivity and lithography characteristics simultaneously. FIG. 2B is a graph showing a radiation-sensitive sensitizer concentration distribution and an acid concentration distribution in the chemically amplified resist material according to the embodiment of the present invention. In the patternwise exposure, the latent image of the resist pattern is superior, while sufficient acid is not generated. However, following the floodwise exposure, an amount of the acid can be increased only in the patternwise exposed regions by the radiation-sensitive sensitizer generated in the patternwise exposure, and sensitivity can be thus improved with a small exposure dose while maintaining a superior latent image of the resist pattern. Since the acid generating mechanism by the radiation-sensitive sensitizer in the floodwise exposure takes place at room temperature, blurring of the latent image upon acid generation is mild, thereby allowing great increase in sensitivity while maintaining the resolution.

Figure 3A:
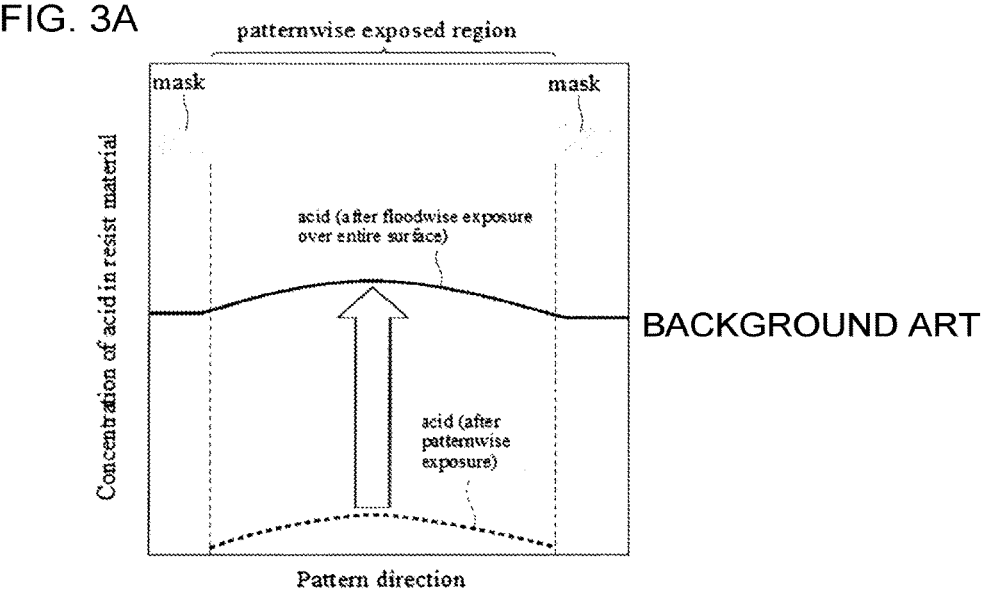
FIG. 3A shows a conceptual diagram showing the acid concentration distribution in the conventional chemically amplified resist material as a graph.
Figure 3B:
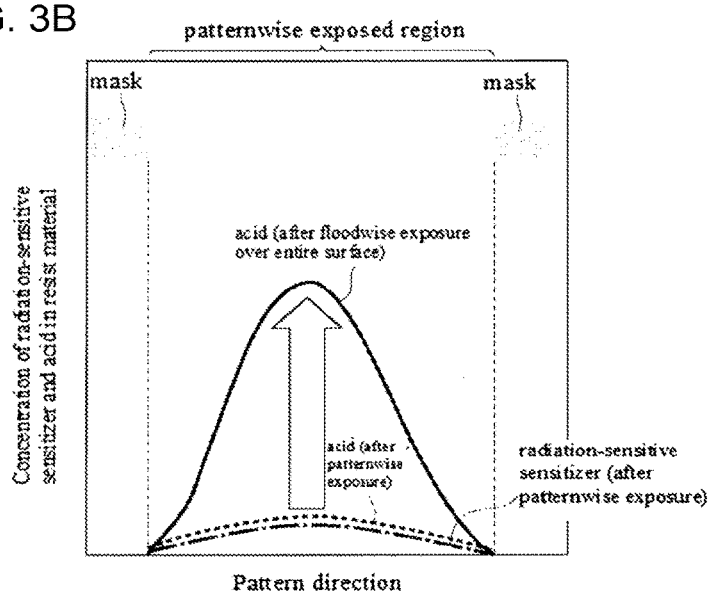
FIG. 3B is a conceptual diagram showing the radiation-sensitive sensitizer concentration distribution and the acid concentration distribution in the chemically amplified resist material according to an embodiment of the present invention as a graph.

FIG. 3A is a graph showing an acid concentration distribution in the conventional chemically amplified resist material, showing an acid concentration distribution in the case of performing both the patternwise exposure and the floodwise exposure by extreme-ultraviolet rays (EUV) and the like. In spite of small amount of the acid generated in the patternwise exposure, a superior latent image of the resist pattern is maintained. However, in the floodwise exposure, the acid is generated in the entire surface of the resist material film. Increasing the exposure dose for improving sensitivity deteriorates a latent image of the resist pattern (reduces lithography characteristics), thereby making it difficult to provide sensitivity and lithography characteristics simultaneously. FIG. 3B is, similarly to FIG. 2B, a graph showing a radiation-sensitive sensitizer concentration distribution and an acid concentration distribution in the chemically amplified resist material according to the embodiment of the present invention. Also in FIG. 3B, similarly to FIG. 2B, an amount of the acid can be increased only in the patternwise exposed regions, and sensitivity can be thus improved with a small exposure dose while maintaining a superior latent image of the resist pattern.

Semiconductor Device

A semiconductor device according to the embodiment of the present invention is produced by using the pattern formed by the above described method. FIG. 6 is a cross sectional view illustrating an example of a production step of the semiconductor device of the embodiment of the present invention.

Figure 6A:
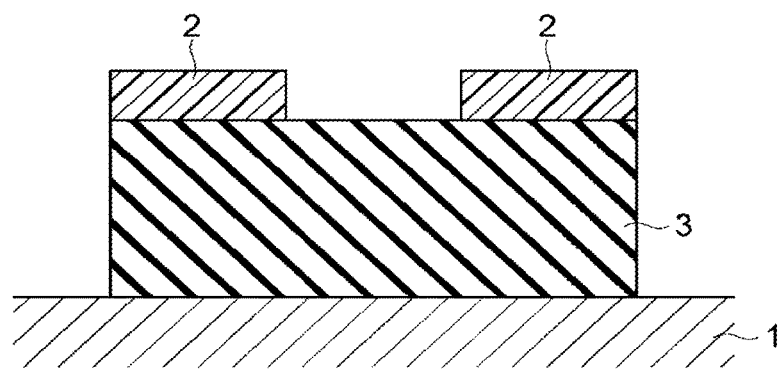
Figure 6B:
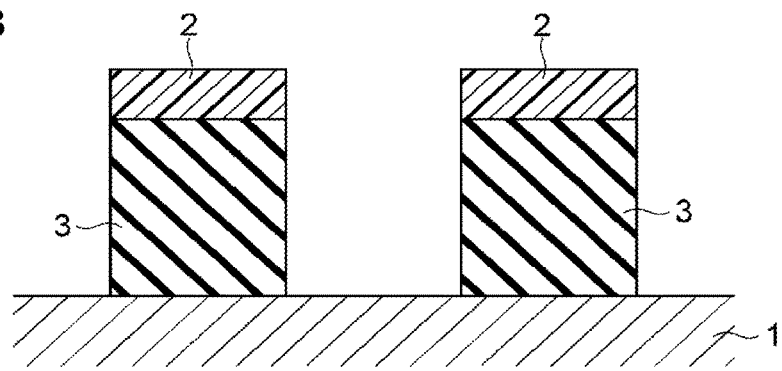
Figure 6C:
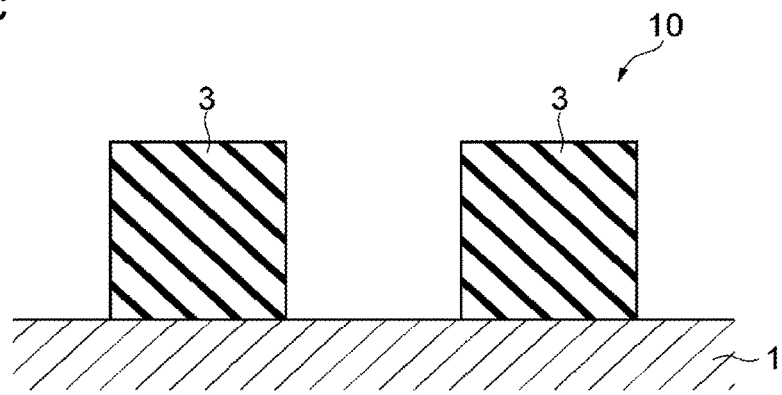

FIG. 6A is a cross-sectional view showing a resist pattern forming step, the cross-sectional view illustrating a semiconductor wafer 1, a film 3 which is to be etched and formed on the semiconductor wafer 1, and a resist pattern 2 formed on the film 3 by the above described pattern-forming method (corresponding to a state after completion of the developing step S6). Examples of the film include: an active layer, an under layer insulating film, a gate electrode film, and an upper layer insulating film. Between the film 3 and the resist pattern 2, an antireflective film, an underlayer film for resist adhesiveness amelioration, or an underlayer film for resist shape amelioration may be provided. In addition, a multi-layer mask structure may also be employed. FIG. 6B is a cross sectional view showing an etching step, the cross-sectional view illustrating a semiconductor wafer 1, the resist pattern 2, and the film 3 being etched with the resist pattern 2 as a mask. The film 3 has been etched according to a shape of openings in the resist pattern 2. FIG. 6C is a cross sectional view of a patterned substrate 10 with the semiconductor wafer 1 and a pattern of the film 3 being etched, after removal of the resist pattern 2.

A semiconductor device can be formed by using a substrate provided with the pattern of the film 3. Examples of the forming method thereof include a method of embedding wiring between the pattern of the film 3 from which the resist pattern 2 has been removed, and then overlaying a device element onto the substrate.

Lithography Mask

A lithography mask according to the embodiment of the present invention is produced by processing a substrate using the resist pattern formed by the above described method. Examples of the production method thereof include a method of using the resist pattern for etching of a surface of a glass substrate or of a hard mask formed on a surface of a glass substrate. Here, the lithography mask includes a transmissive mask using an ultraviolet ray or an electron beam, and a reflection type mask using EUV light. In the case of the lithography mask being a transmissive mask, the lithography mask can be produced by processing by etching while masking a light shielding part or a phase shift part with the resist pattern. On the other hand, in the case of the lithography mask being a reflection type mask, the lithography mask can be produced by processing a light absorbing body with the resist pattern as a mask.

Nanoimprinting Template

A nanoimprinting template according to the embodiment of the present invention can also be produced by using the resist pattern formed by the above described method. Examples of the production method thereof include a method of forming a resist pattern on a surface of a glass substrate or on a surface of a hard mask formed on a surface of a glass substrate, and then processing by etching.

EXAMPLES

Hereinafter, the present invention is explained in detail by way of Examples, but the present invention is not in any way limited to these Examples. Measuring methods of physical property values in the present Examples are described below.

Weight Average Molecular Weight (Mw) and Number Average Molecular Weight (Mn)

Mw and Mn of a polymer were measured by gel permeation chromatography (GPC) with mono-dispersed polystyrene as a standard, using GPC columns (G2000 HXL×2, G3000 HXL×1 and G4000 HXL×1 (each available from Tosoh Corporation) under analysis conditions of: flow rate: 1.0 mL/min; elution solvent: tetrahydrofuran; sample concentration: 1.0% by mass; amount of injected sample: 100 μL; and column temperature: 40° C., using a differential refractometer as a detector.

$^{13}$C-NMR Analysis $^{13}$C-NMR analysis for determination of the proportion of the structural unit in the polymer was conducted by using a nuclear magnetic resonance apparatus ("JNM-ECX400" from JEOL, Ltd.), and DMSO-$d_6$ as a solvent for measurement, with tetramethylsilane (TMS) as an internal standard.

Synthesis of Base Component (1)

Monomers used in the synthesis of the base component (1) are shown below.

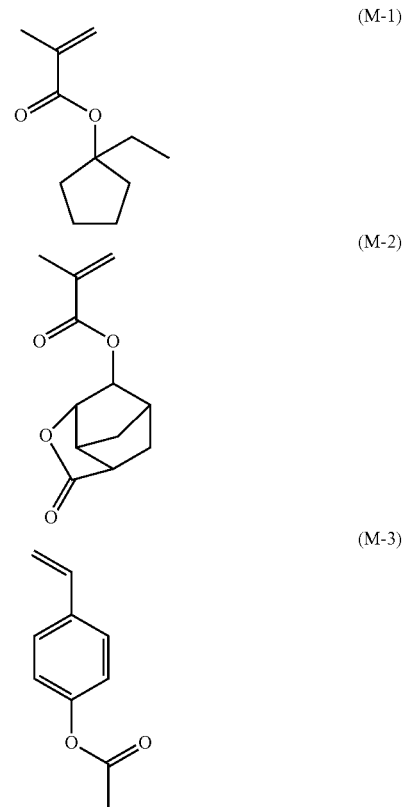

Synthesis Example 1

55 g (50 mol %) of the compound (M-1), 45 g (50 mol %) of the compound (M-2) and 3 g of azobisisobutyronitrile (AIBN) were dissolved in 300 g of methyl ethyl ketone, followed by polymerizing for 6 hrs under a nitrogen atmosphere while maintaining a reaction temperature at 78° C. Following the polymerization, a reaction solution was added to 2,000 g of methanol dropwise to permit solidification of the polymer. Thereafter, the polymer was washed twice with 300 g of methanol and white powder thus obtained was filtered, followed by drying at 50° C. overnight under a reduced pressure, thereby obtaining a polymer (A-1) served as the base component (1). The polymer (A-1) has the Mw of 7,000 and the Mw/Mn of 2.10. In addition, the result of $^{13}$C-NMR analysis indicated that the proportions of the structural units derived from the compound (M-1) and the compound (M-2) were respectively 52 mol % and 48 mol %.

Synthesis Example 2

55 g (42 mol %) of the compound (M-3), 45 g (58 mol %) of the compound (M-1), 3 g of AIBN and 1 g of t-dodecyl mercaptan were dissolved in 150 g of propylene glycol monomethyl ether, followed by polymerizing for 16 hrs under a nitrogen atmosphere while maintaining a reaction temperature at 70° C. Following the polymerization, a reaction solution was added to 1,000 g of n-hexane dropwise to permit solidification and purification of a polymer. Subsequently, 150 g of propylene glycol monomethyl ether was added again to the polymer, then 150 g of methanol, 37 g of trimethylamine and 7 g of water were further added thereto, and a hydrolysis reaction was allowed to proceed for 8 hrs with refluxing at the boiling point to permit deacetylation of the structural unit derived from (M-3). After the reaction, the solvent and triethylamine were distilled off under reduced pressure, the resulting polymer was dissolved in 150 g of acetone, and then the solution thus obtained was added to 2,000 g of water dropwise to permit solidification of the polymer. The white powder thus formed was filtered off, followed by drying at 50° C. overnight under a reduced pressure to obtain a polymer (A-2), which served as (1) base component. The polymer (A-2) had the Mw of 6,000 and the Mw/Mn of 1.90. In addition, the result of $^{13}$C-NMR analysis indicated that the proportions of the structural units derived from p-hydroxystyrene and (M-1) were 50 mol % and 50 mol %, respectively.

TABLE 2

| (1) Base Component | Monomer type | Proportions of structural units (% by mole) | Mw | Mw/Mn |
|---|---|---|---|---|
| Synthesis Example 1 | S-1 | M-1 52 | 7,000 | 2.10 |
|  |  | M-2 48 |  |  |
| Synthesis Example 2 | S-2 | M-1 50 | 6,000 | 1.90 |
|  |  | M-3 50 |  |  |

(2) Component
(b) Radiation-Sensitive Sensitizer Generating Agent

The following compounds were used as the radiation-sensitive sensitizer generating agent (b).
B-1: a compound represented by the following formula (B-1)
B-2: a compound represented by the following formula (B-2)

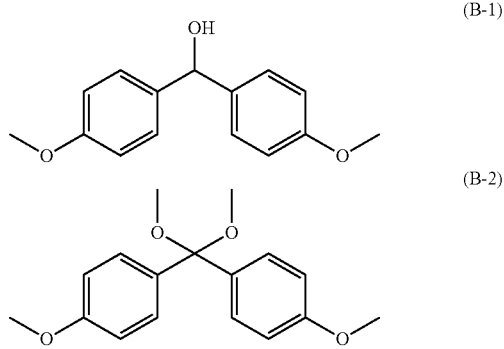

Absorbance Measurement of Component (b)

The component (b) and the sensitizing agent derived from the component (b) are shown together in Table 3. With respect to each of the components (b) and the sensitizing agents derived from the components (b), a 0.0001% by mass cyclohexane solution thereof was prepared. The absorbance of the solution prepared thus was measured using cyclohexane as a reference solvent and a spectrophotometer ("V-670" available from JASCO Corporation).

At each wavelength falling within the range of no less than 250 nm and no greater than 600 nm, the absorbance was determined by subtracting the absorbance of the reference solvent from the absorbance of the solution to be measured. The absorbance was evaluated to be: "transparent" in a case where the measurement value of the absorbance was less than 0.01 over the entire wavelength range of no less than 300 nm and no greater than 450 nm; and "absorbing" in a case where the measurement value of the absorbance was no less than 0.01 at least one wavelength within the entire wavelength range of no less than 300 nm and no greater than 450 nm. The results of the evaluations are shown in Table 4. It is to be noted that the transmittance of cyclohexane which was a solvent used for the measurement of the absorption spectrometry was ascertained to be no less than 95% at each wavelength falling within the range of no less than 250 nm and no greater than 600 nm.

TABLE 3

| | (b) Component | Compound name of component (b) | Sensitizing agent derived from component (b) | Compound name of sensitizing agent derived from component (b) |
|---|---|---|---|---|
| Synthesis Example 3 | B-1 | bis(4-methoxyphenyl)methanol | D-1 | 4,4'-dimethoxybenzophenone |
| Synthesis Example 4 | B-2 | 4,4'-dimethoxybenzophenone dimethyl ketal | D-2 | 4,4'-dimethoxybenzophenone |

TABLE 4

| | (b) Component | Absorbance (300-450 nm) | Sensitizing agent derived from component (b) | Absorbance (300-450 nm) |
|---|---|---|---|---|
| Synthesis Example 3 | B-1 | transparent | D-1 | absorbing |
| Synthesis Example 4 | B-2 | transparent | D-2 | absorbing |

Radiation-Sensitive Acid Generating Agent (c)

C-1: a compound represented by the following formula (C-1)

C-2: a compound represented by the following formula (C-2)

C-3: a compound represented by the following formula (C-3)

C-4: a compound represented by the following formula (C-4)

C-5: a compound represented by the following formula (C-5)

C-6: a compound represented by the following formula (C-6)

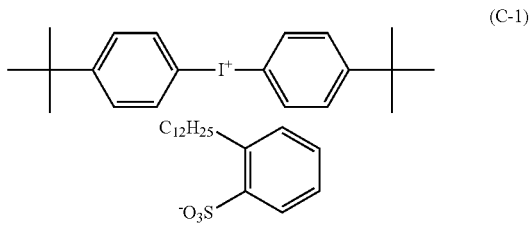

-continued (C-2)
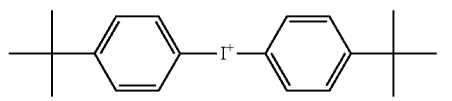

(C-3)
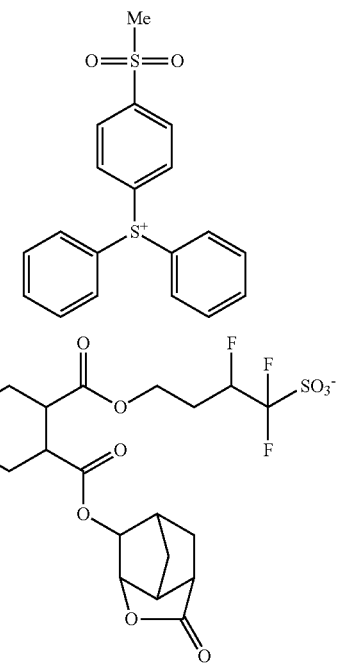

(C-4)
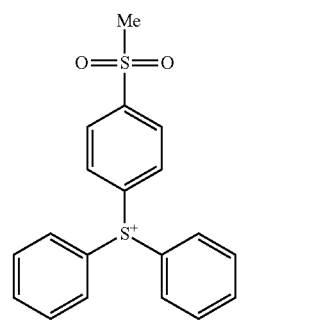
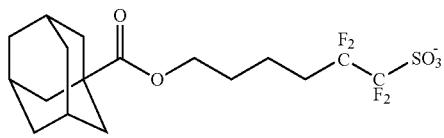

(C-5)
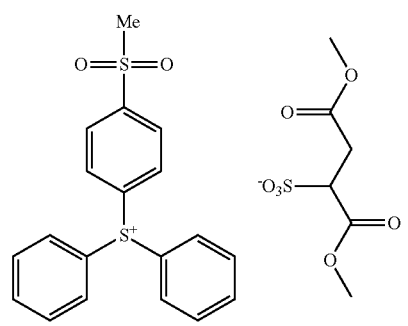

-continued (C-6)
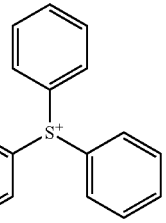
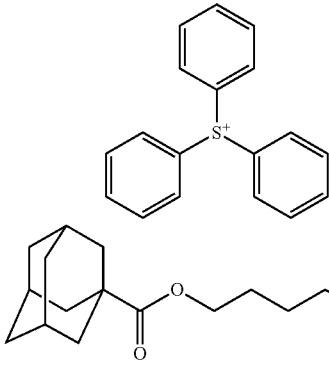

Van der Waals Radius of Acid Generated from Component (2)

With regard to the compounds (C-1) to (C-6), van der Waals volumes of acids generated from these compounds are shown in Table 4.

Energy Released upon Reduction of Cation in Component (2) to Radical

Furthermore, with regard to the compounds (C-1) to (C-6), calculated results of energy released upon reduction of a cation in these compounds to a radical are shown in Table 5. Here, after carrying out structure optimization of each cation and radical, an energy level of each substance was obtained by the B3LYP/LANL2DZ method, and then the energy was calculated from an energy difference between a cation and a radical.

TABLE 5

| (c) Component | van der Waals volume of generated acid ($\times 10^{-28}$ m$^3$) | Energy released from cation (eV) |
| --- | --- | --- |
| C-1 | 3.30 | 5.75 |
| C-2 | 1.65 | 5.75 |
| C-3 | 3.93 | 5.33 |
| C-4 | 3.34 | 5.33 |
| C-5 | 1.72 | 5.33 |
| C-6 | 3.34 | 4.92 |

Preparation of Chemically Amplified Resist Material

Components other than the base component (1) and the component (2) which were used for preparation of the chemically amplified resist material are described below.

First Trapping Agent

E-1: a compound represented by the following formula (E-1) (Radioactive ray-reactive first trapping agent (Radioactive ray-degradable type trapping agent))

E-2: a compound represented by the following formula (E-2) (Radioactive ray-unreactive first trapping agent)

(E-1)
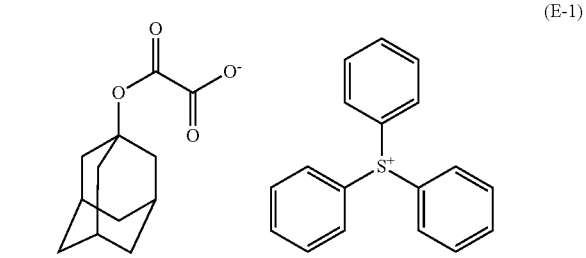

-continued

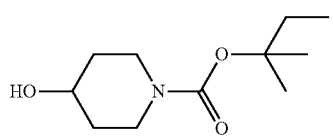
(E-2)

Solvent
G-1: propylene glycol monomethyl ether acetate
G-2: ethyl lactate

Example 1

The chemically amplified resist material (R-1) was prepared by mixing 100 parts by mass of the base component (1) (S-1), 5 parts by mass of (B-1) which served as radiation-sensitive sensitizer generating agent (b), 21 parts by mass of (C-1) which served as radiation-sensitive acid generating agent (c), 2.5 parts by mass of (E-1) which served as the first trapping agent, and 4,300 parts by mass of (G-1) and 1,900 parts by mass of (G-2) which served as the solvent, and then filtering a mixture solution thus obtained with a membrane filter of 0.20 μm in pore size.

Examples 2 to 5 and Comparative Examples 1 to 4

Each chemically amplified resist material was prepared by a similar operation to that for Example 1, except for using components of the types and in proportions specified in Table 6. It is to be noted that "-" indicates the absence of the component.

pattern (1L 1S) obtained by using a mask configured with a line part having a line width of 150 nm and a spaces part formed by neighboring line parts with an interval of 150 nm. After the irradiation with the electron beam for patterning, the following operation (a) or (b) was performed.

Operation (a): Without Floodwise Exposure

After the irradiation with the electron beam, PEB was carried out at 110° C. for 60 sec in the CLEAN TRACK ACT-8. Then, a development was carried out according to the puddle procedure at 23° C. for 1 min using a 2.38% by mass aqueous tetramethylammonium hydroxide (THAM) solution in the CLEAN TRACK ACT-8. After the exposure, the substrate was washed with pure water, followed by drying, whereby a positive resist pattern was formed.

Operation (b): With Floodwise Exposure

After the irradiation with the electron beam, the entire face of the resist film was subjected to the floodwise exposure for 10 min using a black light lamp (Toshiba Corporation, wavelength: 320 nm). Subsequently, in the CLEAN TRACK ACT-8, PEB was carried out under conditions of 110° C. and 60 sec. Thereafter, development, washing and drying was carried out in a similar manner to that in the operation (a), whereby a positive resist pattern was formed.

Examples 2 to 4 and Comparative Examples 1 to 4

Each resist pattern was formed by a similar operation to that for Example 1 except that the chemically amplified resist material as shown in Table 5 was used.

Evaluations

TABLE 6

| | Chemically amplified resist material | (1) Base component type | proportion (parts by mass) | (2) Component component (b) type | proportion (parts by mass) | component (c) type | proportion (parts by mass) | First trapping agent type | proportion (parts by mass) | Solvent type | proportion (parts by mass) |
|---|---|---|---|---|---|---|---|---|---|---|---|
| Example 1 | R-1 | S-1 | 100 | B-1 | 5 | C-1 | 21 | E-1 | 2.5 | G-1/G-2 | 4,300/1,900 |
| Example 2 | R-2 | S-2 | 100 | B-2 | 5 | C-3 | 24 | E-1 | 2.5 | G-1/G-2 | 4,300/1,900 |
| Example 3 | R-3 | S-2 | 100 | B-2 | 5 | C-3 | 24 | E-2 | 2.5 | G-1/G-2 | 4,300/1,900 |
| Example 4 | R-4 | S-2 | 100 | B-2 | 5 | C-4 | 21 | E-2 | 2.5 | G-1/G-2 | 4,300/1,900 |
| Example 5 | R-5 | S-2 | 100 | B-2 | 5 | C-6 | 19 | E-2 | 2.5 | G-1/G-2 | 4,300/1,900 |
| Comparative Example 1 | R-6 | S-1 | 100 | B-1 | 5 | C-2 | 20 | E-1 | 2.5 | G-1/G-2 | 4,300/1,900 |
| Comparative Example 2 | R-7 | S-1 | 100 | — | — | C-1 | 21 | E-1 | 2.5 | G-1/G-2 | 4,300/1,900 |
| Comparative Example 3 | R-8 | S-2 | 100 | B-2 | 5 | C-5 | 16 | E-2 | 2.5 | G-1/G-2 | 4,300/1,900 |
| Comparative Example 4 | R-9 | S-2 | 100 | — | — | C-3 | 24 | E-2 | 2.5 | G-1/G-2 | 4,300/1,900 |

Formation of Resist Pattern

Example 1

The chemically amplified resist material (R-1) was spin-coated onto a silicon wafer in "CLEAN TRACK ACT-8" available from Tokyo Electron Limited, and subjected to PB at 100° C. for 60 sec to form a resist material film having an average thickness of 50 nm. Subsequently, the resist material film was irradiated with an electron beam using a simplified electron beam writer ("HL800D" available from Hitachi, Ltd., power: 50 KeV, current density: 5.0 ampere/cm$^2$) to permit patterning. The patterning was a line and space The positive resist patterns formed in Examples and Comparative Examples described above were evaluated for the sensitivity and the nanoedge roughness according to the following procedure.

Sensitivity

An exposure dose at which a line and space pattern (1L 1S) configured with a line part having a line width of 150 nm and a space part formed by neighboring line parts with an interval of 150 nm was formed to give a line width of 1:1 was defined as "optimal exposure dose", and the "optimal exposure dose" was used as a reference for the sensitivity. The sensitivity was evaluated to be: "AA (extremely favorable)" in the case of the optimal exposure dose being less than 30 μC/cm²; "A (favorable)" in the case of no less than 30 μC/cm² and no greater than 35 μC/cm²; and "B (unfavorable)" in the case of greater than 35 μC/cm². Measured values of the optimal exposure dose and evaluation results of the sensitivity are shown in Table 6.

Nanoedge Roughness

Figure 8:
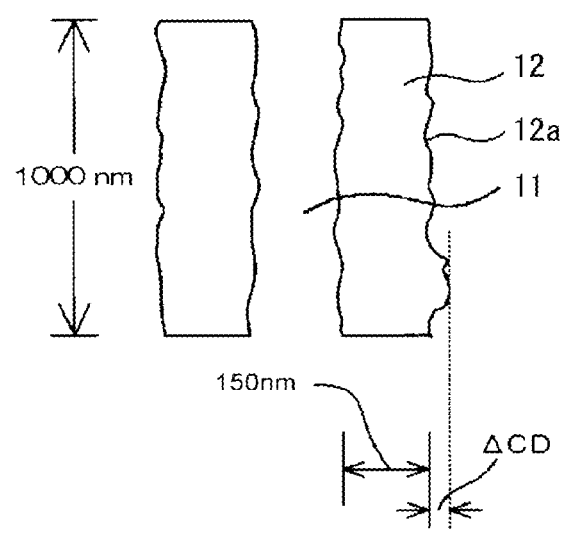
FIG. 8 shows a schematic plan view illustrating the nanoedge roughness of a pattern.
Figure 9:
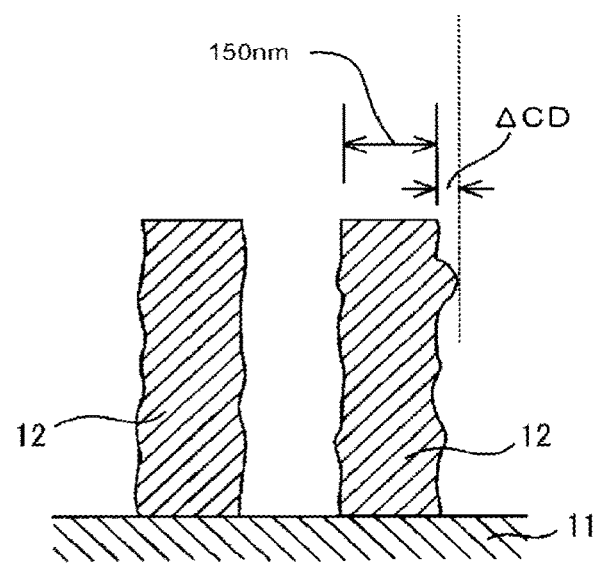
FIG. 9 shows a schematic cross sectional view illustrating the nanoedge roughness of the pattern.

The line patterns of the line and space pattern (1L 1S) were observed using a high-resolution FEB critical dimension measurement device (S-9220, available from Hitachi, Ltd.) at arbitrary twenty points on the line pattern. With respect to the points at which the observation was made, as shown in FIGS. 8 and 9, a difference "ΔCD" between an intended line width of 150 nm and a line width in an area in which irregularities generated along side lateral surface 12a of the line part (resist pattern) 12 of the pattern formed on the substrate (silicon wafer) 11 was most significant was measured. The average value of the ΔCD of the twenty points was used as a standard for nanoedge roughness. The nanoedge roughness was evaluated to be: "AA (extremely favorable)" in the case of the average value of ΔCD (nm) being no greater than 15.0 nm; "A (favorable)" in the case of greater than 15.0 nm and no greater than 16.5 nm; and "B (unfavorable)" in the case of greater than 16.5 nm. It is to be noted that the irregularities shown in FIGS. 8 and 9 are exaggerated. The average values of the ΔCD and evaluation results of the nanoedge roughness are shown in Table 7.

On the other hand, for the Comparative Examples 2 and 4 containing only the component (c), an evaluation for the operation (a) and an evaluation for the operation (b) are substantially equal, and no advantage could be found in employing these chemically amplified resist material in a process carrying out two exposures. Furthermore, in Comparative Examples 1 and 3 in which the van der Waals radius of the generated acid is smaller than $3.0 \times 10^{-28}$ m³, the nanoedge roughness in the operation (b) was high and variance in the shape of pattern was large.

As explained in the foregoing, the chemically amplified resist material of the embodiment of the invention can achieve both high sensitivity and superior lithographic characteristics at a sufficiently high level. Formation of a fine pattern is thus possible even in the case of employing a low-power light source in the patternwise exposure step. The chemically amplified resist material may therefore be suitably used for formation of a resist pattern in a lithography step for various types of electronic device such as a semiconductor device, a liquid crystal device and the like.

Obviously, numerous modifications and variations of the present invention are possible in light of the above teachings. It is therefore to be understood that within the scope of the appended claims, the invention may be practiced otherwise than as specifically described herein.

TABLE 7

| | Chemically amplified resist material | Evaluation results of operation(a) | | | | Evaluation results of operation(b) | | | |
|---|---|---|---|---|---|---|---|---|---|
| | | sensitivity | | nanoedge roughness | | sensitivity | | nanoedge roughness | |
| | | optimum exposure dose (μC/cm²) | evaluation | average value of ΔCD (nm) | evaluation | optimum exposure dose (μC/cm²) | evaluation | average value of ΔCD (nm) | evaluation |
| Example 1 | R-1 | 45.2 | B | 15.9 | A | 32.5 | A | 15.6 | A |
| Example 2 | R-2 | 43.5 | B | 14.3 | AA | 28.9 | AA | 14.8 | AA |
| Example 3 | R-3 | 43.8 | B | 14.4 | AA | 29.1 | AA | 15.3 | A |
| Example 4 | R-4 | 42.9 | B | 14.7 | AA | 29.3 | AA | 15.9 | A |
| Example 5 | R-5 | 44.1 | B | 14.5 | AA | 34.9 | A | 15.0 | AA |
| Comparative Example 1 | R-6 | 44.5 | B | 15.4 | A | 33.2 | A | 16.8 | B |
| Comparative Example 2 | R-7 | 43.2 | B | 15.3 | A | 42.5 | B | 15.4 | A |
| Comparative Example 3 | R-8 | 42.5 | B | 14.9 | AA | 27.3 | AA | 16.8 | B |
| Comparative Example 4 | R-9 | 43.9 | B | 14.6 | AA | 42.8 | B | 14.9 | AA |

As shown in Table 7, Examples containing the components (b) and (c) and in which the van der Waals radius of the acid generated from the component (c) is greater than $3.0 \times 10^{-28}$ m³ were superior in both the sensitivity and the nanoedge roughness in the operation (b) which carries out both the patternwise exposure and the floodwise exposure. In particular, the sensitivity in the operation (b) is greatly improved compared to the sensitivity in the operation (a), indicating that the chemically amplified resist material may be suitably employed in a process carrying out such two exposures. Furthermore, Examples 2 and 3 in which the van der Waals radius of the acid generated is greater than $3.5 \times 10^{-28}$ m³ were particularly superior in the sensitivity in the operation (b). Moreover, Example 2 in which the van der Waals radius of the acid generated is greater than $3.5 \times 10^{-28}$ m³ and the radioactive ray-reactive first trapping agent was contained was particularly superior in the nanoedge roughness in the operation (b).

What is claimed is:

1. A resist-pattern-forming method comprising:
   patternwise exposing a predetermined region of a resist material film made from a photosensitive resin composition comprising a chemically amplified resist material to a first radioactive ray that is ionizing radiation or nonionizing radiation having a wavelength of no greater than 400 nm;
   floodwise exposing the resist material film patternwise exposed, to a second radioactive ray that is nonionizing radiation having a wavelength greater than the nonionizing radiation for the patternwise exposing and greater than 200 nm;
   baking the resist material film floodwise exposed; and
   developing the resist material film baked with a developer solution to form a resist pattern,
   the chemically amplified resist material comprising:
   a base component that is capable of being made soluble or insoluble in the developer solution by an action of an acid; and a generative component that is capable of generating a radiation-sensitive sensitizer and an acid upon an exposure, wherein the generative component comprises:
at least one radiation-sensitive acid-and-sensitizer generating agent;
the at least one radiation-sensitive acid-and-sensitizer generating agent and at least one a radiation-sensitive sensitizer generating agent;
the at least one radiation-sensitive acid-and-sensitizer generating agent and at least one radiation-sensitive acid generating agent;
the at least one radiation-sensitive sensitizer generating agent and the at least one radiation-sensitive acid generating agent; or
the at least one radiation-sensitive acid-and-sensitizer generating agent, the at least one radiation-sensitive sensitizer generating agent, and the at least one radiation-sensitive acid generating agent, wherein
the radiation-sensitive acid-and-sensitizer generating agent generates, upon the exposure to the first radioactive ray, an acid, and a radiation-sensitive sensitizer absorbing the second radioactive ray, and substantially does not generate the acid and the radiation-sensitive sensitizer upon the exposure to the second radioactive ray, in light-unexposed regions that are not exposed to the first radioactive ray in the patternwise exposing, the radiation-sensitive sensitizer generating agent generates, upon the exposure to the first radioactive ray, a radiation-sensitive sensitizer absorbing the second radioactive ray, and substantially does not generate the radiation-sensitive sensitizer upon the exposure to the second radioactive ray, in light-unexposed regions that are not exposed to the first radioactive ray in the patternwise exposing, and the radiation-sensitive acid generating agent generates an acid upon the exposure to the first radioactive ray, and substantially does not generate the acid upon the exposure to the second radioactive ray, in light-unexposed regions that are not exposed to the first radioactive ray in the patternwise exposing, wherein a van der Waals volume of an acid generated from the generative component is no less than $3.0 \times 10^{-28}$ m$^3$ and wherein the radiation-sensitive acid-and-sensitizer generating agent or the radiation-sensitive acid generating agent is an onium salt compound, and an anion of the onium salt compound is represented by formula (1):

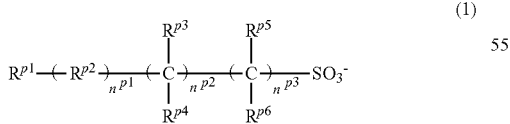

wherein, in the formula (1),
$R^{p1}$ represents a monovalent group having 8 or more ring atoms;
$R^{p2}$ represents a divalent linking group;
$R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms;

$R^{p5}$ and $R^{p6}$ each independently represent a fluorine atom or a monovalent fluorinated hydrocarbon group having 1 to 20 carbon atoms;
$n^{p1}$ is an integer of 0 to 10;
$n^{p2}$ is an integer of 0 to 10; and
$n^{p3}$ is an integer of 2,
wherein in a case where $n^{p1}$ is no less than 2, a plurality of $R^{p2}$s are identical or different, in a case where $n^{p2}$ is no less than 2, a plurality of $R^{p3}$s are identical or different and a plurality of $R^{p4}$s are identical or different, and a plurality of $R^{p5}$s are identical or different and a plurality of $R^{p6}$s are identical or different.

2. The resist-pattern-forming method according to claim 1, wherein
the radiation-sensitive acid-and-sensitizer generating agent or the radiation-sensitive acid generating agent comprises a radiation-sensitive onium cation and the anion, and
energy released upon reduction of the radiation-sensitive onium cation to a radical is no less than 5.0 eV.

3. The resist-pattern-forming method according to claim 1, further comprising a first trapping agent that can trap an acid and a cation, and is radioactive ray-reactive.

4. The resist-pattern-forming method according to claim 3, wherein the first trapping agent is degradable by a radioactive ray.

5. The resist-pattern-forming method according to claim 1, wherein the van der Waals volume of the acid generated from the generative component is no less than $3.32 \times 10^{-28}$ m$^3$.

6. The resist-pattern-forming method according to claim 1, wherein the van der Waals volume of the acid generated from the generative component is no less than $3.5 \times 10^{-28}$ m$^3$.

7. The resist-pattern-forming method according to claim 1, wherein the van der Waals volume of the acid generated from the generative component is no greater than $1.0 \times 10^{-27}$ m$^3$.

8. The resist-pattern-forming method according to claim 1, wherein
the radiation-sensitive acid-and-sensitizer generating agent or the radiation-sensitive acid generating agent comprises a radiation-sensitive onium cation and the anion, and
energy released upon reduction of the radiation-sensitive onium cation to a radical is no less than 5.1 eV.

9. The resist-pattern-forming method according to claim 1, wherein
the radiation-sensitive acid-and-sensitizer generating agent or the radiation-sensitive acid generating agent comprises a radiation-sensitive onium cation and the anion, and
energy released upon reduction of the radiation-sensitive onium cation to a radical is no less than 5.2 eV.

10. The resist-pattern-forming method according to claim 1, wherein
the radiation-sensitive acid-and-sensitizer generating agent or the radiation-sensitive acid generating agent comprises a radiation-sensitive onium cation and the anion, and
a reduction potential of the radiation-sensitive onium cation is from −1.3 V to 0.0V.

11. A chemically amplified resist material comprising:
a base component that is capable of being made soluble or insoluble in a developer solution by an action of an acid; and a generative component that is capable of generating a radiation-sensitive sensitizer and an acid upon an exposure,
wherein the generative component comprises:
at least one radiation-sensitive acid-and-sensitizer generating agent;
the at least one radiation-sensitive acid-and-sensitizer generating agent and at least one a radiation-sensitive sensitizer generating agent;
the at least one radiation-sensitive acid-and-sensitizer generating agent and at least one radiation-sensitive acid generating agent;
the at least one radiation-sensitive sensitizer generating agent and the at least one radiation-sensitive acid generating agent; or
the at least one radiation-sensitive acid-and-sensitizer generating agent, the at least one radiation-sensitive sensitizer generating agent, and the at least one radiation-sensitive acid generating agent,
wherein
the radiation-sensitive acid-and-sensitizer generating agent is capable of generating, upon an exposure to a first radioactive ray that is ionizing radiation or non-ionizing radiation having a wavelength of no greater than 400 nm, an acid, and a radiation-sensitive sensitizer absorbing a second radioactive ray that is nonionizing radiation having a wavelength greater than a wavelength of the first radioactive ray and greater than 200 nm, and substantially does not generate the acid and the radiation-sensitive sensitizer upon an exposure to the second radioactive ray without the exposure to the first radioactive ray,
the radiation-sensitive sensitizer generating agent is capable of generating, upon the exposure to the first radioactive ray, a radiation-sensitive sensitizer absorbing the second radioactive ray, and substantially does not generate the radiation-sensitive sensitizer upon the exposure to the second radioactive ray without the exposure to the first radioactive ray, and
the radiation-sensitive acid generating agent is capable of generating an acid upon the exposure to the first radioactive ray, and substantially does not generate the acid upon the exposure to the second radioactive ray without the exposure to the first radioactive ray,
wherein a van der Waals volume of the acid generated from the generative component is no less than $3.0\times10^{-28}$ m$^3$, and
wherein the radiation-sensitive acid-and-sensitizer generating agent or the radiation-sensitive acid generating agent is an onium salt compound, and an anion of the onium salt compound is represented by formula (1):

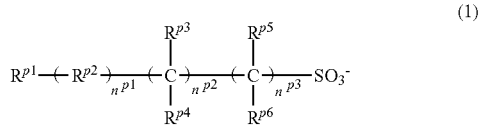

(1)

wherein, in the formula (1),
$R^{p1}$ represents a monovalent group having 8 or more ring atoms;
$R^{p2}$ represents a divalent linking group;
$R^{p3}$ and $R^{p4}$ each independently represent a hydrogen atom, a fluorine atom, a monovalent hydrocarbon group having 1 to 20 carbon atoms or a monovalent fluorinated hydrocarbon group having 1 to 20 carbon atoms;
$R^{p5}$ and $R^{p6}$ each independently represent a fluorine atom or a monovalent fluorinated hydrocarbon group having 1 to 20 carbon atoms;
$n^{p1}$ is an integer of 0 to 10;
$n^{p2}$ is an integer of 0 to 10; and
$n^{p3}$ is an integer of 2,
wherein in a case where $n^{p1}$ is no less than 2, a plurality of $R^{p2}$s are identical or different, in a case where $n^{p2}$ is no less than 2, a plurality of $R^{p3}$s are identical or different and a plurality of $R^{p4}$s are identical or different, and a plurality of $R^{p5}$s are identical or different and a plurality of $R^{p6}$s are identical or different.

12. The chemically amplified resist material according to claim 11, wherein
the radiation-sensitive acid-and-sensitizer generating agent or the radiation-sensitive acid generating agent comprises a radiation-sensitive onium cation and the anion, and
energy released upon reduction of the radiation-sensitive onium cation to a radical is no less than 5.0 eV.

13. The chemically amplified resist material according to claim 11, further comprising a first trapping agent that can trap an acid and a cation, and is radioactive ray-reactive.

14. The chemically amplified resist material according to claim 13, wherein the first trapping agent is degradable by a radioactive ray.

15. The chemically amplified resist material according to claim 11, wherein the van der Waals volume of the acid generated from the generative component is no less than $3.32\times10^{-28}$ m$^3$.

16. The chemically amplified resist material according to claim 11, wherein the van der Waals volume of the acid generated from the generative component is no less than $3.5\times10^{-28}$ m$^3$.

17. The chemically amplified resist material according to claim 11, wherein the van der Waals volume of the acid generated from the generative component is no greater than $1.0\times10^{-27}$ m$^3$.

18. The chemically amplified resist material according to claim 11,
wherein
the radiation-sensitive acid-and-sensitizer generating agent or the radiation-sensitive acid generating agent comprises a radiation-sensitive onium cation and the anion, and
energy released upon reduction of the radiation-sensitive onium cation to a radical is no less than 5.1 eV.

19. The chemically amplified resist material according to claim 11,
wherein
the radiation-sensitive acid-and-sensitizer generating agent or the radiation-sensitive acid generating agent comprises a radiation-sensitive onium cation and the anion, and
energy released upon reduction of the radiation-sensitive onium cation to a radical is no less than 5.2 eV.

20. The chemically amplified resist material according to claim 11,
wherein
the radiation-sensitive acid-and-sensitizer generating agent or the radiation-sensitive acid generating agent comprises a radiation-sensitive onium cation and the anion, and
a reduction potential of the radiation-sensitive onium cation is from −1.3 V to 0.0V.

* * * * *